US009540647B2

(12) United States Patent
Samant et al.

(10) Patent No.: US 9,540,647 B2
(45) Date of Patent: *Jan. 10, 2017

(54) METHODS AND COMPOSITIONS FOR THE TREATMENT OF CANCER

(71) Applicant: University of South Alabama, Mobile, AL (US)

(72) Inventors: Lalita Samant, Vestavia Hills, AL (US); Rajeev Samant, Vestavia Hills, AL (US); Shamik Das, Vestavia Hills, AL (US); Eddie Reed, Mobile, AL (US)

(73) Assignee: University of South Alabama, Mobile, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/919,448

(22) Filed: Oct. 21, 2015

(65) Prior Publication Data

US 2016/0115480 A1 Apr. 28, 2016

Related U.S. Application Data

(63) Continuation of application No. 13/635,893, filed as application No. PCT/US2011/029093 on Mar. 18, 2011, now Pat. No. 9,186,370.

(60) Provisional application No. 61/315,615, filed on Mar. 19, 2010.

(51) Int. Cl.
| A61K 31/70 | (2006.01) |
| C07H 21/02 | (2006.01) |
| C07H 21/04 | (2006.01) |
| C12N 15/113 | (2010.01) |
| G01N 33/50 | (2006.01) |
| G01N 33/574 | (2006.01) |
| A61K 31/704 | (2006.01) |
| A61K 31/7088 | (2006.01) |
| A61K 33/24 | (2006.01) |
| C12Q 1/68 | (2006.01) |

(52) U.S. Cl.
CPC ......... *C12N 15/1135* (2013.01); *A61K 31/704* (2013.01); *A61K 31/7088* (2013.01); *A61K 33/24* (2013.01); *G01N 33/5008* (2013.01); *G01N 33/5011* (2013.01); *G01N 33/57415* (2013.01); *C12N 2310/11* (2013.01); *C12N 2310/14* (2013.01); *C12N 2310/531* (2013.01); *C12N 2320/30* (2013.01); *G01N 2800/56* (2013.01)

(58) Field of Classification Search
None
See application file for complete search history.

(56) References Cited

U.S. PATENT DOCUMENTS

| 4,945,050 A | 7/1990 | Sanford et al. |
| 5,036,006 A | 7/1991 | Sanford et al. |
| 5,100,792 A | 3/1992 | Sanford et al. |
| 5,459,127 A | 10/1995 | Felgner et al. |
| 5,580,859 A | 12/1996 | Felgner et al. |
| 5,589,466 A | 12/1996 | Felgner et al. |
| 5,824,519 A | 10/1998 | Norris et al. |
| 6,271,359 B1 | 8/2001 | Norris et al. |
| 8,273,701 B2 | 9/2012 | Robbins et al. |
| 9,186,370 B2 | 11/2015 | Samant et al. |
| 2004/0259247 A1 | 12/2004 | Tuschl et al. |
| 2005/0085417 A1 | 4/2005 | Wickstrom et al. |
| 2005/0119204 A1 | 6/2005 | Chabas et al. |
| 2007/0009530 A1 | 1/2007 | Altaba et al. |
| 2007/0161588 A1 | 7/2007 | Lawman et al. |
| 2013/0224311 A1 | 8/2013 | Samant et al. |

FOREIGN PATENT DOCUMENTS

| WO | WO 92/05263 | 4/1992 |
| WO | WO 94/21807 | 9/1994 |
| WO | WO 94/26914 | 11/1994 |
| WO | WO 95/18863 | 7/1995 |
| WO | WO 95/21931 | 8/1995 |
| WO | WO 96/17823 | 6/1996 |
| WO | WO 96/25508 | 8/1996 |
| WO | WO 2006/020071 | 2/2006 |
| WO | WO 2007/027421 | 3/2007 |
| WO | WO 2007/067814 | 6/2007 |

OTHER PUBLICATIONS

Ahmad et al. ERCC1-XPF endonuclease facilitates DNA double-strand break repair. Mol Cell Biol. (2008) 28(16): 5082-5092.
Al-Minawi et al. the ERCC1/XPF endonuclease is required for completion of homologous recombination at DNA replication forks stalled by inter-strand cross-links. Nucleic Acids Res. (2009) 37(19): 6400-6413.
Alonso et al. A High-Throughput Study in Melanoma Identifies Epithelial-Mesenchymal Transition as a Major Determinant of Metastasis, Cancer Res. (2007) 67(7): 3450-3460.
Altaha et al. Excision repair cross complementing-group 1: Gene expression and platinum resistance. Int J Mol Med. (2004) 14(6): 959-970.
Beachy et al., Tissue Repair and Stem Cell Renewal in Carcinogenesis, Nature (2004) 432(7015): 324-331.
Beard et al. Transcription Mapping of Mouse Adenovirus Type 1 Early Region 3. Virol. 1990) 175(1): 81-90.
Bellahcéene et al. Small integrin-binding ligand N-linked glycoproteins (SIBLINGs): multifunctional proteins in cancer, Nat. Rev. Cancer (2008) 8(3): 212-226.
Berman et al., Widespread requirements for Hedgehog ligand Stimulation in growth of digestive tract tumours, Nature (2003), 425(6960): 846-851.
Bonovich et al. Adenoviral delivery of A-FOS, an AP-1 dominant negative, selectively inhibits drug resistance in two human cancer cell lines. Cancer Gene Ther. (2002) 9(1): 62-70.

(Continued)

Primary Examiner — Sean McGarry
(74) Attorney, Agent, or Firm — Knobbe, Martens, Olson & Bear LLP

(57) ABSTRACT

Some embodiments of the present invention relate to methods and compositions for treating cancer. More embodiments include methods and compositions for modulating the activity of the Hedgehog pathway.

22 Claims, 99 Drawing Sheets

(56) References Cited

OTHER PUBLICATIONS

Boring et al., Cancer statistics, 1993, CA Cancel J. Clin. (1993) 43(1):7-26.
Brown et al. Osteopontin Expression and Distribution in Human Carcinomas. Am J Pathol. (1994) 145:(3): 610-623
Brummelkamp et al. A system for stable expression of short interfering RNAs in mammalian cells. Science (2002) 296(5567): 550-553.
Burleson et al. Ovarian carcinoma ascites spheroids adhere to extracellular matrix components and mesothelial cell monolayers. Gynecol Oncol. (2004) 93(1): 170-181.
Calegari et al. Tissue-specific RNA interference in postimplantation mouse embryos with endoribonuclease-prepared short interfering RNA. Proc. Natl. Acad. Sci. USA (2002) 99(22): 14236-40.
Carpenter et al., Characterization of two patched receptors for the vertebrate hedgehog protein family, Proc Natl Acad Sci. USA (1998) 95: 13630-40.
Casey et al. β1-Integrins Regulate the Formation and Adhesion of Ovarian Carcinoma Multicellular Spheroids. Am J of Pathol. (2001) 159(6): 2071-2080.
Chae et al. Requirement for sphingosine 1-phospate receptor-1 in tumor angiogenesis demonstrated by in vivo RNA interference. J Clin Invest. (2004) 114(8): 1082-1089.
Chen et al. Hedgehog signal pathway is activated in ovarian carcinomas, correlating with cell proliferation: It's inhibition leads to growth suppression and apoptosis. Cancer Sci. (Jan. 2007) 98(1):68-76.
Chiu et al. RNAi in human cells: basic structural and functional features of small interfering RNA. Mol Cell. (2002) 10(3): 549-561.
Chou et al. In vitro response of MC3T3-E1 pre-osteoblasts within three-dimensional apatite-coated PLGA scaffolds. J Biomed Mater Res B Appl Biomater. (2005) 75(1): 81-90.
Clackson et al. Making antibody fragments using phage display libraries. Nature (1991) 352(6336): 624-628.
Clement et al., HEDGEHOG-GLI1 signaling regulates human glioma growth, cancer stem cell self-renewal and tumorigenicity, Curr Biol. (2007) 17(2): 165-172.
Cook et al. Osteopontin Induces Multiple Changes in Gene Expression that Reflect the Six "Hallmarks of Cancer" in a Model of Breast Cancer Progression. Mol Carcinog. (2005) 43(4): 225-236.
Coppola et al. Correlation of osteopontin protein expression and pathological stage across a wide variety of tumor histologies, Clin Cancer Res. (2004) 10(1Pt 1): 184-190.
Curiel et al. High-Efficiency Gene Transfer Mediated by Adenovirus Coupled to DNA-Polylysine Complexes. Hum. Gene Ther. (1992) 3(2): 147-154.
Dabholkar et al. ERCC1 and ERCC2 expression in malignant tissues from ovarian cancer patients. J Natl Cancer Inst. (1992) 84(19): 1512-1517.
Dabholkar et al. Messenger RNA levels of XPAC and ERCC1 in ovarian cancer tissue correlate with response to platinum-based chemotherapy. J Clin Invest. (1994) 94(2): 703-708.
Das et al. The hedgehog pathway transcription factor GLI1 promotes malignant behavior of cancer cells by up-regulating osteopontin. J Biol Chem. (2009) 284(34): 22888-97.
De Fougerolles et al. RNA interference in vivo: toward synthetic small inhibitory RNA-based therapeutics. Methods Enzymol. (2005) 392: 278-296.
Dean et al. Electroporation as a method for high-level nonviral gene transfer to the lung. Gene Ther. (2003) 10: 1608-1615.
D'Errico et al. Mechanism of oxidative DNA damage repair and relevance to human pathology. Mutat Res.(2008) 659(1-2): 4-14.
Dillon et al. Short- and long-range effects of Sonic hedgehog in limb development. Proc Natl Acad Sci U S A. (2003) 100(18): 10152-10157.
Doudna et al. The chemical repertoire of natural ribozymes. Nature (2002) 418(6894): 222-228.
Duarte et al. S100A4: a novel regulator of mineralization and osteoblast differentiation. J Bone Miner Res. (2003) 18(3): 493-501.
Ebisawa et al. Characterization of bone morphogenetic protein-6 signaling pathways in osteoblast differentiation. J Cell Sci. (1999) 112 ( Pt 20): 3519-3527.
Elbashir et al. Duplexes of 21-nucleotide RNAs mediate RNA interference in cultured mammalian cells. Nature (2001) 411(:494-498.
Fattal et al. Biodegradable polyalkylcyanoacrylate nanoparticles for the delivery of oligonucleotides. J. Control Release (1998) 53(1-3): 137-43.
Felgner et al. Cationic liposome-mediated transfection. Nature (1989) 337(6205): 387-388.
Felgner et al. Lipofection: A highly efficient, lipid-mediated DNA-transfection procedure. Proc. Natl. Acad. Sci. USA (1987) 84:7413-7417.
Fuchs et al. Silencing of disease-related genes by small interfering RNAs. Curr Mol Med. (2004) 4(5): 507-517.
Gaultier et al. Alpha-DNA. IV: Alpha-anomeric and beta-anomeric tetrathymidylates covalently linked to intercalating oxazolopyridocarbazole. Nucleic Acids Res. (1987) 15(16): 6625-6641.
Godard et al. Antisense effects of cholesterol-oligodeoxynucleotide conjugates associated with poly(alkylcyanoacrylate) nanoparticles. Eur. J. Biochem. (1995) 232(2): 404-10.
Gupta et al. Inducible, reversible, and stable RNA interference in mammalian cells. Proc Natl Acad Sci USA (2004) 101(7): 1927-1932.
Hahn et al., Mutations of the Human Homolog of *Drosophila* patched in the nevoid basal cell carcinoma syndrome, Cell (1998) 85: 841-851.
Hallahan et al. The SmoA1 mouse model reveals that notch signaling is critical for the growth and survival of sonic hedgehog-induced medulloblastomas, Cancer Res. (2004) 64(21): 7794-7800.
Hayaski et al. Serum Osteopontin, an Enhancer of Tumor Metastasis to Bone, Promotes B16 Melanoma Cell. J Cell Biochem. (2007) 101(4): 979-986.
Hedge et al. Early steps in the DNA base excision/single-strand interruption repair pathway in mammalian cells. Cell Res. (2008) 18(1): 27-47.
Hunter et al. The Characteristics of Inhibition of Protein Synthesis by Double-stranded Ribonucleic Acid in Reticulocyte Lysates. J Biol Chem. (1975) 250(2): 409-417.
Hutvagner et al. RNAi: nature abhors a double-strand. Curr. Opin. Genet. Dev. (2002) 12(2): 225-232.
Ichim et al. RNA interference: a potent tool for gene-specific therapeutics. Am J Transplant. (2004) 4(8): 1227-1236.
Ingham et al. Hedgehog signaling in animal development: paradigms and principles, Genes Dev. (2001) 15(23): 3059-3087.
Inoue et al. Sequence-dependent hydrolysis of RNA using modified oligonucleotide splints and Rnase H. FEBS Lett. (1987) 215(2): 327-330.
Inoue et al. Synthesis and hybridization studies on two complementary nona(2'-O-methyl)ribonucleotides Nucleic Acids Res. (1987) 15(15): 6131-6148.
Izumi et al. Mammalian DNA base excision repair proteins: their interactions and role in repair of oxidative DNA damage. Toxicology. (2003) 193(1-2): 43-65.
Jacque et al. Modulation of HIV-1 replication by RNA interference. Nature (2002) 418: 435-438.
Jana et al. RNA interference: potential therapeutic targets. Appl Microbiol Biotechnol. (2004) 65(6): 649-657.
Jiang et al. Gel-based application of siRNA to human epithelial cancer cells induces RNAi-dependent apoptosis. Oligonucleotides (2004) 14(4): 239-48.
Johnson et al., Human homolog of patched, a candidate gene for the basal cell nevus syndrome, Science (1996) 272(5368): 1668-1671.
Kaplitt et al. Expression of a Functional Foreign Gene in Adult Mammalian Brain following in Vivo Transfer via a Herpes Simplex Virus Type 1 Defective Viral Vector. Mol Cell Neurosci. (1991) 2: 320-330.
Kasugai et al. Concanavalin A induces formation of osteoclast-like cells in RAW 264.7 mouse macrophage cells. Immunopharmacol Immunotoxicol. (2009) 31(1): 103-107.

(56) References Cited

OTHER PUBLICATIONS

Kelley et al. Redox regulation of the DNA repair function of the human AP endonuclease Ape1/ref-1. Antioxid Redox Signal. (2001) 3(4): 671-683.
Kim et al. Electro-gene therapy of collagen-induced arthritis by using an expression plasmid for the soluble p75 tumor necrosis facor receptor-Fc fusion protein. Gen Ther. (2003) 10: 1216-1224
Kim et al. Inhibition of Ocular Angiogenesis by siRNA Targeting Vascular Endothelial Growth Factor Pathway Genes. American Journal of Pathology (2004) 165(6): 2177-2185.
Kingsley et al. Molecular biology of bone metastasis. Mol Cancer Ther. (2007) 6(10): 2609-2617.
Kinzler et al. The GLI Gene Encodes a Nuclear Protein Which Binds Specific Sequences in the Human Genome. Mol Cell Biol. (1990) 10(2): 634-642.
Kitagawa et al. Vascular endothelial growth factor contributes to prostate cancer-mediated osteoblastic activity. Cancer Res. (2005) 65(23): 10921-10929.
Lambert et al. Nanoparticulate systems for the delivery of antisense oligonucleotides. Adv Drug Deliv Rev. (2001) 47(1): 99-112.
Lampasso et al. The expression profile of PKC isoforms during MC3T3-E1 differentiation. Int J Mol Med. (2006) 17(6): 1125-1131.
Laner-Plamberger et al. Cooperation between GLI and JUN enhances transcription of JUN and selected GLI target genes. Oncogene (200) 28(13): 1639-1651.
Le Gal la Salle et al. An adenovirus vector for gene transfer into neurons and glia in the brain. Science (1993) 259(5097): 988-990.
Lebkowski et al. Adeno-associated Virus: a Vector System for Efficient Introduction and Integration of DNA into a Variety of Mammalian Cell Types. Mol Cell Biol. (1988) 8(10): 3988-3996.
Lee et al. Proliveration, differentiation, and calcification of preosteoblast-like MC3T3-E1 cells cultured onto noncrystalline calcium phosphate glass. J Biomed Mater Res Part A (2004) 69A(1): 188-195.
Lee et al. Cisplatin sensitivity/resistance in UV repair-deficient Chinese hamster ovary cells of complementation groups 1 and 3. Carcinogenesis (1993) 14(10): 2177-2180.
Lee et al. Expression of small interfering RNAs targeted against HIV-1 rev transcripts in human cells. Nat Biotechnol. (2002) 20(5): 500-505.
Lewis, D. L. Efficient delivery of siRNA for inhibition of gene expression in postnatal mice. Nat Genet. (2002) 32(1): 107-108.
Li et al. Association between the level of ERCC-1 expression and the repair of cisplatin-induced DNA damage in human ovarian cancer cells. AntiCancer Res. (2000) 20(2A): 645-652.
Li et al. Cisplatin and phorbol ester independently induce ERCC-1 protein in human ovarian carcinoma cells. Int J Oncol. (1998) 13(5): 987-992.
Li et al. Cisplatin induction of ERCC-1 mRNA expression in A2780/CP70 human ovarian cancer cells. J Biol Chem. (1998) 273(36): 23419-23425.
Li et al. Identification of pancreatic cancer stem cells, Cancer Res., (2007) 67(3): 1030-1037.
Li et al. Modulation of Excision Repair Cross Complementation Group 1 (ERCC-1) mRNA Expression by Pharmacological Agents in Human Ovarian Carcinoma cells. Biochem. Pharmacol. (1999) 57(4): 347-353.
Li et al. Phorbol ester exposure activates an AP-1 mediated increase in ERCC-1 messenger RNA expression in human ovarian tumor cells. Cell Mol Life Sci. (1999) 55(3): 456-466.
Li et al. Effect of interleukin-1α and tumor necrosis factor-α on cisplatin-induced ERCC1 mRNA expression in a human ovarian carcinoma cell line. Anticancer Res. (1998) 18(4a): 2283-2287.
Li et al. GLi1 acts through Snail and E-cadherin to promote nuclear signaling by beta-catenin. Oncogene. (2007) 26(31): 4489-4498.
Liao et al., Aberrant activation of hedgehog signaling pathway in ovarian cancers: effect on prognosis, cell invasion and differentiation. Carcinogenesis (Nov. 2008) 30(1):131-140.

Liang et al. Genomic copy number changes of DNA repair genes ERCC1 and ERCC2 in human gliomas. J Neurooncol. (1995) 26(1): 17-23.
Lin et al. Active site of (A)BC excinuclease. I. Evidence for 5'incision by UvrC through a catalytic site involving Asp399, Asp438, Asp466, and His538 residues. J Biol Chem. (1992) 267(25): 17688-17692.
Liu et al. Hedgehog Signaling and Bmi-1 Regulate Self-renewal of Normal and Malignant Human Mammary Stem Cells, Cancer Res, (2006) 66(12): 6063-6071.
Lohr et al. Effective Tumor Therapy with Plasmid-encoded Cytokines Combined with in Vivo Electroporation. Cancer Res. (2001) 61: 3281-3284.
Ma et al. Hedgehog signaling is activated in subsets of esophageal cancers, Int J Cancer. (2006) 118(1): 139-148.
Ma et al., Frequent activation of the hedgehog pathway in advanced gastric adenocarcinomas, Carcinogenesis (2005) 26(10): 1698-1705.
Machy et al. Gene Transfer from targeted liposomes to specific lymphoid cells by electroporation. Proc. Natl. Acad. Sci. USA (1988) 85: 8027-8031.
Madison et al. Epithelial hedgehog signals pattern the intestinal crypt-villus axis, Development (2005) 132(2): 279-289.
Maeda et al. Induction of osteoblast differentiation indices by statins in MC3T3-E1 cells. J Cell Biochem. (2004) 92(3): 458-471.
Martin TJ. Osteoblast-derived PTHrP is a physiological regulator of bone formation. J Clin Invest. (2005) 115(9): 2322-4.
Mastro et al. Breast Cancer cells induce osteoblast apoptosis: a possible contributor to bone degradation. J Cell Biochem. (2004) 91(2): 265-76.
McAllister et al. Systemic endocrine instigation of indolent tumor growth requires osteopontin, Cell (2008) 133(6): 994-1005.
McIntyre et al. Design and cloning strategies for constructing shRNA expression vectors. BMC Biotechnol. (2006) 6: 1; 8 pgs.
McManus et al. Gene silencing using micro-RNA designed hairpins. RNA (2002) 8(6): 842-850.
Mercer et al. Metastatic breast cancer cells suppress osteoblast adhesion and differentiation. Clin Exp Metastasis. (2004) 21(5): 427-435.
Miao et al. Osteoblast-derived PTHrP is a potent endogenous bone anabolic agent that modifies the therapeutic efficacy of administered PTH 1-34. J Clin Invest. (2005) 115(9): 2402-11.
Miao et al. Parathyroid hormone-related peptide is required for increased trabecular bone volume in parathyroid hormone-null mice. Endocrinology. (2004) 145(8): 3554-62.
Miller et al. Improved Retroviral Vectors for Gene Transfer and Expression. BioTech. (1992) 7(9): 980-990.
Mitra et al. Complexities of DNA base excision repair in mammalian cells. Mol Cells. 1997) 7(3): 305-312.
Miyagishi et al. U6 promoter-driven siRNAs with four uridine 3' overhangs efficiently suppress targeted gene expression in mammalian cells. Nat Biotechnol. (2002) 20(5): 497-500.
Mori et al. Conditioned media from mouse osteosarcoma cells promote MC3T3-E1 cell proliferation using JAKs and P13-K/Akt signal crosstalk. Cancer Sci. (2008) 99(11): 2170-2176.
Motoyama et al., Ptch2, a second mouse Patched gene is co-expressed with Sonic hedgehog, Nat Genet. (1998) 18(2): 104-106.
Nakano et al. Cytokine Gene Therapy for Myocarditis by In Vivo Elextroporation. Hum Gene Ther. (2001) 12: 1289-1297.
Narducci et al. Differentiation of activated monocytes into osteoclast-like cells on a hydroxyapatite substrate: an in vitro study. Ann Anat. (2009) 191(4): 349-355.
Nemoto et al. Osteopontin Deficiency Reduces Experimental Tumor Cell Metastasis to Bone and Soft Tissues. J Bone Miner Res. (2001) 16(4): 652-659.
Ohkawa et al., Activities of HIV-RNA targeted ribozymes transcribed from a 'shot-gun' type ribozyme-trimming plasmid. Nucleic Acids Symp. Ser. (1992) 27: 15-6.
Paddison et al. Short hairpin RNAs (shRNAs) induce sequence-specific silencing in mammalian cells. Genes Dev. (2002) 16(8): 948-958.
Pardridge, W. M. Intravenous, non-viral RNAi gene therapy of brain cancer. Expert Opin Biol Ther. (2004) 4(7): 1103-1113.

(56) References Cited

OTHER PUBLICATIONS

Parker et al. Acquired cisplatin resistance in human ovarian cancer cells is associated with enhanced repair of cisplatin-DNA lesions and reduced drug accumulation. J Clin Invest. (1991) 87(3): 772-777.

Paul et al. Effective expression of small interfering RNA in human cells. Nat Biotechnol. (2002) 20(5): 505-508.

Peacock et al. Hedgehog signaling maintains a tumor stem cell compartment in multiple myeloma, Proc Natl Acad Sci USA (2007) 104(10): 4048-4053.

Rangaswami et al. Osteopontin stimulates melanoma growth and lung metastasis through NIK/MEKK1-dependent MMP-9 activation pathways, Oncol Rep. (2007) 18(4): 909-915.

Reed E., ERCC1 and Clinical Resistance to Platinum-based Therapy. Clin Cancer Res. (2005) 11(17): 6100-6102.

Reed E., ERCC1 Measurements in clinical oncology. N Engl J Med. (2006) 355(10): 1054-1055.

Reed, E. Cisplatin and platinum analogs. in: Cancer Principles and Practice of Oncology, DeVita et al (Eds); 8th Edition. (2008) Lippincott, Williams, and Wilkins; Philadelphia, Chapter 25.5, Pharmacology of Cancer Chemotherapy, pp. 419-426.

Ricci-Vitiani et al. Identification and expansion of human colon-cancer-initiating cells, Nature (2007) 445(7123): 111-115.

Riker et al. The gene expression profiles of primary and metastatic melanoma yields a transition point of tumor progression and metastasis, BMC Med. Genomics (2008) 1:13.

Ruiz I Altaba, A. Gli proteins encode context-dependent positive and negative functions: implications for development and disease. Development. (1999) 126(14): 3205-3216.

Ryther et al. siRNA therapeutics: big potential from small RNAs. Gene Ther. (2005) 12(1): 5-11.

Samant et al. Breast Cancer Metastasis Suppressor I (BRMS I) Inhibits Osteopontin Transcription by abrogating NF-κB Activation, Mol Cancer (2007) 6: 6; 9 pgs.

Samulski et al. A Recombinant Plasmid from which an Infectious Adeno-Associated Virus Genome can be Excised In Vitro and its use to Study Viral Replication. J Virol. (1987) 61(10): 3096-3101.

Samulski et al. Helper-free Stocks of Recombinant Adeno-associated Viruses: Normal Integration does not Require Viral Gene Expression. J Virol. (1989) 63(9): 3822-3828.

Schwab et al. An approach for new anticancer drugs: oncogene-targeted antisense DNA. Ann. Oncol. (1994) 5 Suppl. 4: 55-58.

Sharp P. A. RNA interference—2001. Genes Dev. (2001) 15(5): 485-490.

Shen, W.-G. RNA interference and its current application in mammals. Chin Med J. (Engl) (2004) 117(7): 1084-1091.

Shevde et al. Osteopontin knockdown suppresses tumorigenicity of human metastatic breast carcinoma, MDA-MB-435. Clin Exp Metastasis (2006) 23(2): 123-133.

Sims-Mourtada et al. Hedgehog: an Attribute to Tumor Regrowth after Chemoradiotherapy and a Target to Improve Radiation Response, Clin Cancer Res. (2006) 12(21): 6565-6572.

Soutschek et al. Therapeutic silencing of an endogenous gene by systemic administration of modified siRNAs. Nature (2004) 432(7014): 173-178.

Srinivasan et al. Hypoxia-mediated mitochondrial stress in RAW264.7 cells induces osteoclast-like TRAP-positive cells. Ann N Y Acad Sci. (2007) 1117: 51-61.

Stamataki et al. A Gradient of GLI activity mediates graded Sonic Hedgehog Signaling in the Neural Tube. Genes Dev. (2005) 19(5): 626-641.

States et al. Enhanced XPA mRNA levels in cisplatin-resistant human ovarian cancer are not associated with XPA mutations or gene amplification. Cancer Lett. (1996) 108(2): 233-237.

Stecca et al. A GLI1-p53 inhibitory loop controls neural stem cell and tumour cell numbers. Embo J. (2009) 28(6): 663-676.

Stecca et al., Melanomas require HEDGEHOG-GLI signaling regulated by interactions between GLI1 and the RAS-MEK/AKT pathways, Proc Natl Acad Sci USA, (2007) 104: 5895-5900.

Stratford-Perricaudet et al. Widespread Long-term Gene Transfer to Mouse Skeletal Muscles and Heart. J Clin Invest. (1992) 90: 626-630.

Sugatani et al. PTEN regulates RANKL- and osteopontin-stimulated signal transduction during osteoclast differentiation and cell motility. J Biol Chem. (2003) 278(7): 5001-5008.

Sui et al. A DNA vector-based RNAi technology to suppress gene expression in mammalian cells. Proc Natl Acad Sci USA (2002) 99(6): 5515-5520.

Sun et al. Conditional inactivation of Fgf4 reveals complexity of signalling during limb bud development, Nat Genet. (2000) 25(1): 83-86.

Taira et al. Construction of a novel RNA-transcript-trimming plasmid which can be used both in vitro in place of run-off and (G)-free transcriptions and in vivo as multi-sequences transcription vectors. Nucleic Acids Res. (1991) 19(19): 5125-30.

Takaku, H. Gene silencing of HIV-1 by RNA interference. Antivir Chem Chemother. (2004) 15(2): 57-65.

Taxman et al. Criteria for effective design, construction, and gene knockdown by shRNA vectors. BMC Biotechnol. (2006) 6: 7; 16 pgs.

ten Haaf et al., Expression of the *glioma-associated oncogene homolog* (GLI) I in human bread cancer is associated with unfavourable overall survival. BMC Cancer (Aug. 2009) 9:298; 12 pages.

Tuck et al. Osteopontin-induced migration of human mammary epithelial cells involves activation of EGF receptor and multiple signal transduction pathways, Oncogene. (2003) 1198-1205.

Tuschl, T. Expanding small RNA interference. Nature Biotechnol. (2002) 20(5): 446-448.

Ueno et al. MC3T3-E1-conditioned medium-induced mineralization by clonal rat dental pulp cells. Matrix Biol. (2001) 20(5-6): 347-355.

Ulmer et al. Heterologous Protection Against Influenza by Injection of DNA Encoding a Viral Protein. Science (1993) 259(5102): 1745-1748.

Ventura et al. Activation of HIV-specific riboyme activity by self-cleavage. Nucleic Acids Res. (1993) 21(14): 3249-55.

Verhoeven et al. Catalytic sites for 3' and 5' incision of *Escherichia coli* nucleotide excision repair are both located in UvrC. J Biol Chem. (2000) 275(7): 5120-5123.

Vincent et al. The generation of osteoclasts from RAW 264.7 precursors in defined, serum-free conditions. J Bone Miner Metab. (2009) 27(1): 114-119.

Voronov et al. Beno[a]pyrene inhibits osteoclastogenesis by affecting RANKL-induced activation of NF-kappaB. Biochem Pharmacol. (2008) 75(10): 2034-2044.

Wadhwa et al. Know-how of RNA interference and its applications in research and therapy. Mutat Res. (2004) 567(1): 71-84.

Wang et al. Isolation and characterization of MC3T3-E1 preosteoblast subclones with distinct in vitro and in vivo differentiation/mineralization potential. J Bone Miner Res. (1999) 14(6): 893-903.

Wang et al. Proliferation and differentiation of MC3T3-E1 cells on calcium phosphate/chitosan coatings. J Dent Res. (2008) 87(7): 650-654.

Watkins et al. Hedgehog signalling within airway epithelial progenitors and in small-cell lung cancer. Nature (2003) 422(6929): 313-317.

Williams et al. Introduction of foreign genes into tissues of living mice by DNA-coated microprojectiles. Proc Natl Acad Sci. USA (1991) 88(7): 2726-2730.

Wilson et al. Hepatocyte-directed gene transfer in vivo leads to transient improvement of hypercholesterolemia in low density lipoprotein receptor-deficient rabbits. J Biol Chem. (1992) 267(2): 963-967.

Wu et al. Receptor-mediated Gene Delivery and Expression in Vivo. J. Biol. Chem. (1988) 263(29): 14621-14624.

Wu et al. Receptor-mediated in vitro gene transformation by a soluble DNA carrier system. J Biol Chem. (1987) 262(10): 4429-4432.

Xia et al. SiRNA-mediated gene silencing in vitro and in vivo. Nat Biotechnol. (2002) 20(10): 1006-10.

(56) References Cited

OTHER PUBLICATIONS

Xie et al. A role of PDGFRalpha in basal cell carcinoma proliferation, Proc Natl Acad Sci. USA (2001) 98(16): 9255-9259.

Xu et al. Plant Homologue of Human Excision Repair Gene ERCC1 Points to Conservation of DNA Repair Mechanisms. Plant J. (1998) 13(6): 823-829.

Xu et al., Gli1 promotes cell survival and is predictive of a poor outcome in Era-negative breast cancer. Breast Cancer Res Treat. (Aug. 2010) 123(1):59-71.

Xuan et al. Expression of Indian Hedgehog signaling molecules in breast cancer, J Cancer Res Clin Oncol. (2009) 135(2): 235-240.

Yan et al. Regulation of osteoclastogenesis and RANK expression by TGF-beta1. J Cell Biochem. (2001) 83(2): 320-325.

Yin et al. A causal role for endothelin-1 in the pathogenesis of osteoblastic bone metastases. Proc Natl Acad Sci U S A. (2003) 100(19): 10954-10959.

Young et al. Effect of a DNA nuclear targeting sequence on gene transfer and expression of plasmids in the intact vasculature. Gene Ther. (2003) 10: 1465-1470.

Yu et al. Absence of evidence for allelic loss or allelic gain for ERCC1 or for XPD in human ovarian cancer cells and tissues. Cancer Lett. (2000) 151(2): 127-132.

Yu et al. An ERCC1 splicing variant involving the 5'-UTR of the mRNA may have a transcriptional modulatory function. Oncogene, (2001) 20(52): 7694-7698.

Yu et al. Comparison of two human ovarian carcinoma cell lines (A2780/CP70 and MCAS) that are equally resistant to platinum, but differ at codon 118 of the ERCC1 gene. International Journal of Oncology. (2000) 16(3): 555-560.

Yu et al. RNA interference by expression of short-interfering RNAs and hairpin RNAs in mammalian cells. Proc Natl Acad Sci U S A (2002) 99(9): 6047-6052.

Yu et al. Sonic hedgehog regulates proliferation and differentiation of mesenchymal cells in the mouse metanephric kidney, Development. (2002) 129(22): 5301-5312.

Zhang et al. Identification and characterization of ovarian cancer-initiating cells from primary human tumors. Cancer Res. (2008) 68(11): 4311-4320.

Zhao et al., Expression of Gli1 correlates with the transition of breast cancer cells to estrogen-independent growth. Breast Cancer Res Treat. (Feb. 2009) 119:39-51.

Zheng, B. J., Prophylactic and therapeutic effects of small interfering RNA targeting SARS-coronavirus. Antivir. Ther. (2004) 9(3): 365-374.

Zhu et al. The Human Glioma-associated Oncogene Homolog 1 (GLI1) Family of Transcription Factors in Gene Regulation and Diseases. Curr Genomics. (2010) 11(4): 238-245.

Zietarska et al. Molecular description of a 3D in vitro model for the study of epithelial ovarian cancer (EOC). Mol Carcinog. (2007) 46(10): 872-885.

Zunich et al. Paracrine sonic hedgehog signaling by prostate cancer cells induces osteoblast differentiation. Mol Cancer (2009) 8: 12, 11 pgs.

International Search Report and Written Opinion dated Dec. 27, 2011 for Application No. PCT/US2011/029093, filed Mar. 18, 2011.

International Preliminary Report on Patentability Chapter II dated Sep. 28, 2012 for Application No. PCT/US2011/029093, filed Mar. 18, 2011.

Chen X-L. et al., "Gli-1 siRNA induced apoptosis in Huh7 cells", World J Gastroenterol. (Jan. 2008) 14(4): 582-589.

Cytoplasmic fraction and nuclear fraction of A2780-CP70 Cells in log phase growth, in monolayer. Gli1 localizes to the fraction that has histone deactylase (nuclear), and not to the tubulin fraction (cytoplasm).

- HDAC; a 134 kDa band
- Alpha-Tubulin; 50 kDa
- Gli1; 150kDa 24 hrs after transfection with anti-Gli1 construct (shRNA) into A2780 and A2780/CP70 cells mRNA levels of ERCC1, XPD and XRCC1: T=0, 6, 24, 48, 72 hours after after treated with cisplatin to shGli1 transfected A2780/CP70 cells

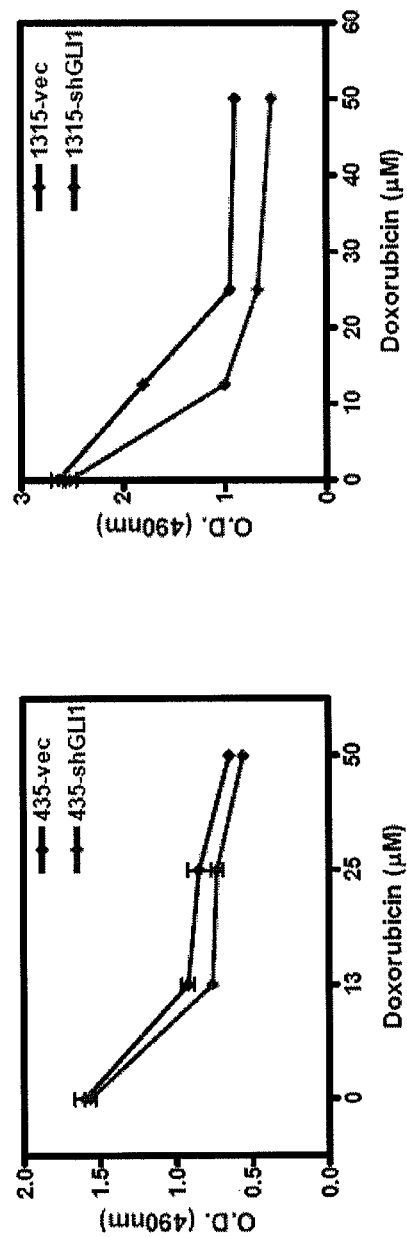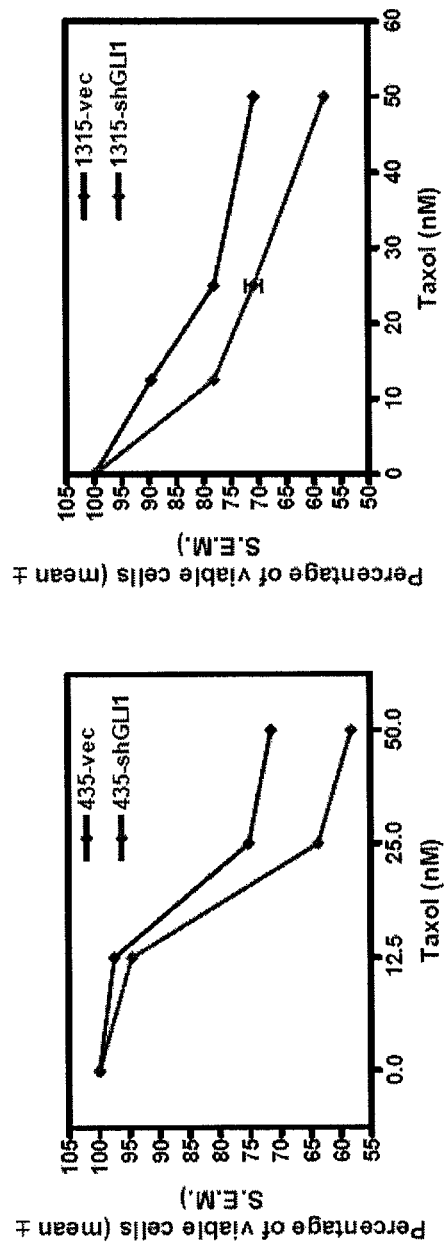
FIG. 62A
FIG. 62B

METHODS AND COMPOSITIONS FOR THE TREATMENT OF CANCER

RELATED APPLICATIONS

This application is a continuation of U.S. Ser. No. 13/635,893 filed Sep. 18, 2012 entitled "METHODS AND COMPOSITIONS FOR THE TREATMENT OF CANCER" which is the U.S. National Phase Application No. PCT/US2011/029093 entitled "METHODS AND COMPOSITIONS FOR THE TREATMENT OF CANCER" filed Mar. 18, 2011 and published in English on Sep. 22, 2011 as WO2011/116351 which claims the benefit of U.S. Provisional Application No. 61/315,615 filed Mar. 19, 2010, the contents of which are incorporated by reference in their entireties.

STATEMENT REGARDING FEDERALLY SPONSORED R&D

This invention was made with government support under Department of Defense IDEA Award 07-1-0400, and National Institute of Health 1R01CA140472-01A1. The government has certain rights in the invention.

REFERENCE TO SEQUENCE LISTING

The present application is being filed along with a Sequence Listing in electronic format. The Sequence Listing is provided as a file entitled USA002C1SEQLIST.TXT, created Oct. 10, 2015, which is approximately 34 Kb in size. The information in the electronic format of the Sequence Listing is incorporated herein by reference in its entirety.

FIELD OF THE INVENTION

Some embodiments of the present invention relate to methods and compositions for treating cancer. More embodiments include methods and compositions for modulating the activity of the Hedgehog pathway.

BACKGROUND

Members of the hedgehog family of signaling molecules mediate many important short- and long-range patterning processes during invertebrate and vertebrate embryonic, fetal, and adult development. In *Drosophila melanogaster*, a single hedgehog gene regulates segmental and imaginal disc patterning. In contrast, in vertebrates, a hedgehog gene family (e.g., in mammals, SHH, DHH, IHH) is involved in the control of proliferation, differentiation, migration, and survival of cells and tissues derived from all three germ layers, including, e.g., left-right asymmetry, CNS development, somites and limb patterning, chondrogenesis, skeletogenesis and spermatogenesis.

Hedgehog signaling occurs through the Hedgehog pathway which includes interactions between hedgehog ligand with the hedgehog receptor, Patched (Ptch), and the co-receptor Smoothened (Smo). There are two mammalian homologs of Ptch, Ptch-1 and Ptch-2 ("collectively "Ptch"), both of which are 12 transmembrane proteins containing a sterol sensing domain (Motoyama et al., Nature Genetics 18: 104-106 (1998), Carpenter et al., P.N.A.S. (U.S.A.) 95: 13630-40 (1998)). The interaction of Hedgehog with Ptch triggers a signaling cascade that results in the regulation of transcription by zinc-finger transcriptions factors of the Gli family.

Malignant tumors (cancers) are the second leading cause of death in the United States, after heart disease (Boring et al., CA Cancel J. Clin. 43:7 (1993)). Cancer features can include an the increase in the number of neoplastic cells which proliferate to form a tumor mass; invasion of adjacent tissues by these neoplastic tumor cells; and generation of malignant cells which eventually spread via the blood or lymphatic system to regional lymph nodes and to distant sites. Cancer manifests itself in a wide variety of forms, characterized by different degrees of invasiveness and aggressiveness.

Reactivation of the Hedgehog pathway has been implicated in a wide variety of cancers and carcinogenesis. The earliest examples of Hedgehog signaling in cancers came from the discovery that Gorlin's syndrome, in which patients frequently suffer basal cell carcinomas and are also predisposed to medulloblastomas and rhabdomysocarcomas, is due to an inactivating mutation in Ptch, resulting in Hedgehog pathway activation (Hahn et al 1998 Cell 85:841; Johnson et al. 1996, Science 272:1668). Subsequently inactivating mutations in Ptch and/or activating mutations in Smo were found to be responsible for sporadic basal cell carcinomas (Xie et al. 1998, Nature 391: 90).

Hedgehog pathway proteins and genes have also been implicated in esophageal cancer (Ma, X., et al. Int J Cancer, 118: 139-148, 2006; Berman, D. et al. Nature, 425: 846-851, 2003) and are highly expressed in the majority of chemotherapy-resistant esophageal cancer specimens (Sims-Mourtada, J. et al. Clin Cancer Res, 12: 6565-6572, 2006). More cancers where the Hedgehog pathway are involved include biliary tract cancers (Berman, D. et al. Nature, 425: 846-851, 2003), melanoma (Stecca, B., et al. Proc Natl Acad Sci USA, 104: 5895-5900, 2007), and stomach cancer (Berman, D. et al. Nature, 425: 846-851, 2003; Ma, X., et al. Carcinogenesis, 26: 1698-1705, 2005). Tumors that contain highly proliferative "tumor stem cells" and which represent areas of therapy include glial cell cancers (Clement, V., et al. Curr Biol, 17: 165-172, 2007), prostate cancers (Li, C., Heidt, et al. Cancer Res, 67: 1030-1037, 2007), breast cancers (Liu, S., et al. Cancer Res, 66: 6063-6071, 2006), multiple myelomas (Peacock, C. D., et al. PNAS, 104: 4048-4053, 2007), and colon cancers (Ricci-Vitiani, L., et al. Nature, 445: 111-115, 2007).

In addition, the Hedgehog pathway plays a role in regulating cancer stem cells, which are discrete tumor cell populations that display highly enhanced survival, self-renewal, and tumorigenicity properties (Beachy, P. A., et al. Nature, 432: 324-331, 2004). Activation of the Hedgehog pathway has been shown to play a role in cancer stem cells of the breast (Liu, S., et al. Cancer Res, 66: 6063-6071, 2006), central nervous system (Clement, V., Curr Biol, 17: 165-172, 2007) as well as in hematological malignancies (Peacock, C. D., PNAS, 104: 4048-4053, 2007).

Modulators of the Hedgehog pathway are described herein.

SUMMARY

Some embodiments of the present invention relate to methods and compositions for treating cancer. More embodiments include methods and compositions for modulating the activity of the Hedgehog pathway.

Some embodiments include methods for killing or retarding the growth of at least one neoplastic cell, comprising reducing the expression level of a nucleic acid encoding GLI1, such as the expression level of a nucleic acid encoding GLI1-130, or the expression level of GLI1 protein such as the expression level of the GLI1-130 protein in the cell.

In some aspects of such embodiments, the level of a nucleic acid encoding GLI1, such as the level of a nucleic acid encoding GLI1-130, or the level of GLI1 protein such as the level of the GLI1-130 protein is reduced by contacting the cell with an isolated nucleic acid selected from a small hairpin RNA (shRNA), a small interfering RNA (siRNA), a micro RNA (miRNA), an antisense polynucleotide, and a ribozyme.

In some aspects of such embodiments, the nucleic acid comprises a sequence encoding GLI1 or a fragment thereof, a sequence encoding antisense GLI1 or a fragment thereof, or an antisense nucleic acid complementary to a sequence encoding GLI1 or a fragment thereof.

In some aspects of such embodiments, the nucleic acid comprises a sequence selected from SEQ ID NO.s:01-10.

In some aspects of such embodiments, the nucleic acid comprises SEQ ID NO:01.

In some aspects of such embodiments, the at least one neoplastic cell is selected from a breast cancer cell, melanoma cell, prostate cancer cell, colorectal cancer cell, head and neck cancer cell, lung cancer cell, colon cancer cell, oesophageal cancer cell, gastric cancer cell, testicular cancer cell, and ovarian cancer cell.

In some aspects of such embodiments, the cell is a mammalian cell.

In some aspects of such embodiments, the mammalian cell is a human cell.

In some aspects of such embodiments, the cell is in vivo.

In some aspects of such embodiments, the cell is in vitro.

In some aspects of such embodiments, the nucleic acid encoding GLI1 comprises a nucleic acid encoding GLI1-130, or the GLI1 protein comprises GLI1-130 isoform.

Some embodiments include methods for treating or ameliorating cancer in a subject comprising reducing the level of a nucleic acid encoding GLI1 or the level of GLI1 protein in a cell of the subject.

In some aspects of such embodiments, the expression level of a nucleic acid encoding GLI1 such as the expression level of a nucleic acid encoding GLI1-130, or the expression level of GLI1 protein such as the expression level of the GLI1-130 protein is reduced by administering an isolated nucleic acid to the subject, wherein the nucleic acid is selected from a small hairpin RNA (shRNA), a small interfering RNA (siRNA), a micro RNA (miRNA), an antisense polynucleotide, and a ribozyme.

In some aspects of such embodiments, the nucleic acid comprises a sequence encoding GLI1, such as GLI-130, or a fragment thereof, a sequence encoding antisense GLI1, a sequence encoding antisense GLI1-130, or a fragment thereof, or an antisense nucleic acid complementary to a sequence encoding GLI1-130 or a fragment thereof.

In some aspects of such embodiments, the nucleic acid comprises a sequence selected from SEQ ID NO.s:01-10.

In some aspects of such embodiments, the nucleic acid comprises SEQ ID NO:01.

In some aspects of such embodiments, the cancer is selected from breast cancer, melanoma, prostate cancer, colorectal cancer, head and neck cancer, lung cancer, colon cancer, oesophageal cancer, gastric cancer, testicular cancer, and ovarian cancer.

In some aspects of such embodiments, the subject is a mammal.

In some aspects of such embodiments, the mammal is a human.

In some aspects of such embodiments, the nucleic acid encoding GLI1 comprises a nucleic acid encoding GLI1-130, or the GLI1 protein comprises GLI1-130 isoform.

Some embodiments include isolated nucleic acids comprising a sequence encoding GLI1, such as a sequence encoding GLI1-130, or a fragment thereof, or a sequence encoding antisense GLI1, such as a sequence encoding antisense GLI1-130, or a fragment thereof, an antisense nucleic acid complementary to a sequence encoding GLI1 or a fragment thereof, such as an antisense nucleic acid complementary to a sequence encoding GLI1-130 or a fragment thereof, wherein the nucleic acid reduces the level of a nucleic acid encoding GLI1, such as the level of a nucleic acid encoding GLI1-130, or the level of GLI1 protein, such as the level of GLI1-130 protein in a cell.

In some aspects of such embodiments, the nucleic acid is selected from a small hairpin RNA (shRNA), a small interfering RNA (siRNA), a micro RNA (miRNA), an antisense polynucleotide, and a ribozyme.

In some aspects of such embodiments, the isolated nucleic acid comprises a sequence selected from SEQ ID NO.s:01-10.

In some aspects of such embodiments, the isolated nucleic acid comprises SEQ ID NO:01.

Some embodiments include isolated nucleic acids comprising a sequence encoding GLI1-130 or a fragment thereof, a sequence encoding antisense 130 or a fragment thereof, or an antisense nucleic acid complementary to a sequence encoding GLI1-130 or a fragment thereof, wherein the nucleic acid reduces the level of a nucleic acid encoding GLI1-130 or the level of GLI1-130 protein in a cell.

In some aspects of such embodiments, the nucleic acid is selected from a small hairpin RNA (shRNA), a small interfering RNA (siRNA), a micro RNA (miRNA), an antisense polynucleotide, and a ribozyme.

In some aspects of such embodiments, the isolated nucleic acid comprises a sequence selected from SEQ ID NO.s:01-10.

In some aspects of such embodiments, the isolated nucleic acid comprises SEQ ID NO:01.

Some embodiments include vectors comprising the isolated nucleic acid of any one of the nucleic acids provided herein.

Some embodiments include cells comprising the isolated nucleic acid of any one of the nucleic acids provided herein.

Some embodiments include pharmaceutical compositions comprising the nucleic acid of any one of the nucleic acids provided herein, and a pharmaceutically acceptable carrier.

Some embodiments include methods for killing or retarding the growth of at least one cell comprising: reducing the level of a nucleic acid encoding GLI1, such as GLI1-130, or the level of GLI1 protein, such as GLI1-130 protein, in the cell; and contacting the cell with an effective amount of the therapeutic compound, wherein the effective amount is reduced compared to a cell wherein the level of a nucleic acid encoding GLI1, such as a nucleic acid encoding GLI1-130, or the level of GLI1 protein, such as GLI1-130 protein, is not reduced.

In some aspects of such embodiments, the level of a nucleic acid encoding GLI1, such as a nucleic acid encoding GLI1-130, or the level of GLI1 protein, such as GLI1-130 protein, is reduced by contacting the cell with an isolated nucleic acid selected from a small hairpin RNA (shRNA), a small interfering RNA (siRNA), a micro RNA (miRNA), an antisense polynucleotide, and a ribozyme.

In some aspects of such embodiments, the nucleic acid comprises a sequence encoding GLI1, such as a sequence encoding GLI1-130, or a fragment thereof, a sequence encoding antisense GLI1, such as a sequence encoding antisense GLI1-130, or a fragment thereof, or an antisense nucleic acid complementary to a sequence encoding GLI1 or a fragment thereof, such as an antisense nucleic acid complementary to a sequence encoding GLI1-130 or a fragment thereof.

In some aspects of such embodiments, the nucleic acid comprises a sequence selected from SEQ ID NO.s:01-10.

In some aspects of such embodiments, nucleic acid comprises SEQ ID NO:01.

In some aspects of such embodiments, the therapeutic compound comprises a chemotherapeutic agent.

In some aspects of such embodiments, the chemotherapeutic agent is selected from a platinum-based compound such as cisplatin, carboplatin, nedaplatin, oxaliplatin, satraplatin, and triplatin tetranitrate, a nitrogen mustard such as cyclophosphamide, mechlorethamine, uramustine, melphalan, chlorambucil, and ifosfamide, a nitrosourea such as carmustine, lomustine, and streptozocin, an alkyl sulfonate such as busulfan, thiotepa, procarbazine, and altretamine.

In some aspects of such embodiments, the chemotherapeutic agent is selected from taxol and doxirubicin.

In some aspects of such embodiments, the therapeutic compound is an agent for which increased expression of ERRC1, XPD, or XRCC1 results in increased cellular resistance.

In some aspects of such embodiments, increased activity of the nucleotide excision repair pathway results in increased cellular resistance to the therapeutic compound.

In some aspects of such embodiments, increased activity of the base excision repair pathway results in increased cellular resistance to the therapeutic compound.

In some aspects of such embodiments, the cellular resistance further comprises clinical resistance to the therapeutic compound.

In some aspects of such embodiments, the at least one cell comprises at least one neoplastic cell.

In some aspects of such embodiments, the at least one neoplastic cell is selected from a breast cancer cell, melanoma cell, prostate cancer cell, colorectal cancer cell, head and neck cancer cell, lung cancer cell, colon cancer cell, oesophageal cancer cell, gastric cancer cell, testicular cancer cell, and ovarian cancer cell.

In some aspects of such embodiments, the cell is a mammalian cell.

In some aspects of such embodiments, the mammalian cell is a human cell.

In some aspects of such embodiments, the cell is in vivo.

In some aspects of such embodiments, the cell is in vitro.

In some aspects of such embodiments, the nucleic acid encoding GLI1 comprises a nucleic acid encoding GLI1-130, or the GLI1 protein comprises GLI1-130 isoform.

Some embodiments include methods for reducing the dosage of a therapeutic agent needed to treat a disorder in a subject comprising reducing the level of a nucleic acid encoding GLI1, such as a nucleic acid encoding GLI1-130, or the level of GLI1 protein, such as GLI1-130 protein, in a cell of the subject.

In some aspects of such embodiments, the level of a nucleic acid encoding GLI1, such as a nucleic acid encoding GLI1-130, or the level of GLI1 protein, such as GLI1-130 protein is reduced by administering to the subject an isolated nucleic acid selected from a small hairpin RNA (shRNA), a small interfering RNA (siRNA), a micro RNA (miRNA), an antisense polynucleotide, and a ribozyme.

In some aspects of such embodiments, the nucleic acid comprises a sequence encoding GLI1, such as a sequence encoding GLI1-130, or a fragment thereof, a sequence encoding antisense GLI1, such as a sequence encoding antisense GLI1, or a fragment thereof, or an antisense nucleic acid complementary to a sequence encoding GLI1 or a fragment thereof.

In some aspects of such embodiments, the nucleic acid comprises a sequence selected from SEQ ID NO.s:01-10.

In some aspects of such embodiments, the nucleic acid comprises SEQ ID NO:01.

In some aspects of such embodiments, the therapeutic compound comprises a chemotherapeutic agent.

In some aspects of such embodiments, the chemotherapeutic agent is selected from a platinum-based compound such as cisplatin, carboplatin, nedaplatin, oxaliplatin, satraplatin, and triplatin tetranitrate, a nitrogen mustard such as cyclophosphamide, mechlorethamine, uramustine, melphalan, chlorambucil, and ifosfamide, a nitrosoureas such as carmustine, lomustine, and streptozocin, an alkyl sulfonate such as busulfan, thiotepa, procarbazine, and altretamine.

In some aspects of such embodiments, the chemotherapeutic agent comprises a platinum-based compound.

In some aspects of such embodiments, the platinum-based compound comprises cisplatin.

In some aspects of such embodiments, the chemotherapeutic agent is selected from taxol and doxirubicin.

In some aspects of such embodiments, the therapeutic compound is an agent for which increased expression of ERRC1, XPD, or XRCC1 results in increased cellular resistance.

In some aspects of such embodiments, increased activity of the nucleotide excision repair pathway results in increased cellular resistance to the therapeutic compound.

In some aspects of such embodiments, increased activity of the base excision repair pathway results in increased cellular resistance to the therapeutic compound.

In some aspects of such embodiments, the cellular resistance further comprises clinical resistance to the therapeutic compound.

In some aspects of such embodiments, the disorder comprises cancer.

In some aspects of such embodiments, the cancer is selected from breast cancer, melanoma, prostate cancer, colorectal cancer, head and neck cancer, lung cancer, colon cancer, oesophageal cancer, gastric cancer, testicular cancer, and ovarian cancer.

In some aspects of such embodiments, the subject is a mammal.

In some aspects of such embodiments, the mammal is a human.

In some aspects of such embodiments, the nucleic acid encoding GLI1 comprises a nucleic acid encoding GLI1-130, or the GLI1 protein comprises GLI1-130 isoform.

Some embodiments include methods for identifying a therapeutic compound comprising: contacting a target cell with a test compound; and determining whether the test compound reduces the level of a nucleic acid encoding GLI1, such as a nucleic acid encoding GLI1-130, or the level of GLI1 protein, such as GLI1-130 protein, in the target cell.

Some aspects of such embodiments also include comparing the level of a nucleic acid encoding GLI1, such as a nucleic acid encoding GLI1-130, or the level of GLI1 protein, such as GLI1-130 protein, in a target cell which has not been contacted with the test compound to the level of a nucleic acid encoding, such as a nucleic acid encoding GLI1-130, or the level of GLI1 protein, such as GLI1-130 protein, in a target cell contacted with the test compound.

Some aspects of such embodiments also include determining whether the test compound reduces the level of c-jun (Ser 63) protein in the target cell.

Some aspects of such embodiments also include comparing the level of c-jun (Ser 63) protein in a target cell which has not been contacted with the test compound to the level of c-jun (Ser 63) protein in a target cell contacted with the test compound.

Some aspects of such embodiments also include determining whether the test compound does not substantially decrease the level of GLI2 protein or a nucleic acid encoding GLI1 in the target cell.

Some aspects of such embodiments also include comparing the level of GLI2 protein in a target cell which has not been contacted with the test compound to the level of GLI2 protein in a target cell contacted with the test compound.

Some aspects of such embodiments also include determining whether the test compound reduces the level of OPN protein in the target cell.

Some aspects of such embodiments also include comparing the level of OPN protein in a target cell which has not been contacted with the test compound to the level of OPN protein in a target cell contacted with the test compound.

In some aspects of such embodiments, the target cell comprises a neoplastic cell.

In some aspects of such embodiments, the neoplastic cell is selected from a breast cancer cell, melanoma cell, prostate cancer cell, colorectal cancer cell, head and neck cancer cell, lung cancer cell, colon cancer cell, oesophageal cancer cell, gastric cancer cell, testicular cancer cell, and ovarian cancer cell.

In some aspects of such embodiments, the target cell is a mammalian cell.

In some aspects of such embodiments, the mammalian cell is a human cell.

In some aspects of such embodiments, the nucleic acid encoding GLI1 comprises a nucleic acid encoding GLI1-130, or the GLI1 protein comprises GLI1-130 isoform.

Some embodiments include methods for assessing the effectiveness of a compound or agent in treating a disorder comprising measuring the level of a nucleic acid encoding OPN or the level of OPN protein in a subject who has been contacted with the compound or agent.

Some aspects of such embodiments, also include comparing the level of a nucleic acid encoding OPN or the level of OPN protein in a subject having the disorder who has been contacted with the compound or agent to the level of a nucleic acid encoding OPN or the level of OPN protein in a subject who does not have the disorder.

Some aspects of such embodiments, also include comparing the level of a nucleic acid encoding OPN or the level of OPN protein in a subject having the disorder who has been contacted with the compound or agent to the level of a nucleic acid encoding OPN or the level of OPN protein in a subject who has not been contacted with the compound or agent.

In some aspects of such embodiments, a decrease in the level of a nucleic acid encoding OPN or the level of OPN protein is indicative of a favorable prognosis.

In some aspects of such embodiments, the agent is a nucleic acid is selected from the group consisting of a small hairpin RNA (shRNA), a small interfering RNA (siRNA), a micro RNA (miRNA), an antisense polynucleotide, and a ribozyme.

In some aspects of such embodiments, the nucleic acid comprises a sequence encoding GLI1, such a sequence encoding GLI1130, or a fragment thereof, a sequence encoding antisense GLI1, such as a sequence encoding antisense GLI1-130, or a fragment thereof, or an antisense nucleic acid complementary to a sequence encoding GLI1 or a fragment thereof, such as an antisense nucleic acid complementary to a sequence encoding GLI1-130 or a fragment thereof.

In some aspects of such embodiments, the nucleic acid comprises a sequence selected from SEQ ID NO.s:01-10.

In some aspects of such embodiments, the nucleic acid comprises SEQ ID NO:01.

In some aspects of such embodiments, the disorder comprises cancer.

In some aspects of such embodiments, the cancer is selected from breast cancer, melanoma, prostate cancer, colorectal cancer, head and neck cancer, lung cancer, colon cancer, oesophageal cancer, gastric cancer, testicular cancer, and ovarian cancer In some aspects of such embodiments, the subject is a mammal.

In some aspects of such embodiments, the mammal is a human.

Some embodiments include methods for assessing the potential effectiveness of a nucleic acid as a therapeutic agent comprising determining whether the nucleic acid reduces the level of a nucleic acid encoding GLI1, such as a nucleic acid encoding GLI1-130, or the level of GLI1 protein, such as GLI1-130 protein in a cell, wherein the nucleic acid is identified as having potential effectiveness as a therapeutic agent if the nucleic acid reduces the level of the nucleic acid encoding GLI1, such as a nucleic acid encoding GLI1-130, or the level of GLI1 protein, such as GLI1-130 protein in said cell.

Some aspects of such embodiments, also include determining whether the nucleic acid has no substantial effect on the level of a nucleic acid encoding GLI2 or the level of GLI2 protein in a cell, wherein the nucleic acid is identified as having potential effectiveness a therapeutic agent if the nucleic acid has no substantial effect on the level of the nucleic acid encoding GLI2 or the level of the GLI2 protein in said cell.

In some aspects of such embodiments, the nucleic acid encoding GLI1 comprises a nucleic acid encoding GLI1-130, or the GLI1 protein comprises GLI1-130 isoform.

Some embodiments include nucleic acids identified as having potential effectiveness as a therapeutic agent by any one of the methods provided herein.

Some embodiments include methods of regulating transcription from the OPN promoter in a cell comprising regulating the activity of Hedgehog (Hh).

In some aspects of such embodiments, the activity of Hedgehog (Hh) is regulated by regulating the amount or activity of a nucleic acid encoding GLI1 or the amount or activity of GLI1 protein.

In some aspects of such embodiments, regulating the amount or activity of a nucleic acid encoding GLI1, such as GLI1-130, or the amount or activity of GLI1 protein, such as GLI1-130 protein comprises administering to said cell an isolated nucleic acid selected from a small hairpin RNA (shRNA), a small interfering RNA (siRNA), a micro RNA (miRNA), an antisense polynucleotide, and a ribozyme.

In some aspects of such embodiments, the nucleic acid comprises a sequence encoding GLI1, such as GLI1-130, or a fragment thereof, a sequence encoding antisense GLI1, such as GLI1-130 or a fragment thereof, or an antisense nucleic acid complementary to a sequence encoding GLI1 or a fragment thereof, such as an antisense nucleic acid complementary to a sequence encoding GLI1-130 or a fragment thereof.

In some aspects of such embodiments, the nucleic acid comprises a sequence selected from SEQ ID NO.s:01-10.

In some aspects of such embodiments, the nucleic acid comprises SEQ ID NO:01.

In some aspects of such embodiments, the Hedgehog (Hh) comprises Sonic Hedgehog (SHh).

In some aspects of such embodiments, the cell comprises a neoplastic cell.

In some aspects of such embodiments, the neoplastic cell is selected from a breast cancer cell, melanoma cell, prostate cancer cell, colorectal cancer cell, head and neck cancer cell, lung cancer cell, colon cancer cell, oesophageal cancer cell, gastric cancer cell, testicular cancer cell, and ovarian cancer cell.

In some aspects of such embodiments, the cell is a mammalian cell.

In some aspects of such embodiments, the mammalian cell is a human cell.

In some aspects of such embodiments, the cell is in vivo.

In some aspects of such embodiments, the cell is in vitro.

Some embodiments include methods of regulating osteoclast differentiation in a cell comprising regulating the activity of Hedgehog (Hh) in said cell.

In some aspects of such embodiments, the activity or effects of Hedgehog (Hh) are regulated by regulating the levels or activity of OPN.

In some aspects of such embodiments, the activity of Hedgehog (Hh) is regulated by regulating the amount or activity of a nucleic acid encoding GLI1, such as GLI1-130, or the amount or activity of GLI1 protein, such as GLI-130 protein.

In some aspects of such embodiments, regulating the amount or activity of a nucleic acid encoding GLI1, such as GLI1-130, or the amount or activity of GLI1 protein, such as GLI1-130 protein, comprises administering to said cell an isolated nucleic acid selected from a small hairpin RNA (shRNA), a small interfering RNA (siRNA), a micro RNA (miRNA), an antisense polynucleotide, and a ribozyme.

In some aspects of such embodiments, the nucleic acid comprises a sequence encoding GLI1, such as GLI1-130, or a fragment thereof, a sequence encoding antisense GLI1, such as GLI1-130, or a fragment thereof, or an antisense nucleic acid complementary to a sequence encoding GLI1, such as GLI-130, or a fragment thereof.

In some aspects of such embodiments, the nucleic acid comprises a sequence selected from SEQ ID NO.s:01-10.

In some aspects of such embodiments, the nucleic acid comprises SEQ ID NO:01.

In some aspects of such embodiments, the Hedgehog (Hh) comprises Sonic Hedgehog (SHh).

In some aspects of such embodiments, the cell comprises a neoplastic cell.

In some aspects of such embodiments, the neoplastic cell comprises a breast cancer cell.

In some aspects of such embodiments, the cell is a mammalian cell.

In some aspects of such embodiments, the mammalian cell is a human cell.

In some aspects of such embodiments, the cell is in vivo.

In some aspects of such embodiments, the cell is in vitro.

Some embodiments include methods of diminishing the levels of osteolysis in an individual having breast cancer comprising regulating the activity of Hedgehog (Hh).

In some aspects of such embodiments, the activity or effects of Hedgehog (Hh) are regulated by regulating the levels or activity of OPN.

In some aspects of such embodiments, the activity of Hedgehog (Hh) is regulated by regulating the amount or activity of a nucleic acid encoding GLI1 or the amount or activity of GLI1 protein.

In some aspects of such embodiments, regulating the amount or activity of a nucleic acid encoding GLI1, such as GLI1-130, or the amount or activity of GLI1 protein, such as GLI1-130 protein, comprises administering to said individual an isolated nucleic acid selected from a small hairpin RNA (shRNA), a small interfering RNA (siRNA), a micro RNA (miRNA), an antisense polynucleotide, and a ribozyme.

In some aspects of such embodiments, the nucleic acid comprises a sequence encoding GLI1, such as GLI1-130, or a fragment thereof, a sequence encoding antisense GLI1, such as GLI1-130, or a fragment thereof, or or an antisense nucleic acid complementary to a sequence encoding GLI1, such as GLI-130, or a fragment thereof.

In some aspects of such embodiments, the nucleic acid comprises a sequence selected from SEQ ID NO.s:01-10.

In some aspects of such embodiments, the nucleic acid comprises SEQ ID NO:01.

In some aspects of such embodiments, the Hedgehog (Hh) comprises Sonic Hedgehog (SHh).

Some embodiments include methods for assessing the extent to which breast cancer has metastasized to the bone comprising determining the level of expression of at least one protein selected from the group consisting of OPN, CTSK, and MMP9 or a nucleic acid encoding at least one of said OPN, CTSK, or MMP9 proteins in a bone sample.

Some embodiments include uses of an isolated nucleic acid comprising a sequence encoding GLI1 or a fragment thereof, a sequence encoding antisense GLI1 or a fragment thereof, or an antisense nucleic acid complementary to a sequence encoding GLI1 or a fragment thereof for treatment of a disorder.

In some aspects of such embodiments, the isolated nucleic acid is selected from a small hairpin RNA (shRNA), a small interfering RNA (siRNA), a micro RNA (miRNA), an antisense polynucleotide, and a ribozyme.

In some aspects of such embodiments, the nucleic acid comprises a sequence selected from SEQ ID NO.s:01-10.

In some aspects of such embodiments, the nucleic acid comprises SEQ ID NO:01.

In some aspects of such embodiments, the disorder is selected from breast cancer, melanoma, prostate cancer, colorectal cancer, head and neck cancer, lung cancer, colon cancer, oesophageal cancer, gastric cancer, testicular cancer, and ovarian cancer.

In some aspects of such embodiments, the nucleic acid comprises a sequence encoding GLI1-130 or a fragment thereof, a sequence encoding antisense GLI1-130 or a fragment thereof, or an antisense nucleic acid complementary to a sequence encoding GLI1-130 or a fragment thereof for treatment of a disorder.

Some embodiments include isolated nucleic acids comprising a sequence encoding GLI1 or a fragment thereof, a sequence encoding antisense GLI1 or a fragment thereof, or an antisense nucleic acid complementary to a sequence encoding GLI1 or a fragment thereof for use as a medicament.

In some aspects of such embodiments, the isolated nucleic acid is selected from a small hairpin RNA (shRNA), a small interfering RNA (siRNA), a micro RNA (miRNA), an antisense polynucleotide, and a ribozyme.

In some aspects of such embodiments, the nucleic acid comprises a sequence selected from SEQ ID NO.s:01-10.

In some aspects of such embodiments, the nucleic acid comprises SEQ ID NO:01.

In some aspects of such embodiments, the nucleic acid comprises a sequence encoding GLI1-130 or a fragment thereof, a sequence encoding antisense GLI1-130 or a fragment thereof, or an antisense nucleic acid complementary to a sequence encoding GLI1-130 or a fragment thereof.

Some embodiments include uses of an isolated nucleic acid comprising a sequence encoding GLI1 or a fragment thereof, a sequence encoding antisense GLI1 or a fragment thereof, or an antisense nucleic acid complementary to a sequence encoding GLI1 or a fragment thereof for the preparation of a medicament for treating a disorder.

In some aspects of such embodiments, the isolated nucleic acid is selected from a small hairpin RNA (shRNA), a small interfering RNA (siRNA), a micro RNA (miRNA), an antisense polynucleotide, and a ribozyme.

In some aspects of such embodiments, the nucleic acid comprises a sequence selected from SEQ ID NO.s:01-10.

In some aspects of such embodiments, the nucleic acid comprises SEQ ID NO:01.

In some aspects of such embodiments, the disorder is selected from breast cancer, melanoma, prostate cancer, colorectal cancer, head and neck cancer, lung cancer, colon cancer, oesophageal cancer, gastric cancer, testicular cancer, and ovarian cancer.

In some aspects of such embodiments, the nucleic acid comprises a sequence encoding GLI1-130 or a fragment thereof, a sequence encoding antisense GLI1-130 or a fragment thereof, or an antisense nucleic acid complementary to a sequence encoding GLI1-130 or a fragment thereof for treatment of a disorder.

BRIEF DESCRIPTION OF THE DRAWINGS

FIG. 2 (panel B) and FIG. 2 (panel C) show graphs of OPN expression in MCC012A, MCC012F, and MDA-MB-435 cells treated with cyclopamine. FIG. 2 (panel B) shows that cyclopamine treatment significantly (* indicates $p<0.0001$) decreases the levels of OPN mRNA (assessed by qRT-PCR) in MCC012A and MCC012F cells. FIG. 2 (panel C) shows that cyclopamine significantly (* indicates $p<0.0001$) decreases the levels of OPN mRNA in a dose-dependent manner in MDA-MB-435 cells. Specifically, cells were treated with the indicated concentrations of cyclopamine in Dulbecco's modified minimum essential medium, F-12 supplemented with 0.5% fetal bovine serum. This medium was replaced with fresh cyclopamine-containing medium after 12 h. Cells were harvested for assay after 24 h of cyclopamine treatment. RNA was assessed by real-time RT-PCR for OPN transcript levels.

FIG. 2 (panel D) shows a graph of reporter gene activity in MCC012A and MCC012F cell lines. Cyclopamine causes a dose-dependent decrease in the OPN promoter activity (200 ng of pGL3-OPN transfected) in MCC012A and MCC012F cell lines. In the MCC012F cells, at the doses tested (10 μM and 20 μM), cyclopamine caused a significant ($p=0.042$ and $0.002$, respectively) decrease in OPN promoter activity. In the MCC012A cell line, cyclopamine (10 μM) caused a noticeable, but not significant ($p=0.06$) decrease in OPN promoter activity. Treatment with 20 μM cyclopamine caused a significant decrease ($p=0.0006$) in OPN promoter activity. Tomatidine had no effect on the promoter activity of OPN.

FIG. 2 (panel E) shows a Western blot of OPN in MDA-MB-435 cells treated with dimethyl sulfoxide (DMSO), 10 μM and 20 μM cyclopamine. The conditioned media were assayed for OPN. OPN in the secretome were decreased upon treatment with cyclopamine.

FIG. 2 (panel F) and FIG. 2 (panel G) show graphs of reporter gene activity in cells (MDA-MB-435) transfected with the OPN promoter construct (200 ng) and treated with increasing concentrations of either SHH (FIG. 2, panel F) or IHH (FIG. 2, panel G). The Hedgehog ligands stimulate OPN promoter activity. The asterisk above the graph indicates that the activity of the OPN promoter was significantly ($p<0.0001$) higher than that of the corresponding control (untreated) group for all concentrations of IHH and SHH tested.

FIG. 2 (panel H) shows a graph of reporter gene activity in metastatic melanoma cell lines treated with SHH or IHH. Triggering the Hedgehog pathway by treatment with the ligands, SHH and IHH, results in a significant increase in OPN promoter activity in metastatic melanoma cell lines, MCC012A ($p=0.0004$ for SHH and $p<0.0001$ for IHH treatments) and MCC012F ($p=0.0078$ for SHH and $p=0.0032$ for IHH).

FIG. 2 (panel I) shows a graph of OPN expression in MDA-MB-435 cells (1 million) were treated with cyclopamine or tomatidine (20 μM). SHH was able to rescue the inhibitory effects of cyclopamine on OPN transcript levels. After 12 hr, the medium of one cyclopamine-treated set was replaced with medium containing recombinant SHH (100 nM). The experiment was terminated after 24 h of the start of the initial cyclopamine treatment. RNA was assessed by real-time RT-PCR for OPN transcript levels. Error bars represent mean±S.E.

FIG. 3 (panel B), FIG. 3 (panel C), and FIG. 3 (panel D) show graphs of SHH, GLI1, and OPN expression in various cell lines, respectively. The metastatic melanoma cell lines express significantly ($p<0.0001$ in all cases) higher levels of the transcripts of SHH, the transcription factor, GLI1 and OPN compared to the primary melanoma-derived cell lines, MCC013.

FIG. 4 (panel A), lower panel) shows a graph of reporter gene activity for various reporter constructs. Mutations of the putative GLI1-binding site make the OPN promoter insensitive to the effects of GLI1. The OPN promoter (−112 to −352 (pGL3-OPN-352)) was significantly activated (p<0.0001) in response to GLI1. Cells (MDA-MB-435) were transfected with either 100 ng of pGL3, pGL3-OPN-352, or pGL3-OPN-352$^{Mut}$ and 300 ng of pLNCX or pLNCX-GLI1. Empty pGL3 vectors (devoid of promoter) co-transfected with empty pLNCX vectors served as control. The inset box outlines the consensus GLI1-binding site and defines the GLI1-binding site in the OPN promoter. The underlined nucleotides are distinct from the ones in the consensus site. The GLI1-binding site in the OPN promoter is abolished in OPN-352$^{Mut}$; the bases in bold have been altered to change from a GLI1-binding site to a NotI restriction enzyme site. Asterisk indicates that the activation of the promoter activity (pGL3-OPN-352) is statistically significant (p<0.0001) compared with pGL3 alone.

FIG. 4 (panel B) shows a graph of reporter gene activity for various reporter constructs in treated cells. pGL3-OPN-352 shows a significant (p<0.0001) activation in the activity in the presence of Hedgehog ligands. In contrast to pGL3-OPN-352, pGL3-OPN-352$^{Mut}$ is resistant to the effects of Hedgehog ligands.

FIG. 4 (panel C) shows a ChIP assay in MDA-MB-435 cells, showing that GLI1 interacts with the OPN promoter. The antibodies used for immunoprecipitation are indicated. Lane 1, PCR using primers encompassing the GLI1-binding site; lanes 2 and 3, PCR using a kit provided the ChIP-positive control and ChIP-negative primers, respectively; and lane 4, PCR using primers amplifying a region of the OPN promoter that is approximately 1 kb upstream of the GLI1-binding site. Error bars represent mean±S.E.

FIG. 5 (panel B) shows a graph of viable transfected cells post transfection. Knock-down of GLI1 causes the cells to proliferate slower in culture (p>0.05). FIG. 5 (panel C) shows a Western blot of transfected cells. The expression of the OPN receptor, CD44 is not altered in the cells with a stable knockdown of endogenous Immunoblot of CD44 in the vector-only, scrambled transfectants and the GLI1-silenced (KO1 and KO4) cells.

FIG. 6 (panel B) shows a graph of real time RT-PCR for various transfected cells. Expression of GLI1 mRNA in KO1 to KO4 was notably lower than the controls (vector-only and scrambled transfected). FIG. 6 (panel C) shows a Western blot of cells transfected with vector-only, scrambled transfectants and KO1 and KO4 cells, and probed for expression of markers of EMT (vimentin, SNAI2, and N-cadherin). β-tubulin served as a loading control. Error bars represent mean±S.E. shRNA to GLI1 abrogates expression of OPN and brings about a partial reversal of EMT FIG. 7 (panel A) shows a graph of cell movement for various transfectants. Abrogating GLI1 expression (KO1 and KO4) reduced the ability of cells to move and fill in a wound in the cell monolayer (p>0.05). FIG. 7 (panel C) shows a graph of cell invasion for various transfectants. Silencing endogenous expression of GLI1 significantly decreases the ability of cells to invade (p<0.0001) through Matrigel. The readings of KO1 and KO4 were compared with the corresponding scrambled control-transfected cells to determine statistical significance. In all cases, the vector-only cells were comparable with the scrambled control cells (p>0.1). FIG. 7 (panel D) shows a graph of tumor diameter over time for various transfectants. GLI1-silenced cells were compromised for their tumorigenicity. Tumor measurements are represented as mean tumor diameter±S.E. As compared with the scrambled control cells both KO1 (p=0.0028) and KO4 (p=0.0018) formed significantly slower growing tumors. FIG. 7 (panel E) shows a graph of pulmonary metastases for various transfectants. The GLI1 KO1 (p=0.0012) and KO4 (p=0.0005) cells were significantly impaired in their ability to form spontaneous metastases. Error bars represent mean±S.E. Silencing endogenous GLI1 expression diminishes attributes of motility, invasion, migration, and proliferation and negatively impacts tumorigenicity and metastasis.

FIG. 9 (panel B) shows a graph of cell migration for various transfectants. In the migration assay, OPN-treated cells migrate in significantly larger numbers (p<0.0001) compared with untreated cells. As compared with KO1, the KO/OPN stable transfectants migrate in significantly greater numbers (p<0.0001). FIG. 9 (panel C) shows a graph of cell invasion for various transfectants. As compared with the respective untreated cells, the OPN-treated cells invade in significantly larger numbers (KO1, p<0.0001; and KO4, p=0.0038). In contrast to KO1, the KO/OPN stable transfectants invade in significantly larger numbers (p<0.0001). FIG. 9 (panel D) shows a graph of cell motility for various transfectants. In the wound healing assay, although the KO/OPN and KO1+OPN cells are able to move significantly faster than the respective control KO1 cells (p=0.0269 and p=0.0066, respectively), the motility of KO4 cells treated with OPN follows a similar fast trend (p=0.15). (KO1+OPN and KO4+OPN represent experimental conditions wherein the cells were cultured in OPN-containing medium for 24 h and assayed in the presence of OPN. KO/OPN represents the GLI1-knocked down cells that have been stably transfected with OPN.) FIG. 9 (panel E) shows a graph of tumor diameter over time for various transfectants. Restoration of OPN in GLI1-silenced cells results in enhanced ability of the cells to grow as xenografts in athymic nude mice. Tumor measurements are represented as mean tumor diameter±S.E. As compared with the vector-only (pSUPERIOR) and Gli1-silenced (KO1) cells, the two clones, KO1/OPN.5 and KO1/OPN.8, both formed significantly faster growing tumors (p<0.05). Error bars represent mean±S.E. Restoring the availability of OPN-initiated signaling in GLI1-silenced cells reinstates their motility and ability to migrate and invade

FIG. 15 (right panel) shows a graph of nodule formation in osteoblasts treated with recombinant SHH and IHH. SHH and IHH promote differentiation of the pre-osteoblastic MC3T3-E1 clone 14 cells compared to differentiation medium (DM) alone.

FIG. 54 (panel B) shows a graph depicting an OPN promoter construct (200 ng) and the β-galactosidase plasmid (200 ng) were co-transfected into RAW264.7 cells. Luciferase activity was assayed 24 hours post-SHH treatment and normalized to β-galactosidase. Each group was assessed in triplicate. The data is depicted as relative luciferase activity and is representative of three independent experiments. The increase in OPN promoter activity is significantly (p<0.05) higher for the indicated groups relative to the control (untreated) cells.

FIG. 54 (panel C) shows a Western blot depicting SHH treatment of the RAW264.7 cells (at the nM concentrations indicated) stimulates the expression of OPN. Cells were lysed 24 hours post SHH treatment and OPN and β-actin were assessed by immunoblotting.

FIG. 54 (panel D) shows a graph depicting densitometric analyses of the immunoblotting results. The results are represented as band intensity relative to respective loading control. Band intensities are represented as arbitrary units.

FIG. 55 (panel B) shows a graph depicting conditioned serum-free medium from breast cancer cells, MDA-MB-231, SUM159 and SUM1315 significantly (*p<0.01) increases the numbers of multinucleate, TRAP-positive cells. The addition of Hh ligand neutralizing antibody, 5E1, to differentiation conditions, notably (^ p<0.05) reduces the efficiency of breast cancer cell-conditioned medium to elicit osteoclast differentiation.

FIG. 55 (panel C) shows a Western blot depicting breast cancer cells (MCF10CA clone d, MDAMB-231, SUM159 and SUM1315) express IHH and SHH ligands. Shown is an immunoblot of the lysate from the breast cancer cells. β-tubulin serves as a loading control.

FIG. 55 (panel D) shows photomicrographs depicting TRAP-stained osteoclasts formed in response to various differentiation conditions. The bar represents 100 μm. (a) Growth medium (GM); (b) & (e) Differentiation medium (DM); DM supplemented with (c) recombinant OPN (100 ng/ml); (d) SHH (100 nM); (f) DM+5E1 (2.5 μg/ml); DM supplemented with conditioned medium from (g) MDA-MB-231 cells; (i) SUM159 cells; (k) SUM1315 cells; 5E1 (2.5 μg/ml) added to DM supplemented with conditioned medium from (h) MDA-MB-231; (j) SUM159 and (l) SUM1315 cells. The osteoclasts are marked within circles in panel (c). The data was recorded at 10× magnification using the Nikon Eclipse TS 100 microscope and is represented as a percentage of multinucleate TRAP-positive cells relative to the total number of cells in the field. The data was verified by two independent experiments.

FIG. 56 (panel B) shows photomicrographs depicting the areas resorbed by the differentiated osteoclasts in response to various differentiation conditions. The bar represents 100 μm. (a) Growth medium (GM); (b) Differentiation medium (DM); DM supplemented with (c) SHH (100 nM); (d) recombinant OPN (100 ng/ml). The arrows point to the area resorbed.

FIG. 56 (panel C) shows a graph depicting conditioned serum-free medium from breast cancer cells, SUM159, MDA-MB-231, and SUM1315 significantly (*p<0.01) increases the resorption activity of osteoclasts. Addition of the Hh ligand neutralizing antibody, 5E1, to differentiation conditions notably (^ p<0.05) decreases the resorption activity of osteoclasts induced by the secretome of breast cancer cells. The difference in the area resorbed by DM and DM+5E1 is not statistically significant (p=0.06). Data is represented as a percentage of the area resorbed relative to the total area in the field of view (this corresponds to 568197.12 μm2). The experiment was repeated once.

FIG. 56 (panel D) shows photomicrographs depicting the areas resorbed by the differentiated osteoclasts in response to various differentiation conditions. The bar represents 100 μm. Differentiation medium (DM) (a); DM supplemented with (b) 5E1 (2.5 μg/ml); conditioned medium from (c) SUM159 cells (e) MDA-MB-231; (g) SUM1315 cells. (d) (f) and (h) 5E1 (2.5 μg/ml) added to DM supplemented with conditioned medium from SUM159 cells, MDA-MB-231 cells and SUM1315 cells respectively.

FIG. 57 (panel B) shows photomicrographs depicting differentiation assessed by TRAP staining. Differentiation conditions included (a) DM; (b) DM+cyclopamine; conditioned medium from (c) SUM159, (e) MDA-MB-231 & SUM1315 cells (g). Images (d), (f) & (h) represent resorption in presence of conditioned media from SUM159, MDA-MB-231, and SUM1315 cells supplemented with cyclopamine. Images were acquired at 10× magnification using the Nikon Eclipse TS 100 microscope.

FIG. 57 (panel C) shows a graph depicting Hh signaling in osteoclasts by the Smoothened (SMOH) inhibitor, cyclopamine (20 μM) significantly (*p<0.0001) compromises their ability to resorb matrix when stimulated with conditioned medium from breast cancer cells.

FIG. 57 (panel D) shows photomicrographs depicting resorption activity assessed by TRAP staining. Differentiation conditions were used as described for cells depicted in FIG. 57 (panel B).

FIG. 58 (panel D) shows a Western blot depicting expression of proteases Cathepsin K and MMP9 is regulated by Hh signaling. The expression of OPN, MMP9 and Cathepsin K (CTSK) were assessed by immunoblotting. The graph represents densitometric analyses of the immunoblotting results. The results are represented as band intensity in arbitrary units relative to respective loading control.

FIG. 59 (panel B) shows a graph depicting relative expression of MMP9 in various treated cells.

FIG. 59 (panel C) shows a graph depicting percent area resorped for various treated cells.

FIG. 59 (panel D) depicts photomicrographs showing the areas resorbed by the differentiated osteoclasts in response to various differentiation conditions. The bar represents 100 μm. (a) Differentiation medium (DM); (b) DM on KO osteoclasts; (c) recombinant SHH (100 nM); (d) recombinant SHH on KO osteoclasts; (e) & (i) DM supplemented with conditioned medium from MDA-MB-231 cells and SUM1315 cells respectively; (f) & (j) represent osteoclasts silenced for OPN expression on day 6 (KO); (g) & (k) represent differentiation conditions in presence of the 5E1 antibody (2.5 μg/ml); (h) & (1) represent osteoclasts cultured in presence of 5E1 antibody that were silenced for OPN expression on day 6 (KO). (*p<0.05).

FIG. 60 (panel B) shows photomicrographs depicting differentiation of (a) control SUM1315 cells or (b) cells transfected with vector control (scr1: pSuperior.egfp.neo) or (c) transfected with shRNA targeting GLI1 or (d) transfected with pSuper vector control (scr2) or (e) transfected with shRNA targeting OPN.

FIG. 60 (panel C) shows a graph depicting percent area resorbed for various treated cells (p=0.0001 and p=0.0005 respectively).

FIG. 60 (panel D) shows photomicrographs depicting resorption of (a) control SUM1315 cells or (b) cells transfected with vector control (scr1: pSuperior.egfp.neo) or (c) transfected with shRNA targeting GLI1 or (d) transfected with pSuper vector control (scr2) or (e) transfected with shRNA targeting OPN.

FIG. 62A shows graphs depicting MDA-MB-435 cells (left panel) or SUM1315 cells (right panel) transfected with vector or vector encoding shGLI1 RNA and treated with various concentrations of doxorubicin. FIG. 62B shows graphs depicting MDA-MB-435 cells (left panel) or SUM1315 cells (right panel) transfected with vector or vector encoding shGLI1 RNA and treated with various concentrations of taxol.

Neutralization of Hh ligand caused a significant decrease in the levels of PTHrP. SUM1315+5E1 (^p=0.04); MDA-MB-231+5E1 (^p=0.0001), SUM159+5E1 (^p=0.01), MDA-MB-435+5E1 (^p<0.0001). The expression of RANKL and PTHrP were assessed by real time qRT-PCR after 14 days of differentiation.

Figure 72:
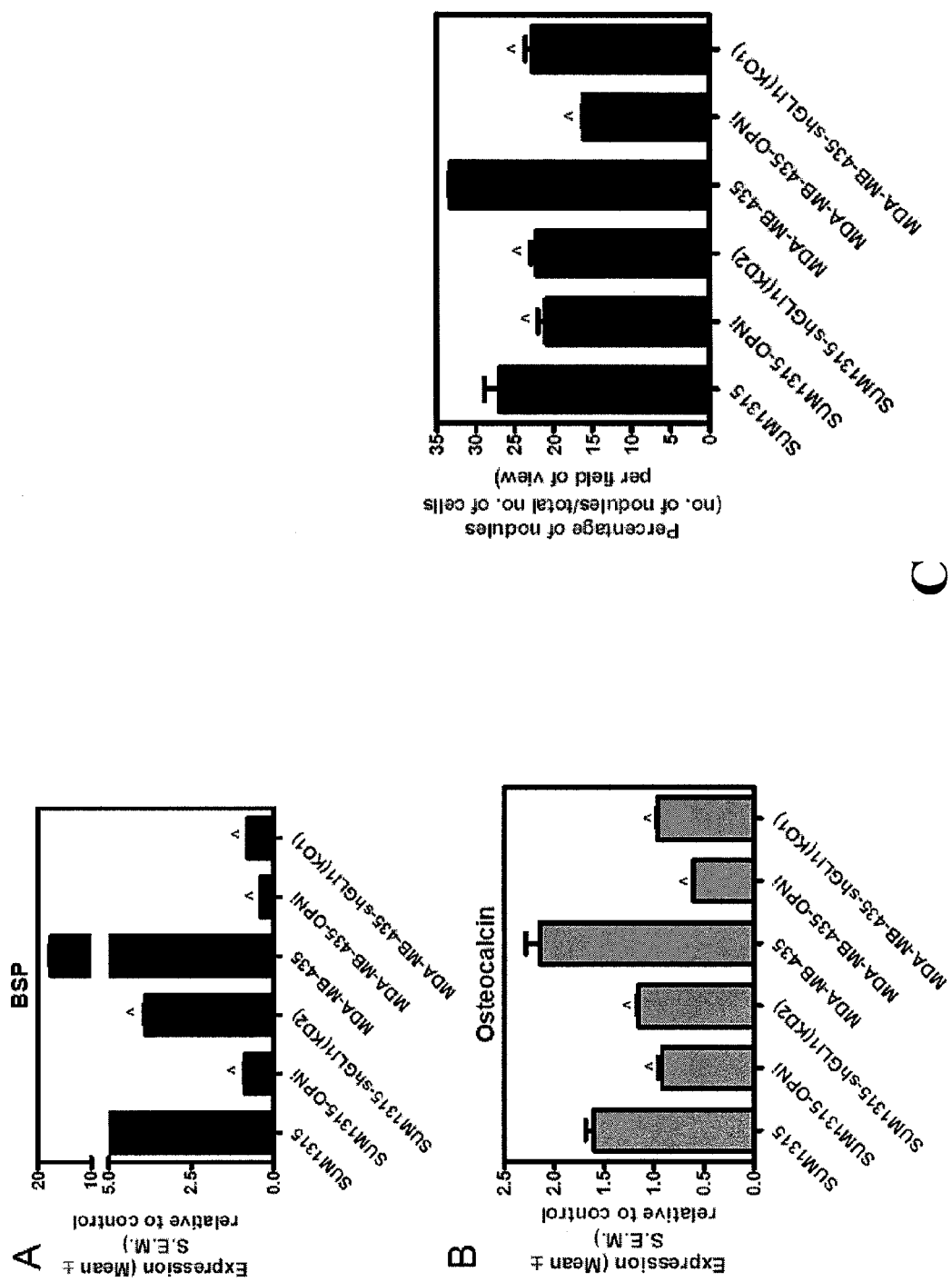

FIG. 72 depicts tumor cells competent for Hh signaling and OPN expression are efficient at inducing osteoblast differentiation. Stable silencing of OPN (OPNi) or GLI1 (KD2 and KO1) significantly reduces the expression of (A) BSP [Relative to SUM1315, SUM1315-OPNi (^p=0.008) and KD2 (^p=0.0004) show lower BSP; Relative to MDA-MB-435, 435-OPNi and KO1 have decreased BSP (^p<0.0001)], (B) osteocalcin [SUM1315-OPNi (^p=0.0013) and KD2 (^p=0.0004); 435-OPNi and KO1 (^p<0.0001)], and (C) the mineralization capacity of the osteoblasts [SUM1315-OPNi (^p=0.04) and KD2 (^p=0.04); 435-OPNi (^p<0.0001) and KO1 (^p=0.0003)]. The expression of BSP and osteocalcin were assessed by real time qRT-PCR and the nodules were assessed after Alizarin Red S staining after 14 days of differentiation.

Figure 73:
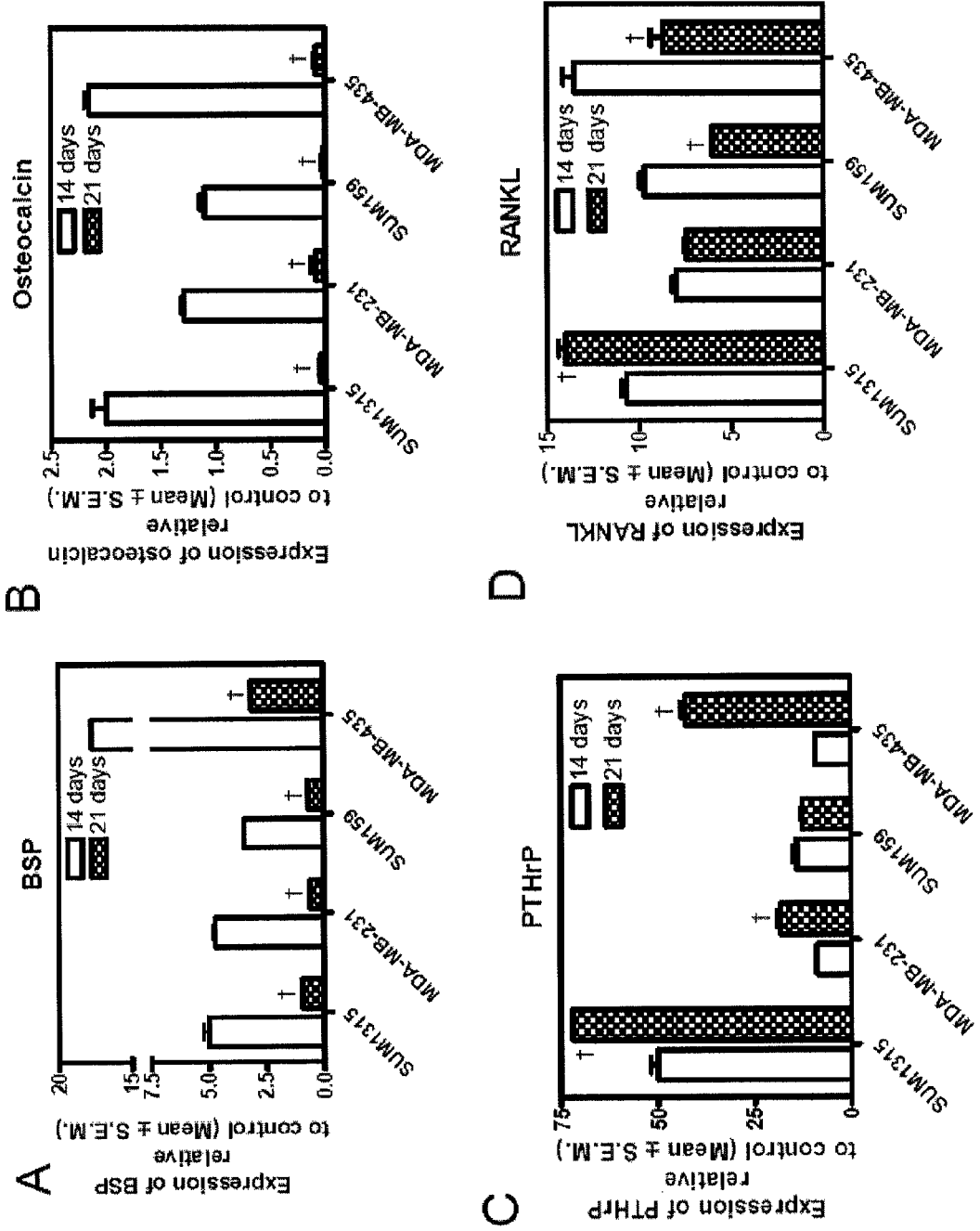
Figure 73:
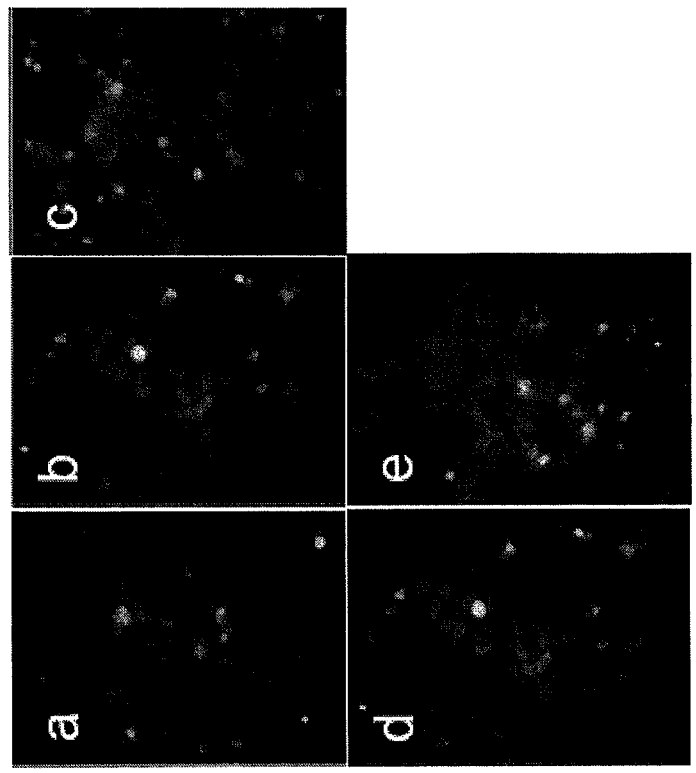
Figure 73:
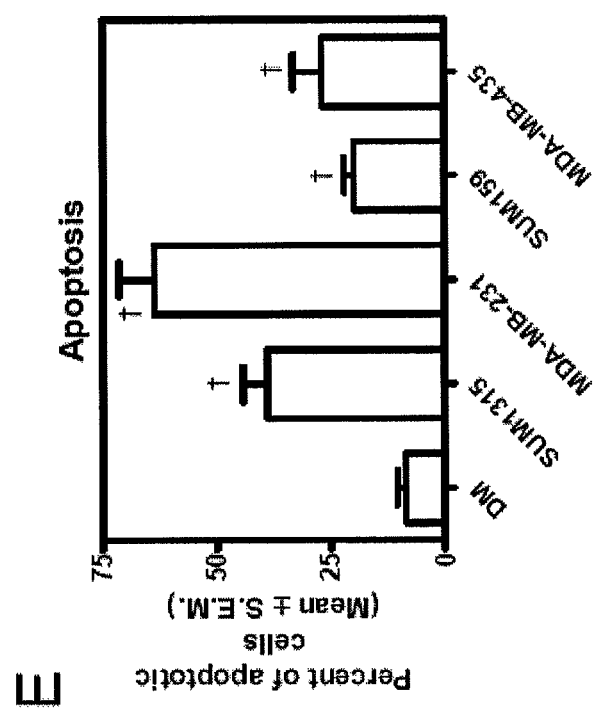

FIG. 73 depicts extended differentiation in presence of tumor cell-conditioned media preserves RANKL and PTHrP expression but promotes osteoblast apoptosis. MC3T3 cells were grown in differentiation supplemented with conditioned media from cancer cells for either 14 days or 21 days. At the end of each time point RNA was harvested from the differentiated osteoblastic cells and levels of BSP, osteocalcin, PTHrP and RANKL were assessed by qRT-PCR. (A) There is a significant decrease in the levels of BSP at 21 days relative to 14 days of differentiation for all four tumor cell lines assessed (†p<0.0001 for all tumor cells). (B) The levels of osteocalcin significantly decrease at 21 days relative to 14 days of differentiation (†p<0.0001 for all tumor cells). (C) The levels of PTHrP remained at elevated levels at 21 days post-initiation of differentiation (SUM1315: †p=0.0005; MDA-MB-231: †p=0.0006; SUM159: p>0.05; MDA-MB-435: p<0.0001). (D) The levels of RANKL also remained elevated 21 days after differentiation. (SUM1315: †p=0.0023; MDA-MB-231: p=0.07; SUM159: †p=0.0002; MDA-MB-435: †p=0.004). The levels of RANKL and PTHrP were assessed by qRT-PCR. (E) Assessment of apoptosis was done at the end of 21 days post initiation of differentiation. Fluorescein conjugated TUNEL staining was performed to assay for apoptosis followed by nuclear staining with DAPI and cytoskeleton staining with phalloidin. Percentage of apoptotic cells was calculated as the number of cells with green fluorescence in the nucleus divided by the total number of cells (represented by the blue DAPI stain) in each field of view. Enhanced apoptosis of osteoblasts was noted in presence of conditioned media from all tumor cells (SUM1315 (†p=0.005), MDA-MB-231 (†p=0.002), SUM159 (†p=0.01), MDA-MB-435 (†p=0.04)). Representative images shown depict apoptosis recorded for a: DM; b: SUM1315; c: MDA-MB-231; d: SUM159; e: MDA-MB-435.

Figure 74:
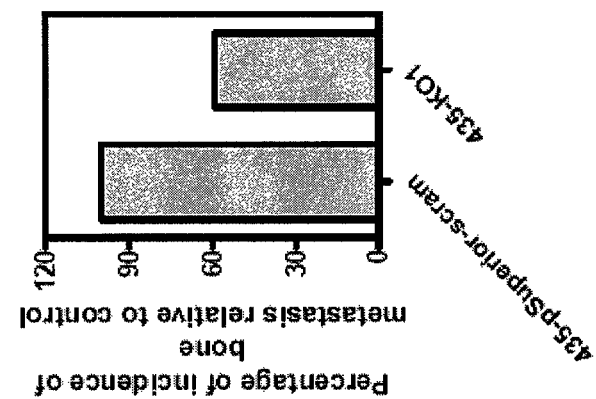

FIG. 74 depicts active Hh signaling in tumor cells causes osteolysis. Tumor cells were injected into the left cardiac ventricle of athymic mice; mice were euthanized 4-6 weeks later and radiographically imaged and assessed for osteolysis at the tibio-femoral junction. As represented in the Table, cells that were silenced for GLI1 expression showed an attenuated ability of osteolysis. The percent incidence of osteolysis is depicted in the adjacent graph.

Figure 75:
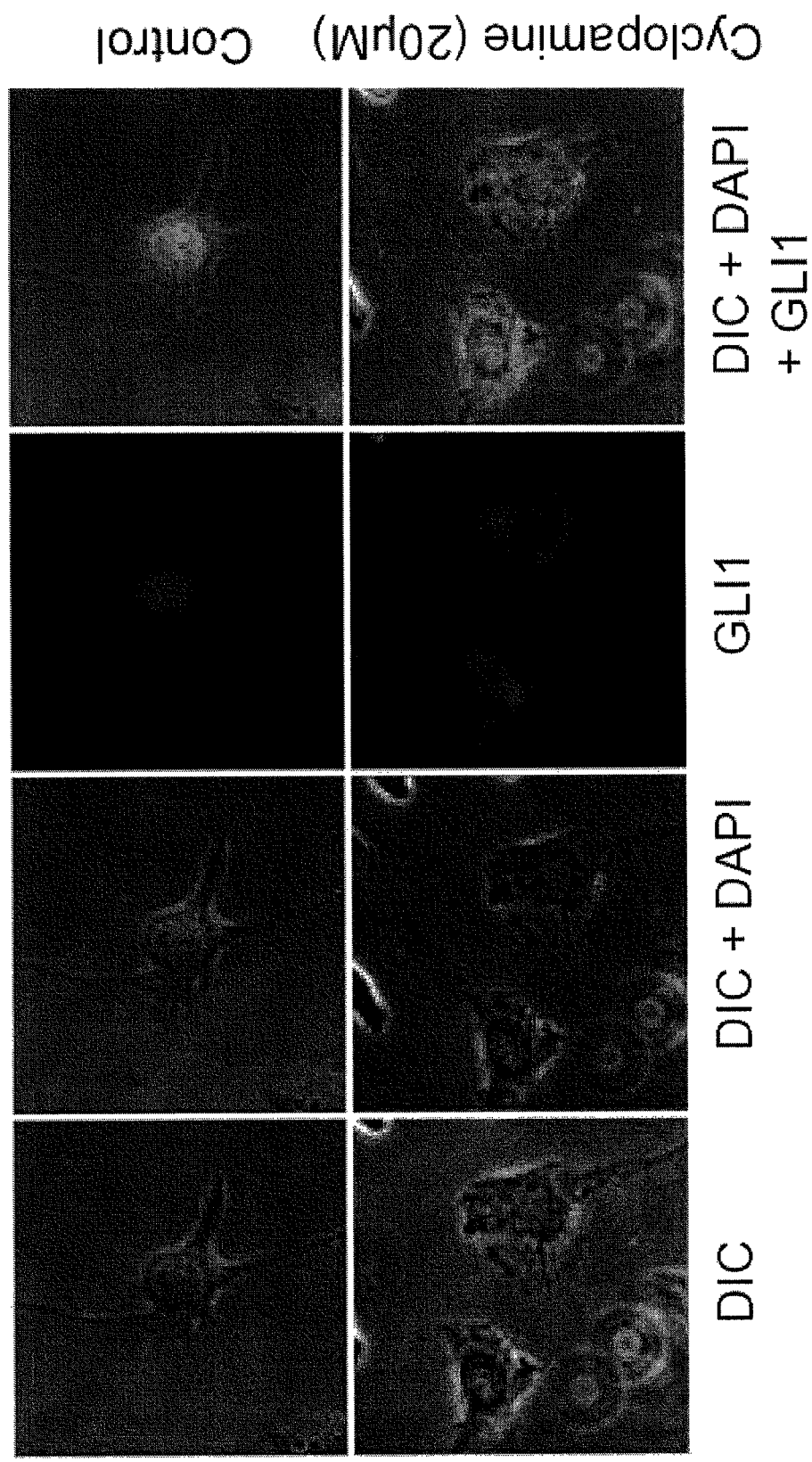
Figure 75:
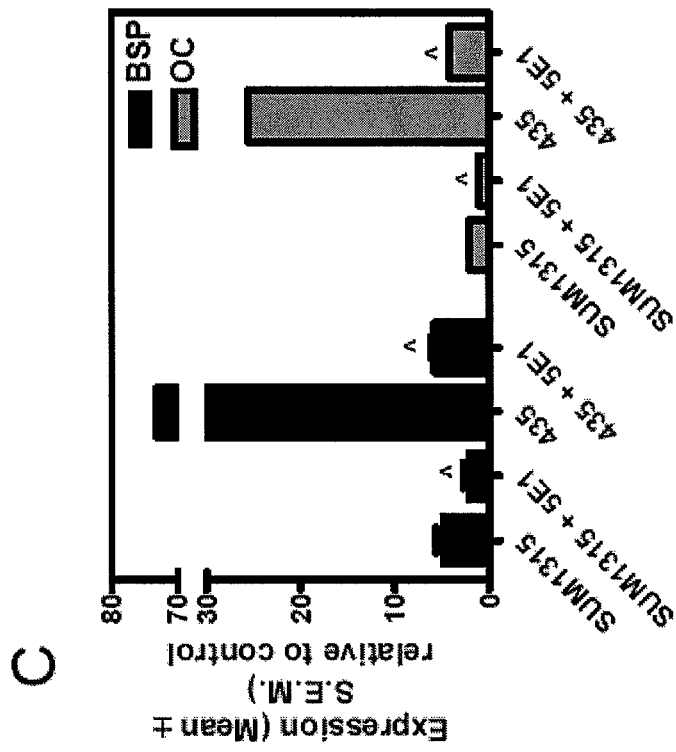
Figure 75:
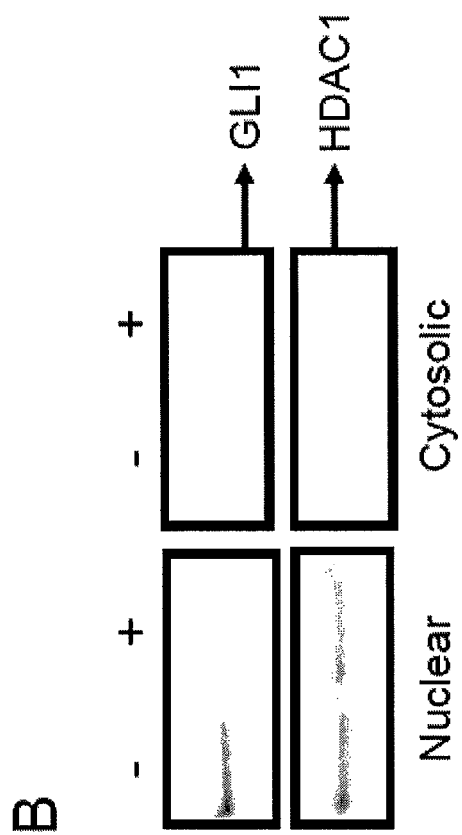

FIG. 75 (A) The Hh pathway inhibitor, cyclopamine restricts GLI1 to the cytosol. hFOB cells were cultured in absence (control) or in presence of cyclopamine (20 µM) for 24 h. The cells were fixed in 4% formaldehyde, permeabilized in 0.5% Triton-X and probed with anti-GLI1 antibody followed Alexa.Fluor 488-coupled second antibody (Molecular Probes). Cells were observed under either DIC or fluorescence (at 488 nm for Alexa.Fluor) and 461 nm for DAPI. Photomicrographs were acquired at using Axiovert 200 M Fluorescence Microscope (Zeiss). In the composite shown, GLI1 is stained green. (B) Cyclopamine treatment causes GLI1 to accumulate in the cytosol. Nuclear and cytosolic fractions were prepared after treating hFOB cells with cyclopamine. HDAC1 is used as a marker of purity of the nuclear fraction. (C) Hh ligands produced by the tumor cells upregulates expression of BSP and osteocalcin in the osteoblasts 14 days after initiation of differentiation. Deprivation of the Hh ligands from the tumor cell-conditioned medium using the 5E1 neutralizing antibody caused a significant reduction in the levels of BSP (SUM1315+5E1: ^p=0.01; 435+5E1: ^p<0.0001) and osteocalcin (OC) (SUM1315+5E1: ^p=0.001; 435+5E1: ^p<0.0001).

Figure 76:
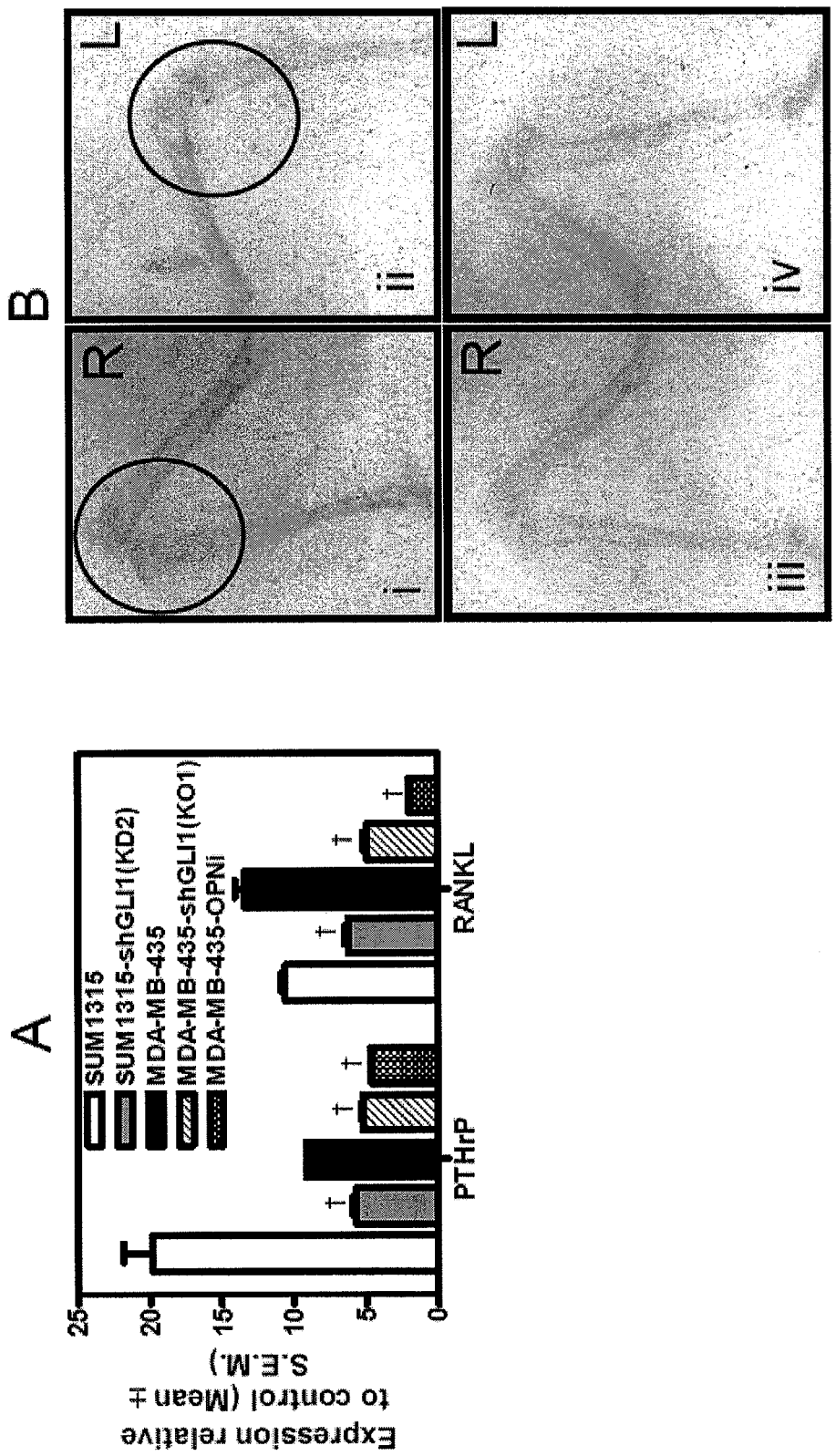
Figure 76:
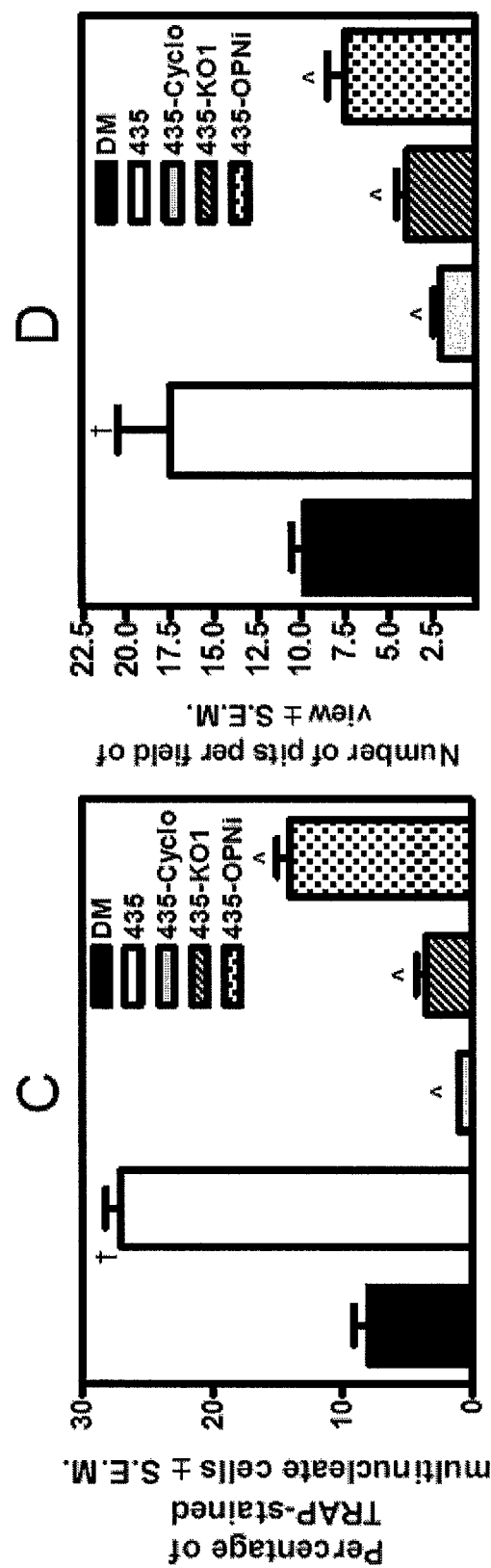

FIG. 76 (A) Expression of GLI1 and OPN in the tumor cells enhances their ability to induce RANKL and PTHrP by the osteoblasts. Abrogation of GLI1 expression in the SUM1315 cells reduces the expression of RANKL (KD2: †p=0.02) and PTHrP (KD2: †p=0.02003) elicited by the conditioned media from these cells. Likewise, conditioned medium from MDA-MB-435 cells abrogated for GLI1 was less efficient at inducing expression of RANKL (KO1: †p<0.0001) and PTHrP (KO1: †p<0.0001) by the osteoblasts. Ablating expression of OPN also caused a significant reduction in eliciting the expression of RANKL (OPNi: †p<0.0001) and PTHrP (OPNi: †p<0.0001) in osteoblasts. (B) Abrogating GLI1 expression reduces the incidence and intensity of osteolysis inflicted by MDA-MB-435 cells. Radiographic images (i) and (ii) represent osteolysis in mice injected with MDA-MB-435-vector control cells. Images (iii) and (iv) represent absence of evidence of osteolysis in mice injected with MDA-MB-435-KO1 (silenced for GLI1) cells. Cells were injected via the intracardiac route. (C) Interfering with Hh signaling decreases with the ability of tumor cells to induce osteoclast differentiation. Relative to DM, the conditioned medium from the MDA-MB-435 cells causes the development of significantly increased numbers of TRAP-positive multinucleate osteoclasts (†p=0.0004). There was a significant reduction in this ability following interference with Hh signaling in the tumor cells with cyclopamine treatment (^p<0.0001) or silencing GLI1 (^p<0.0001). Silencing OPN from the tumor cells also significantly reduced (^p=0.001) their ability to elicit osteoclast differentiation. Osteoclast differentiation was scored using the TRAP assay following the manufacturer's protocol (Sigma). (D) Interfering with Hh signaling decreases with the ability of tumor cells to enhance resorptive activity of osteoclasts. Conditioned medium from the MDA-MB-435 cells significantly enhances (†p=0.006) the ability of DM to induce resorptive activity of osteoclasts. Cyclopamine treatment (^p=0.007) or GLI1-silencing (^p=0.016) or OPN-silencing (^p=0.03) of the tumor cells significantly reduced their ability to activate the resorptive function of osteoblasts. The ability of the osteoclasts to resorb bone matrix was tested using osteoclast activity assay (OAAS plates, Osteogenic Core Technologies).

DETAILED DESCRIPTION

Some embodiments of the present invention relate to methods and compositions for treating disorders relating to increased activity of the Hedgehog pathway. Some embodiments include methods and compositions for modulating the activity of the Hedgehog pathway. Additional methods and compositions relate to treating neoplastic cells and cancer.

The Hedgehog pathway has a central role in developmental patterning (ontogeny), in the maintenance of stem or progenitor cells in many adult tissues, and has been demonstrated to be active in multiple cancer types. Active Hedgehog signaling is also reported to influence the tumor stromal microenvironment and support stem cells in the tumor in an undifferentiated, proliferative state.

Figure 1:
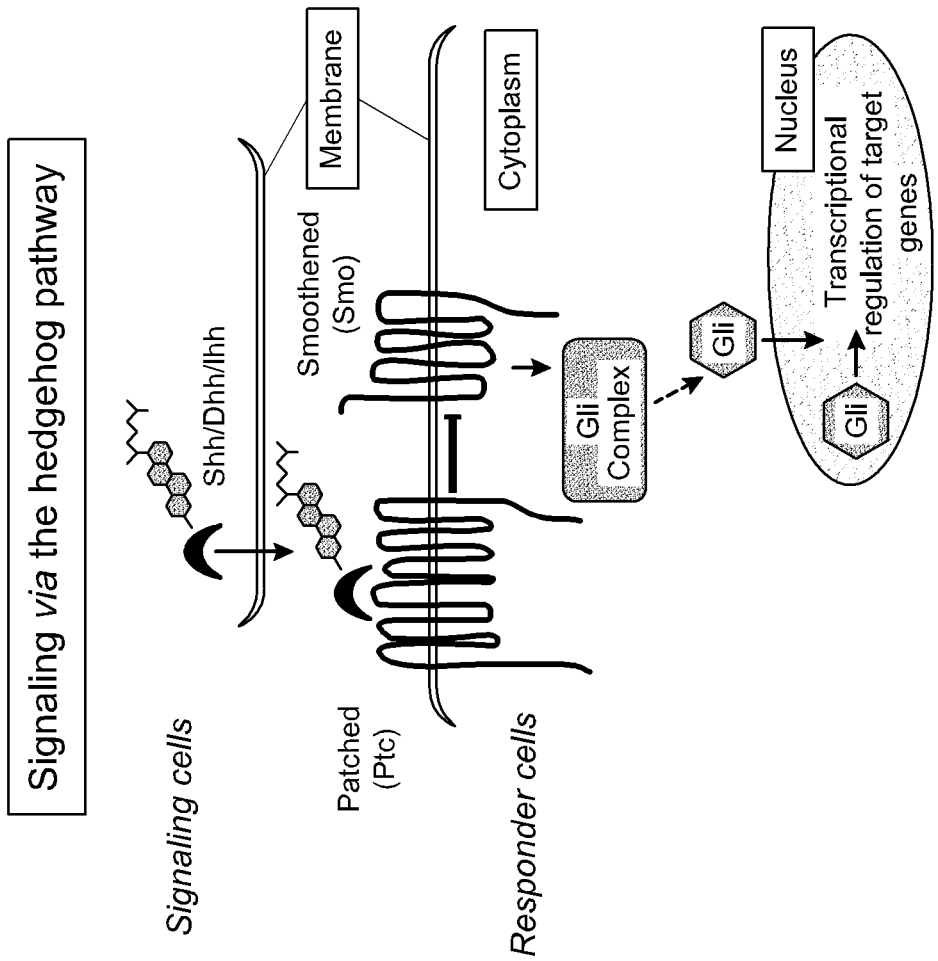
FIG. 1 shows a schematic diagram of signaling via the Hedgehog pathway.

Hedgehog signaling in mammalian cells is mediated by the GLI family of zinc finger transcription factors comprising GLI1, GLI2, and GLI3. GLI1 is a strong transcriptional activator; GLI2 has both activator and repressor functions; and GLI3 is mostly a repressor. In the Hedgehog ligand-dependent pathway, in the absence of the ligand, Desert hedgehog (DHH), Indian hedgehog (IHH), or Sonic hedgehog (SHH), the Hedgehog signaling pathway is inactive, GLI1 is sequestered in the cytoplasm and repressed for its transcription activity. Binding the Hedgehog ligands to the receptor patched-1 or patched-2 (PTCH1 or -2) changes the GLI code: the transmembrane protein, Smoothened (Smo) is activated, and GLI1 is activated by release from a large protein complex and translocates to the nucleus to function as a transcriptional activator (Ingham, P. W., et al. (2001) Genes Dev. 15, 3059-3087; FIG. 1).

GLI1 is encoded by two alternatively spliced transcripts which give rise to at least five different protein isoforms, some of which exist in more than one form. As used herein the term "GLI1 protein" includes all of these isoforms, including the isoforms listed in Table 4 below. As used herein the term "nucleic acid encoding GLI1" includes nucleic acids encoding all of the GLI1 isoforms, including the isoforms listed in Table 4 below.

Signaling via the Hedgehog pathway plays a determinative role in the development of the dorsal brain, near the sites of origin of melanogenic precursors. The Hedgehog pathway is required for normal proliferation of human melanocytes in vitro and for proliferation and survival of human melanoma in vivo. Activation of Hedgehog signaling results in transcriptional activation of the expression of several genes including insulin-like growth factor-binding protein, cyclin D2, and osteopontin (OPN).

Expression of GLI1 and OPN increase progressively with the progression of melanoma from primary cutaneous cancer to metastatic melanoma in clinically derived specimens. OPN is a direct transcriptional target of GLI1. OPN expression is stimulated in the presence of Hedgehog ligands and inhibited in the presence of the Smo inhibitor, cyclopamine. Transcriptional silencing of GLI1 negatively impacts OPN expression and compromises the ability of cancer cells to proliferate, migrate, and invade in vitro and interferes with their ability to grow as xenografts and spontaneously metastasize in nude mice. These altered attributes can be rescued by re-expressing OPN in the GLI1-silenced cells, suggesting that OPN is a critical downstream effector of active GLI1 signaling. These findings suggest that the GLI1-mediated upregulation of OPN promotes malignant behavior of cancer cells. Expression levels of GLI1 and OPN are significantly elevated in surgically excised metastatic melanoma specimens compared with surgically obtained basal and squamous cell carcinomas and primary melanoma samples. The Hedgehog pathway acts via OPN to regulate malignant behavior of cancer cells. Thus, there exists a clinically relevant relationship between OPN and Hedgehog signaling.

Embodiments of the present invention relate to the finding that reducing the expression of GLI1 reduces the metastatic potential of particular cells. Some embodiments of the present invention relate to methods and compositions for reducing the expression level of GLI1 protein or the expression level of a nucleic acid encoding GLI1 in a cell or a subject. Some such methods and compositions can be useful to kill or retard the growth of neoplastic cells. More such methods can be useful to treat a disorder in a subject in which the disorder is related to an increase in the activity of the Hedgehog pathway. Such disorders can include cancer, for example, ovarian cancer and breast cancer.

More embodiments include methods and compositions for increasing the sensitivity of cells to therapeutic compounds. Such methods can be useful to reduce the dosage of a therapeutic agent to treat a subject. For example, some methods and compositions provided herein can be used to increase the sensitivity of cells to chemotherapeutic compounds. In some such methods, the effective amount of a chemotherapeutic compound to treat a subject can be reduced.

The role of the Hedgehog pathway has been documented in several cancer histotypes (e.g., Watkins, D. N., et al. (2003) Nature 422, 313-317). The activities of this pathway have been attributed to several mediators, such as platelet-derived growth factor (Xie, J., et al. (2001) Proc. Natl. Acad. Sci. U.S.A. 98, 9255-9259), fibroblast growth factor (Sun, X., et al. (2000) Nat. Genet. 25, 83-86), bone morphogenic protein (Yu, J., et al. (2002) Development 129, 5301-5312), Notch (Hallahan, A. R., et al. (2004) Cancer Res. 64, 7794-7800), and Wnt (Madison, B. B., et al. (2005) Development 132, 279-289), which have been identified as Hedgehog target genes in various models. However, few universal target genes have been identified across different systems and much work still needs to be done to determine how Hedgehog overexpression contributes to tumorigenesis.

Studies provided herein indicate that signaling via the Hedgehog pathway can transcriptionally up-regulate OPN, an oncogene that has been widely reported to promote tumorigenesis, tumor progression, and metastasis in several cancer types. The regulation of OPN by the transcription factor GLI1 is integral to the malignant behavior of cancer cells as evidenced by the impaired ability of tumor cells to migrate, invade, and grow in vivo as xenografts when endogenous GLI1 expression is silenced. OPN is a secreted protein that influences multiple downstream signaling events that allows cancer cells to resist apoptosis, invade through extracellular matrix, evade host immunity (Bellahce'ne, A., et al. (2008) Nat. Rev. Cancer 8, 212-226), and influence growth of indolent tumors (McAllister, S. S., et al. (2008) Cell 133, 994-1005). OPN induces integrin and CD44-mediated migration via hepatocyte growth factor, its receptor, Met, and epidermal growth factor and enhances the invasive ability of cells by inducing the expression of proteases such as MT1-matrix metalloproteinase, matrix metalloproteinase-2, and urokinase plasminogen activator (Tuck, A. B., et al. (2003) Oncogene 22, 1198-1205). Clinically, OPN expression is up-regulated in several malignancies including breast cancer, melanoma, prostate cancer, colorectal cancer, and head and neck cancer (Coppola, D., et al. (2004) Clin. Cancer Res. 10, 184-190). OPN constitutes a component of the secretome of several melanoma-derived cell lines and is expressed in metastatic breast cancer cell lines (Riker, A. I., et al. (2008) BMC Med. Genomics 1, 13). Studies have reported an increase in levels of OPN in melanoma-derived cell lines (Rangaswami, H., et al. (2007) Oncol. Rep. 18, 909-915).

Expression of OPN is 13-fold higher when comparing thin melanomas to metastatic melanomas. Expression of GLI1 increases notably as cutaneous cancer progresses from a stage of melanoma in situ to intermediate and thick melanoma to metastatic melanoma. The increase in GLI1 expression is paralleled by an increase in OPN levels. Overall, such observations underscore the role of enhanced Hedgehog signaling via increased GLI1 transcriptional activity in potentiating the malignant behavior of melanoma cells and contributing to disease progression.

The Hedgehog pathway is aberrantly active in several cancer types, including breast cancer and melanoma (Xuan, et al. (2009) J. Cancer Res. Clin. Oncol. 135, 235-240). Hedgehog pathway components were detected in nevi, melanoma, and lymph node metastases of melanoma (Stecca, B., et al. (2007) Proc. Natl. Acad. Sci. U.S.A. 104, 5895-5900). Overexpression of GLI1 induced the expression of Snail, whereas blockade of Hedgehog signaling by the inhibitor cyclopamine suppressed pancreatic cancer invasion and metastasis by inhibiting EMT (Li, X., Deng, et al. (2007) Oncogene 26, 4489-4498). Experiments described herein are consistent with such findings in view of the observation of a loss of mesenchymal markers by abrogating GLI1 expression. EMT-related genes (N-cadherin, OPN, and osteonectin) have been reported to contribute to the promotion of the metastatic phenotype in primary cutaneous malignant melanomas by supporting specific adhesive, invasive, and migratory properties (Alonso, S. R., et al. (2007) Cancer Res. 67, 3450-3460). Moreover, these findings support observations provided herein showing that GLI1 silencing attenuates malignancy-associated attributes, such as invasion, migration, and motility. Results provided herein show that GLI1 silencing retards the tumor (xenograft) rate in the early phase. In the experiments described herein, after day 11 post-injection, the growth of GLI1-silenced tumors proceeded at the same rate as that of controls. This data has multiple implications, for example, it is likely that over time, a revertant population outgrew the GLI1-silenced cells. These revertants may have either lost the effects of RNA interference or may have by-passed the requirement for GLI1 signaling. In this case, the cells may have utilized other signaling pathways to up-regulate OPN. In addition, trace levels of OPN secreted by GLI1-silenced cells (FIG. 6A) can accumulate in the local microenvironment from the growing tumor and may have stimulated cell growth. Overall, GLI1 silencing had a pronounced effect on tumor malignancy in vivo by reducing metastasis.

The MDA-MB-435 cell line was used as a model as it produces abundant levels of OPN (Samant, R. S., et al. (2007) Mol. Cancer 6:6). This model system, which endogenously expresses high levels of OPN, supports a role for the Hedgehog pathway in regulating malignant cell behavior. Moreover, findings provided herein can have implications on multiple cancer histotypes that overexpress OPN (Brown, L. F., et al. (1994) Am. J. Pathol. 145, 610-623).

Hedgehog ligands and OPN, the signaling intermediate of the active Hedgehog pathway, are secreted molecules. This allows them to influence the behavior of cells in the tumor microenvironment. OPN has been documented to influence the behavior of cells in a paracrine manner. Although serum OPN influences the migratory behavior of melanoma cells and tumor-derived OPN inhibits nitric-oxide synthase activity of macrophages, OPN produced by fibroblasts is able to influence growth of pre-neoplastic cells (Hayashi, C., et al. (2007) J. Cell. Biochem. 101, 979-986). Thus, active Hedgehog signaling in a subset of cancer cells can potentially be amplified by secretion of OPN into the tumor microenvironment. The secreted OPN, in turn, can promote malignant behavior in neighboring cancer cells, regardless of the status of the Hedgehog pathway.

In addition, whereas OPN is capable of long-range signaling, the secreted Hedgehog ligand proteins participate in short-range signaling and can move many cell diameters from their source of production and often control developmental outcomes in a concentration-dependent manner. For example, during ventral spinal cord patterning, SHH forms a ventral-to-dorsal gradient with different concentrations specifying distinct pools of neural progenitors (Stamataki, D., et al. (2005) Genes Dev. 19, 626-641). It is likely that such a situation also prevails in a tumor; in which case, the Hedgehog ligands produced by a subpopulation of cells within a tumor can trigger activation of the pathway in the recipient cell.

Hedgehog Pathway and Bone Metastasis

Levels of OPN are significantly elevated in the tumors and plasma of patients with metastatic breast cancer and are notably associated with decreased patient survival (Cook, A. C., et al. (2005). Mol Carcinog 43, 225-236). Tumor cells upregulate OPN synthesis and secretion by osteoblasts and cause pathologic activation of osteoclasts, resulting in a net loss of bone (Nemoto H, R. S., et al. (2001). J Bone Miner Res 16, 652-659). Thus, OPN enhances metastasis of breast cancer to bone. OPN is a transcriptional target of Gli1. Gli1 is a transcription factor of the Hedgehog pathway that activates transcription of Hedgehog-target genes. The Hedgehog pathway is activated in a variety of cancer types, thus making it a putative therapeutic target.

Hedgehog Pathway and Osteoclastogenesis and Osteolysis

Breast cancer cells preferentially metastasize to the bone. Once within bone, an interaction ensues between breast cancer cells and the cells within the bone microenvironment. Breast cancer cells secrete various factors that stimulate osteoblasts and osteoclasts and other cells within the bone; these in turn secrete factors that stimulate the tumor cells, creating a vicious cycle that nurtures the development and propagation of bone metastases. OPN forms a component of a "bonemetastasis signature" of breast cancer cells i.e., breast cancer cells that metastasized to bone had increased OPN expression. Furthermore, OPN functionally enhanced incidence of bone metastases by breast cancer cells in concert with interleukin-11. OPN is one of the abundant non-collagenous proteins in bone. It is a bone matrix protein that promotes osteoclast function and is consistently overexpressed in highly metastatic cells. Ultrastructural immunocytochemical studies show that the most prominent accumulation of OPN is seen at cement lines in remodeling bone, and at laminae limitantes at bone surfaces. It is localized to cell-matrix and matrix-matrix interfaces in mineralized tissue, where it is deposited as the result of osteoclast action. Moreover, OPN appears to be an important component in the communication between osteoclasts and osteoblasts, and there is strong evidence for the involvement of OPN in the formation, migration and attachment of osteoclasts and in their resorptive activity. Importantly, interfering with the adhesion of osteoclasts to osteopontin by RGD-peptides abolishes their resorptive activity.

Nearly 42% of primary breast tumors express moderate to strong levels of OPN and 83% of bone metastases resulting from these tumors express OPN. OPN expression, specifically within the tumor cells, reciprocally correlates with patient survival. Clinical studies have revealed a correlation between plasma OPN, tumor burden and prognosis in patients with breast cancer metastasis. The levels of OPN in plasma of patients with breast cancer are significantly higher in those with bone metastasis compared to those who do not have bone metastasis. Moreover, the level of OPN increases with progression of the disease. Among these women, those with highest levels of OPN (more than 2000 µg/ml) show poor survival compared to those with OPN levels between 1000-1500 µg/ml. Whether the circulating OPN impacts 'homing' of breast cancer cells to bone is still not known. Functionally, OPN expression is vital to the tumorigenic ability of cells. Expression of OPN in OPN-negative breast cancer cells increases their adhesion to bone marrow cells and OPN knock-out mice display significantly lower incidence of bone metastases. In bone, tumor derived OPN plays a vital role in the establishment of vasculature by mediating adhesion to endothelial cells, co-operating with VEGF, and preventing apoptosis of the endothelial cells.

Expression of OPN is regulated, in part, by the Hedgehog (Hh) pathway. The Hh pathway has been reported to be aberrantly activated in breast cancer. In the absence of the ligand, Desert hedgehog (DHH) or Indian hedgehog (IHH) or Sonic hedgehog (SHH), the Hh signaling pathway is inactive. Ligand molecules bind to the receptor Patched (PTCH) thereby alleviating PTCH-mediated suppression of smoothened (SMOH), leading to activation of the pathway through the transcription of target genes mediated by the GLI transcription factors. As described herein, breast cancer cells express Hh ligands. These ligands can mediate a crosstalk directly with osteoclasts and activate expression of OPN in the osteoclasts; this promotes osteoclast maturation and resorptive activity. As such, breast cancer cells can directly influence osteoclast development and activity.

Hedgehog Pathway and Resistance to Chemotherapy

Cells may develop resistance to a range of chemotherapeutic compounds by reverting to a stem cell-like state. The Hedgehog pathway including genes such as GLI1 play a role in the development and maintenance of a stem cell-like phenotype (Peacock C D, et al. Proc Natl Acad Sci USA 104:4048-4053, 2007). Work on the proximal molecular causes of cellular and clinical resistance to platinum compounds has focused on DNA damage and repair, the nucleotide excision repair (NER) pathway, and ERCC1.

Nucleotide Excision Repair

More than 30 genes are involved in the NER process, which includes activities such as DNA damage recognition, helicase functions of XPB and XPD, damage excision, and gap-filling and ligation (Reed, E. Cisplatin and platinum analogs. in: Cancer Principles and Practice of Oncology; 8th Edition. Lippincott, Williams, and Wilkins; Philadelphia, pp 419-26, 2008). Understanding the molecular and pharmacologic control of NER, allows development of new platinum anticancer agents, and non-platinum agents that damage DNA and/or modulate DNA repair.

In NER, the DNA damage excision step is rate-limiting to the process, where the last sub-step is the 5' incision into the DNA strand, relative to the site of covalent damage. This 5' incision occurs after the 3'→5' and 5'→3' helicase functions of the repairosome, and after the 3' incision. The 5' incision is executed by the ERCC1-XPF heterodimer.

ERCC1

ERCC1 is highly conserved across organisms (Xu H, et al. The Plant Journal 13:823-829, 1998). The *E. coli* homologue is UvrC, which performs the 5' incision during the conduct of the NER process. Exon VIII of ERCC1 has high homology with uvrC of *E coli* (Lin J-J, et al. J Biol Chem 267:17688-17692, 1992). In *E. coli*, the uvrABC protein complex executes NER-types of DNA repair. Within the *E. coli* complex, uvrC executes the 5' and the 3' DNA strand-cutting steps that excise platinum-DNA damage (Verhoeven E E A, et al. J Biol Chem 275:5120-5123, 2000). In mammalian NER, exon VIII of ERCC1 may serve the same DNA-strand cutting function as uvrC in *E. coli*. An alternatively spliced form of ERCC1 exists in human malignant and non-malignant tissues, which lacks exon VIII. This alternatively spliced variant of ERCC1 may possibly have an inhibitory role for NER, in human cells. These NER activities appear to be distinct from the ERCC1 roles in double strand break repair (Ahmad A, et al. Mol Cell Biol 28:5082-5092, 2008).

Some studies have utilized paired Chinese hamster ovary (CHO) cells having functional ERCC1 or non-functional ERCC1 (Lee, K B., et al. Carcinogenesis, 14:2177-2180, 1993). CHO cells lacking a functional ERCC1 (43:3B cells) were super-sensitive to IC50 doses of cisplatin, and showed no detectable ability to repair cisplatin-DNA adduct. In CHO cells having a functional ERCC1 (83:J5 cells), cisplatin-DNA adduct repair capability was intact and there was an increased level of cellular resistance to cisplatin.

ERCC1 is biomarker for the overall activity of NER in human cell lines and tissues (Reed E. New Eng J. Med 355:1054-1055, 2006; Reed E. Clinical Cancer Research, 11:6100-6102, 2005). Non-functionality of ERCC1 results in a severe DNA repair deficit phenotype, in vitro or in vivo.

In NER, the ERCC1-XPF heterodimer executes the 5' incision into the DNA strand, freeing the DNA segment that has covalent bulky DNA damage (Ahmad A, et al. Mol Cell Biol 28:5082-5092, 2008). The ERCC1-XPF heterodimer also plays a role in drug-cross-link induced double-strand break repair, via an end joining mechanism that is Ku86-independent. Detailed structure-function analyses of both proteins show that XPF is a scaffold protein (Al-Minawi A Z, et al. Nucleic Acids Res 27 Aug. 2009).

Cisplatin damages DNA by inducing double strand breaks, single strand breaks, platinum-DNA adducts, and DNA-platinum-protein adducts. ERCC1 plays a role in cellular resistance to cisplatin including excision of platinum-DNA damage from cellular DNA, and repair of double-strand breaks (Altaha R et al. Int J Mol Med, 14:959-970, 2004).

In human ovarian cancer tissues, high levels of ERCC1 mRNA have been observed in tissues from patients that were clinically resistant to platinum therapy; and low levels of ERCC1 mRNA have been observed in tissues from patients that were clinically sensitive to platinum therapy (Dabholkar, M., et al. J Nat'l Cancer Inst, 84:1512-1517, 1992).

In human ovarian cancer cells, ERCC1 is up-regulated from 1 hr treatment with cisplatin (Li Q, et al. J Biol Chem, 273:23419-23425, 1998). Subsequent to treating cells with IC50 dose of cisplatin, A2780-CP70 human ovarian cancer cells increase expression of mRNA and protein for c-jun and c-fos, with mRNA levels peaking at 1-2 hr and c-jun protein levels peaking at 3-5 hr after treatment. Phosphorylation of c-jun protein has been observed to be greatly enhanced at 1 hr after cisplatin treatment, and peaks at 15-fold over baseline at 3-5 hr after cisplatin treatment. Phosphorylation activates c-jun protein, which in turn activates AP1, which leads to increased transcription of ERCC1. ERCC1 mRNA levels peak levels at 3-4 hr. ERCC1 protein levels begin to rise within 1 hr, and peak at 24 hr.

In cisplatin-treated cells, ERCC1 mRNA degrades with a half-life of 24 hr, in contrast to a half-life of 14 hr in untreated cells. This suggests mechanisms that are activated in response to DNA damage that prolong the period during which ERCC1 may be active.

More studies suggest that ERCC1 up-regulation through AP1 may occur through the JNK/SAPK pathway, or the ERK pathway (Li Q, et al. Cellular and Molecular Life Sciences, 55:456-466, 1999). The ERK pathway can be activated by cell exposure to phorbol ester.

Modulating expression levels of ERCC1 may modulate DNA repair activities in a cell, and alter cellular sensitivity to agents that affect DNA repair, such as cisplatin. In one study, a dominant negative AdA-FOS construct to inhibit AP1 binding was transfected into the human ovarian cell line, A2780-CP70, prior to cisplatin exposure (Li Q, et al. Effect of interleukin-1 and tumor necrosis factor on cisplatin-induced ERCC1 mRNA expression in a human ovarian carcinoma cell line. Anticancer Research, 18: 2283-2287, 1998). ERCC1 up-regulation was severely blunted after cisplatin exposure, platinum-DNA adduct repair was severely reduced, and cells were several-fold more sensitive to cisplatin treatment. A series of compounds were assessed for their ability to blunt ERCC1 up-regulation. All agents that blunted ERCC1 up-regulation, also inhibited platinum-DNA adduct repair and enhanced sensitivity to cisplatin. The following compounds blunted ERCC1 up-regulation: heavy metals including platinum, chromium; cycloheximide; α-amanitin; actinomycin D; interleukin 1-α; lactacystin; N-acetyl-leucyl-leucyl-norleucinal; SU5416; cyclosporin A; and herbimycin A.

The ERCC1 gene is alternatively spliced. One splice variant lacks exon VIII, an exon which has high homology to uvrC in E. coli. The occurrence of the variant lacking exon VIII, correlates to a decrease in the ability of cells to repair platinum-DNA adduct, namely, the higher the percent alternatively spliced ERCC1, the lower the DNA adduct repair capability. Another splice variant of ERCC1 mRNA involves the 5' UTR, and may involve transcriptional regulation by the gene RFX1 (Yu J J, et al. Oncogene, 20:7694-7698, 2001).

A specific polymorphism at codon 118 of the NER gene ERCC1 in exon IV may be clinically relevant (Yu J J, et al. International Journal of Oncology, 16:555-560, 2000). This polymorphism is associated with reduced mRNA expression of the gene, reduced protein expression, reduced platinum-DNA adduct repair, enhanced cellular sensitivity to cisplatin, and more favorable clinical outcomes from platinum-based chemotherapy in patients with cancers including ovarian cancer, lung cancer, and colorectal cancer.

Loss of heterozygosity may occur in some ovarian cancer cells and tissues for the 19q region that contains ERCC1 (Yu, J J, et al. Cancer Letters, 151:127-132, 2000). This has also been observed in malignant gliomas, with changes in gene copy number for ERCC1 and for XPD (Liang, B. C., et al. J Neuro Oncol, 26:17-23, 1995). These changes do not appear to correlate with alterations in mRNA or protein expression of these genes, or with observed clinical outcomes. Indeed, variations in XPA mRNA expression have been observed in the absence of mutations or changes in gene copy number (States, J. C. et al. Cancer Letters, 108:233-237, 1996).

Coordinate Expression of NER Genes in Human Ovarian Cancer Tissues

ERCC1, XPA, XPB, and XPD of the NER repairosome appear to be coordinately up-regulated and down-regulated in tissues such as human ovarian cancer, non-malignant bone marrow, and human brain (e.g., Dabholkar, M., et al. J Clin Invest, 94:703-708, 1994).

In a study using human ovarian cancer, genes of the NER pathway including ERCC1, XPA, XPB, and CSB were examined, along with the genes, MDR1 and MT-II. The NER genes were up-regulated in platinum-resistant tissues together in the absence of upregulation of MDR1 and of MT-II. Tissues that responded to chemotherapy, namely, platinum-sensitive tissues, consistently showed low level expression of these NER genes. In another study, human ovarian cancer tumors were examined for coordinate mRNA expression of ERCC1, XPB, and XPD. Five different histological types were investigated: clear cell, endometriod, serous, mucinous, and undifferentiated tumors. Clear cell tumors of the ovary are known for being particularly chemoresistant. In this study, clear cell tumors had consistently higher mRNA levels of ERCC1, XPB, and XPD, and the degree of coordinate expression was statistically significantly greater in clear cell tumors, than in any of the other histologies.

In another study, evidence of coordinate expression of NER genes was investigated in human brain tissues using malignant, and adjacent non-malignant specimens. In high grade gliomas, there was strong coordinate mRNA expression of ERCC1 and XPA, as assessed by linear regression analysis. When malignant and non-malignant glial tissues were assayed from the same patients, there was poor coordinate expression of ERCC1 mRNA. This suggests that during the conversion of cells from the normal to the malignant state, ERCC1 is altered and possibly all of NER is altered. This type of circumstance has been confirmed using different DNA repair genes in an examination of direct reversal of DNA damage caused by methylating agents.

In sum, genes in the NER pathway seem to display several common essential characteristics in human malignant tissues that have some degree of clinical sensitivity to cisplatin and other platinum analogues. For example, higher levels of expression of mRNA and of protein are seen in platinum-resistant tissues, as compared to platinum-sensitive tissues. In addition, the degree to which NER is tightly coordinated between the various genes involved in the process, contributes to that tissue's ability to repair platinum-DNA damage and resist platinum-based therapy.

Base Excision Repair

The base excision repair pathway is an evolutionarily conserved mechanism for repair of several types of DNA lesions, including oxidative lesions, alkylation, and incorporation of inappropriate bases (Hegde, M. L., et al. (2008) Cell Res. 18, 27-47). The primary source of these lesions is reactive oxygen species, whether generated endogenously or due to genotoxic agents. The base excision repair pathway functions to maintain genomic integrity via a high fidelity repair process and is thus anti-mutagenic and anti-carcinogenic (D'Errico, M., et al. (2008) Mutat Res. 659, 4-14). This pathway usually has four or five enzymatic steps, involving a DNA glycosylase, such as OGG1 or NTH1, an AP endonuclease (REF1/APE1), a DNA polymerase, such as POLB and POLD, and a DNA ligase (LIG1 or LIG3) (Mitra, S., et al. (1997) Mol Cells. 7, 305-312). DNA glycosylases such as OGG1 and NTH1, recognize specific subsets of damaged bases, excise the damaged base, and may also incise at the site of the excised base due to an intrinsic lyase activity. REF1/APE1 (an example of a mammalian AP endonuclease) then cleaves the abasic site to form a 3'-OH end and a 5' deoxyribose phosphate end. The remaining steps may utilize a "long patch" or "short patch" pathway involving repair DNA synthesis and strand ligation by different sets of proteins. The preferred substrates for the DNA glycosylases OGG1 (8-oxoguanine glycosylase 1) and NTH1 (homolog of E. coli endonuclease III) are 8-oxoguanine (8-OxoG) and thymine glycol (TG) lesions, respectively. REF1/APE1 (redox factor 1/apurinic endonuclease 1) is a multifunctional enzyme with apurinic/apyrimidinic (AP) endonuclease activity and 3',5'-exonuclease, 3'-diesterase, and 3'-phosphatase activities. REF1/APE1 also has transcriptional regulatory activity independently of its function in base excision repair (Izumi, T., et al. (2003) Toxicology. 193, 43-65; Kelley, M. R., et al. (2001) Antioxid Redox Signal. 3, 671-683). Finally, the XRCC1 protein (X-ray repair, cross-complementing defective, in Chinese hamster, 1) associates with several other proteins—polynucleotide kinase (PNK), DNA polymerase-β (POLB), and DNA ligase III (LIG3)—to form a complex that repairs the single-strand DNA breaks generated during the base excision repair process.

Cancer Stem Cells and Drug Resistance

Human ovarian cancer cells grown under conditions that support a sub-population that grows in spheroids selects for cells that have a more potent ability to form new independent cancers (Zhang S, et al. Cancer Res 68:4311-4320, 2008). As few as 100 spheroid forming cells could form new independent tumors when transferred to nude mice, while as many as 100,000 cells grown in monolayer, were unable to form independent tumors. The cancer initiating cells (cancer stem cells) become much more drug resistant to a variety of agents, including platinum compounds such as cisplatin and paclitaxel. Such cells may also express a set of molecular markers that differ from the same cell line, grown in monolayer, such as CD117, CD44, and Nestin. Cancer initiating cells have been investigated in other malignancies including prostate cancer, breast cancer, and lung cancer (Zietarska M, et al. Molecular Carcinogenesis 46:872-885, 2007; Burleson K et al. Gynecologic Oncology 93: 170-181, 2004; Casey R C, et al. Am J of Pathology 159:2071-2080, 2001).

Ovarian cancer stem cells may be responsible for persistent low volume disease after induction of a clinical complete response. The inability to eradicate such cells may be a function of cell dormancy, the relative inability of any chemotherapy to have a meaningful effect on cells in the dormant state or these cells may represent a state of extreme drug resistance at the molecular level.

Methods and Compositions to Reduce Activity of the Hedgehog Pathway

Some embodiments relate to compositions and/or methods for reducing activity of the Hedgehog pathway. In some embodiments, the level of GLI1 protein, such as the GLI1-130 isoform, or the level of a nucleic encoding GLI1, such as a nucleic acid encoding the GLI1-130 isoform, can be reduced in the cell of a subject. Methods to reduce the level of GLI1 protein, such as the GLI1-130 isoform, or the level of a nucleic encoding GLI1, such as a nucleic acid encoding the GLI1-130 isoform, in a cell or a subject can be useful to kill or retard the growth of a cell or can be useful to treat or ameliorate certain disorders in a subject.

In some embodiments, the methods or compositions described herein result in a decrease of the amounts of GLI1 protein, such as the GLI1-130 isoform, or a nucleic acid encoding GLI1, such as a nucleic acid encoding the GLI1-130 isoform, within a cell, such as endogenous GLI1, or an mRNA encoding GLI1. In some embodiments, the methods or compositions described herein provide a decrease in GLI1 protein, such as the GLI1-130 isoform, or a decrease in a nucleic acid encoding GLI1, such as a nucleic acid encoding the GLI1-130 isoform, within a cell of at least about 10%, at least about 20%, at least about 30%, at least about 40%, at least about 50%, at least about 60%, at least about 70%, at least about 80%, at least about 90%, and at least about 100%.

The level of GLI1 protein, such as the GLI1-130 isoform, or the level of a nucleic encoding GLI1, such as a nucleic acid encoding the GLI1-130 isoform, can be reduced using RNA interference or antisense technologies. RNA interference is an efficient process whereby double-stranded RNA (dsRNA), also referred to herein as siRNAs (small interfering RNAs) or ds siRNAs (double-stranded small interfering RNAs), induces the sequence-specific degradation of targeted mRNA in animal or plant cells (Hutvagner, G. et al. (2002) Curr. Opin. Genet. Dev. 12:225-232); Sharp, P. A. (2001) Genes Dev. 15:485-490).

In mammalian cells, RNA interference can be triggered by various molecules, including 21-nucleotide duplexes of siRNA (Chiu, Y.-L. et al. (2002) Mol. Cell. 10:549-561. Clackson, T. et al. (1991) Nature 352:624-628; Elbashir, S. M. et al. (2001) Nature 411:494-498), or by micro-RNAs (miRNA), functional small-hairpin RNA (shRNA), or other dsRNAs which can be expressed in vivo using DNA templates with RNA polymerase III promoters (Zheng, B. J. (2004) Antivir. Ther. 9:365-374; Paddison, P. J. et al. (2002) Genes Dev. 16:948-958; Lee, N. S. et al. (2002) Nature Biotechnol. 20:500-505; Paul, C. P. et al. (2002) Nature Biotechnol. 20:505-508; Tuschl, T. (2002) Nature Biotechnol. 20:446-448; Yu, J.-Y. et al. (2002) Proc. Natl. Acad. Sci. USA 99(9):6047-6052; McManus, M. T. et al. (2002) RNA 8:842-850; Sui, G. et al. (2002) Proc. Natl. Acad. Sci. USA 99(6):5515-5520, each of which are incorporated herein by reference in their entirety).

The scientific literature is replete with reports of endogenous and exogenous gene expression silencing using siRNA, highlighting their therapeutic potential (Gupta, S. et al. (2004) PNAS 101:1927-1932; Takaku, H. (2004) Antivir Chem. Chemother 15:57-65; Pardridge, W. M. (2004) Expert Opin. Biol. Ther. 4(7):1103-1113; Shen, W.-G. (2004) Chin. Med. J. (Engl) 117:1084-1091; Fuchs, U. et al. (2004) Curr. Mol. Med. 4:507-517; Wadhwa, R. et al. (2004) Mutat. Res. 567:71-84; Ichim, T. E. et al. (2004) Am. J. Transplant 4:1227-1236; Jana, S. et al. (2004) Appl. Microbiol. Biotechnol. 65:649-657; Ryther, R. C. C. et al. (2005) Gene Ther. 12:5-11; Chae, S-S. et al. (2004) J. Clin. Invest 114:1082-1089; de Fougerolles, A. et al. (2005) Methods Enzymol. 392:278-296, each of which is incorporated herein by reference in its entirety).

Therapeutic silencing of endogenous genes by systemic administration of siRNAs has been described in the literature (Kim, B. et al. (2004) American Journal of Pathology 65:2177-2185; Soutschek, J. et al. (2004) Nature 432:173-178; Pardridge, W. M. (2004) Expert Opin. Biol. Ther. 4(7):1103-1113, each of which is incorporated herein by reference in its entirety).

siRNAs induce a sequence-specific reduction in expression of a gene by the process of RNAi. Thus, siRNA is the intermediate effector molecule of the RNAi process. Some nucleic acid molecules or constructs provided herein include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA of GLI1 and the other strand is identical or substantially identical to the first strand. However, it will be appreciated that the dsRNA molecules may have any number of nucleotides in each strand which allows them to reduce the level of GLI1 protein, such as the GLI1-130 isoform, or the level of a nucleic acid encoding GLI1. The dsRNA molecules provided herein can be chemically synthesized, or can be transcribed in vitro from a DNA template, or in vivo from, e.g., shRNA. The dsRNA molecules can be designed using any method known in the art.

An example method for designing dsRNA molecules is provided in the pSUPER RNAi SYSTEM™ (OligoEngine, Seattle, Wash.). The system provides inducible expression of a siRNA in a transfected cell. To effect silencing of a specific gene, a pSUPERIOR vector is used in concert with a pair of custom oligonucleotides that include a unique 19-nt sequence derived from the mRNA transcript of the gene targeted for suppression (the "N-19 target sequence"). The N-19 target sequence corresponds to the sense strand of the pSUPER-generated siRNA, which in turn corresponds to a 19-nt sequence within the mRNA. In the mechanism of RNAi, the antisense strand of the siRNA duplex hybridizes to this region of the mRNA to mediate cleavage of the molecule. These forward and reverse oligonucleotides are annealed and cloned into the vector so that the desired siRNA duplex can be generated. The sequence of the forward oligonucleotide includes the unique N-19 target in both sense and antisense orientation, separated by a 9-nt spacer sequence. The resulting transcript of the recombinant vector is predicted to fold back on itself to form a 19-base pair stem-loop structure. The stem-loop precursor transcript is quickly cleaved in the cell to produce a functional siRNA (T. R. Brummelkamp, et al, Science 296, 550 (2002)). More example methods are provided in Taxman D. J. et al. (2006) BMC Biotechnol. 6:7; and McIntyre G. J. et al. (2006) BMC Biotechnol. 6:1, each of which is incorporated by reference in its entirety.

Nucleic acids provided herein can include both unmodified siRNAs and modified siRNAs as known in the art. For example, in some embodiments, siRNA derivatives can include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Nucleic acids provided herein can include nucleic acids that can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert, G. et al. (2001) Drug Deliv. Rev. 47(1): 99-112 (describes nucleic acids loaded to polyalkylcyanoacrylate (PACA) nanoparticles); Fattal et al. (1998) J. Control Release 53(1-3): 137-43 (describes nucleic acids bound to nanoparticles); Schwab et al. (1994) Ann. Oncol. 5 Suppl. 4:55-58 (describes nucleic acids linked to intercalating agents, hydrophobic groups, polycations or PACA nanoparticles); and Godard, G. et al. (1995) Eur. J. Biochem. 232(2):404-10 (describes nucleic acids linked to nanoparticles). Because RNAi is believed to progress via at least one single stranded RNA intermediate, the skilled artisan will appreciate that ss-siRNAs (e.g., the antisense strand of a ds-siRNA) can also be designed as described herein and utilized according to the claimed methodologies.

Synthetic siRNAs can be delivered to cells by methods known in the art, including cationic liposome transfection and electroporation. However, these exogenous siRNA generally show short term persistence of the silencing effect (4 to 5 days in cultured cells), which may be beneficial in certain embodiments. To obtain longer term suppression of expression for targeted genes, such as GLI1, and to facilitate delivery under certain circumstances, one or more siRNA duplexes, e.g., ds siRNA, can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T. (2002) Nature Biotechnol. 20:446-448) capable of expressing functional double-stranded siRNAs; (Lee, N. S. et al. (2002) Nature Biotechnol. 20:500-505; Miyagishi, M. and Taira, K. (2002) Nature Biotechnol. 20:497-500; Paul, C. P. et al. (2002) Nature Biotechnol. 20:505-508; Yu, J.-Y. et al. (2002) Proc. Natl. Acad. Sci. USA 99(9):6047-6052; Sui, G. et al. (2002) Proc. Natl. Acad. Sci. USA 99(6):5515-5520). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression. Constructs containing siRNA sequence(s) under the control of a T7 promoter also make functional siRNAs when co-transfected into the cells with a vector expressing T7 RNA polymerase (Jacque J.-M. et al. (2002) Nature 418:435-438). A single construct may contain multiple sequences coding for siRNAs, such as multiple regions of the GLI1 gene, such as a nucleic acid encoding the GLI1 mRNA, and can be driven, for example, by separate Pol III promoter sites.

Nucleic acids provided herein can include micro RNA (miRNAs) which can regulate gene expression at the post transcriptional or translational level. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zheng, B. J. (2004) Antivir. Ther. 9:365-374). When expressed by DNA vectors containing polymerase III promoters, micro-RNA designed hairpins can silence gene expression, such as GLI1 expression.

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002) Nature Biotechnol. 20(10):1006-10). In vitro infection of cells by such recombinant adenoviruses allows for diminished endogenous target gene expression. Injection of recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari, F. et al. (2002) Proc. Natl. Acad. Sci. USA 99(22):14236-40). In adult mice, efficient delivery of siRNA can be accomplished by the "high-pressure" delivery technique, a rapid injection (within 5 seconds) of a large volume of siRNA containing solution into animal via the tail vein (Lewis, D. L. (2002) Nature Genetics 32:107-108). Nanoparticles, liposomes and other cationic lipid molecules can also be used to deliver siRNA into animals. A gel-based agarose/liposome/siRNA formulation is also available (Jiamg, M. et al. (2004) Oligonucleotides 14(4):239-48).

Nucleic acids provided herein can include an antisense nucleic acid sequence selected such that it is complementary to the entirety of GLI1 or to a portion of GLI1. In some embodiments, a portion can refer to at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, and at least about 80%, at least about 85%, at least about 90%, at least about 95%. In some embodiments, a portion can refer up to 100%. An example mRNA sequence (SEQ ID NO:11) of human GLI1 is shown in TABLE 1.

TABLE 1

|  |  |
|---:|---|
| 1 | cccagactcc agccctggac cgcgcatccc gagcccagcg cccagacaga gtgtccccac |
| 61 | accctcctct gagacgccat gttcaactcg atgacccccac caccaatcag tagctatggc |
| 121 | gagccctgct gtctccggcc cctccccagt caggggccc ccagtgtggg gacagaagga |
| 181 | ctgtctggcc cgcccttctg ccaccaagct aacctcatgt ccggccccca cagttatggg |
| 241 | ccagccagag agaccaacag ctgcaccgag ggcccactct tttcttctcc ccggagtgca |
| 301 | gtcaagttga ccaagaagcg ggcactgtcc atctcacctc tgtcggatgc cagcctggac |
| 361 | ctgcagacgg ttatccgcac ctcacccagc tccctcgtag ctttcatcaa ctcgcgatgc |
| 421 | acatctccag gaggctccta cggtcatctc tccattggca ccatgagccc atctctggga |
| 481 | ttcccagccc agatgaatca ccaaaaaggg ccctcgcctt cctttggggt ccagccttgt |
| 541 | ggtccccatg actctgcccg gggtgggatg atcccacatc ctcagtcccg ggaccctttc |
| 601 | ccaacttgcc agctgaagtc tgagctggac atgctggttg gcaagtgccg ggaggaaccc |
| 661 | ttggaaggtg atatgtccag ccccaactcc acaggcatac aggatcccct gttggggatg |
| 721 | ctggatgggc gggaggacct cgagagagag gagaagcgtg agcctgaatc tgtgtatgaa |
| 781 | actgactgcc gttgggatgg ctgcagccaa gaatttgact cccaagagca gctggtgcac |
| 841 | cacatcaaca gcgagcacat ccacggggag cggaaggagt tcgtgtgcca ctggggggc |
| 901 | tgctccaggg agctgaggcc cttcaaagcc cagtacatgc tggtggttca catgcgcaga |
| 961 | cacactggcg agaagccaca caagtgcacg tttgaagggt gccggaagtc atactcacgc |
| 1021 | ctcgaaaacc tgaagacgca cctgcggtca cacacgggtg agaagccata catgtgtgag |
| 1081 | cacgagggct gcagtaaagc cttcagcaat gccagtgacc gagccaagca ccagaatcgg |
| 1141 | acccattcca atgagaagcc gtatgtatgt aagctccctg gctgcaccaa acgctataca |
| 1201 | gatcctagct cgctgcgaaa acatgtcaag acagtgcatg gtcctgacgc ccatgtgacc |
| 1261 | aaacggcacc gtggggatgg cccctgcct cgggcaccat ccatttctac agtggagccc |
| 1321 | aagagggagc gggaaggagg tcccatcagg gaggaaagca gactgactgt gccagagggt |
| 1381 | gccatgaagc cacagccaag ccctggggcc cagtcatcct gcagcagtga ccactccccg |
| 1441 | gcagggagtg cagccaatac agacagtggt gtggaaatga ctggcaatgc aggggcagc |
| 1501 | actgaagacc tctccagctt ggacgaggga ccttgcattg ctggcactgg tctgtccact |
| 1561 | cttcgccgcc ttgagaacct caggctggac cagctacatc aactccggcc aatagggacc |
| 1621 | cggggtctca aactgcccag cttgtcccac accggtacca ctgtgtcccg ccgcgtgggc |
| 1681 | cccccagtct ctcttgaacg ccgcagcagc agctccagca gcatcagctc tgcctatact |
| 1741 | gtcagccgcc gctcctccct ggcctctcct ttccccccctg ctccccacc agagaatgga |
| 1801 | gcatcctccc tgcctggcct tatgcctgcc cagcactacc tgcttcgggc aagatatgct |
| 1861 | tcagccagag gggtggtac ttcgcccact gcagcatcca gcctggatcg gataggtggt |
| 1921 | cttcccatgc ctccttggag aagccgagcc gagtatccag gatacaaccc caatgcaggg |

TABLE 1-continued

```
1981  gtcacccgga gggccagtga cccagcccag gctgctgacc gtcctgctcc agctagagtc
2041  cagaggttca agagcctggg ctgtgtccat accccaccca ctgtggcagg gggaggacag
2101  aactttgatc cttacctccc aacctctgtc tactcaccac agcccccag catcactgag
2161  aatgctgcca tggatgctag agggctacag gaagagccag aagttgggac ctccatggtg
2221  ggcagtggtc tgaacccta tatggacttc ccacctactg atactctggg atatggggga
2281  cctgaagggg cagcagctga gccttatgga gcgaggggtc caggctctct gcctcttggg
2341  cctggtccac ccaccaacta tggccccaac ccctgtcccc agcaggcctc atatcctgac
2401  cccacccaag aaacatgggg tgagttccct tcccactctg ggctgtaccc aggccccaag
2461  gctctaggtg gaacctacag ccagtgtcct cgacttgaac attatggaca agtgcaagtc
2521  aagccagaac aggggtgccc agtgggtct gactccacag gactggcacc ctgcctcaat
2581  gcccacccca gtgagggcc cccacatcca cagcctctct tttcccatta ccccagccc
2641  tctcctcccc aatatctcca gtcaggcccc tatcccagc cacccctga ttatcttcct
2701  tcagaaccca ggccttgcct ggactttgat tccccaccc attccacagg gcagctcaag
2761  gctcagcttg tgtgtaatta tgttcaatct caacaggagc tactgtggga gggtgggggc
2821  agggaagatg ccccgccca ggaaccttcc taccagagtc ccaagtttct ggggggttcc
2881  caggttagcc caagccgtgc taaagctcca gtgaacacat atggacctgg ctttggaccc
2941  aacttgccca atcacaagtc aggttcctat cccacccctt caccatgcca tgaaaattt
3001  gtagtggggg caaatagggc ttcacatagg gcagcagcac cacctcgact tctgccccca
3061  ttgcccactt gctatgggcc tctcaaagtg ggaggcacaa accccagctg tggtcatcct
3121  gaggtgggca ggctaggagg gggtcctgcc ttgtaccctc ctcccgaagg acaggtatgt
3181  aaccccctgg actctcttga tcttgacaac actcagctgg actttgtggc tattctggat
3241  gagccccagg ggctgagtcc tcctccttcc catgatcagc ggggcagctc tggacatacc
3301  ccacctccct ctgggccccc aacatggct gtgggcaaca tgagtgtctt actgagatcc
3361  ctacctgggg aaacagaatt cctcaactct agtgcctaaa gagtagggaa tctcatccat
3421  cacagatcgc atttcctaag gggtttctat ccttccagaa aaattggggg agctgcagtc
3481  ccatgcacaa gatgccccag ggatgggagg tatgggctgg gggctatgta tagtctgtat
3541  acgttttgag gagaaatttg ataatgacac tgtttcctga taataaagga actgcatcag
3601  aaaaaaaaaa aaaaaaaa
```

RefSeq Span/Primary identifier:

1-3482/X07384.1

3483-3483/AC022506.38

3484-3618/BC013000.2

An antisense oligonucleotide can have a length of at least about 5 nucleotides, at least about 7 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, and at least about 100 nucleotides. An antisense nucleic acid of the invention can be constructed using chemical synthesis and enzymatic ligation reactions using procedures known in the art. For example, an antisense nucleic acid can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation, namely, RNA transcribed from the inserted nucleic acid will be of an antisense orientation to a target nucleic acid of interest. The antisense nucleic acid molecules can be administered to a subject (e.g., systemically or locally by direct injection at a tissue site, or generated in situ such that they hybridize with or bind to cellular mRNA and/or genomic DNA encoding GLI1 to thereby inhibit its expression. Alternatively, antisense nucleic acid molecules can be modified to target particular cells and then administered systemically. For systemic administration, antisense molecules can be modified such that they specifically bind to receptors or antigens expressed on a selected cell surface, e.g., by linking the antisense nucleic acid molecules to peptides or antibodies that bind to particular cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In some embodiments, antisense oligonucleotide include α-anomeric nucleic acid molecules. An α-anomeric nucleic acid molecule forms specific double-stranded hybrids with complementary RNA in which, contrary to the usual beta-units, the strands run parallel to each other (Gaultier, C. et al. (1987) Nucleic Acids. Res. 15:6625-6641). The antisense nucleic acid molecule can also comprise a 2'-o-methylribonucleotide, or a chimeric RNA-DNA analogue (Inoue, H. et al. (1987) Nucleic Acids Res. 15:6131-6148; Inoue, H. et al. (1987a) FEBS Lett. 215:327-330).

Additional methods or compositions described herein to reduce the level of GLI1 protein, such as the GLI1-130 isoform, or a nucleic acid encoding GLI1, such as a nucleic acid encoding the GLI1-130 isoform, within a cell, such as endogenous GLI1, or an mRNA encoding GLI1, can utilize ribozymes. In general, a ribozyme is a catalytic RNA molecule that cleaves RNA in a sequence specific manner. Ribozymes that cleave themselves are known as cis-acting ribozymes, while ribozymes that cleave other RNA molecules are known as trans-acting ribozymes. The term "cis-acting ribozyme sequence" as used herein refers to the sequence of an RNA molecule that has the ability to cleave the RNA molecule containing the cis-acting ribozyme sequence. A cis-acting ribozyme sequence can contain any sequence provided it has the ability to cleave the RNA molecule containing the cis-acting ribozyme sequence. For example, a cis-acting ribozyme sequence can have a sequence from a hammerhead, axhead, or hairpin ribozyme. In addition, a cis-acting ribozyme sequence can have a sequence from a hammerhead, axhead, or hairpin ribozyme that is modified to have either slow cleavage activity or enhanced cleavage activity. For example, nucleotide substitutions can be made to modify cleavage activity (Doudna and Cech, Nature, 418:222-228 (2002)). Examples of ribozyme sequences that can be used with the methods and compositions described herein include those described in U.S. Pat. No. 6,271,359, and U.S. Pat. No. 5,824,519, incorporated by reference in their entireties. One example method for preparing a ribozyme is to synthesize chemically an oligodeoxyribonucleotide with a ribozyme catalytic domain (approximately 20 nucleotides) flanked by sequences that hybridize to the target mRNA. The oligodeoxyribonucleotide is amplified by using the substrate binding sequences as primers. The amplified product is cloned into a eukaryotic expression vector. A ribozyme can be expressed in eukaryotic cells from the appropriate DNA vector. If desired, the activity of the ribozyme may be augmented by its release from the primary transcript by a second ribozyme (Ohkawa et al., Nucleic Acids Symp. Ser., 27: 15-6 (1992); Taira et al., Nucleic Acids Res., 19: 5125-30 (1991); Ventura et al., Nucleic Acids Res., 21, 3249-55 (1993).

Methods of Treatment

Some embodiments relate to compositions and/or methods for treating or ameliorating disorders related to an increased activity of the Hedgehog pathway. In some embodiments, treating such disorders can include decreasing the level of a nucleic acid encoding GLI1, such as a nucleic acid encoding the GLI1-130 isoform, in the cell of a subject. In some embodiments, a composition can include an isolated nucleic acid having activity to reduce the levels of GLI1, such as a nucleic acid having activity to reduce the levels of the GLI1-130 isoform, in a cell of a subject. Examples of such nucleic acids are described herein and include a sequence encoding GLI1 or a fragment thereof, or a sequence encoding antisense GLI1 or a fragment thereof. Such nucleic acids can be useful for RNA interference or antisense technologies. A fragment of a polynucleotide sequence will be understood to include any nucleotide fragment having, for example, at least about 5 successive nucleotides, at least about 12 successive nucleotides, at least about 15 successive nucleotides, at least about 18 successive nucleotides, or at least about 20 successive nucleotides of the sequence from which it is derived. An upper limit for a fragment can include, for example, the total number of nucleotides in a full-length sequence encoding a particular polypeptide. Methods to select for nucleic sequences that have activity to reduce the level of a protein, such as GLI1 protein, including the GLI1-130 isoform, or the level of a nucleic acid encoding a polypeptide, such as an mRNA encoding GLI1, including an mRNA encoding the GLI1-130 isoform, in a cell or a subject, are also provided herein.

In some embodiments, a nucleic acid having activity to reduce GLI1 protein expression, such as the GLI1-130 isoform protein expression, or the level of a nucleic acid encoding GLI1, such as a nucleic acid encoding the GLI1-130 isoform, in a cell of a subject is further operably linked to a regulatory sequence. Regulatory sequences include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990), the disclosure of which is incorporated herein by reference in its entirety. Regulatory sequences include those which direct constitutive expression of a nucleotide sequence in many types of host cell and those which direct expression of the nucleotide sequence only in certain host cells (e.g., tissue-specific regulatory sequences). Tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, promoters as follows may be used to target gene expression in other tissues. Examples of more tissue specific promoters include in (a) pancreas: insulin, elastin, amylase, pdr-I, pdx-I, glucokinase; (b) liver: albumin PEPCK, HBV enhancer, a fetoprotein, apolipoprotein C, α-I antitrypsin, vitellogenin, NF-AB, Transthyretin; (c) skeletal muscle: myosin H chain, muscle creatine kinase, dystrophin, calpain p94, skeletal α-actin, fast troponin 1; (d) skin: keratin K6, keratin KI; (e) lung: CFTR, human cytokeratin IS (K 18), pulmonary surfactant proteins A, B and C, CC-10, Pi; (f) smooth muscle: sm22 α, SM-α-actin; (g) endothelium: endothelin-I, E-selectin, von Willebrand factor, TIE, KDR/flk-I; (h) melanocytes: tyrosinase; (i) adipose tissue: lipoprotein lipase, adipsin, acetyl-CoA carboxylase, glycerophosphate dehydrogenase, adipocyte P2; (j) blood: P-globin; and (k) mammary: MMTV, and whey acidic protein (WAP).

In certain embodiments, it may be desirable to activate transcription at specific times after administration of a vector comprising a nucleic acid having activity to reduce GLI1 protein level, such as the level of the GLI1-130 isoform, or the level of a nucleic acid encoding GLI1, such as the level of a nucleic acid encoding the GLI1-130 isoform, in a cell. This may be done with such promoters as those that may be regulated by hormone or cytokine. For example, in a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful with the nucleic acids described herein. Cytokine and inflammatory protein responsive promoters that could be used include K and T Kininogen, c-fos, TNF-α, C-reactive protein, haptoglobin, serum amyloid A2, C/EBP α, IL-1, IL-6, Complement C3, IL-8, α-1 acid glycoprotein, α-1 antitrypsin, lipoprotein lipase, angiotensinogen, fibrinogen, c-jun (inducible by phorbol esters, TNF a, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), α-2 macroglobulin and α-1 antichymotrypsin. It is envisioned that any of the promoters described herein, alone or in combination with another, may be useful depending on the action desired.

Nucleic acid constructs having activity to reduce GLI1 protein levels, such as the level of GLI1-130 isoform, or the level of a nucleic acid encoding GLI1, such as the level of a nucleic acid encoding the GLI1-130 isoform, in a cell and described herein can be introduced in vivo as naked DNA plasmids, for example, using transfection, electroporation (e.g., transcutaneous electroporation), microinjection, transduction, cell fusion, DEAE dextran, calcium phosphate precipitation, use of a gene gun, or use of a DNA vector transporter (Wu et al. J. Biol. Chem., 267:963-967, 1992; Wu and Wu J. Biol. Chem., 263:14621-14624, 1988; and Williams et al. Proc. Natl. Acad. Sci. USA 88:2726-2730, 1991). A needleless delivery device, such as a BIOJECTOR® needleless injection device can be utilized to introduce nucleic acid constructs in vivo. Receptor-mediated DNA delivery approaches can also be used (Curiel et al. Hum. Gene Ther., 3:147-154, 1992; and Wu and Wu, J. Biol. Chem., 262:4429-4432, 1987). Methods for formulating and administering naked DNA to mammalian muscle tissue are disclosed in U.S. Pat. Nos. 5,580,859 and 5,589,466, both of which are herein incorporated by reference in their entireties. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931), the disclosures of which are incorporated herein by reference in their entireties.

Alternatively, electroporation can be utilized conveniently to introduce nucleic acid constructs, having activity to reduce GLI1 protein levels, such as the level of the GLI1-130 isoform, or the level of a nucleic acid encoding GLI1, such as the level of a nucleic acid encoding the GLI1-130 isoform, in a cell and described herein, into cells. Electroporation is well known by those of ordinary skill in the art (see, for example: Lohr et al. Cancer Res. 61:3281-3284, 2001; Nakano et al. Hum Gene Ther. 12:1289-1297, 2001; Kim et al. Gene Ther. 10:1216-1224, 2003; Dean et al. Gene Ther. 10:1608-1615, 2003; and Young et al. Gene Ther 10:1465-1470, 2003). For example, in electroporation, a high concentration of vector DNA is added to a suspension of host cell (such as isolated autologous peripheral blood or bone marrow cells) and the mixture shocked with an electrical field. Transcutaneous electroporation can be utilized in animals and humans to introduce heterologous nucleic acids into cells of solid tissues (such as muscle) in vivo. Typically, the nucleic acid constructs are introduced into tissues in vivo by introducing a solution containing the DNA into a target tissue, for example, using a needle or trochar in conjunction with electrodes for delivering one or more electrical pulses. For example, a series of electrical pulses can be utilized to optimize transfection, for example, between 3 and ten pulses of 100 V and 50 msec. In some cases, multiple sessions or administrations are performed.

Another well known method that can be used to introduce nucleic acid constructs, having activity to reduce GLI1 protein levels, such as the GLI1-130 isoform protein levels, or the level of a nucleic acid encoding GLI1, such as the level of a nucleic acid encoding the GLI1-130 isoform, in a cell and described herein, into host cells is biolistic transformation. One method of biolistic transformation involves propelling inert or biologically active particles at cells, e.g., U.S. Pat. Nos. 4,945,050, 5,036,006; and 5,100,792, the disclosures of which are hereby incorporated by reference in their entireties. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the exogenous DNA. Alternatively, the target cell can be surrounded by the plasmid so that the plasmid is carried into the cell by the wake of the particle.

Alternatively, nucleic acid constructs, having activity to reduce GLI1 protein levels, such as the GLI1-130 isoform protein levels, or the level of a nucleic acid encoding GLI1, such as the level of a nucleic acid encoding the GLI1-130 isoform, in a cell and described herein, can be introduced in vivo by lipofection. Synthetic cationic lipids designed to limit the difficulties and dangers encountered with liposome mediated transfection can be used to prepare liposomes for in vivo transfection of a gene encoding a marker (Felgner et al. Proc. Natl. Acad. Sci. USA 84:7413-7417, 1987; Mackey, et al. Proc. Natl. Acad. Sci. USA 85:8027-8031, 1988; Ulmer et al. Science 259:1745-1748, 1993, the disclosures of which are incorporated herein by reference in their entireties). The use of cationic lipids can promote encapsulation of negatively charged nucleic acids, and also promote fusion with negatively charged cell membranes (Felgner and Ringold Science 337:387-388, 1989, the disclosure of which is incorporated by reference herein in its entirety). Particularly useful lipid compounds and compositions for transfer of nucleic acids are described in WO95/18863 and WO96/17823, and in U.S. Pat. No. 5,459,127, incorporated herein by reference in their entireties.

In some embodiments, the nucleic acid constructs, having activity to reduce GLI1 protein levels, such as the GLI1-130 isoform protein levels, or the level of a nucleic acid encoding GLI1, such as the level of a nucleic acid encoding the GLI1-130 isoform, in a cell and described herein, are viral vectors. Methods for constructing and using viral vectors are known in the art (See e.g., Miller and Rosman, BioTech., 7:980-990, 1992). Preferably, the viral vectors are replication defective, that is, they are unable to replicate autonomously in the target cell. In some cases, the replication defective virus retains the sequences of its genome that are necessary for encapsulating the viral particles. DNA viral vectors commonly include attenuated or defective DNA viruses, including, but not limited to, herpes simplex virus (HSV), papillomavirus, Epstein Barr virus (EBV), adenovirus, adeno-associated virus (AAV), Moloney leukemia virus (MLV) and human immunodeficiency virus (HIV) and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al. Mol. Cell. Neurosci., 2:320-330, 1991, the disclosure of which is incorporated herein by reference in its entirety), defective herpes virus vector lacking a glycoprotein L gene (See for example, Patent Publication RD 371005 A, incorporated herein by reference in its entirety), or other defective herpes virus vectors (See e.g., WO 94/21807; and WO 92/05263, incorporated herein by reference in their entireties); an attenuated adenovirus vector, such as the vector described by Stratford-Perricaudet et al. (J. Clin. Invest., 90:626-630 1992; La Salle et al., Science 259:988-990, 1993, the disclosure of which is incorporated herein by reference in its entirety); and a defective adeno-associated virus vector (Samulski et al., J. Virol., 61:3096-3101, 1987; Samulski et al., J. Virol., 63:3822-3828, 1989; and Lebkowski et al., Mol. Cell. Biol., 8:3988-3996, 1988, the disclosures of which are incorporated herein by reference in their entireties).

In some embodiments, the viral vectors, having activity to reduce GLI1 protein levels, such as the GLI1-130 isoform protein levels, or the level of a nucleic acid encoding GLI1, such as the level of a nucleic acid encoding the GLI1-130 isoform, in a cell and described herein, may be adenovirus vectors. Adenoviruses are eukaryotic DNA viruses that can be modified to efficiently deliver a nucleic acid of the disclosure to a variety of cell types. Various serotypes of adenovirus exist. Of these serotypes, preference is given, within the scope of the present disclosure, to type 2, type 5 or type 26 human adenoviruses (Ad 2 or Ad 5), or adenoviruses of animal origin (See e.g., WO94/26914 and WO2006/020071, the disclosures of which are incorporated herein by reference in their entireties). Those adenoviruses of animal origin that can be used within the scope of the present disclosure include adenoviruses of canine, bovine, murine (e.g., Mav1, Beard et al. Virol., 75-81, 1990, the disclosure of which is incorporated herein by reference in its entirety), ovine, porcine, avian, and simian (e.g., SAV) origin. In some embodiments, the adenovirus of animal origin is a canine adenovirus, such as a CAV2 adenovirus (e.g. Manhattan or A26/61 strain (ATCC VR-800)).

Some embodiments include pharmaceutical compositions comprising a nucleic acid which reduces GLI1 protein levels, such as the GLI1-130 isoform protein levels, or the level of a nucleic acid encoding GLI1, such as the level of a nucleic acid encoding the GLI1-130 isoform, and a suitable carrier. While any suitable carrier known to those of ordinary skill in the art may be employed in the pharmaceutical compositions described herein, the type of carrier will typically vary depending on the mode of administration. Compositions described herein may be formulated for any appropriate manner of administration, including for example, topical, oral, nasal, mucosal, intravenous, intracranial, intraperitoneal, subcutaneous and intramuscular administration. Carriers for use within such pharmaceutical compositions are biocompatible, and may also be biodegradable. In certain embodiments, the formulation preferably provides a relatively constant level of active component release.

The pharmaceutical compositions described herein can further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions described herein may be formulated as a lyophilizate.

Pharmaceutical compositions described herein can be administered to a subject, such as a mammal, such as a human. Pharmaceutical compositions can be administered at a therapeutically effective amount. A "therapeutically effective amount" is a quantity of a chemical composition (such as a nucleic acid construct, vector, or polypeptide) used to achieve a desired effect in a subject being treated. Pharmaceutical compositions may be administered either prior to or following surgical removal of primary tumors and/or treatment such as administration of radiotherapy or conventional chemotherapeutic drugs. Pharmaceutical compositions may be administered in combination with at least one additional therapeutic compound, such as a chemotherapeutic compound.

Indications

Methods and compositions described herein can be used to treat disorders that relate to increased activity of the Hedgehog pathway. Examples of such disorders include cancers, for example, breast cancer, melanoma, prostate cancer, colorectal cancer, head and neck cancer, lung cancer, colon cancer, oesophageal cancer, gastric cancer, testicular cancer cell, and ovarian cancer. More examples include any cancer that may be treated with the therapeutic compounds described herein.

Methods to Increase Sensitivity of Cells to Therapeutic Compounds

It has been discovered that reducing GLI1 protein levels or the level of a nucleic acid encoding GLI1 in a cell increases the sensitivity of the cell to particular therapeutic compounds. Accordingly, some embodiments relate to methods for increasing the sensitivity of a cell or a subject to a therapeutic compound. As will be understood, increasing the sensitivity of a cell or a subject to a therapeutic compound can decrease the therapeutically effective amount of a therapeutic compound needed to treat the cell or subject.

In some embodiments, a cell or a subject may be treated with an agent that reduces GLI1 protein levels, such as the GLI1-130 isoform protein levels, or the level of a nucleic acid encoding GLI1, such as the level of a nucleic acid encoding the GLI1-130 isoform. Reducing GLI1 protein levels, such as the GLI1-130 isoform protein levels, or the level of a nucleic acid encoding GLI1, such as the level of a nucleic acid encoding the GLI1-130 isoform, in certain cells can increase the sensitivity of those cells to particular therapeutic compounds. Such cells can include cells in which GLI1 expression is increased compared to normal cells, for example, in certain neoplastic cells. More examples include cells in which the activity of DNA repair mechanisms is increased compared to normal cells. Such DNA repair mechanisms can include nucleotide excision repair, and base excision repair.

Therapeutic compounds for which the therapeutic dosage may be reduced can include chemotherapeutic compounds. Examples of chemotherapeutic compounds include platinum-based compounds such as cisplatin, carboplatin, nedaplatin, oxaliplatin, satraplatin, and triplatin tetranitrate, nitrogen mustards such as cyclophosphamide, mechlorethamine, uramustine, melphalan, chlorambucil, and ifosfamide, nitrosoureas such as carmustine, lomustine, and streptozocin, alkyl sulfonates such as busulfan, thiotepa, procarbazine, and altretamine. In more embodiments, chemotherapeutic compounds can include compounds in which an increased cellular resistance to the chemotherapeutic compound correlates to an increased expression of ERRC1, XPD, XRCC1, or c-jun such as c-jun (Ser 63). More embodiments, include therapeutic compounds for which increased activity of the base excision repair pathway results in increased cellular resistance to the therapeutic compounds. More embodiments, include therapeutic compounds for which increased activity of the nucleotide excision repair pathway results in increased cellular resistance to the therapeutic compounds.

Methods for Identifying Agents

More embodiments include methods of identifying compounds and agents useful for the methods and compositions described herein. Some such methods can be useful to evaluate test compounds useful to treat disorders related to increased activity of the Hedgehog pathway. More methods can be useful to evaluate test compounds useful to increase the sensitivity of certain cells to particular therapeutic compounds.

In some embodiments, a test compound is evaluated by contacting the cell with the test compound. A test compound that reduces the level of GLI1 protein, such as the level of the GLI1-130 isoform, or the level of a nucleic acid encoding GLI1, such as the level of a nucleic acid encoding the GLI1-130 isoform, may be useful to decrease the activity of the Hedgehog pathway. Such a test compound can be useful to treat or ameliorate disorders related to increased activity of the Hedgehog pathway. More methods include comparing the level of a nucleic acid encoding GLI1, such as the level of a nucleic acid encoding the GLI1-130 isoform, or the level of GLI1 protein, such as the level of the GLI1-130 isoform, in a target cell to the level of a nucleic acid encoding GLI1, such as the level of a nucleic acid encoding the GLI1-130 isoform, or the level of GLI1 protein, such as the level of GLI1-130 isoform, in a target cell contacted with the test compound.

More methods can also include selecting a test compound that, in addition to reducing the level of the GLI1 protein, such as the level of the GLI1-130 isoform or the level of a nucleic acid encoding GLI1, such as the level of a nucleic acid encoding the GLI1-130 isoform, also reduces the level of c-jun (Ser 63) protein in a target cell, where c-jun (Ser 63) is a c-jun protein phosphorylated at the Serine 63 residue. More methods can also include selecting a test compound that also inhibits or reduces the upregulation of the level of c-jun (Ser 63) protein in a target cell. Upregulation of c-jun (Ser 63) can be in response to a chemical compounds that upregulates c-jun (Ser 63).

More methods can also include selecting a test compound that, in addition to reducing the level of the GLI1 protein, such as the level of the GLI1-130 isoform or the level of a nucleic acid encoding GLI1, such as the level of a nucleic acid encoding the GLI1-130 isoform, also reduces the level of ERCC1 protein or a nucleic acid encoding ERCC1 in a target cell. More methods can also include selecting a test compound that also inhibits or reduces upregulation of the level of ERCC1 protein or a nucleic acid encoding ERCC1 in a target cell. The upregulation of ERCC1 protein or a nucleic acid encoding ERCC1 in a target cell can be in response to a chemical compound that upregulates ERCC1.

More methods can also include selecting a test compound that, in addition to reducing the level of the GLI1 protein, such as the level of the GLI1-130 isoform or the level of a nucleic acid encoding GLI1, such as the level of a nucleic acid encoding the GLI1-130 isoform, also reduces the level of XPD protein or a nucleic acid encoding XPD in a target cell. More methods can also include selecting a test compound that also inhibits or reduces upregulation of the level of XPD protein or a nucleic acid encoding XPD in a target cell. The upregulation of XPD protein or a nucleic acid encoding XPD in a target cell can be in response to a chemical compound that upregulates XPD.

More methods can also include selecting a test compound that, in addition to reducing the level of the GLI1 protein, such as the level of the GLI1-130 isoform or the level of a nucleic acid encoding GLI1, such as the level of a nucleic acid encoding the GLI1-130 isoform, also reduces the level of XRCC1 protein or a nucleic acid encoding XRCC1 in a target cell. More methods can also include selecting a test compound that also inhibits or reduces upregulation of the level of XRCC1 protein or a nucleic acid encoding XRCC1 in a target cell. The upregulation of XRCC1 protein or a nucleic acid encoding XRCC1 in a target cell can be in response to a chemical compound that upregulates XRCC1.

More methods can also include selecting a test compound that while reducing the level of the GLI1 protein, such as the level of the GLI1-130 isoform or the level of a nucleic acid encoding GLI1, such as the level of a nucleic acid encoding the GLI1-130 isoform, also does not reduce the level of GLI2 protein or a nucleic acid encoding GLI2 in a cell. More methods can also include selecting a test compound that does not substantially reduce the level of GLI2 protein or a nucleic acid encoding GLI2 in a cell. As used herein the term "not substantially reduce" and grammatical equivalents can refer to a reduction of no more than about 1%, no more than about 2%, no more than about 3%, no more than about 4%, no more than about 5%, no more than about 6%, no more than about 7%, no more than about 8%, no more than about 9%, and no more than about 10%.

Test compounds that do not reduce or substantially reduce the level of GLI2 protein or a nucleic acid encoding GLI2 in a cell, and also have activity that reduces the level of GLI1 protein, such as the GLI1-130 isoform, or the level of a nucleic acid encoding GLI1, such as a nucleic acid encoding the GLI1-130 isoform, are particularly advantageous, as these compounds may selectively inhibit a tumor cell's, for example, a neoplastic cell's, ability to up-regulate those processes/pathways that promote tumor cell survival.

Examples of chemical compounds that can upregulate target cell levels of c-jun (Ser 63) protein, ERCC1 protein, XPD protein, or XRCC1 protein are well known and include chemotherapeutic agents, such as cisplatin. Examples of test compounds can include chemical compounds, nucleic acids, for example, nucleic acids encoding GLI1 or fragments thereof, or antisense GLI1 or fragments thereof.

Methods for Assessing the Effectiveness of a Compound or Agent

More methods include assessing the effectiveness of a compound or agent in treating a disorder. In some such methods, treatment can include methods and/or compositions that reduce the level of GLI1 protein, such as the level of the GLI1-130 isoform, or the level of a nucleic acid encoding GLI1, such as the level of a nucleic acid encoding the GLI1-130 isoform, in a cell of a subject. The effectiveness of the compound or agent can be evaluated by measuring the level of OPN protein or the level of of a nucleic acid encoding OPN in a sample from the subject. The measuring can be carried out in vivo or ex vivo. More methods can include comparing the level of a nucleic acid encoding OPN or the level of OPN protein in the sample to the level of a nucleic acid encoding OPN or the level of OPN protein in a subject who does not have the disorder, and/or a subject who has not been contacted with the compound or agent. In some embodiments, a decrease in the level of a nucleic acid encoding OPN or the level of OPN protein is indicative of a favorable prognosis.

More methods include methods for assessing the potential effectiveness of a nucleic acid as a therapeutic agent. Some such methods include determining whether the nucleic acid reduces the level of a nucleic acid encoding GLI1, such as the level of a nucleic acid encoding the GLI1-130 isoform, or the level of GLI1 protein, such as the level of the GLI1-130 isoform, in a cell. In such methods, the nucleic acid can be identified as having potential effectiveness as a therapeutic agent if the nucleic acid reduces the level of the nucleic acid encoding GLI1, such as the level of a nucleic acid encoding the GLI1-130 isoform, or the level of the GLI1 protein, such as the level of the GLI1-130 isoform, in said cell. In further embodiments, methods can also include determining whether a nucleic acid has no substantial effect on the level of a nucleic acid encoding GLI2 or the level of GLI2 protein in a cell. In some such embodiments, the nucleic acid is identified as having potential effectiveness a therapeutic agent if the nucleic acid has no substantial effect on the level of the nucleic acid encoding GLI2 or the level of the GLI2 protein in said cell.

More embodiments include nucleic acids identified as having potential effectiveness as a therapeutic agent by the methods described herein.

EXAMPLES

Example 1

Figure 2:
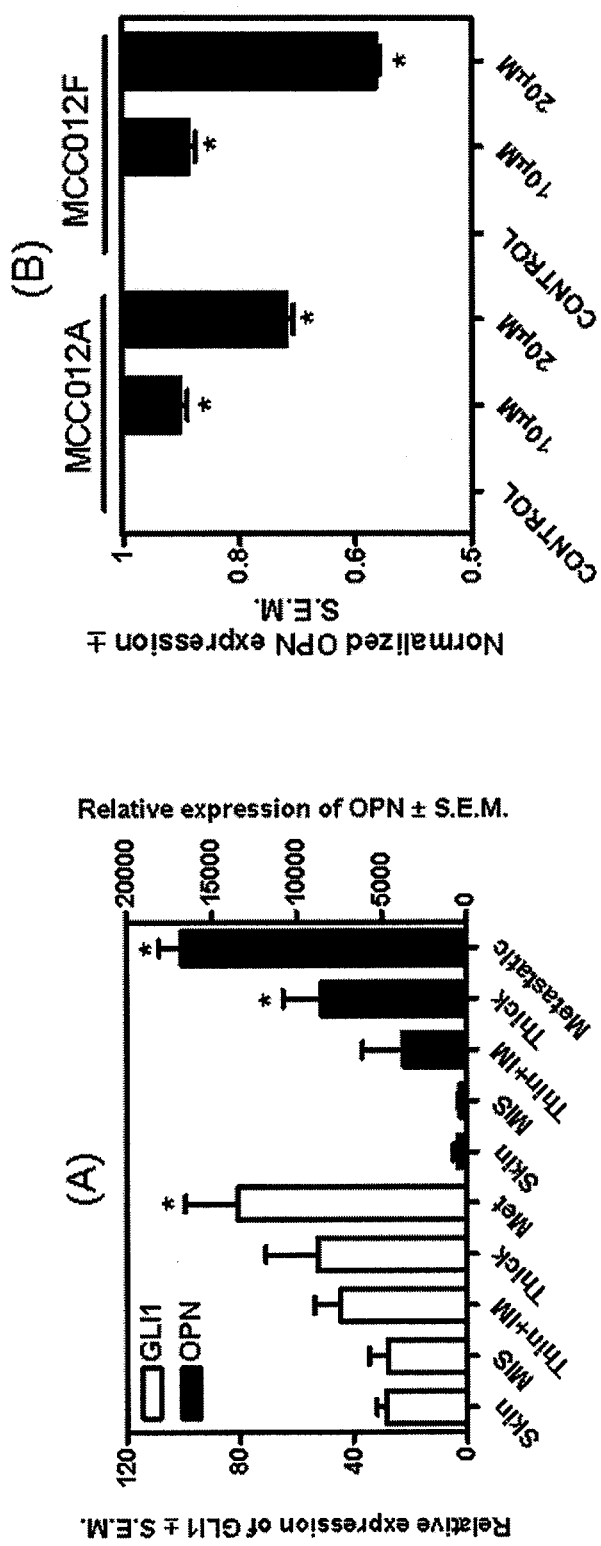
FIG. 2 (panel A) shows a graph of GLN1 and OPN expression in various primary cutaneous cancer and metastatic melanoma. Gene microarray analysis (utilizing a Human Genome U133 Plus 2.0 array from Affymetrix, Inc.) was used to compare 40 metastatic melanoma samples, composed of 22 bulky, macroscopic (replaced) lymph node metastases, 16 subcutaneous and 2 distant metastases (adrenal and brain), to 16 primary cutaneous melanoma specimens (Riker, A. I., et al. (2008) BMC Med. Genomics 1:13). The expression levels of GLI1 and OPN increase progressively beyond the stage of MIS through the stage of metastatic melanoma. Thin, thin melanomas (<1.5 mm in Breslow thickness); IM, intermediate thickness (between 1.5 and 4.0 mm in Breslow thickness); thick, melanomas (that are >4.0 mm in Breslow thickness). The left y-axis denotes the scale for GLI1 expression and the right y-axis corresponds to OPN levels. As compared with MIS, the increase in GLI1 in the metastatic melanoma samples is statistically significant ($p=0.020$). The increase in OPN expression in the thick and metastatic melanoma specimens is statistically significant compared with the corresponding OPN levels in the MIS specimens ($p=0.018$ and $0.0018$, respectively).
Figure 2:
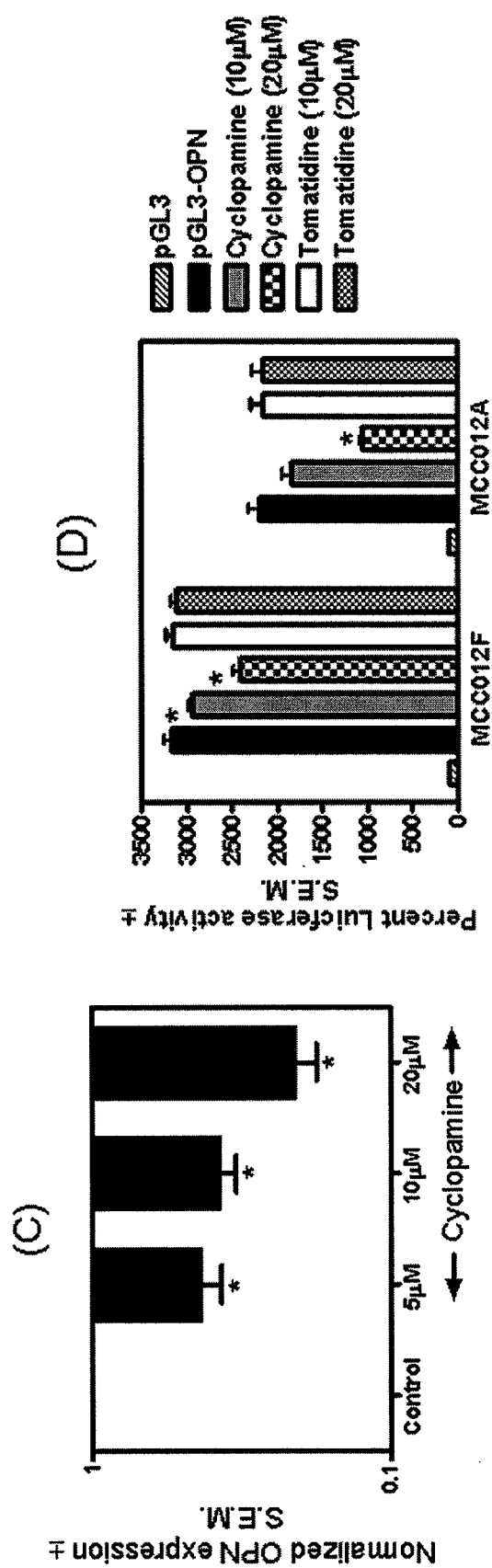
Figure 2:
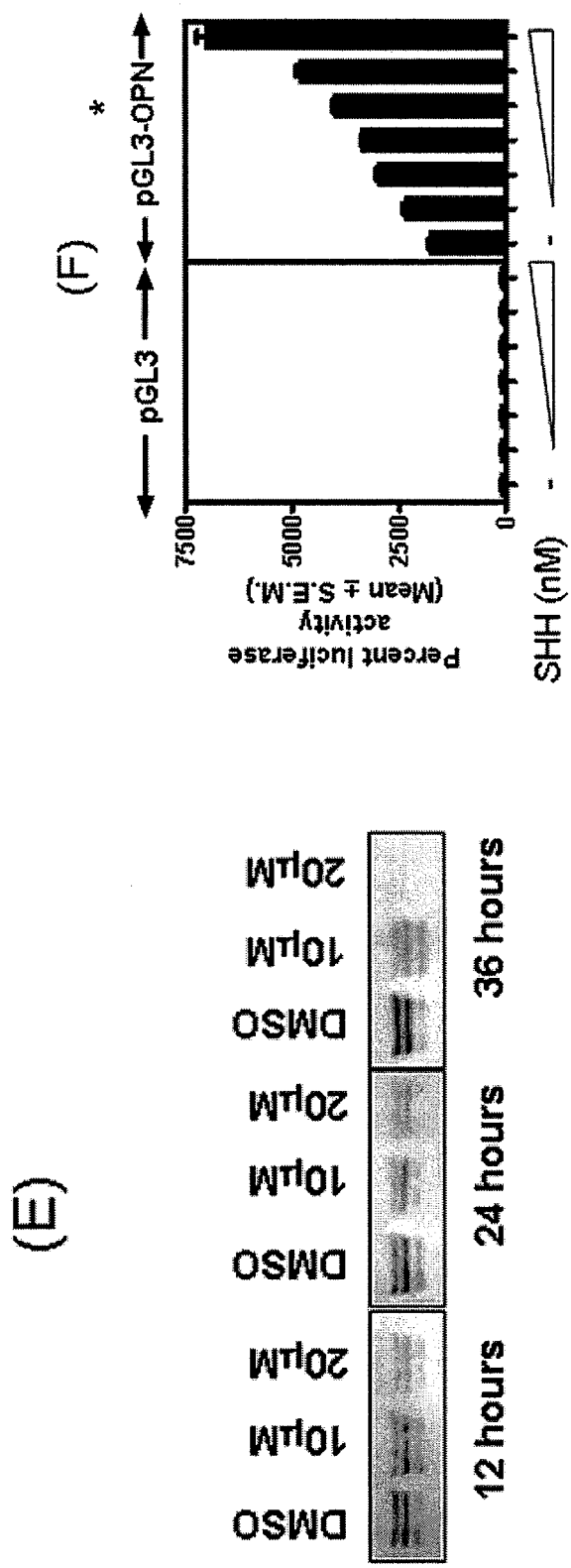
Figure 2:
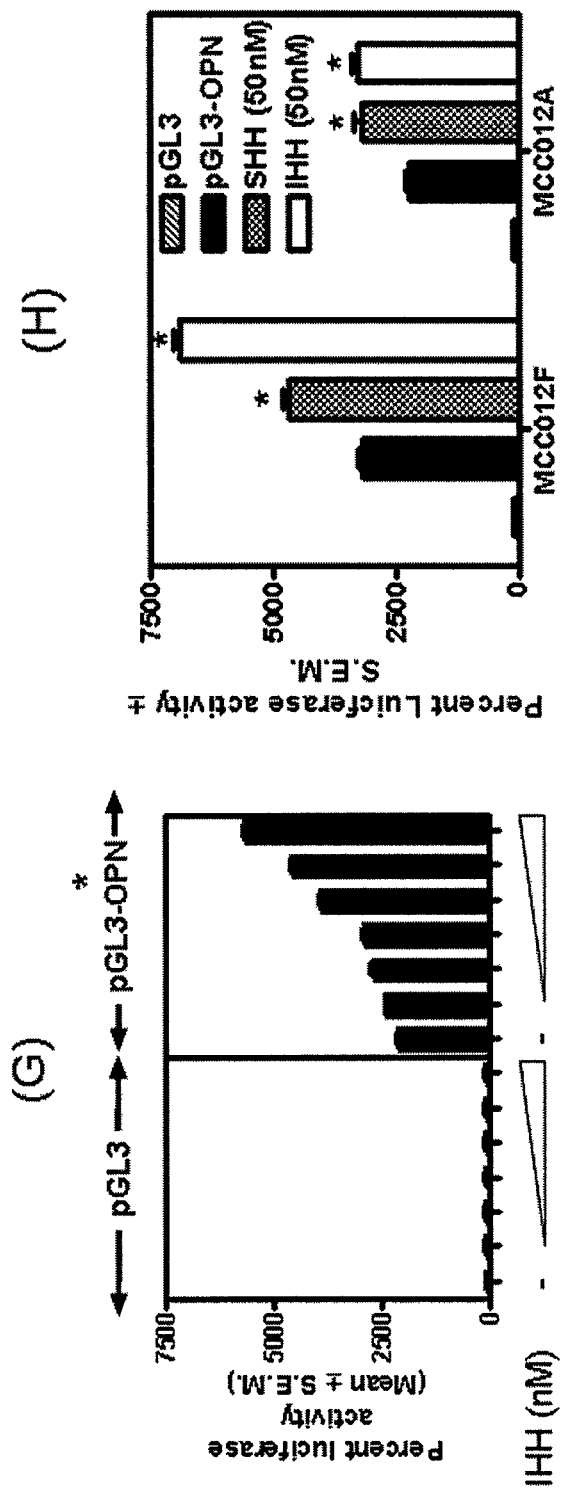
Figure 2:
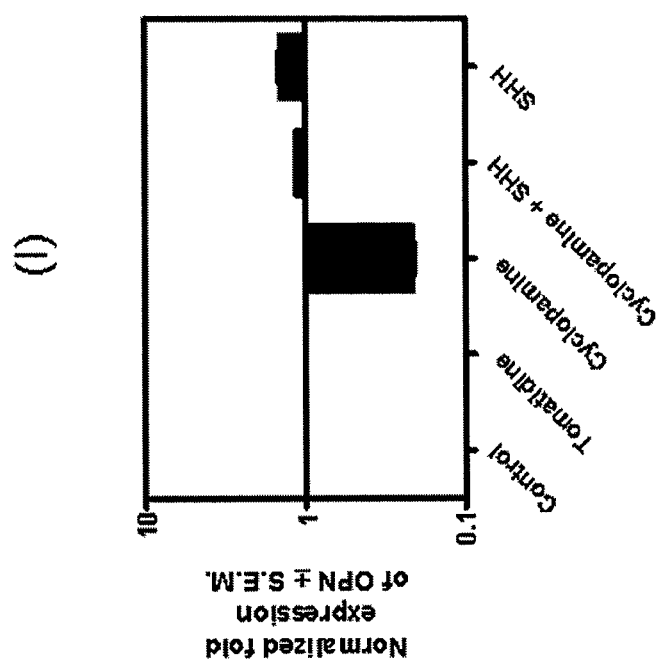

Expression Levels of GLI1 and OPN Increase with the Development and Progression of Melanoma Activation of the Hedgehog pathway results in nuclear translocation of GLI1 transcription factors and up-regulation of target genes. Microarray analysis of genes that were differentially regulated by the Hedgehog pathway revealed that OPN expression was up-regulated. Clinically derived primary cutaneous cancers and melanoma specimens were profiled by gene expression analysis and it was shown that the expression of OPN was increased 67.3-fold in metastatic melanoma samples when compared with primary cancer samples. This data set was queried for the changes in the expression of GLI1 and OPN with disease progression. As seen in FIG. 2 (panel A), the expression of GLI1 and OPN increase with the progression of the disease to metastatic melanoma. Specifically, the expression of GLI1 notably increases in thin (up to 1.5 mm in Brelsow thickness) and intermediate (up to 4.0 mm in Brelsow thickness) melanoma specimens and continues to increase as the condition progresses to thick melanoma (>4 mm in Breslow thickness) and beyond into metastatic melanoma. The increase in GLI1 expression in the metastatic melanoma specimens is significantly higher (p<0.05) as compared with the melanoma in situ (MIS) specimens. In parallel, the expression of OPN also increases as the MIS progresses to thin/intermediate melanoma and beyond into thick and metastatic melanoma. The levels of OPN expression in the thick and metastatic melanoma specimens are significantly greater compared with the corresponding OPN levels in the MIS specimens (p=0.018 and 0.0018, respectively). The relative expression of GLI1 in metastatic melanoma averages (±S.E.) 80.6±18.5 units, whereas the relative expression of OPN peaks at 16,760±1324 units. This finding underscores the fact that small changes in expression of the transcription factor, GLI1, correlates with changes of a large magnitude in the levels of OPN.

Example 2

OPN is Transcriptionally Up-Regulated by the Hedgehog Pathway

Figure 3:
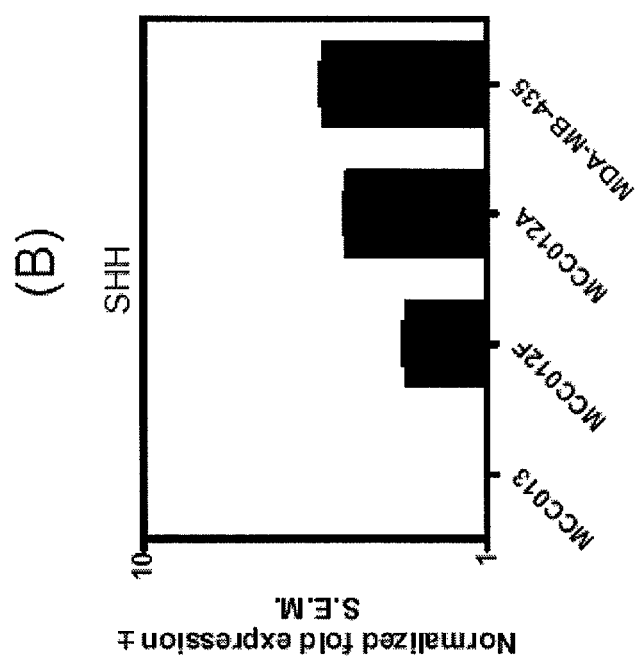
FIG. 3 (panel A) shows a Western blot of cell lysates from the metastatic melanoma cell lines, MCC12A, MCC12F and MDA-MB-435. β-actin served as a loading control. Each cell line expresses the Hedgehog receptor (PTCH) and the Hedgehog ligand (SHH).
Figure 3:
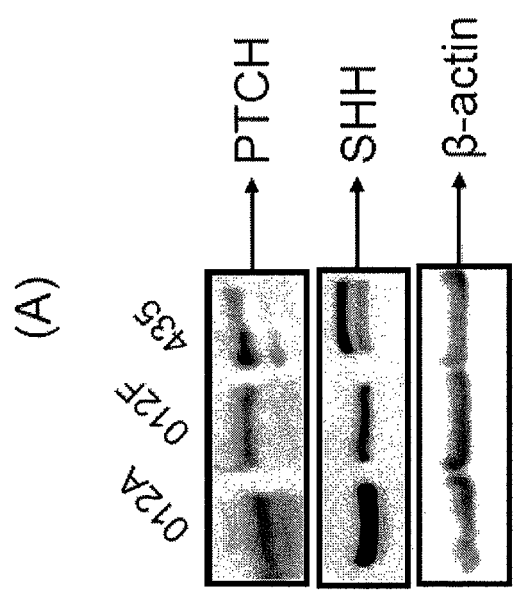
Figure 3:
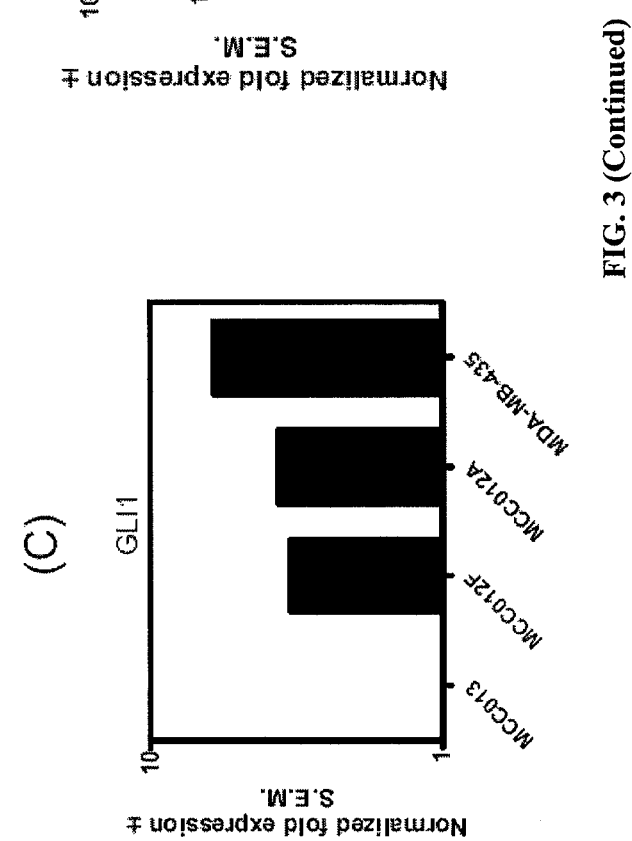

To determine whether OPN expression is regulated by Hedgehog pathway signaling three metastatic melanoma-derived cell lines, MCC012A, MCC012F, and MDAMB-435 were studied. To establish autocrine Hedgehog signaling, the cell lines should express the Hedgehog pathway products, including the receptor PTCH, the ligand SHH, and the transcription factor GLI1. As seen in FIG. 3, all three melanoma cell lines express Hedgehog pathway members indicating that the cell lines are capable of autocrine Hedgehog signaling. The expression of these Hedgehog members is significantly greater (p<0.0001) in metastatic melanoma cell lines compared with that in the primary melanoma-derived cell line, MCC013. All the three metastatic melanoma cell lines also express significantly higher levels of OPN (p<0.0001) compared with MCC013 (FIG. 3D).

The effect of the Hedgehog inhibitor, cyclopamine, was tested on OPN levels (19). As seen in FIG. 2 (panel B) and FIG. 2 (panel C), cyclopamine significantly (p<0.05) decreases the levels of OPN mRNA in a dose-dependent manner in two metastatic melanoma-derived cell lines, MCC012A and MCC012F, and in MDA-MB-435 cells (p<0.0001), suggesting that blocking the Hedgehog pathway interferes with the transcription of OPN. Cyclopamine treatment also decreases the activity of the OPN promoter in a dose-dependent manner (FIG. 2, panel D). In contrast, tomatidine, the structural analog of cyclopamine, had no effect on the promoter activity of cyclopamine.

The decreases in the levels of OPN mRNA are also reflected in the decreased levels of OPN protein in the secretome of cyclopamine-treated cells (FIG. 2, panel E). This effect was more pronounced at time intervals of 24 and 36 h post-treatment, when a lower concentration of cyclopamine was also able to inhibit OPN. In contrast to the inhibitory effect of cyclopamine, treatment of MDA-MB-435 cells with SHH and IHH ligands (FIG. 2, panel F and FIG. 2, panel G) significantly (p<0.0001) up-regulated the promoter activity of OPN in a dose-dependent manner. Similarly, SHH and IHH caused a significant up-regulation in promoter activity of OPN in MCC012A (p<0.01) and MCC012F (p<0.005) (FIG. 2, panel H). SHH was also able to reverse and rescue the inhibitory effects of cyclopamine on the levels of the OPN transcript thereby re-instating Hedgehog signaling (FIG. 2, panel I).

Example 3

GLI1 Up-Regulates OPN

Signaling via the Hedgehog pathway culminates in the transcription of target genes by the GLI transcription factors. The role of transcription factor GLI1 in mediating the effects of the Hedgehog pathway on OPN was tested. The promoter region of human OPN was scanned (up to 1 kb upstream of transcription start site) for GLI1-binding sites using TFSEARCH and identified a putative GLI1 binding site at position −243 to −259 (5'-TGCTGAATGCCCATCCC-3' (SEQ ID NO:12)).

Figure 4:
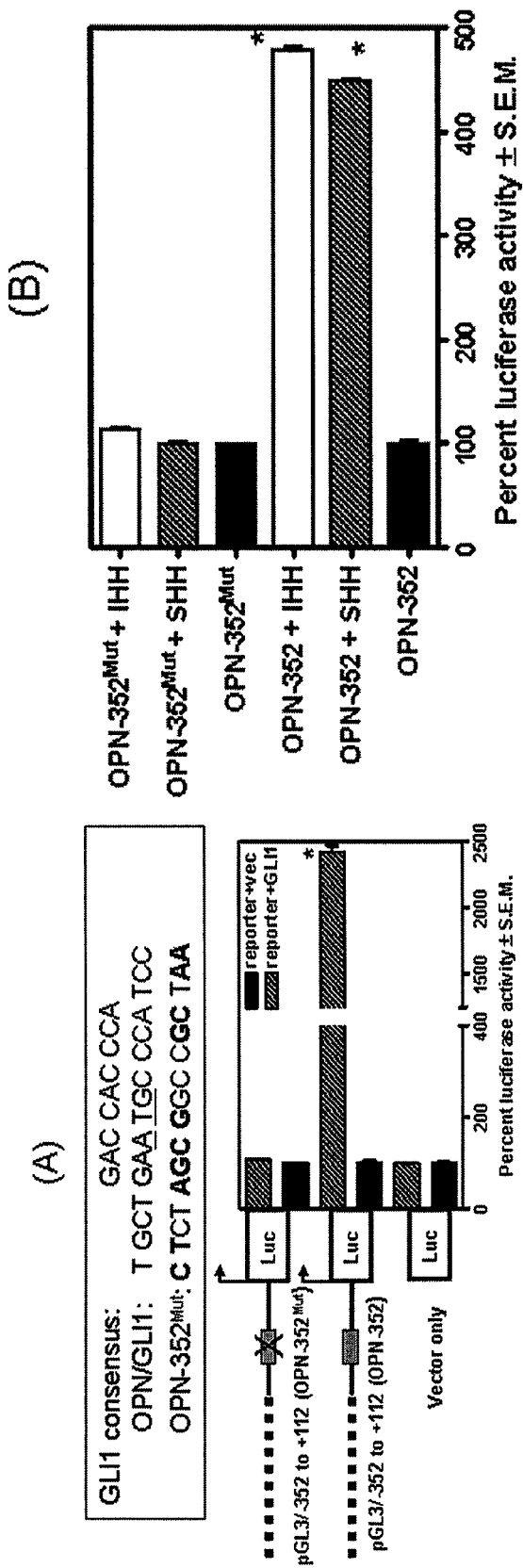
FIG. 4 (panel A), upper panel) shows the putative GLI1-binding site in the OPN promoter.
Figure 4:
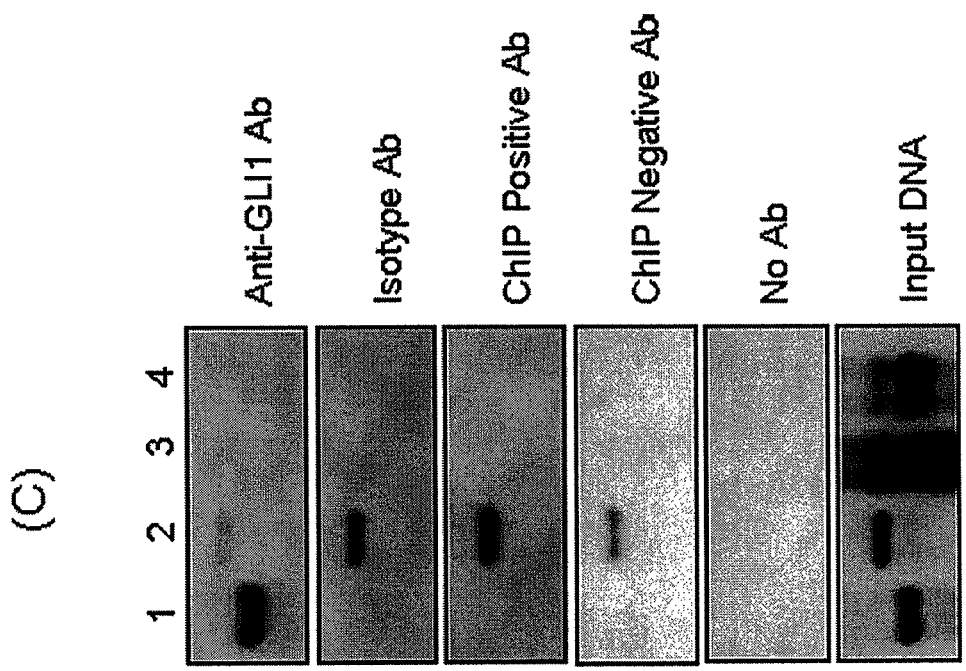

As shown in FIG. 4 (panel A), co-transfection of a GLI1 expressing construct with an OPN promoter construct (OPN-352; encompassing the −352 to −112 region) brought about a significant (p<0.0001) increase in the activity of the OPN promoter. The putative GLI1-binding site in the OPN promoter differs from the consensus GLI1-binding site by 3 nucleotides as shown in FIG. 4 (panel A). This site was abolished from the OPN-352 promoter and replaced it with a NotI site, keeping the distance from the transcription site unchanged; no other transcription factor-binding site was generated by this replacement. This mutant OPN construct, OPN-352$^{Mut}$, was unable to respond to GLI1, indicating that this site on the OPN promoter was critical to its ability to be activated by transcription factor GLI1 (FIG. 4, panel A). Additionally, OPN-2$^{Mut}$ is refractory to the effects of SHH and IHH. As seen in FIG. 4 (panel B), whereas OPN-352 (bearing the GLI1-recognition site) shows a notable increase ((p<0.0001) in promoter activity in the presence of stimulation by SHH and IHH, OPN-352$^{Mut}$ is immune to the potentially activating effects of SHH and IHH.

To determine whether GLI1 physically associates with the OPN promoter, cross-linked chromatin from MDA-MB-435 cells was immunoprecipitated with an anti-GLI1 antibody and amplified the region of the OPN promoter that bears the GLI1 recognition sequence (FIG. 4, panel C), implying that GLI1 associates with the OPN promoter. Specificity of the ChIP assay was controlled by performing PCR of the chromatin immunoprecipitated using primers located approximately 1 kb upstream of the GLI1 recognition sequence (16) in the OPN promoter. The absence of a product using these primers confirms specificity of the pulldown. Thus, the data shows that OPN is transcriptionally activated by GLI1.

Example 4

Knockdown of Endogenous GLI1 Blunts the Malignant Behavior of Tumor Cells

To evaluate the functional effects of active Hedgehog signaling stable cell lines that were knocked down for GLI1 expression by RNA interference were generated. The efficacy of three shRNA constructs for silencing GLI1 expression was assessed. TABLE 2 shows details of the region in GLI1 transcript that was targeted by the shRNAs used to assess efficacy of silencing GLI1

TABLE 2

| shRNA notations | Oligo-nucleotide designation | SEQ ID NO | Targeted GLI1 mRNA sequence | Position from start codon per Genbank sequence X07384 |
|---|---|---|---|---|
| GLI1 shRNA-1 | X07384_314 | SEQ ID NO: 01 | CCTCGTAGC TTTCATCAA C | 314 |
| GLI1 shRNA-2 | X07384_325 | SEQ ID NO: 02 | TCATCAACT CGCGATGCA C | 325 |
| GLI1 shRNA-3 | X07384_1108 | SEQ ID NO: 03 | CCAAACGCT ATACAGATC C | 1108 |

Figure 5:
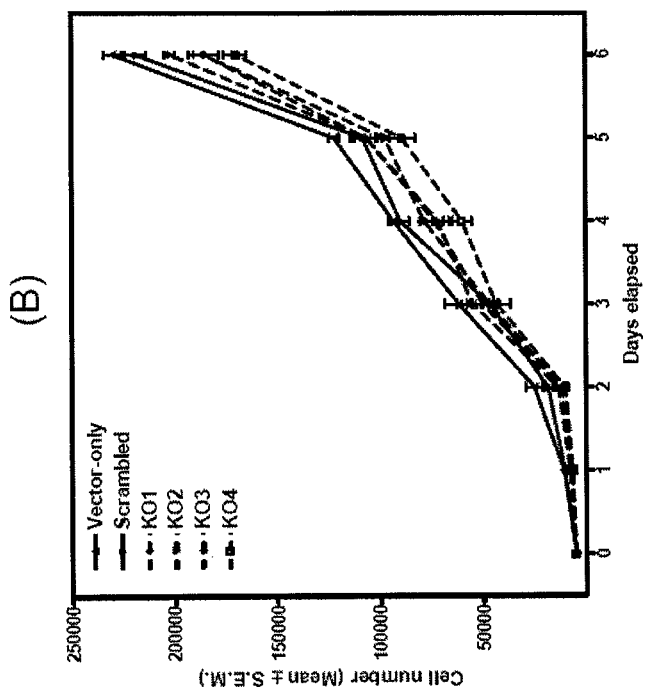
FIG. 5 (panel A) shows a Western blot of MDA-MB-435 cells transfected with shRNA constructs predicted to target GLI1 (cloned into pSUPERIOR). Cells were assessed for OPN and GLI1 by western blotting. shRNA-1 and -2 are effective at silencing GLI1. Concomitantly, cells transfected with shRNA 1 & 2 show decreased OPN expression.
Figure 5:
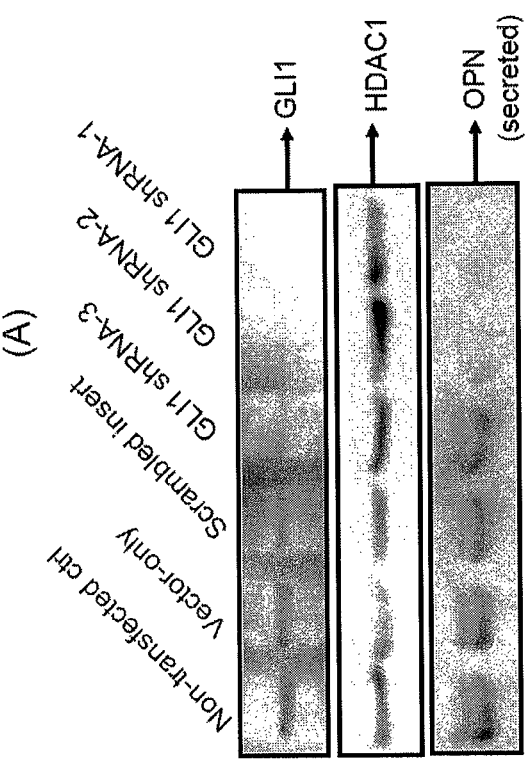
Figure 5:
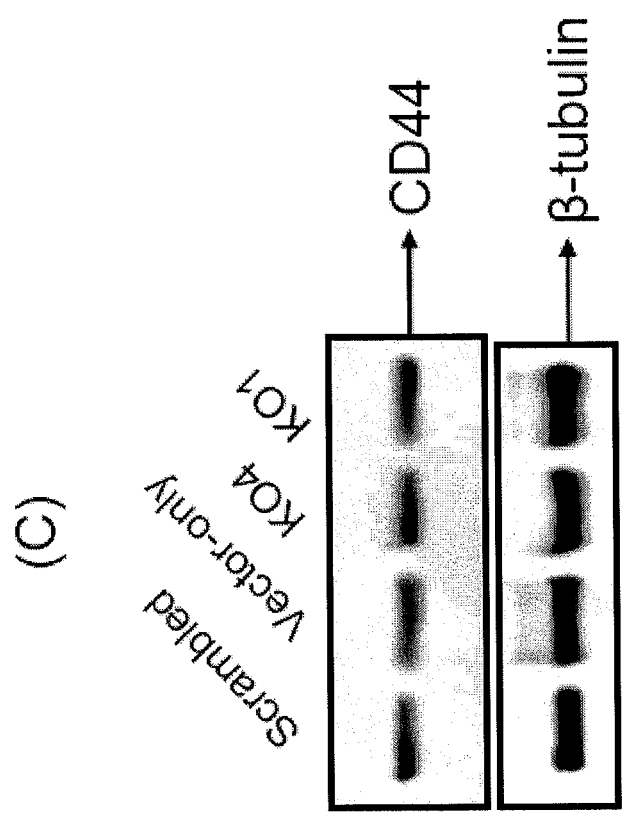
Figure 6:
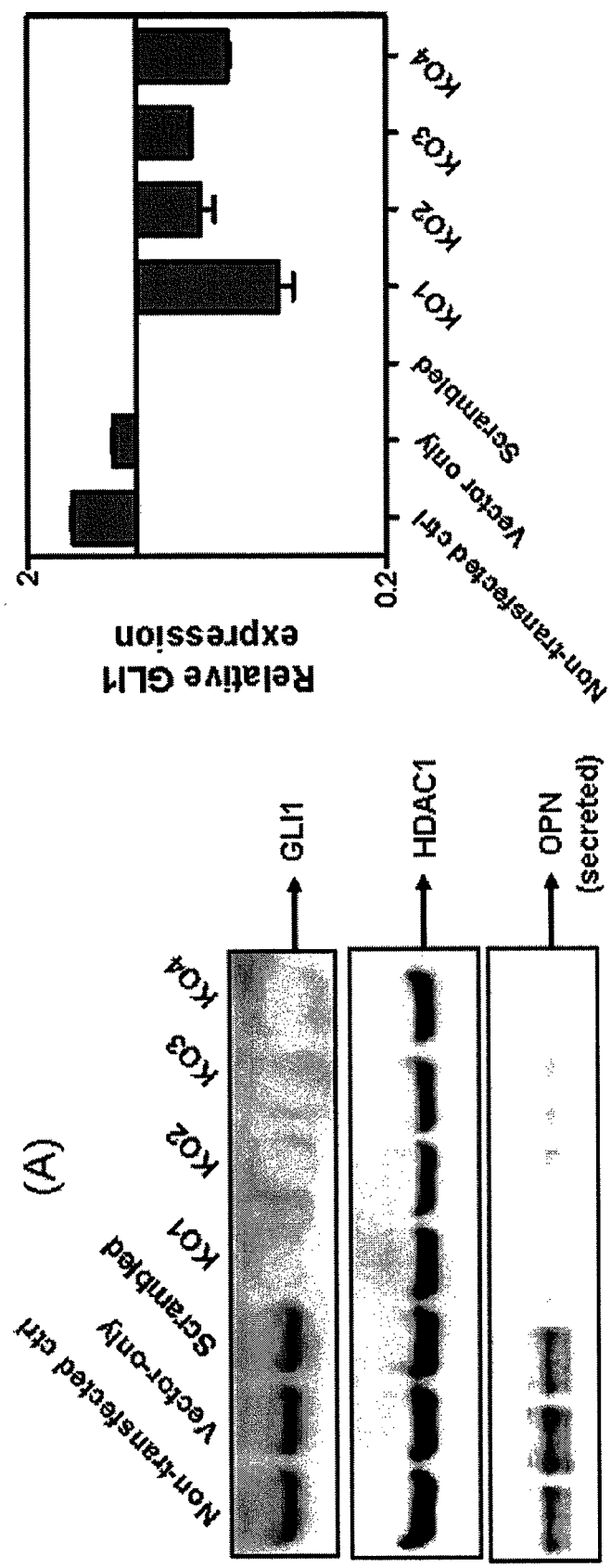
FIG. 6 (panel A) shows a Western blot of MDAMB-435 cells stably transfected with shRNA to GLI1. Clones KO1 to KO4 were stably silenced for GLI1 and show notably reduced OPN expression.
Figure 6:
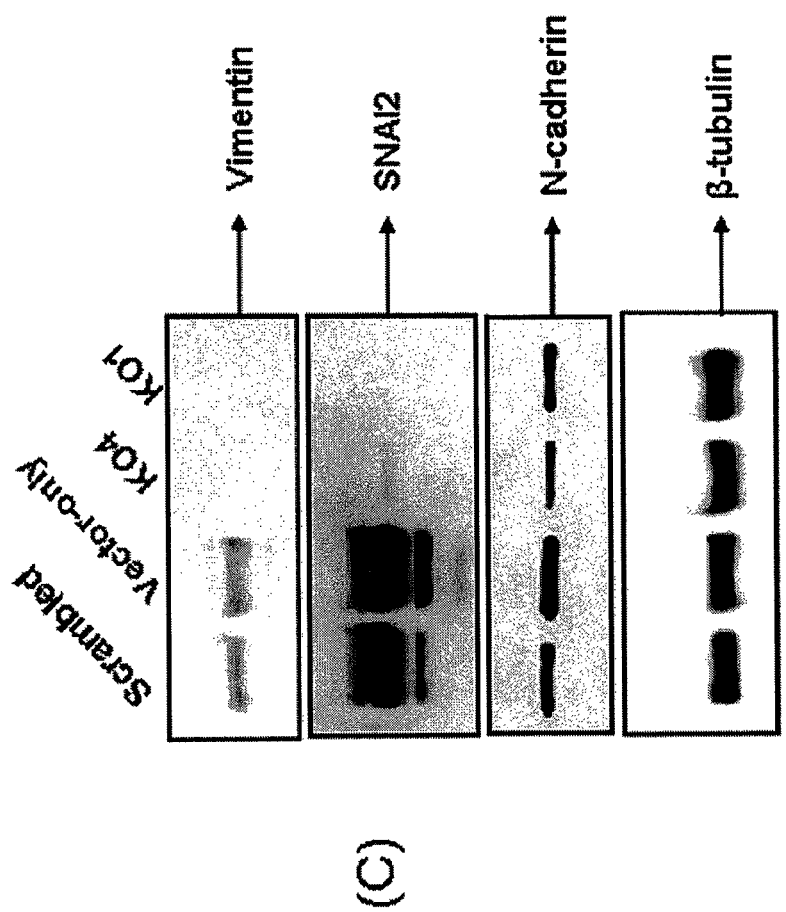

The two shRNA constructs that demonstrated more effective GLI1 silencing, shRNA-1 and shRNA-2, overlap in the region they target. Using vector construct GLI1 shRNA-1 (FIG. 5, panel A), four clones stably silenced for GLI1 expression were generated. All four clones also showed significantly reduced OPN expression. Of the four stable clones, clones KO1 and KO4 expressed the least amount of GLI1 followed by clones KO2 and KO3 (FIG. 6, panel A and FIG. 6, panel B). KO1 and KO4 were used for further detailed studies. TABLE 3 shows candidate sequences based on human mRNA for GLI1 protein that may be used to generate more shRNA constructs.

TABLE 3

| SEQ ID NO | Targeted GLI1 mRNA sequence | Position from start codon per Genbank sequence X07384 |
|---|---|---|
| SEQ ID NO: 01 | CCTCGTAGCTTTCATCAAC | 314 |
| SEQ ID NO: 02 | TCATCAACTCGCGATGCAC | 325 |
| SEQ ID NO: 03 | CCAAACGCTATACAGATCC | 1108 |
| SEQ ID NO: 04 | CCCTCGTAGCTTTCATCAA | 313 |
| SEQ ID NO: 05 | CGTAGCTTTCATCAACTCG | 317 |
| SEQ ID NO: 06 | GTAGCTTTCATCAACTCGC | 318 |
| SEQ ID NO: 07 | TAGCTTTCATCAACTCGCG | 319 |
| SEQ ID NO: 08 | TTCATCAACTCGCGATGCA | 324 |
| SEQ ID NO: 09 | CATCAACTCGCGATGCACA | 326 |
| SEQ ID NO: 10 | ATCAACTCGCGATGCACAT | 327 |

The Hedgehog pathway has been reported to influence the expression of signature proteins that mediate epithelial-mesenchymal transition (EMT). Hence GLI1-knocked down clones KO1 and KO4 for the status of these signature markers were examined. As seen in FIG. 6 (panel C), expression of vimentin, SNAI2, and N-cadherin were notably decreased in KO1 and KO4 suggesting loss of the mesenchymal phenotype in GLI1-knocked down cells. Concomitant expression of E-cadherin in KO1 and KO4 was not documented.

Figure 7:
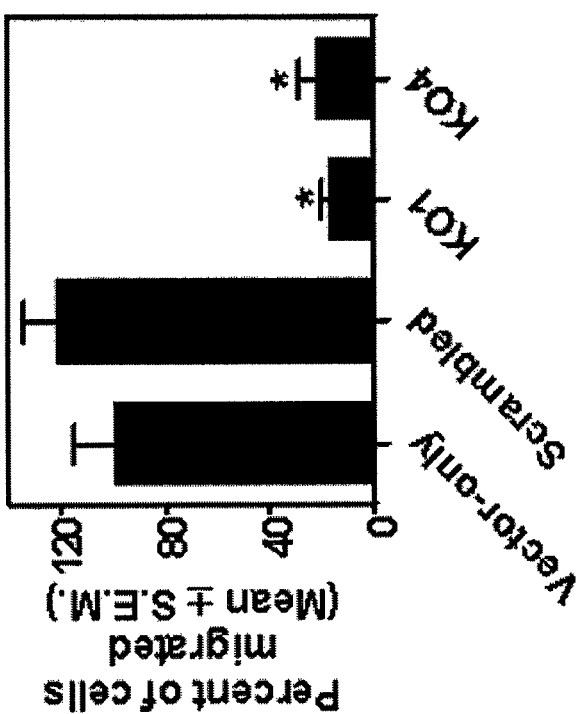
FIG. 7 (panel B) shows a graph of cell migration for various transfectants. Silencing endogenous expression of GLI1 significantly decreases the ability of cells to migrate (p<0.0001) across gelatin-coated filters.
Figure 7:
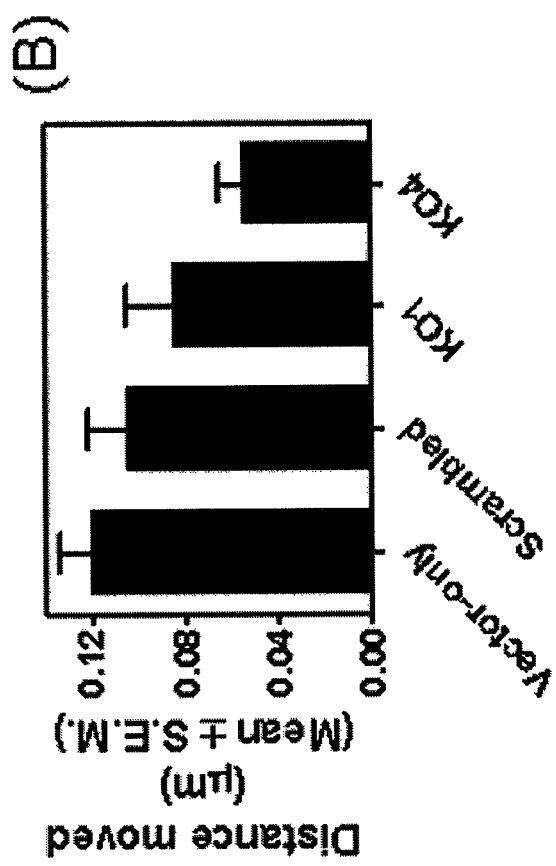
Figure 7:
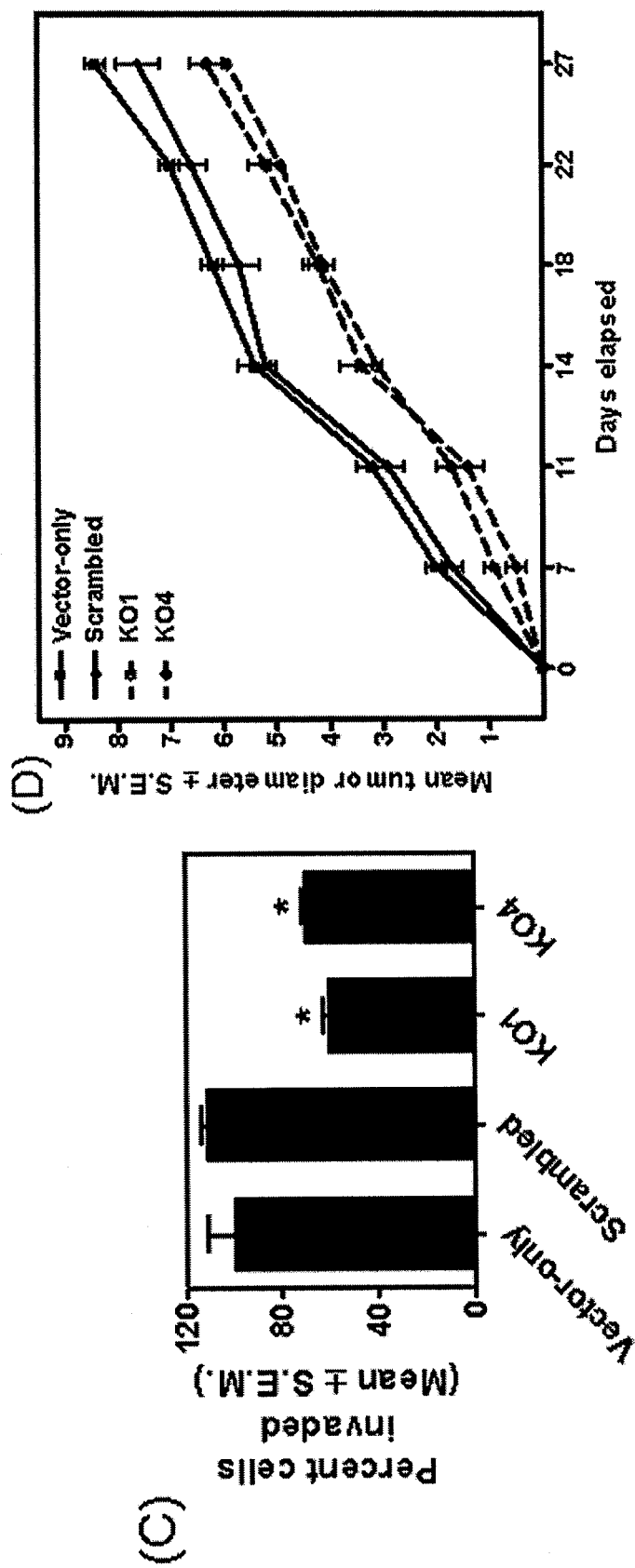
Figure 7:
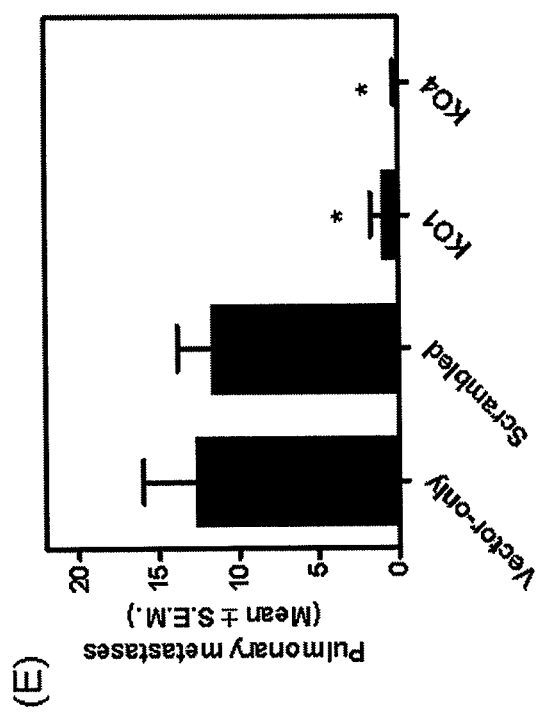
Figure 8:
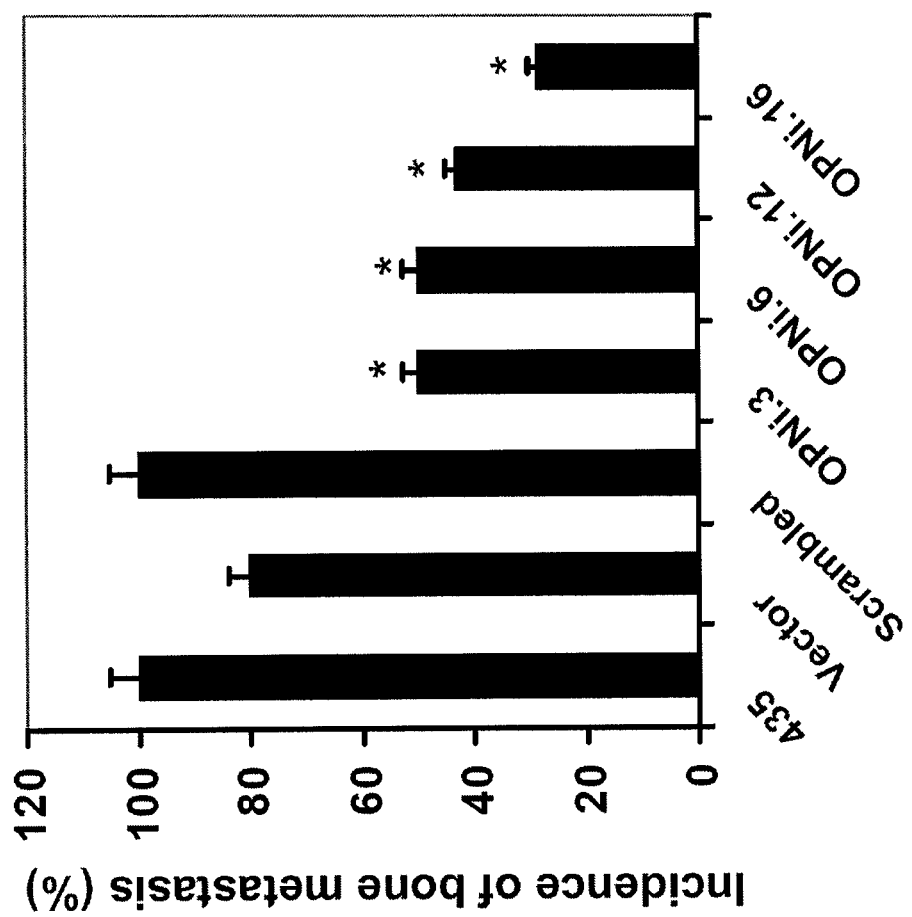
FIG. 8 shows a graph of the incidence of bone metastases for various transfectants.

GLI1-silenced cells for their in vitro attributes of aggressiveness, viz. cell migration, invasion, and motility were tested. Although GLI1 silencing had no significant effect on cell motility measured with a scratch assay (FIG. 7, panel A), cells in which GLI1 has been silenced showed statistically significant (p<0.0001) decreases in cell migration and invasion measured in modified Boyden chamber assays (FIG. 7, panel B and FIG. 7, panel C). There was no statistically significant (p<0.05) effect of GLI1 silencing on cell proliferation in vitro (FIG. 5, panel B). To examine the effect of GLI1 knockdown on the ability of cells to grow tumors as xenografts, GLI1-silenced cells and the corresponding vector-only and scrambled control cells were injected into athymic nude mice. Although there was no change in the tumor take rate, there was slower growth rate of GLI1-silenced cells up to day 11 (FIG. 7, panel D); the rate of growth subsequent to day 11 was similar between control and silenced cells. The implications of these observations are discussed further herein. In general, cells silenced for GLI1 showed a significantly (p<0.005) slower growth of tumors over the monitored time course. This was also reflected in the significantly (p<0.005) decreased numbers of pulmonary metastases (FIG. 7E) resulting from spontaneous metastasis of the injected cells. FIG. 8 shows the incidence of bone metastasis for cells transfected with constructs that inhibit OPN. GLI1-silencing reduced the incidence of bone metastasis. In summary, the results suggest that GLI1 silencing has little or no effect on proliferation or primary xenograft growth, but has a marked effect on metastasis. Thus, expression of GLI1 plays a functionally important role in the malignant behavior of tumor cells.

Example 5

OPN Mediates the Effect of GLI1 on Malignant Cell Behavior

Figure 9:
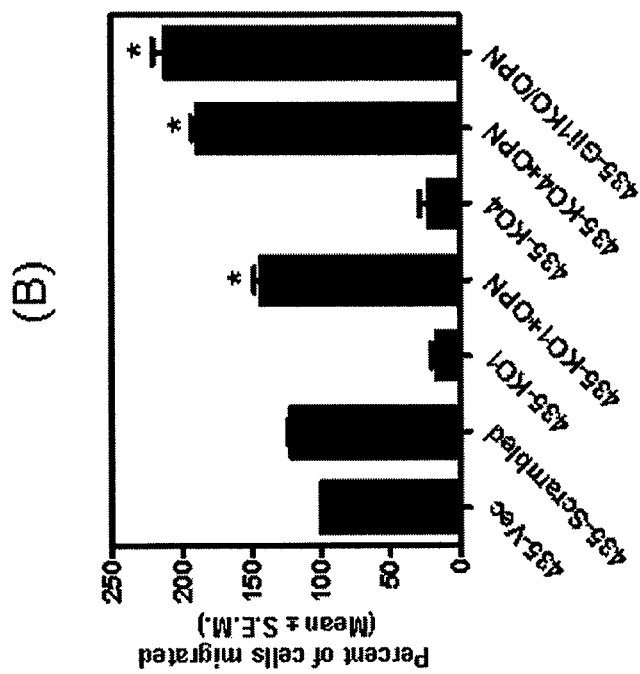
FIG. 9 (panel A) shows an immunoblot representing the restored OPN in cells that have been stably knocked down for GLI1 (GLI1 KO; and consequently express decreased levels of OPN). GLI1 KO cells were stably transfected with empty vector, pcDNA3.1, or pcDNA3.1 expressing OPN.
Figure 9:
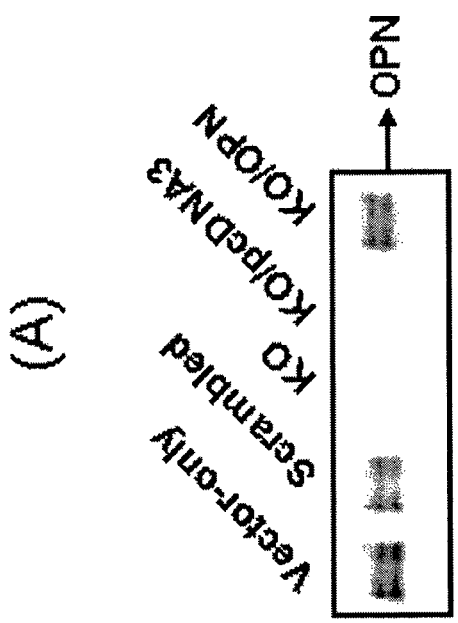
Figure 9:
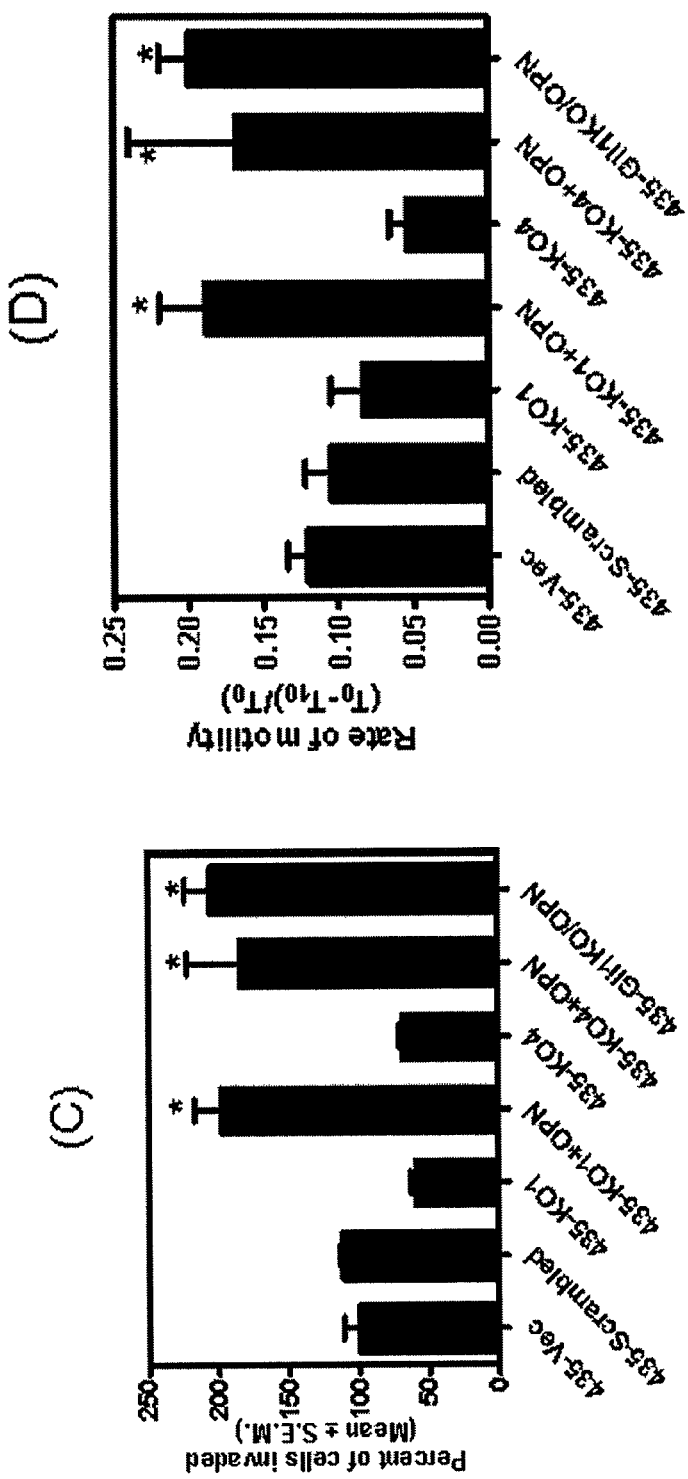
Figure 9:
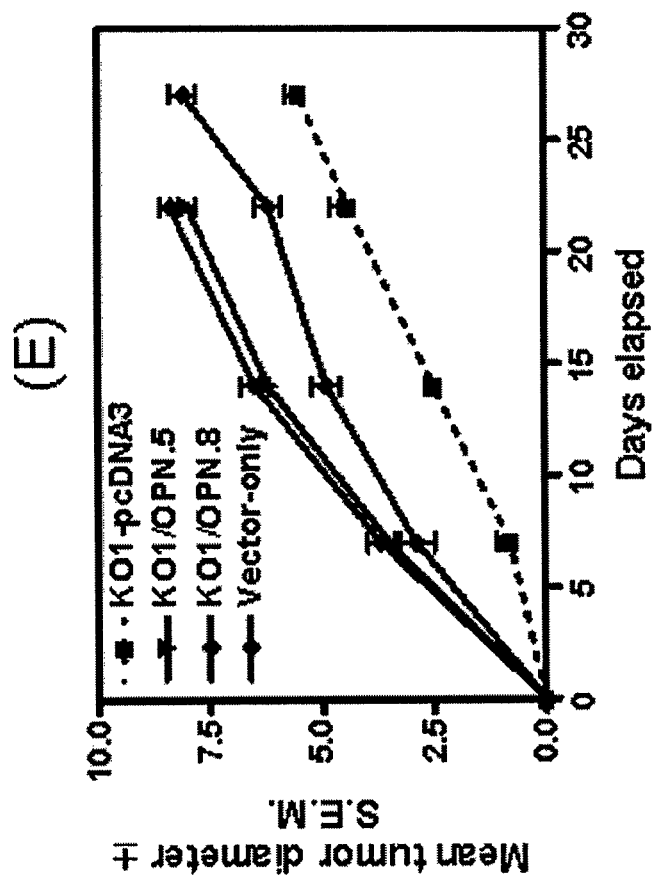

To determine the role of OPN in mediating GLI1 effects the effects of OPN in GLI1-KO cells was restored. This was assessed in two ways: (a) the GLI1-knocked down cells were treated with recombinant OPN and (b) the GLI1-knocked down cells were stably transfected with a plasmid construct expressing human OPN (FIG. 9, panel A). These cells were then monitored in vitro for properties of migration, invasion, and motility. When the GLI1-knocked down cells were cultured in the presence of OPN, KO1 and KO4 cells were restored for the ability to migrate (p<0.0001) (FIG. 9, panel B) and invade through MATRIGEL (FIG. 9, panel C) in much larger numbers (p<0.005) compared with untreated cells. Motility of GLI1-silenced cells was also restored in KO1 cells (p<0.05) and KO4 cells in the presence of recombinant OPN (p<0.05) (FIG. 9, panel D). The levels of the OPN receptor, CD44, were comparable in the vector-only and KO cells (FIG. 5, panel C), implying that both cell types should be receptive and responsive to OPN.

Similarly, stably restoring the expression of OPN (FIG. 9 panel A) in the GLI1-knocked down cells reinstated the ability of the cells to chemotactically migrate through a filter (8 μm pores) (FIG. 9, panel B), invade through MATRIGEL (FIG. 9, panel C), and restore the ability of the cells to move laterally (in a scratch motility/wound healing assay) (FIG. 9, panel D). Restoration of OPN expression in GLI1-silenced (KO1) cells caused the cells to form rapidly growing tumors in mice (FIG. 9, panel E). As compared with KO1 cells transfected with empty vector (KO1-pcDNA3), the two clones restored for OPN, viz. KO1/OPN.5 and KO1/OPN.8, formed tumors that grew faster than control cells. This implied that regulation of OPN by the Hedgehog pathway plays a role in the malignant properties of cancer cells.

Example 6

Experimental Procedures

Cell Culture—The melanoma cell lines, MCC012A and MCC012F, used were established from two subcutaneous metastatic nodules from the same patient. Cells were grown in a Dulbecco's modified minimum essential medium, F-12 mixture (1:1) (Invitrogen) supplemented with 5% heat inactivated fetal bovine serum (Atlanta Biologicals, Lawrenceville, Ga.), 200 μM sodium pyruvate (Invitrogen), and 20 μM non-essential amino acids (Invitrogen). All cells were maintained in a humidified 5% $CO_2$ environment. MDA-MB-435 cells were also cultured under similar conditions.

Generation of Stable Transfectants—Endogenous GLI1 from MDA-MB-435 cells was silenced using shRNAs (short hairpin RNA) cloned into pSuperior.neo+gfp plasmid (OligoEngine, Seattle, Wash.) (TABLE 1). Introduction of double-stranded RNA has proven to be a powerful tool to suppress gene expression through a process known as RNA interference (P. A. Sharp, Genes Dev. 13, 139 (1999)). However, in some mammalian cells this can provoke a strong cytotoxic response (T. Hunter, T. Hunt, R. J. Jackson, H. D. Robertson, J. Biol. Chem. 250, 409 (1975)). This non-specific effect can be circumvented by use of synthetic short [21- to 22-nucleotide (nt)] interfering RNAs (siRNAs), which can mediate strong and specific suppression of gene expression (S. M. Elbashir et al., Nature 411, 494 (2001)). shRNAs included a target sequence sense strand, a short hairpin, and a target sequence antisense strand.

Stable vector only and non-targeting (scrambled control) transfectants were also generated. Stable transfectants were selected on medium supplemented with 500 μg/ml Geneticin (Invitrogen). The four GLI1-knocked down clones chosen were based on the extent of GLI1 knockdown and were termed KO1, KO2, KO3, and KO4. The expression of OPN was restored in the KO1 cells by transfecting with pcDNA3.1-OPN. A corresponding vector-only transfectant was also generated. Transfectants were selected on medium containing Geneticin (500 μg/ml) and hygromycin (750 μg/ml). Serum-free conditioned medium harvested from approximately $3.0\times10^6$ cells after 24 hr was assayed for OPN by immunoblotting. To test the inhibitory effect of cyclopamine on Hedgehog pathway activation, cells were cultured in Dulbecco's modified minimum essential medium supplemented with 0.5% fetal bovine serum and treated for the indicated time intervals with dimethyl sulfoxide (vehicle control), 10 and 20 μM cyclopamine (Sigma).

Western Blotting Analysis—Whole cell lysates were collected in Nonidet P-40 buffer (150 mM NaCl, 50 mM Tris, 1% Nonidet P-40). Isolation of cytosolic and nuclear fractions was done as previously reported (15). Total protein (30 μg) was resolved by SDS-PAGE gel and transferred to polyvinylidene difluoride membranes. Membranes were immunoblotted overnight at 4° C. with antibodies to OPN (catalog number 905-629; Assay Designs, Ann Arbor, Mich.), GLI1 (sc-20687; Santa Cruz Biotechnology, Santa Cruz, Calif.), CD44 (HCAM) (sc-7946; Santa Cruz Biotechnology), vimentin (sc-32322; Santa Cruz Biotechnology), N-cadherin (catalog 18-0224; Invitrogen), SNAI2 (catalog H00006591-MO2; Novus Biologicals, Littleton, Colo.), SHH (sc-1194; Santa Cruz Biotechnology), or PTCH1 (sc-6149; Santa Cruz Biotechnology). Equal loading was confirmed with anti-β-actin (Sigma) antibody. The purity of cytosolic and nuclear fractions was confirmed with anti-β-tubulin (catalog 2146; Cell Signaling, Danvers, Mass.) or anti-HDAC1 (catalog 2062; Cell Signaling) antibodies, respectively. Secreted OPN was assessed by loading an equal quantity of protein from the serum-free conditioned medium. Corresponding horseradish peroxidase conjugated secondary antibodies were used for detection; blots were developed with SuperSignal enhanced chemiluminescence substrate (Pierce) and imaged using a Fuji LAS3000 imager.

Expression Constructs—OPN promoter activity was assessed by a luciferase reporter assay using the human OPN promoter construct (OPN-352) cloned into pGL3-basic vector (Promega) (Samant, R. S., et al. (2007) Mol. Cancer 6: 6). The putative GLI1 binding site (Kinzler, K. W., and Vogelstein, B. (1990) Mol. Cell. Biol. 10, 634-642) (5'-TGCTGAATGCCCATCCC-3') in the OPN promoter was disrupted using an inside-out PCR and replaced with a NotI site using primers: (SEQ ID NO: 13) forward, 5'-CTCA-GCGGCCGCTAATAAATGAAAAAGC-3' and (SEQ ID NO: 14) reverse, 5'-GTTAGCGGCCGCTGAGAGTTCCA-GGAAG-3'. The resultant construct, referred to as OPN-352$^{Mut}$ has a mutated GLI1-binding site.

Luciferase Assay—Cells (40,000) were transfected with pGL3-OPN-352 or pGL3-OPN-352$^{Mut}$ in combination with pLNCX or pLNCX-GLI1 as previously described (16). Empty pGL3 vector was used as control. Hedgehog ligands were added to the well 6 h prior to harvesting the cells (approximately 33 hr of initiation of transfection) for assay. Readings were normalized to total protein content. Each parameter was studied in triplicate and the experiment repeated at least 3 times. The data are represented as percent luciferase activity, which was derived as a percent of the relative light units in treated groups compared with the untreated groups.

Quantitative RT-PCR (qRT-PCR)—cDNA was generated using High Capacity Reverse Transcriptase Kit (Applied Biosystems, Foster City, Calif.). Real time PCR was performed using a Bio-Rad iQ5 Real-Time Detection system (Bio-Rad). All reactions were done as three independent replicates. All assays were done using the TaqMan Gene Expression Assays from Applied Biosystems. OPN (SPP1: Hs 00959010_m1) transcript levels were normalized to glyceraldehyde-3-phosphate dehydrogenase (Hs 99999905_m1) levels (δCT), which was used to calculate changes in OPN expression ($2^{-\delta\delta CT}$). To analyze the effect of cyclopamine treatment on OPN expression, untreated samples were set as calibrator (control) and compared with their respective treated samples. GLI1 and SHH (Hs 00179843_m1) expressions were also similarly assessed with glyceraldehyde-3-phosphate dehydrogenase as an endogenous control. To analyze the knockdown effectiveness, "scrambled transfectants" of MDA-MB-435 was set as calibrator.

Chromatin Immunoprecipitation Assay—MDA-MB-435 cells were utilized for chromatin immunoprecipitation using the ChIP-IT Express enzymatic kit (Active Motif, Carlsbad, Calif.) following the manufacturer's protocol using GLI1 (N-16) X TransCruz antibody (Santa Cruz Biotechnology; sc-6153 X). The recovered DNA was PCR amplified using primers: forward, (SEQ ID NO: 15) 5'-GTTTTTC-CCTACTTTCTCCC-3' and reverse, (SEQ ID NO: 16) 5'-CCAAAAACGCACACACAC-3' to amplify a 145-bp segment of the OPN promoter containing the putative GLI1 binding site. The specificity of the pull-down was confirmed by amplifying a region approximately 1 kb upstream from the PCR product containing the GLI1 site tested. The primers used were: (SEQ ID NO: 17) 5'-TTCCCCCTAC-CAAATGTTCA-3' and (SEQ ID NO: 18) 5'-TGCTG-CAAAAGTAATTGTGGTT-3'. The PCR generates a 151-bp product. This segment lacks a predicted GLI1-binding site.

In Vitro Proliferation Assay—Cells (5000) of each cell type were seeded per well in separate 96-well plates. Cells were allowed to grow in complete medium for 6 days. Every day after initial seeding cells were harvested by trypsinization and counted in a hemocytometer. Counting for each cell type for each day was done in triplicate.

Motility Assay—These experiments were performed as previously described (Shevde, L. A., et al. (2006) Clin. Exp. Metastasis 23, 123-133). Images were acquired at $T_0$, the reading at the initial time, and at $T_{10}$ (10 h later). The experiment was conducted in duplicate and cell motility was calculated as $(T_0-T_{10})/T_0$, which represents the rate of movement over a 10-h period. For OPN add-back experiments the cells were pretreated for 12 h with 100 ng/ml human OPN (recombinant R & D Systems) and the assay conducted in the presence of OPN. Each experimental group was assessed in duplicate and data were recorded in three fields per well. Thus, six data points were recorded and analyzed per experimental group.

Invasion and Migration Assays—These experiments were performed as previously outlined (18) using a modified Boyden chamber assay. OPN add-back experiments for migration and invasion were conducted as described above with an additional step of pre-treating the cells for 24 h with rOPN. OPN was added to the upper and lower chambers (100 ng/ml) to ensure the OPN was present during the entire duration of the experiment. Each experimental group was assessed as three independent replicates.

In Vivo Assay—One million (100 μl) cells were injected into the third mammary fat pad of 6-week-old female athymic nude mice (Harlan Sprague-Dawley, Indianapolis, Ind.). Orthogonal tumor measurements were taken twice a week. The mean tumor diameter was calculated by taking the square root of the product of orthogonal measurements. Spontaneous metastasis was monitored as previously described (18). Eight mice were used for each group and the entire experiment was repeated once. All animals were maintained under the guidelines of the National Institutes of Health and University of South Alabama. All protocols were approved and evaluated by the Institutional Animal Care and Use Committee.

Statistical Analysis—Statistical differences between groups were assessed using the Mann-Whitney test, t test, or analysis of variance, using GraphPad Prism 4 software. Statistical significance was determined if the analysis reached 95% confidence. The precise p values are listed in the corresponding figure legends. In figures, the error bars represent mean±S.E.

Example 7

Molecular Analysis of the Crosstalk Between Breast Cancer Cells, Osteoblasts and Osteoclasts Involving the Hedgehog Pathway and OPN Cell lines used: Breast cancer (BC) cells: Two metastatic breast cancer cell lines (i) MDA-MB-231 and (ii) SUM 159. Osteoblasts (OB): Two osteoblast cell lines. (i) hFOB and, (ii) MC3T3-E1 pre-osteoblast cells. Both lines produce OPN. Differentiation of the MC3T3-E1 cells, clone 14 was studied when cultured under conditions that induce differentiation (presence of ascorbic acid and β-glycerophosphate) (Zunich, S. M., et al. (2009) Mol Cancer 8, 12).

Osteoclasts (OC): Osteoclasts (i) RAW264.7 cells of the macrophage/monocyte lineage were cultured under conditions to differentiate them into osteoclasts (Narducci, P., et al. (2009) Ann Mat; Voronov, I., Li, K, et al. (2008); and Biochem Pharmacol 75, 2034-2044).

Example 8

Effects of Breast Cancer Cells on Osteoblasts

Figure 10:
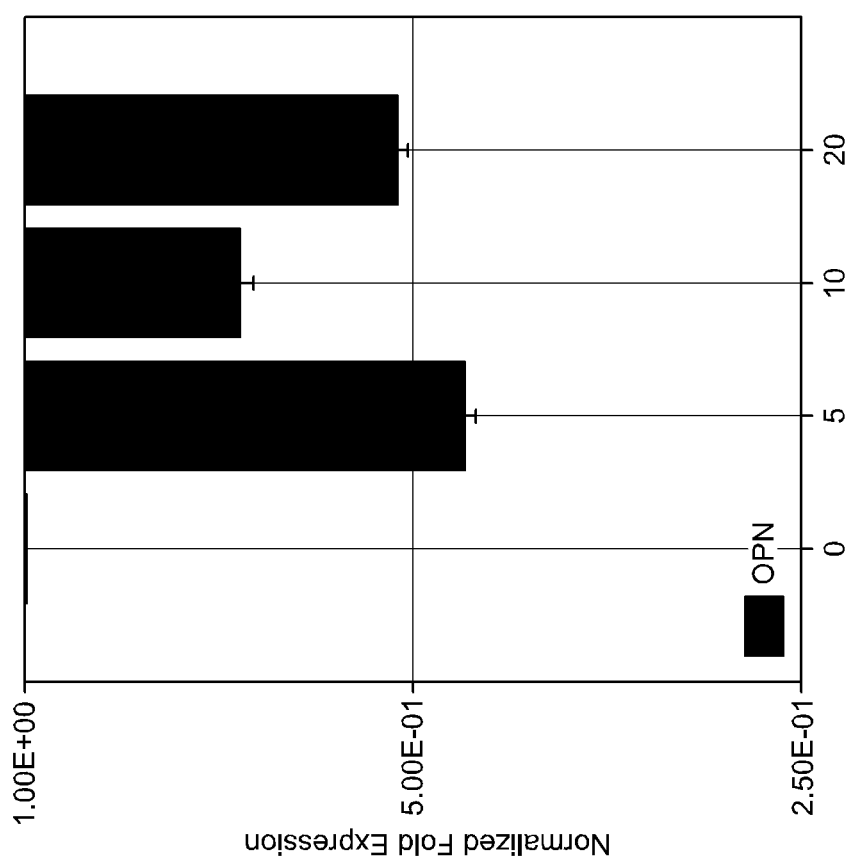
FIG. 10 shows a graph of OPN expression in hFOB cells treated with cyclopamine treatment (5 µM, 10 µM, 20 µM). Treatment decreases OPN mRNA levels in the hFOB cells (assessed by quantitative real-time RT-PCR).
Figure 11:
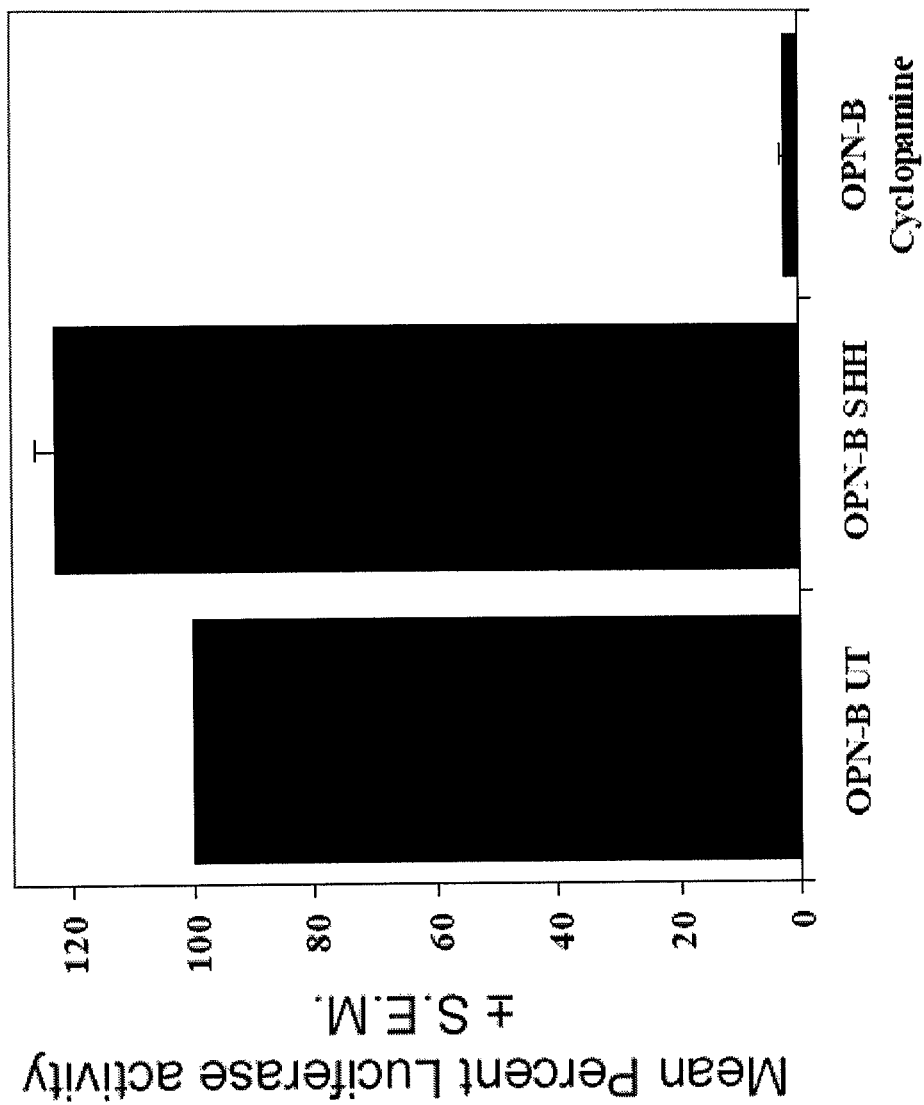
FIG. 11 shows a graph of reporter gene activity in hFOB cells treated with recombinant Sonic Hedgehog (SHH). SHH activates the OPN promoter (OPN-B). Conversely, cyclopamine inhibits OPN in the cells compare to the untreated control (UT) cells.
Figure 12:
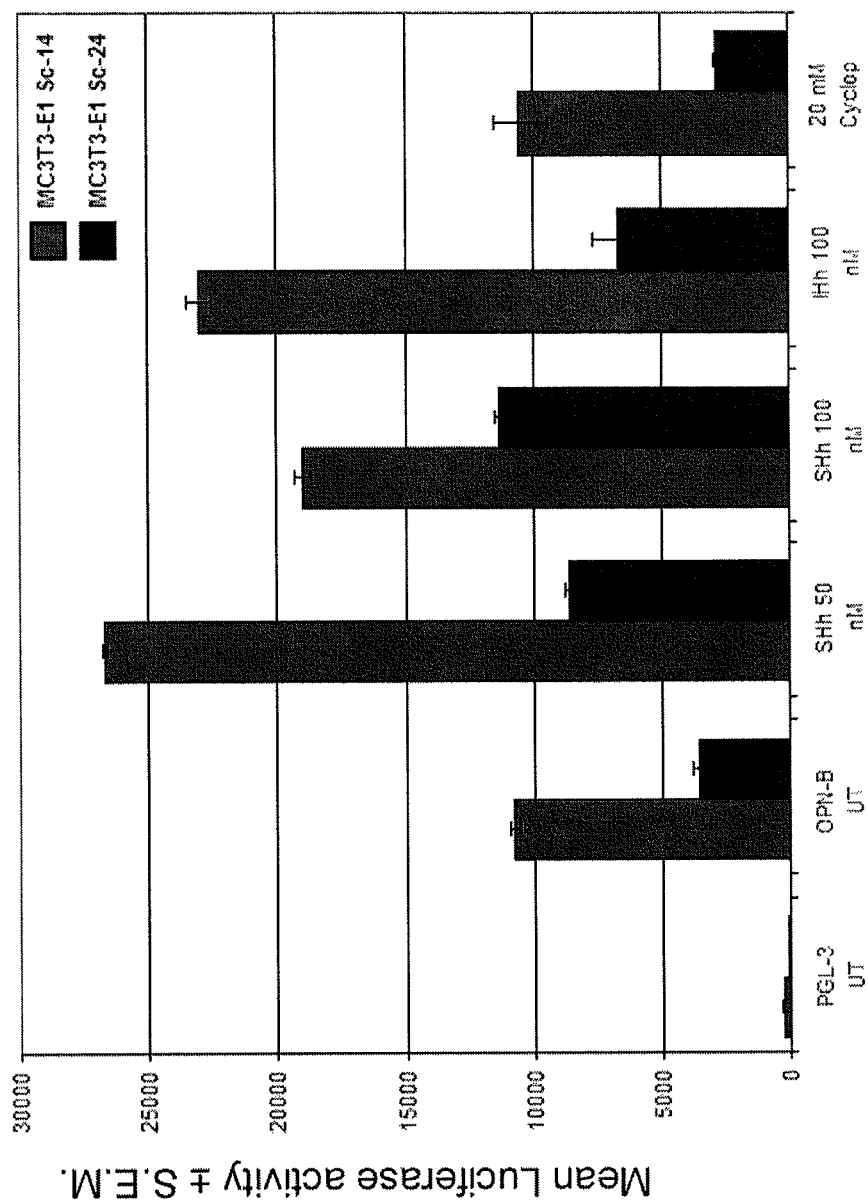
FIG. 12 shows a graph reporter gene activity in MC3T3-E1 pre-osteoblastic cells (clones 14 and 24) treated with Recombinant Sonic Hedgehog (SHH) and Indian Hedgehog (IHH). SHH and IHH activate OPN promoter. Conversely, cyclopamine treatment (20 µM) inhibits Hedgehog-activated OPN in the MC3T3-E1 cells.

The role of the Hedgehog pathway in regulating the expression of OPN in the two osteoblastic cell lines, hFOB and MC3T3-E1 was assessed. Referring to FIG. 10 and FIG. 11, in hFOB cells, treatment with cyclopamine inhibited the transcription of OPN and the ligand, sonic hedgehog (SHH) stimulated the promoter of OPN. Similar observations were seen in the MC3T3-E1 cells (FIG. 12). This that OPN is regulated via the Hedgehog pathway in these two cell lines.

Figure 13:
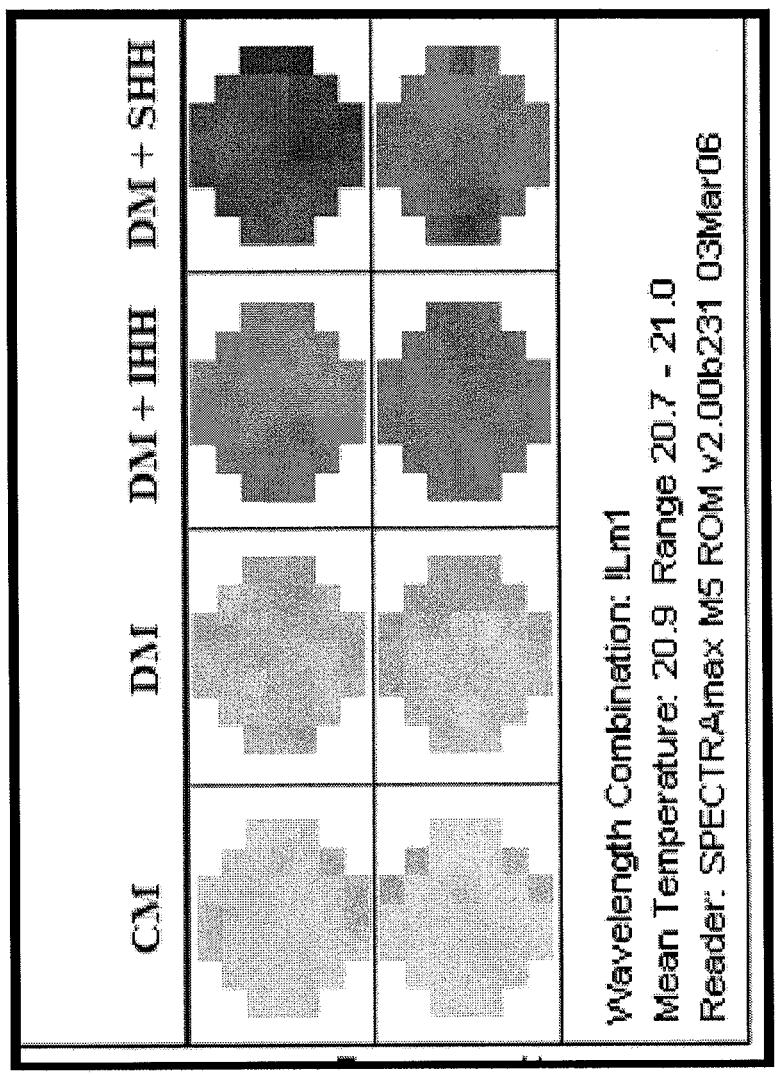
FIG. 13 shows a photograph of the Alizarin Red S staining of osteoblast differentiation/mineralization following treatment with recombinant SHH and IHH FIG. 14 (panel A), FIG. 14 (panel B), and FIG. 14 (panel C) show photomicrographs of Alizarin Red-stained osteoblasts, showing mineralization following differentiation in medium alone (FIG. 14, panel A), and treatment with recombinant IHH (FIG. 14, panel B) and SHH (FIG. 14, panel C).
Figure 14:
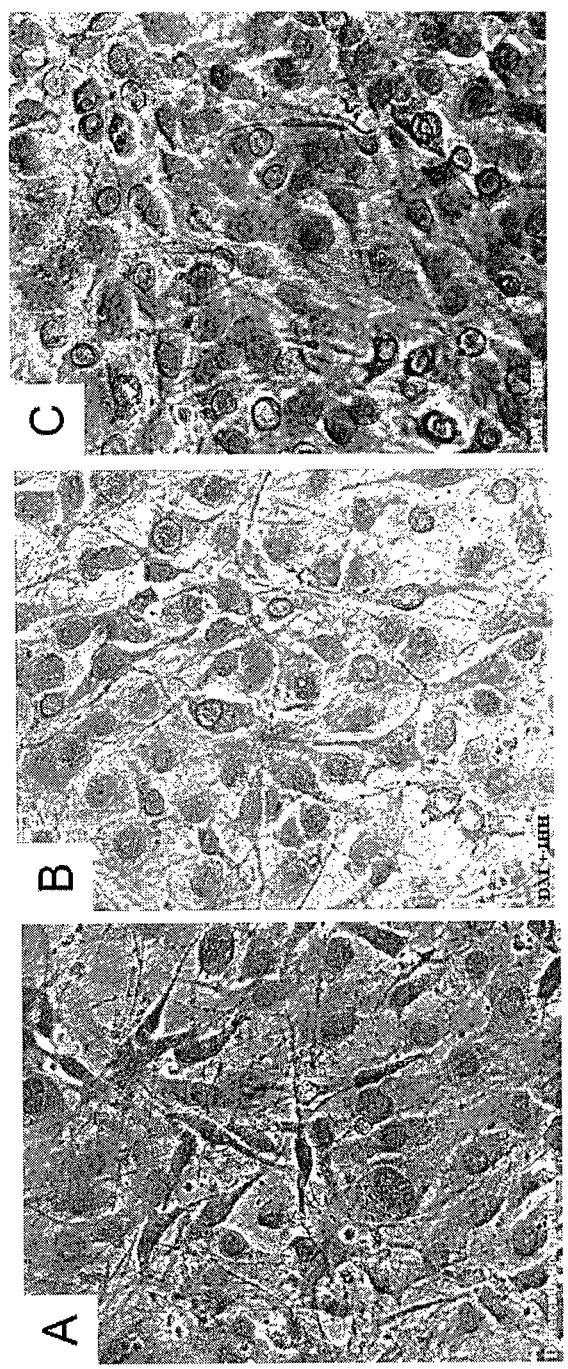
Figure 15:
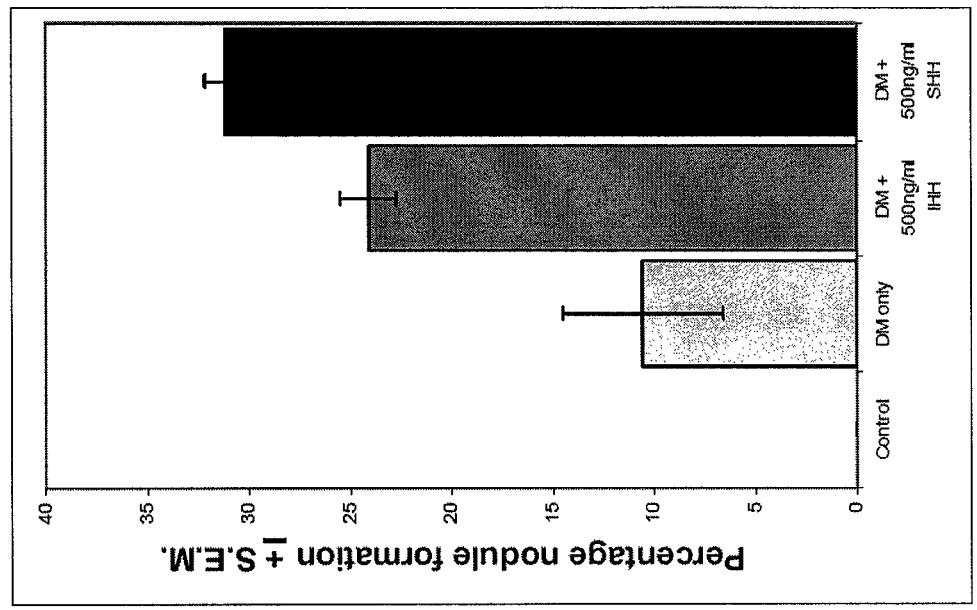
FIG. 15 (left panel) shows a graph of relative absorbance of Alizarin Red-stained osteoblasts treated with recombinant SHH and IHH.
Figure 15:
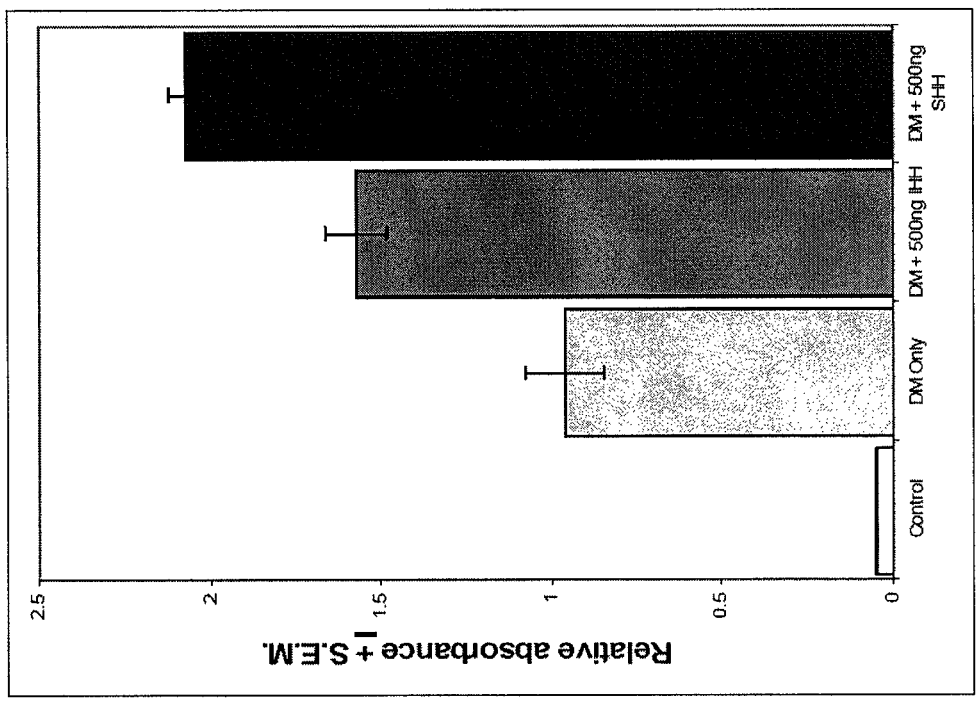

The procedure for differentiation of osteoblasts was standardized. MC3T3-E1 cells were cultured in the presence of ascorbic acid and β-glycerophosphate. Mineralization was examined by Alizarin RedS staining (Ueno, A., et al. (2001). Matrix Biol 20, 347-355; Lee, Y. K., et al. (2004). J Biomed Mater Res A 69, 188-195; Duarte, W. R., et al. (2003). S100A4: a novel negative regulator of mineralization and osteoblast differentiation. J Bone Miner Res 18, 493-501). Referring to FIG. 13 and FIG. 14, differentiation was evident by intense red staining in presence of differentiation medium and in differentiation medium containing SHH compared to the control, growth medium. This was also evident in the intensity of absorbance and in the numbers of mineralized nodules formed (counted under the microscope) (FIG. 15).

Figure 16:
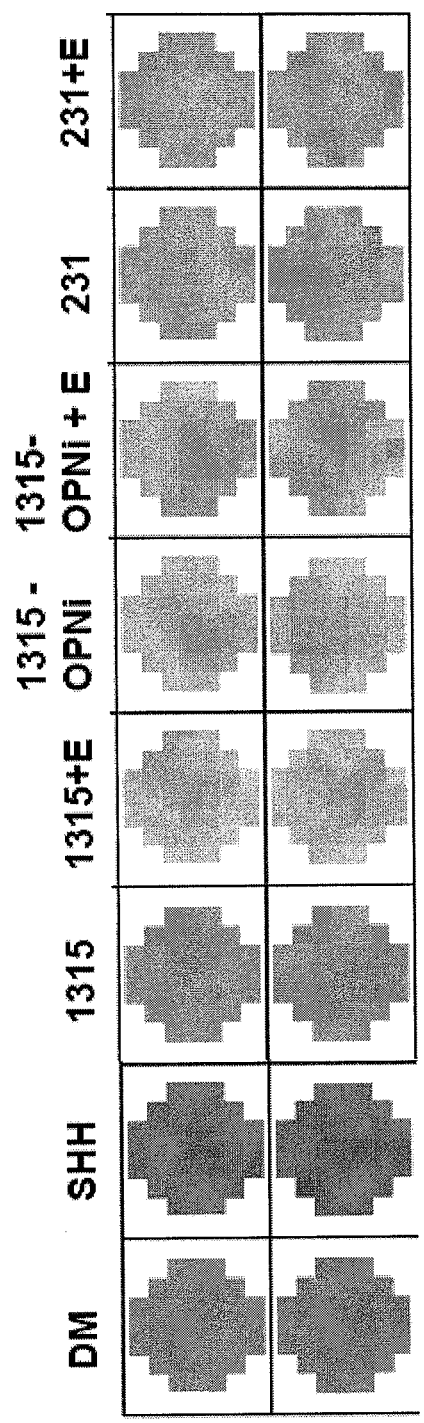
FIG. 16 is a photograph of the Alizarin Red S staining of osteoblast differentiation/mineralization following treatment with recombinant SHH and conditioned medium from two breast cancer cell lines, SUM1315 (1315) and MDA-MB-231 (231) in the presence of SHH-neutralizing antibody 5E1 (E) and/or in the presence of RNA interference-induced silencing of OPN (OPNi).
Figure 17A:
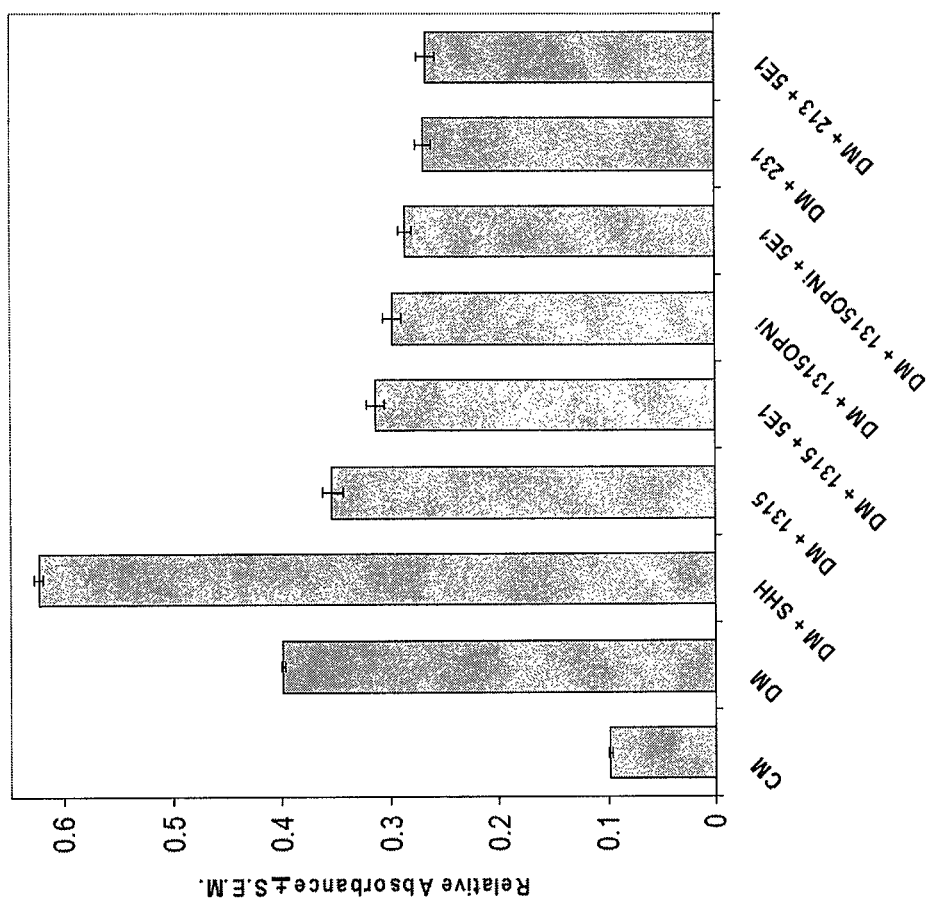
FIG. 17A is a graph of relative absorbance of Alizarin Red-stained osteoblasts treated with recombinant SHH.
Figure 17B:
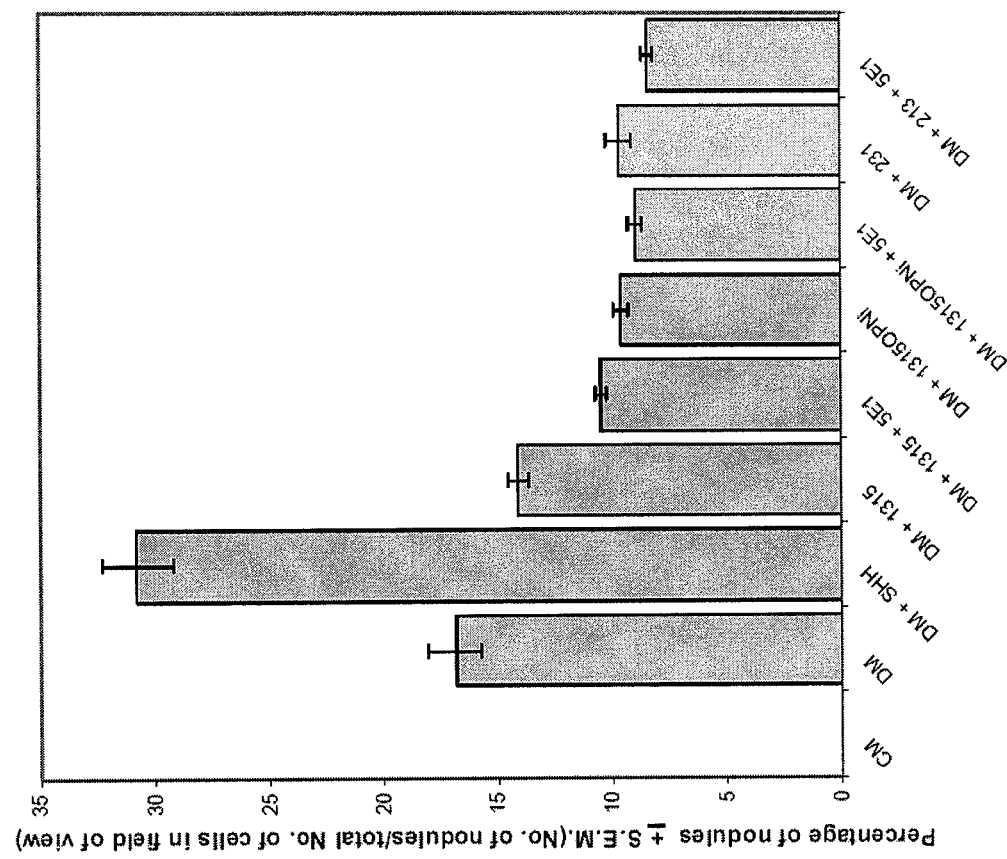
FIG. 17B is a graph of nodule formation in osteoblasts treated with recombinant SHH. Treatment with recombinant SHH promotes differentiation of the pre-osteoblastic MC3T3-E1 clone 14 cells. Conditioned medium (SFM) from the MDA-MB-231 and SUM1315 cells interferes with osteoblast differentiation & mineralization compared to differentiation medium (DM) alone.

The effect of conditioned culture medium from breast cancer cells on the differentiation of osteoblasts was assessed. Referring to FIG. 16 and FIG. 17, the medium from breast cancer cells (SUM1315 and MDA-MB-231) interfered with osteoblast differentiation and reduced the mineralization capability as determined by absorbance following Alizarin Red S staining (FIG. 17A) and number of nodules (FIG. 17B). SHH is important for osteoblast differentiation. Also, there was a progressive decrease in the mineralization when the conditioned medium from the SUM1315 cells and MDA-MB-231 cells was spiked with the 5E1 antibody which neutralizes SHH.

OPN expression by the SUM1315 cells influences osteoblast differentiation. Referring to FIG. 17B, medium from the SUM1315 cells abrogated for OPN expression (OPNi) by RNAi-mediated silencing, also showed a decrease in osteoblast differentiation.

Figure 18:
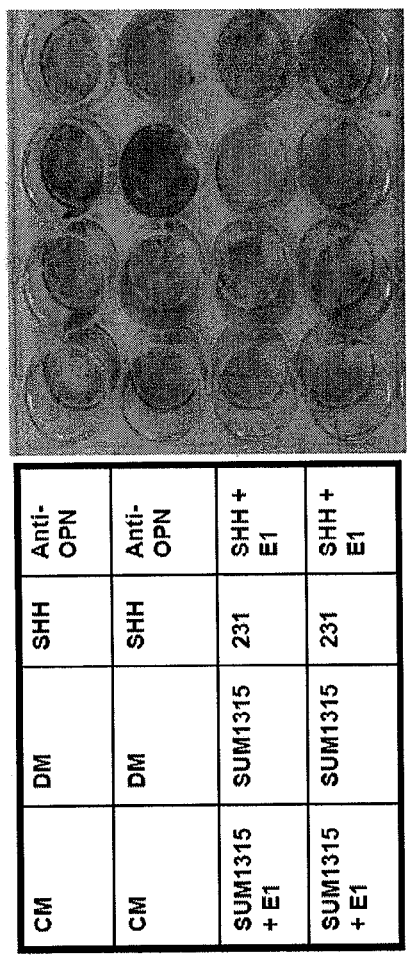
FIG. 18 shows an alkaline phosphatase assay for osteoblast differentiation shows that conditioned medium (SFM) from the MDA-MB-231 and SUM1315 cells interferes with osteoblast differentiation compared to differentiation medium (DM) alone. Treatment with recombinant SHH promotes differentiation of the pre-osteoblastic MC3T3-E1 clone 14 cells. A neutralizing SHH antibody (E1) reduces differentiation.
Figure 18:
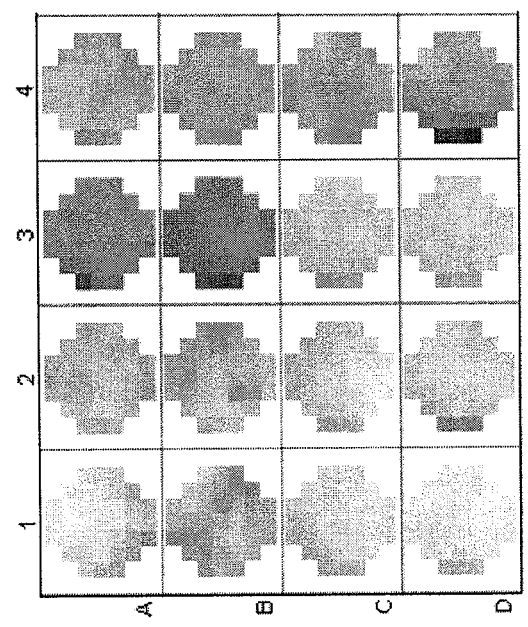
Figure 18:
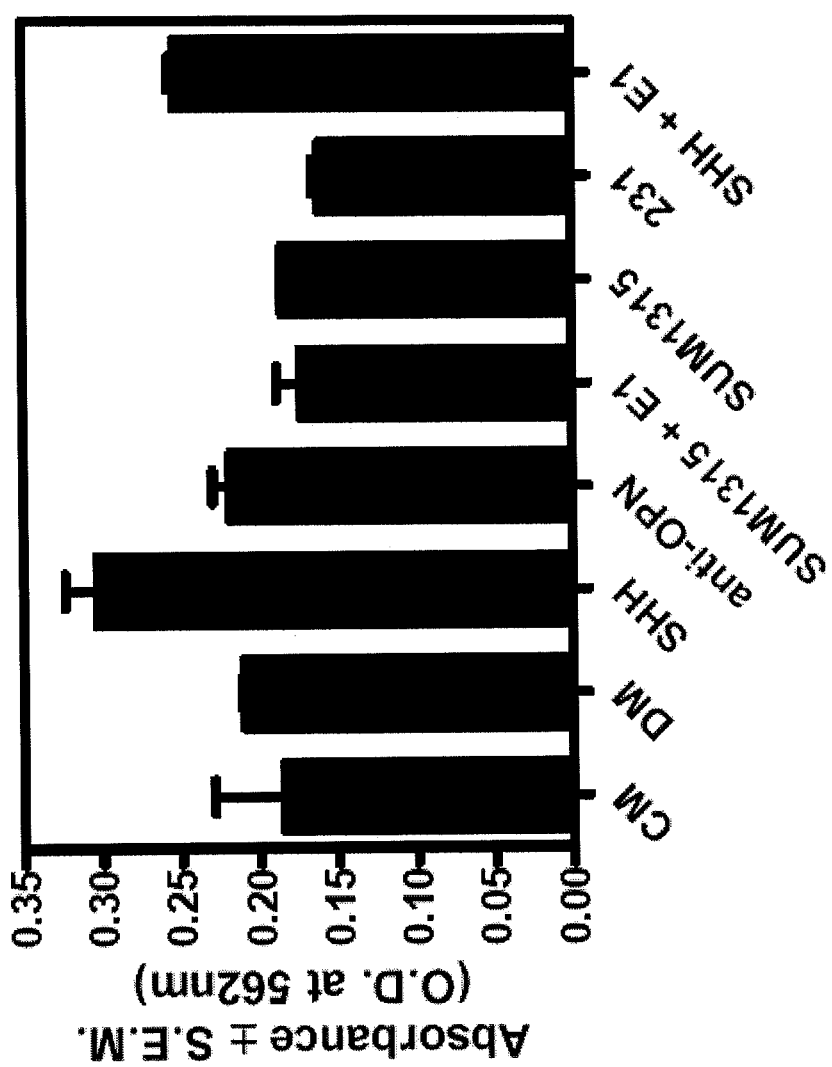

Differentiated osteoblasts were stained for their alkaline phosphatase activity. Alkaline phosphatase is a reliable marker of osteoblast differentiation (Ebisawa, T., et al. (1999). J Cell Sci 112 (Pt 20), 3519-3527; Mori, K., et al. (2008). Cancer Sci 99, 2170-2176; Kitagawa, Y., et al. (2005). Cancer Res 65, 10921-10929; Mercer, R. R., et al. (2004). Clin Exp Metastasis 21, 427-435). Referring to FIG. 18, conditioned medium from the breast cancer cells reduced the levels of alkaline phosphatase in the osteoblasts. As a control, the total phosphatase level in the cells was assessed. Referring to FIG. 18, the conditioned medium from the SUM1315 cells and the MDA-MB-231 cells interfered with osteoblast differentiation. A darker intensity of the brown staining of the alkaline phosphatase stained wells suggests that SHH and OPN promoted osteoblast differentiation.

Figure 19A:
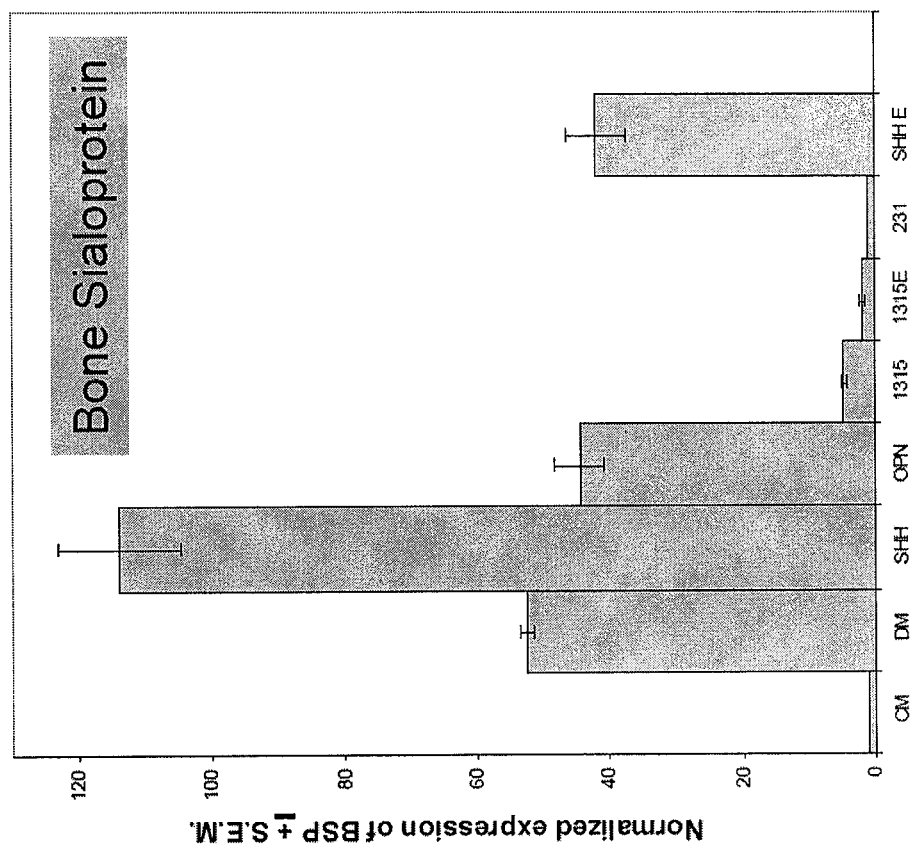
FIG. 19A and FIG. 19B show quantitative real-time RT-PCR analysis of Bone Sialoprotein and Osteocalcin, respectively, as markers of osteoblast differentiation also show that conditioned medium (SFM) from the MDA-MB-231 and SUM1315 cells interferes with osteoblast differentiation compared to differentiation medium (DM) alone. Treatment with recombinant SHH promotes differentiation of the pre-osteoblastic MC3T3-E1 clone 14 cells. A neutralizing SHH antibody (E1) reduces differentiation.
Figure 19B:
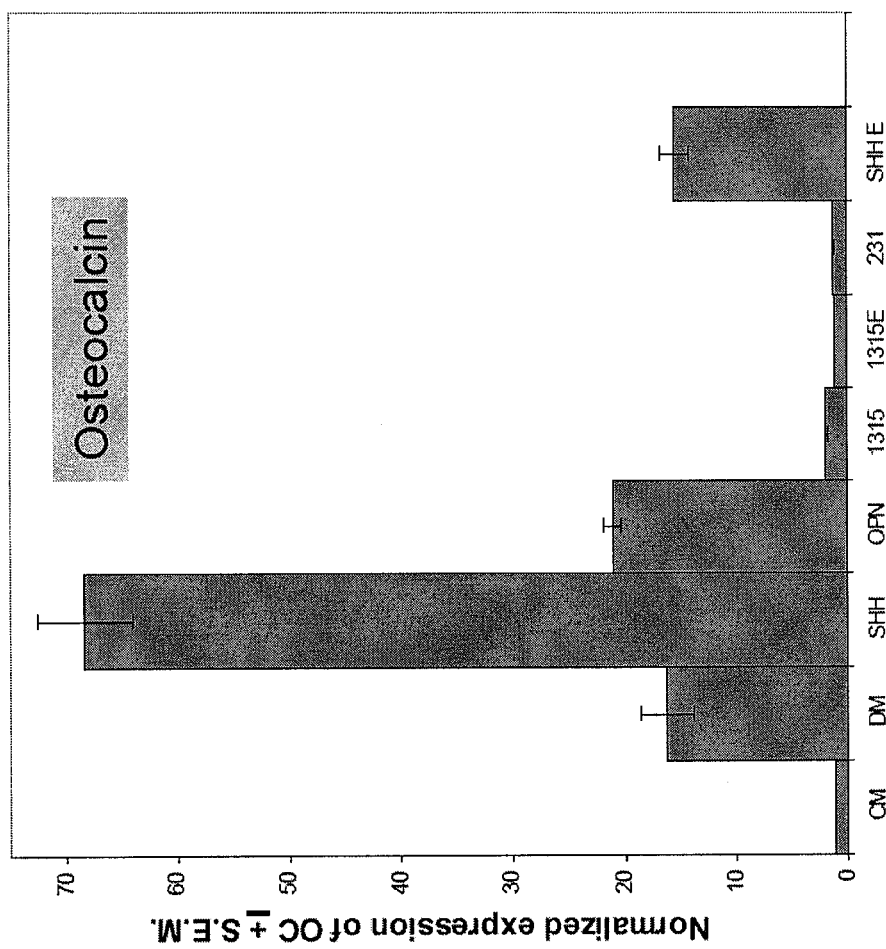

The expression of sialoprotein and osteocalcin, two bonafide markers of osteoblast differentiation viz. bone was assessed (Wang, J., et al. (2008) J Dent Res 87, 650-654; Lampasso, J. D., et al. (2006) Int J Mol Med 17, 1125-1131; Chou, Y. F., et al. (2005). J Biomed Mater Res B Appl Biomater 75, 81-90; Wang, D., et al. (1999) J Bone Miner Res 14, 893-903; Maeda, T., et al. (2004). J Cell Biochem 92, 458-471). Referring to FIG. 19, the expression of the two molecules was reduced when the osteoblast differentiation was performed in presence of conditioned medium from the breast cancer cells. Consistent with other observation, SHH appears to play a positive role in impacting the osteoblast differentiation. In sum, these data suggest that the breast cancer cells inhibit differentiation of osteoblasts.

Example 9

Effects of Breast Cancer Cells on Osteoclasts

Figure 20:
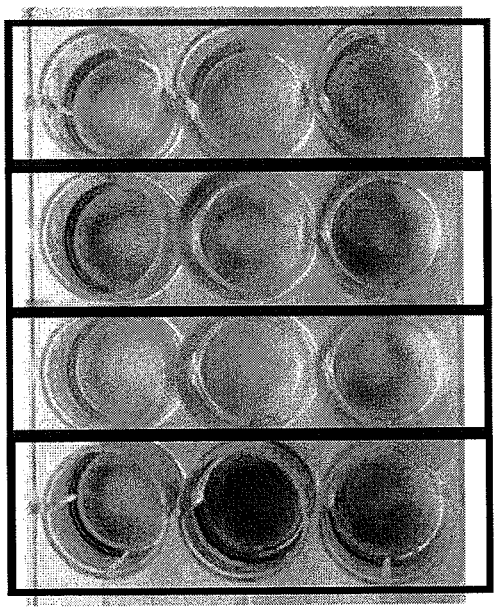
FIG. 20 shows a photomicrograph of RAW cells cultured under conditions incorporating RANKL (RANK-Ligand) and M-CSF (macrophage colony stimulating factor) to induce their differentiation into osteoclast-like cells. TRAP (Tartarate-resistant acid phosphatase) staining for osteoclast differentiation is shown in red boxes. The wells boxed in black represent staining for the total phosphatase in the RAW264.7 cells.
Figure 21:
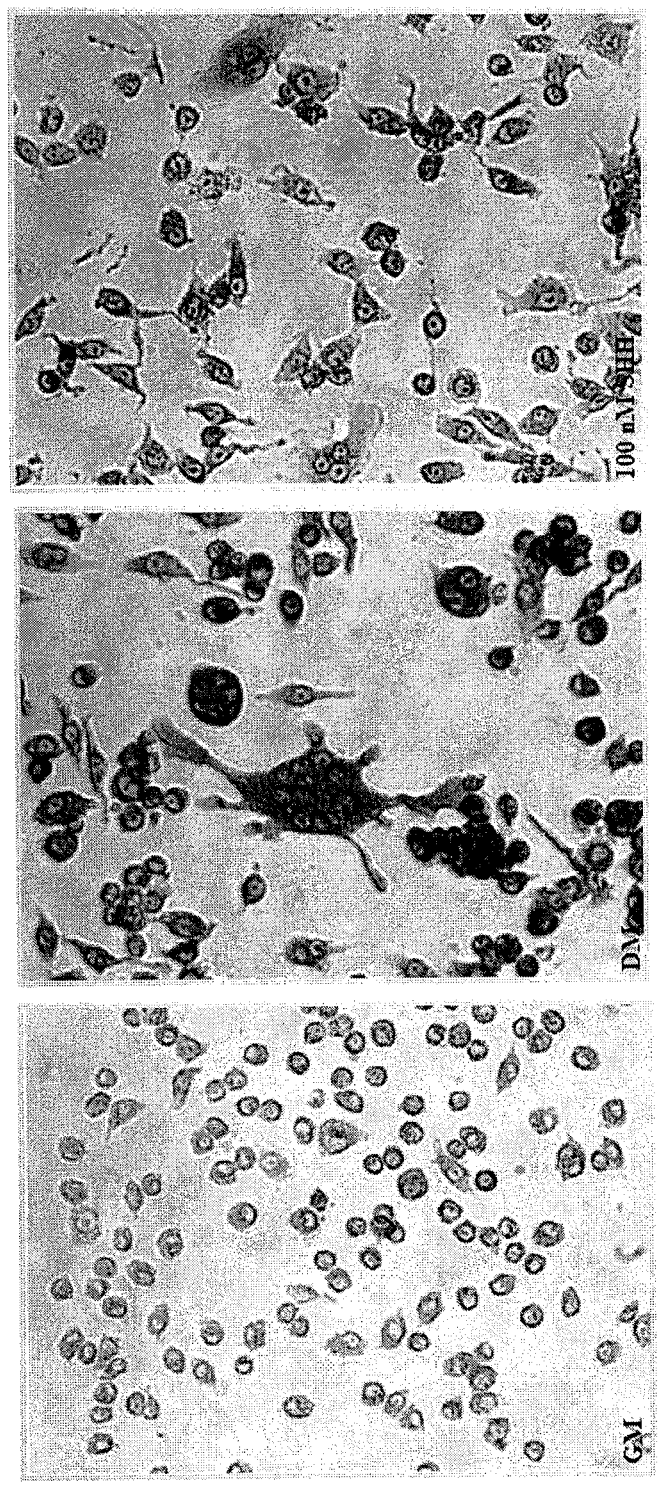
FIG. 21 shows photomicrographs of RAW cells in growth medium (GM, left panel) and in differentiation medium (DM, middle panel) containing RANKL (RANK-Ligand) and M-CSF (macrophage colony stimulating factor, right panel). The giant, multinucleate cells represent differentiated osteoclast-like cells. Recombinant SHH (100 nM) potentiates differentiation.
Figure 22:
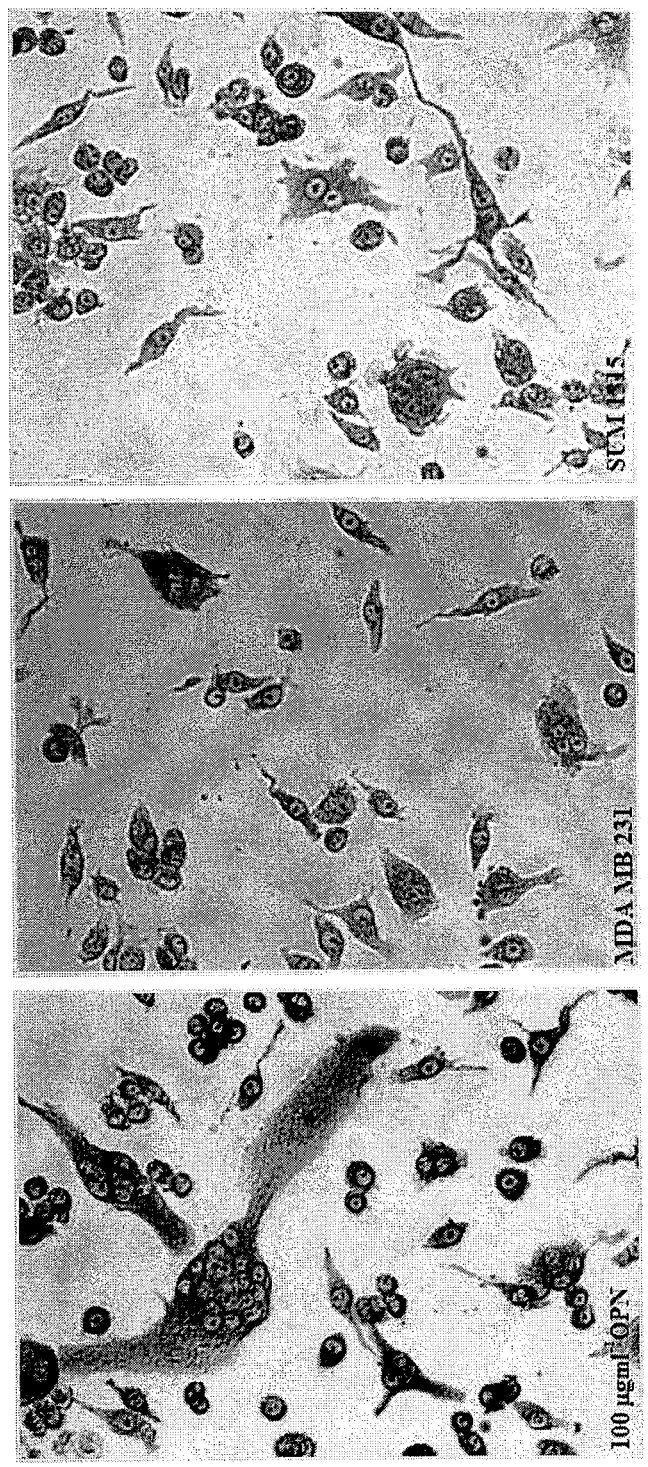
FIG. 22 shows photomicrographs of RAW cells in differentiation medium (DM) containing RANKL (RANK-Ligand) and M-CSF (macrophage colony stimulating factor) and osteopontin (OPN). Left panel: cells treated with OPN; center panel: cells treated with conditioned medium from MDA-MB-231 cells; right panel: cells treated with conditioned medium from SUM1315 cells. The giant, multinucleate cells represent differentiated osteoclast-like cells. Conditioned medium from the breast cancer cells, MDA-MB-231 and SUM 1315 potentiates differentiation.
Figure 23:
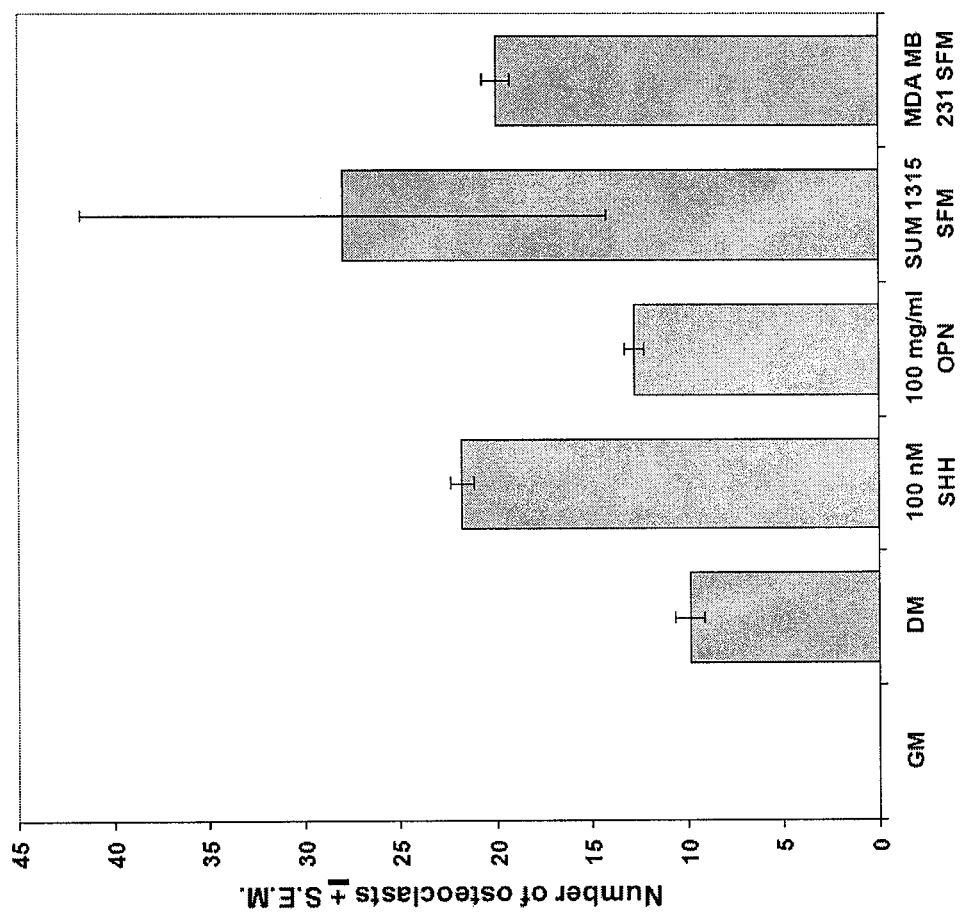
FIG. 23 shows a graph of osteoclast number treated with various compounds. Conditioned medium from the breast cancer cells, MDA-MB-231 and SUM 1315 potentiates osteoclast differentiation. DM represents differentiation medium containing RANKL (RANK-Ligand) and M-CSF (macrophage colony stimulating factor). Recombinant SHH (sonic hedgehog) and OPN (osteopontin) also stimulate osteoclast differentiation. TRAP stained cells containing 3 or more nuclei were scored as osteoclasts.

Effects of breast cancer cells-conditioned medium on the differentiation of osteoclasts were examined. Pre-osteoblastic RAW cells were cultured in the presence of M-CSF and RANKL. The effects of conditioned medium from breast cancer cells on osteoclast differentiation were also assessed (FIG. 20). Differentiated osteoclasts were stained for TRAP (tartarate-resistant acid phosphatase) activity (Kasugai, C., et al. (2009) Immunopharmacol Immunotoxicol 31, 103-107; Yan, T., et al. (2001) J Cell Biochem 83, 320-325; Srinivasan, S., et al. (2007) Ann N Y Acad Sci 1117, 51-61; Vincent, C., et al. (2009) J Bone Miner Metab 27, 114-119). The presence of giant cells containing multiple nuclei is diagnostic of osteoclast-like cells. FIG. 21 and FIG. 22 show that conditioned medium from the SUM1315 cells and the MDA-MB-231 cells potentiated the numbers of differentiated osteoclasts. SHH and OPN also promote osteoclast differentiation. The numbers of osteoclasts in these wells were counted. As seen in FIG. 23, the numbers of osteoclasts increased in the presence of medium conditioned by breast cancer cells. In sum, these data suggest that the breast cancer cells potentiate differentiation of osteoclasts.

Example 10

Hedgehog Pathway, Osteoclastogenesis and Osteolysis

Experimental Procedures

Cell lines—Human metastatic breast cancer cells, MDA-MB-231, were cultured in Dulbecco's Modified Eagle's Medium (DMEM/F12; Invitrogen, Carlsbad, Calif.), supplemented with 2 mM L-glutamine, 1 mM sodium pyruvate, 0.02 mM non-essential amino acids, 5% fetal bovine serum, FBS (Atlanta Biologicals, Norcross, Ga.), without antibiotics or antimycotics (cDME/F12). SUM1315 and SUM159 cells (DiMeo, T. A., et al. (2009) Cancer Res 69, 5364-5373) (Asterand, Detroit, Mich.) were cultured in DMEM/F12 supplemented with 5 mg/ml insulin, 5% FBS (Atlanta Biologicals) and either 10 ng/ml EGF or 1 ng/ml hydrocortisone, without antibiotics or antimycotics. The SUM1315 cells are derived from a metastasis in a patient with infiltrating ductal carcinoma; SUM159 cells were derived from a primary breast tumor with metaplastic carcinoma. RAW264.7 (ATCC, TIB 71) cells, a murine pre-osteoclastic line capable of differentiation and mineralization in culture (in presence of RANKL and MCSF), were grown in DMEM with L-glutamine (ATCC, 30-2002) supplemented with 10% FBS. A 2× differentiation medium (DM) was formulated for the RAW 264.7 cells comprising RAW264.7 growth medium supplemented with 20% FBS, RANKL (100 ng/ml)

and M-CSF (40 ng/ml) (Matsubara, T., et al. J Bone Miner Res 25, 1068-1076). Conditioned media was harvested from breast cancer cells and mixed in a 1:1 ratio with double strength differentiation medium to assess the effect on osteoclast differentiation. 1×DM was used as control or wherever SHH (R & D Systems, Minneapolis, Minn.) or OPN (R & D Systems) was used alone. The medium on the RAW264.7 cells was replenished every 48 hours. In order to assess the effect of secreted Hh ligands, the neutralizing 5E1 antibody was used (Developmental Studies Hybridoma Bank, at the University of Iowa, Iowa). The amount of 5E1 antibody used for the studies was determined following titration of the antibody with respect to its effects on osteoclast differentiation. Medium was supplemented with 5E1 (2.5 µg/ml) and was changed on alternate days until the end of the experiment. The effect of OPN on osteoclast activity was assessed by transfecting an OPN shRNA-expressing construct on day 6 post-induction of differentiation. Fresh DM was added the following day and cells were allowed to grow for another 12 hours before termination of experiment. GLI1 expression was silenced in the SUM1315 cells using shRNA targeting GLI1 into pSuperior. gfp+neo (Oligoengine, WA, USA). Silencing of OPN expression was done using OPN-targeting shRNA cloned into pSuper (Oligoengine)

Osteoclast differentiation and activity assays—Tartarate-resistant acid phosphatase (TRAP) assay was conducted for RAW 264.7 following the manufacturer's protocol (Sigma, St. Louis, Mo.). This assay was indicative of the extent of differentiation. OAAS plates (Osteogenic Core Technologies, Choongnam, Republic of Korea) were utilized to measure osteoclastic activity. RAW 264.7 cells (25×103) were inoculated in 48-well plates. Cells were treated with serum-free conditioned media from breast cancer cells or 100 nM SHH or 100 ng/ml OPN on the following day. Media was changed every two days and the experiments were terminated either on day 6 (day 7 for knockdown experiments, with transfections being done on the sixth day). At the completion, cells were detached with 5% sodium hypochlorite and the wells were observed under a Nikon Eclipse TS 100 microscope at 10× magnification. To test the inhibitory effect of cyclopamine on osteoclast differentiation and activity, RAW264.7 cells were cultured in differentiation medium supplemented with 20 µM cyclopamine (Sigma) dissolved in DMSO (Sigma). Medium containing cyclopamine was changed every 48 hrs. The percentage of area resorbed was calculated using the NIS-Elements BR. 3.1 software.

Western Blotting Analysis—Whole cell lysates were collected in NP-40 buffer (150 mM NaCl, 50 mM Tris, 1% NP-40). Total protein (30 µg) was resolved by SDS-PAGE gel and transferred to PVDF membranes. Membranes were immunoblotted overnight at 4° C. with antibodies to either SHH (Santacruz, Calif., USA) or IHH (Santacruz). Equal loading was confirmed with anti-β-tubulin (Cell Signaling, Danvers, Mass.). To assess OPN expression upon SHH treatment, 105 cells were grown in 6-well plates in the presence of SHH. After 24 hours the cells were lysed in NP-40 buffer and 30 µg of each experimental group assessed by immunoblotting. To assess for the expression of OPN, MMP9 and CTSK, at the end of Day 6 of differentiation, all the different experimental groups were kept in serum free medium for 24 hrs and both, the conditioned media and whole cell lysates were collected and immunoblotted using antibodies to either anti-mouse OPN (Millipore, Bedford, Mass.), or CTSK (SantaCruz Biotech). Equal loading was confirmed with anti-β-actin (Sigma) antibody. Secreted MMP9 (Santa Cruz Biotech) was assessed by loading equal quantity of protein from the serum-free conditioned medium. Corresponding HRP conjugated secondary antibodies were used for detection; blots were developed with SuperSignal enhanced chemiluminescence substrate (Pierce, Rockford, Ill.) and imaged using a Fuji LAS3000 imager. Detection and quantification of proteins was done using Fuji LAS 3000 apparatus and Multigauge V3.1 software (Fujifilm, Valhalla, N.Y.). Band intensities were measured in arbitrary Units (AU). Relative band intensity was obtained as a ratio of individual band intensity to that of the corresponding β-actin band.

Luciferase Assay—Cells were co-transfected with the OPN promoter construct, pGL3-OPNB and pSV-β-galactosidase (Promega) (Das, S., et al. (2009) J Biol Chem 284, 22888-22897). Empty pGL3 vector was used as control. Different concentrations of SHH ligand were added to the well the next day. Cells were lysed in Reporter Lysis buffer (Promega) 24 hrs post addition of SHH and both β-galactosidase assay and luciferase assays were done following manufacturer's protocol. Readings were normalized to β-galactosidase. Each parameter was studied in triplicate and the experiment repeated at least 3 times.

Quantitative RT-PCR (qRT-PCR)—cDNA was generated using High Capacity Reverse Transcriptase Kit (Applied Biosystems, Foster City, Calif.). Real time PCR was performed in two cycles using a BioRad iQ5 Real-Time Detection system (Bio-Rad, Hercules, Calif.): the first cycle of 95° C. for 10 mins followed by 40 repeats of the second cycle comprising 95° C. for 15 sec followed by 60° C. for 1 min. All reactions were done in triplicate. Transcript levels were normalized to GAPDH levels (dCT) which was used to calculate changes in gene expression (2-ddCT). In order to assess levels of OPN, CTSK, and MMP9 cells (50×103) were seeded in each well of 12-well plates. Following the experimental regime as described herein (for Osteoclast differentiation/activity) RNA was isolated using Trizol (Invitrogen) and assessed as described herein. The details of the primers used were as follows: OPN (Spp1; Mm00436767_m1), Matrixmetalloprotease 9 (MMP9; Mm00600163_m1), Cathepsin K (Ctsk; Mm00484036_m1), SHH (Hs00179843_m1), GLI1 (Hs01110766_m1), OPN (Hs00959010_m1), hGAPDH (Hs99999905_m1) and GAPDH (Mm99999915_g1).

Statistical analysis—Statistical differences between groups were assessed using the Mann-Whitney test, t-test or ANOVA, using GraphPad Prism 4 software. Statistical significance was determined if the analysis reached 95% confidence. The precise p values are listed in the corresponding figure legends. In all figures the error bars represent standard error of the mean (S.E.M.).

Hh Signaling Activates OPN Expression in Pre-Osteclasts

Figure 54:
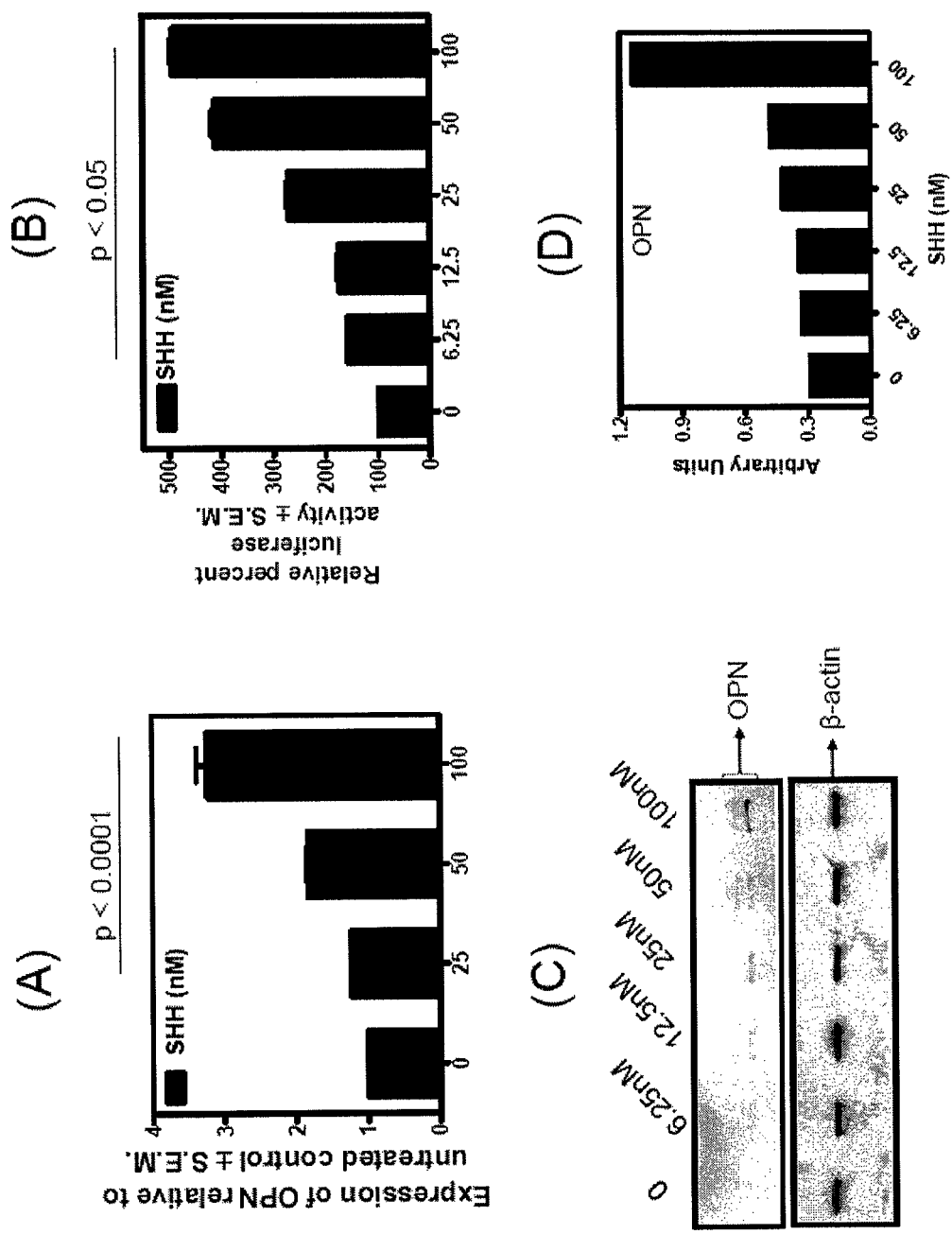
FIG. 54 (panel A) shows a graph depicting RAW264.7 cells treated with the indicated concentrations of recombinant SHH. The levels of OPN were assessed by real-time quantitative RT-PCR. Relative to untreated cells, the cells treated with SHH expressed significantly greater levels of OPN mRNA (p<0.0001).

In melanoma, activated Hh signaling culminates in the transcription of OPN by GLI1, the transcription factor of the Hh pathway. The ability of pre-osteoclastic RAW264.7 cells to regulate OPN in response to Hh ligands was assessed. As seen in FIG. 54 (panel A), the RAW264.7 cells show a dose-dependent significant (p<0.0001) increase in OPN mRNA levels in response to SHH. The increases in OPN mRNA levels are due to an increase in the activity of the OPN promoter in response to SHH (FIG. 54, panel B) indicating that OPN is under regulation of the Hh pathway in this system. This is also reflected in increased protein levels of OPN upon SHH treatment (FIG. 54, panel C and FIG. 54, panel D).

Figure 55:
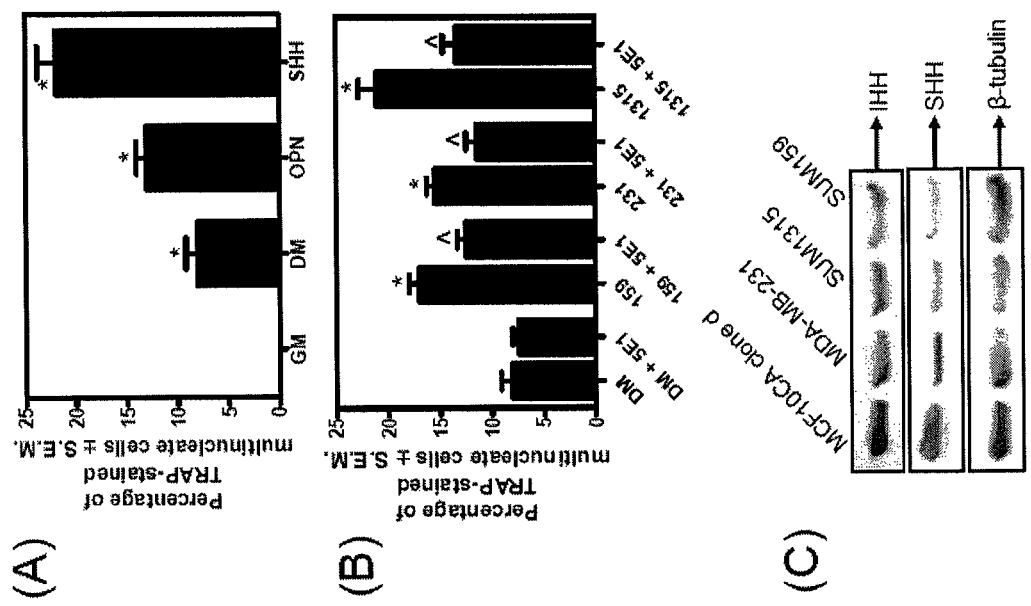
FIG. 55 (panel A) shows a graph depicting differentiation medium (DM) supports differentiation of RAW264.7 into osteoclasts. Supplementing DM with recombinant human OPN (100 ng/ml) or SHH (100 nM) significantly (* indicates p<0.005) increases the numbers of multinucleate (>3 nuclei) TRAP-positive cells.
Figure 55:
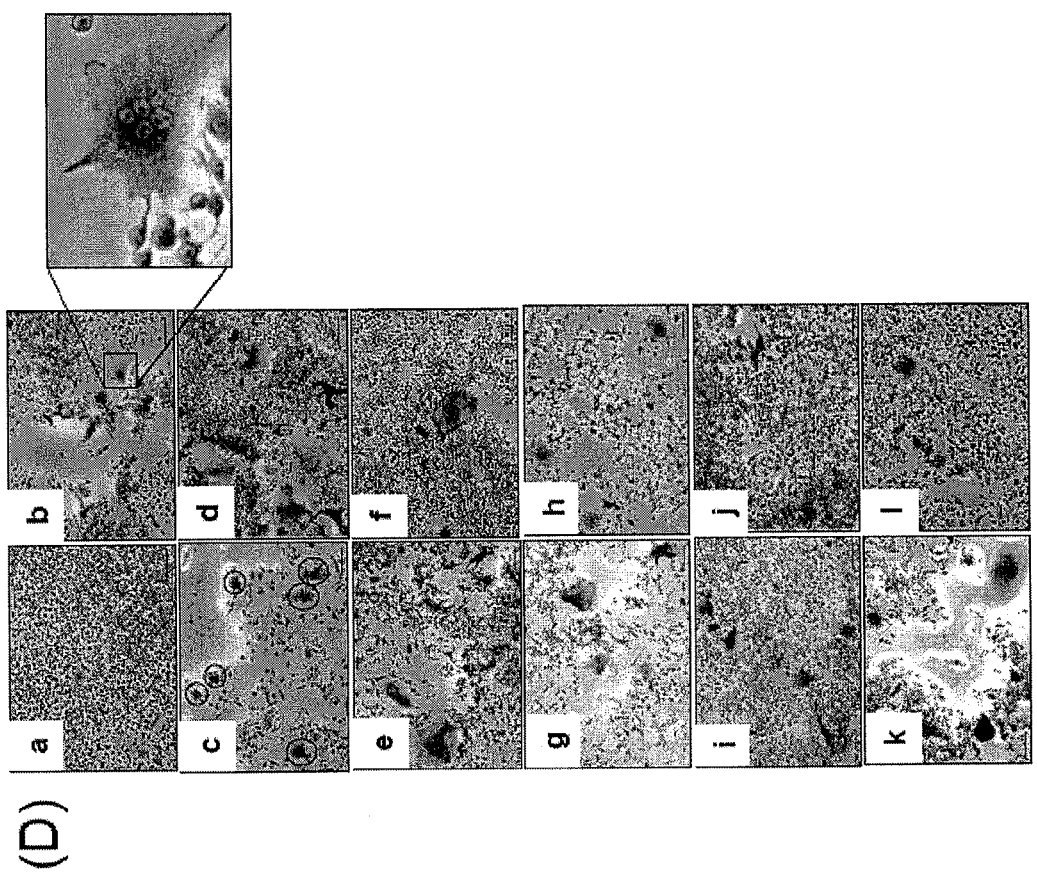

Breast Cancer Cells Enhance Osteoclast Differentiation and Activity Via Hh Signaling The Hh pathway may have a role in bone development and homeostasis, OPN is critical to osteoclast activity, specifically their motility (Sugatani, T., et al. (2003) J Biol Chem 278, 5001-5008). Since both, SHH and OPN are secreted molecules, the effects of recombinant SHH and OPN on influencing differentiation of RAW264.7 cells were evaluated. Osteoclast differentiation was scored by staining the cells for TRAP, an indication of differentiated osteoclasts. multinucleate (>3 nuclei per cell) TRAP-positive cells were scored. As seen in FIG. 55 (panel A), compared to differentiation medium (DM) alone, DM supplemented with SHH or OPN causes a significant ($p<0.005$) increase in the numbers of TRAP stained multinucleate cells, indicating that activation of the Hh pathway enhances osteoclast differentiation. Moreover, OPN-initiated signaling also appears to influence osteoclast differentiation.

Breast cancer cells potentiate osteoclast activity leading to increased osteolysis. This is brought about, in part, by factors secreted by the breast cancer cells (Kingsley, L. A., et al. (2007) Mol Cancer Ther 6, 2609-2617). In order to determine the effects of factors secreted by the breast cancer cells on osteoclast differentiation, the conditioned medium of breast cancer cells was mixed in equal proportion with double strength DM and assessed the effects on differentiation of the RAW264.7 cells was assessed. As seen in FIG. 55 (panel B), the conditioned medium from three breast cancer cell lines (MDA-MB-231, SUM159 and SUM1315) significantly increases ($p<0.01$) the formation of TRAP-positive multinucleate cells.

Breast cancer cells express SHH and IHH (FIG. 55, panel C). The Hh ligands are synthesized in cells and are secreted from the cells and are expressed at the exterior surface of the cell membrane or form a component of the secretome of the cells (Dillon, R., et al. (2003) Proc Natl Acad Sci USA 100, 10152-10157). In order to determine if Hh ligands produced by breast cancer cells influence osteoclast differentiation, the Hh ligand neutralizing antibody, 5E1, was added to the differentiation conditions. The 5E1 antibody is a Hh pathway antagonist that is widely used in Hh-related studies in developmental biology and cancer. The 5E1 antibody blocks binding of all three mammalian Hh ligands to PTCH, thereby inhibiting Hh signaling. Thus, using 5E1 provides a tool to effectively block Hh signaling. As seen in FIG. 55 (panel B) and FIG. 55 (panel D), the addition of 5E1 significantly ($p<0.05$) diminishes the ability of the breast cancer cell conditioned medium to influence osteoclast differentiation. This suggests that Hh ligands secreted by breast cancer cells potentiate osteoclast differentiation.

Figure 56:
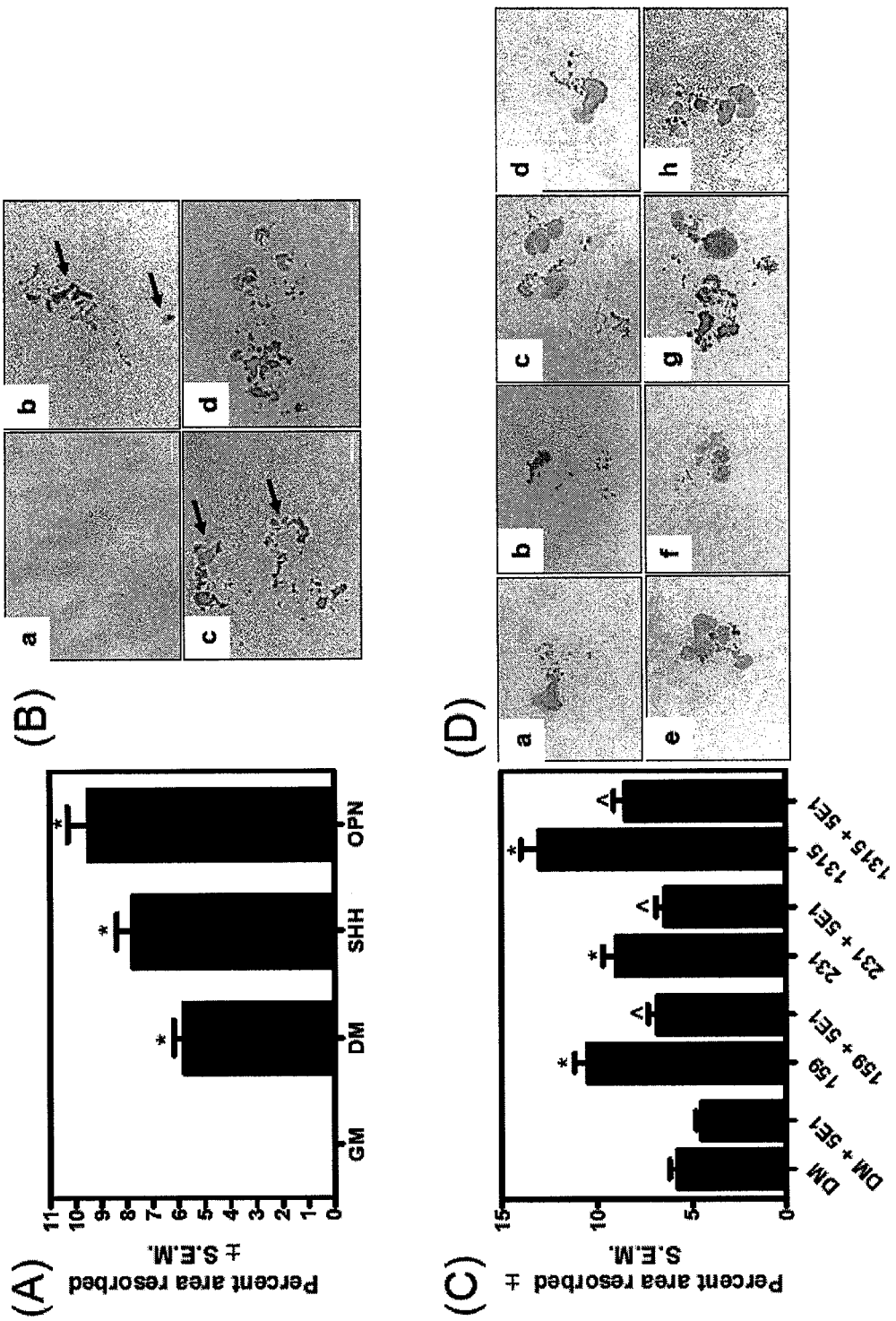
FIG. 56 (panel A) shows a graph depicting recombinant human OPN (100 ng/ml) and SHH (100 nM) significantly (* indicates p<0.001) increases the resorption activity of the differentiated osteoclasts. RAW254.7 cells were induced for differentiation on OAAS plates. At the end of the assay the area resorbed was quantified.

In order to determine the effects of Hh signaling on osteoclast activity, the osteoclasts on plates were cultured coated with a mineralized bone matrix. The area resorbed was estimated. As seen in FIG. 56 (panel A) and FIG. 56 (panel B), the DM supplemented with SHH or OPN notably enhances ($p<0.001$) osteoclast activity ($p<0.05$). Further, the conditioned medium from all three breast cancer cells enhances the ability of osteoclasts to resorb the matrix (FIG. 56, panel C and FIG. 56, panel D). While the medium from all three breast cancer cells lines stimulates osteoclasts, ($p<0.01$), the medium from SUM1315 cells maximally potentiated osteoclast activity, more than the MDA-MB-231 and SUM159 cells. Conversely, depleting the Hh ligands from the secretome of the breast cancer cells using 5E1 antibody compromises its ability to resorb the matrix. Thus, overall the results indicate that the Hh ligands secreted by breast cancer cells augment osteoclast differentiation and activity.

Activation of Hh Signaling is Related to Osteoclast Activity

Figure 57:
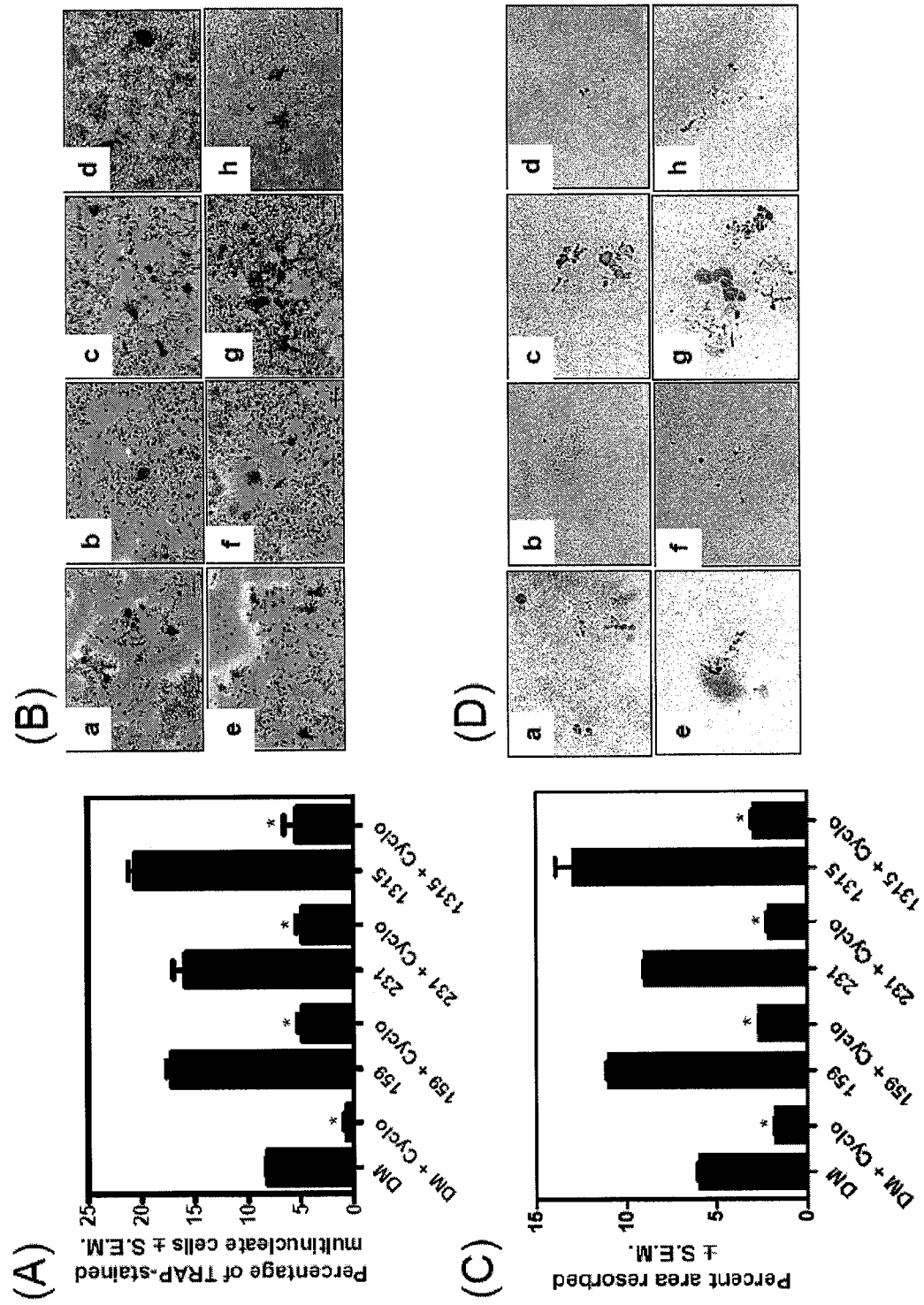
FIG. 57 (panel A) shows a graph depicting inhibition of Hh signaling in osteoclasts by the Smoothened (SMOH) inhibitor, cyclopamine (20 μM) significantly (*p<0.0001) compromises their ability to differentiate. RAW264.7 cells were cultured under differentiating conditions in the presence of breast cancer cell-conditioned medium/and cyclopamine (20 μM).

In order to assess the role of Hh signaling in osteoclasts in determining their maturation and activity, the differentiation medium was supplemented with the SMOH inhibitor, cyclopamine. As seen in FIG. 57, cyclopamine significantly ($p<0.0001$) reduced the ability of DM to elicit differentiation (FIG. 57, panel A and FIG. 57, panel B) of the preosteoclasts into TRAP-positive, multinucleate osteoclasts, without impacting their viability. The ability of breast cancer cell-conditioned medium to potentiate differentiation and resorptive activity of the osteoclasts was also remarkably compromised in presence of cyclopamine (FIG. 57, panel A—57, panel D). Thus, these results suggest that activation of Hh signaling is an essential event for osteoclast maturation and activity.

Figure 58:
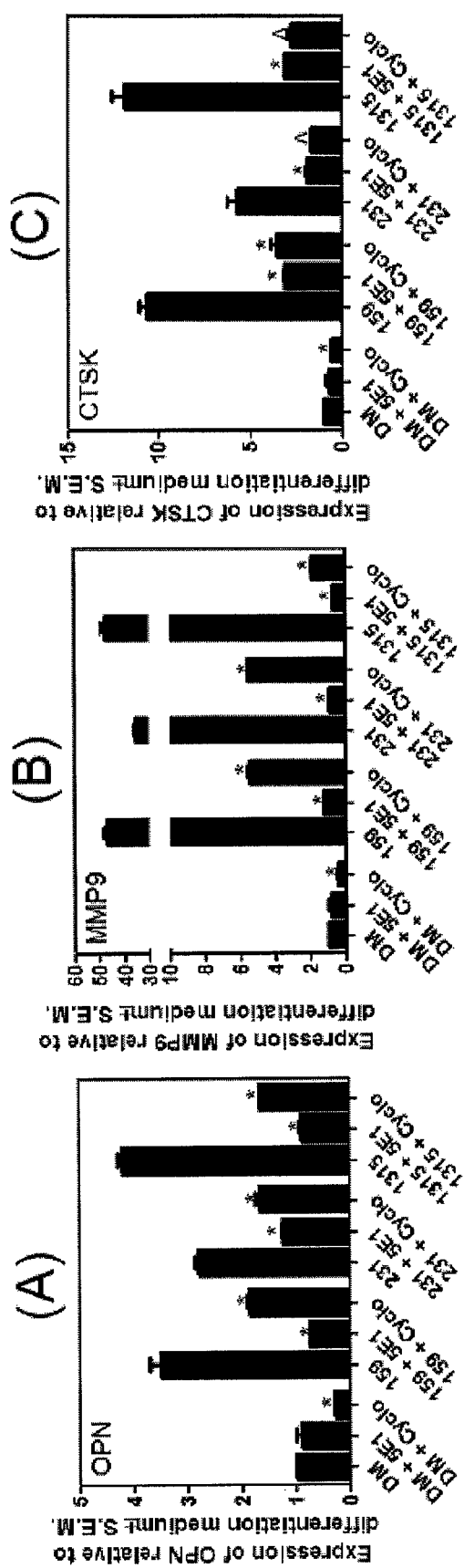
FIG. 58 (panel A), FIG. 58 (panel B), and FIG. 58 (panel C) show graphs depicting the levels in treated cells of OPN, MMP9, and Cathepsin K (CTSK), respectively. The levels were assessed by real-time quantitative RT-PCR and normalized to GAPDH. The levels of gene expression are represented relative to the expression in DM alone. Three breast cancer cell lines: MDA-MB-231, SUM159 and SUM1315 were evaluated. Neutralizing antibody 5E1 significantly decreased levels of OPN (* p<0.01), CTSK (*p<0.001) and MMP9 (*p<0.0001). Cyclopamine significantly decreased levels of OPN (* p<0.0001), CTSK (*p<0.0001) and MMP9 (*p<0.0001; ^p<0.005).
Figure 58:
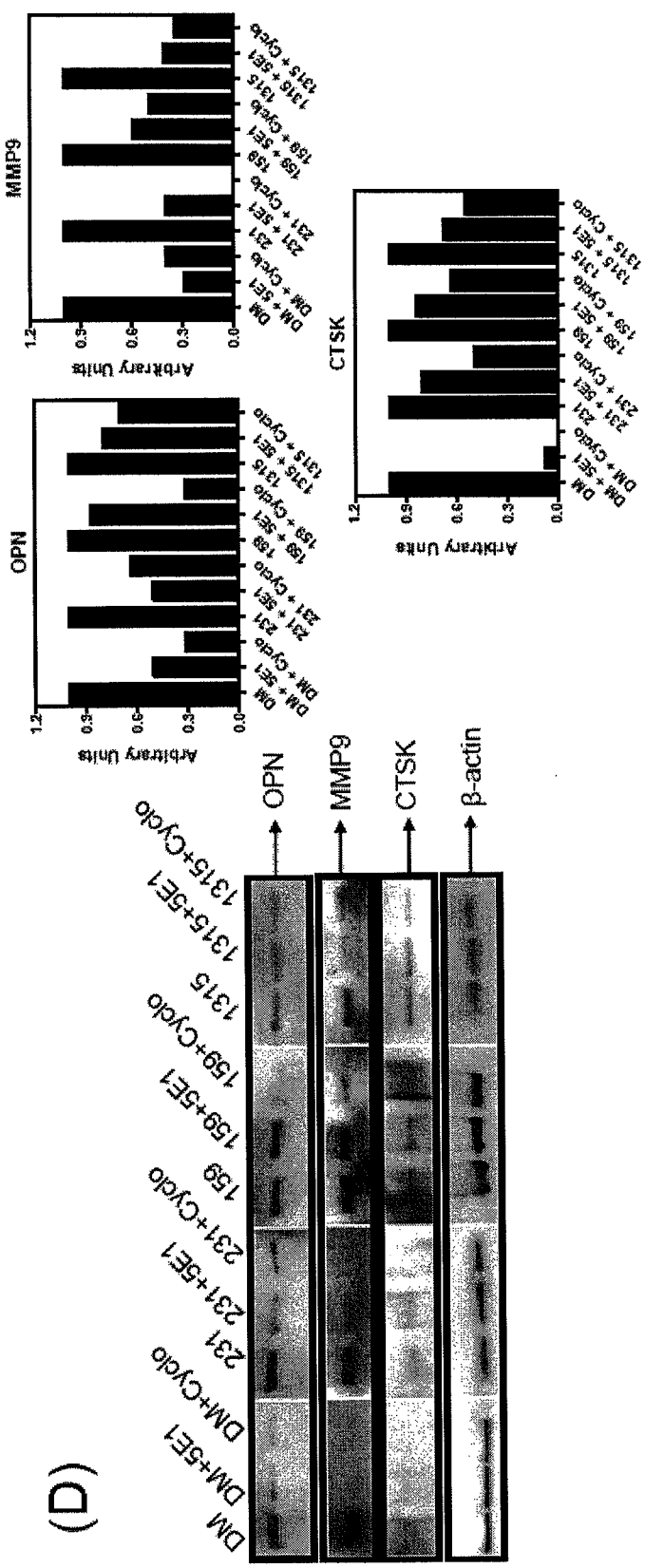

Breast Cancer Initiated Hh Signaling Activates OPN, CTSK and MMP9 Expression by the Osteoclasts While OPN enhances osteoclast motility and overall activity, activation of osteoclasts is functionally dictated by the expression of proteases such as MMP9 and cathepsin K (CTSK). Thus, in order to assess if Hh signaling initiated by breast cancer cells influences the ability of the differentiated osteoclasts to express these key molecules, the expression of OPN, MMP9 and CTSK was assessed by a real-time quantitative PCR. As seen in FIG. 58 (panels A-C), compared to DM alone, conditioned medium from breast cancer cells increases the expression of OPN, MMP9 and CTSK. While neutralization of Hh ligands by the 5E1 antibody from the conditioned medium of SUM159 and SUM1315 cells caused a severe reduction ($p<0.001$) in the expression of OPN by osteoclasts, the MDA-MB-231 cells showed a moderate, but significant ($p<0.01$) decrease in OPN expression. The decrease in CTSK and MMP9 expression by the osteoclasts was also statistically significant ($p<0.001$ & $p<0.0001$ respectively) in presence of the 5E1 antibody, suggesting that the Hh ligands secreted by the breast cancer cells play a critical role in upregulating the expression of OPN, CTSK and MMP9. Hh signaling in the pre-osteoclasts was inhibited by supplementing DM with cyclopamine. As seen in FIG. 58, panel A—58, panel D, cyclopamine significantly reduces the expression of OPN, MMP9 and CTSK by the osteoclasts. The overall decrease in the expression of OPN, MMP9 and CTSK is likely due to an overall negative impact on differentiation as a result of interfering with Hh signaling in the pre-osteoclasts. The data suggests that inhibiting Hh signaling in the pre-osteoclasts makes them refractory to the stimulative effects provoked by breast cancer cells.

Hh Signaling-Initiated OPN Expression in Osteoclasts is Essential for the Expression of MMP9 and CTSK Hh signaling transcriptionally promotes the expression of OPN (FIG. 54). In order to determine if the transcriptional activation of OPN is essential for the expression of MMP9 and CTSK by the osteoclasts in response to breast cancer cell-derived Hh ligands, the expression of OPN from the osteoclasts was abrogated using RNA interference on Day 6, after the osteoclast differentiation is complete.

Figure 59:
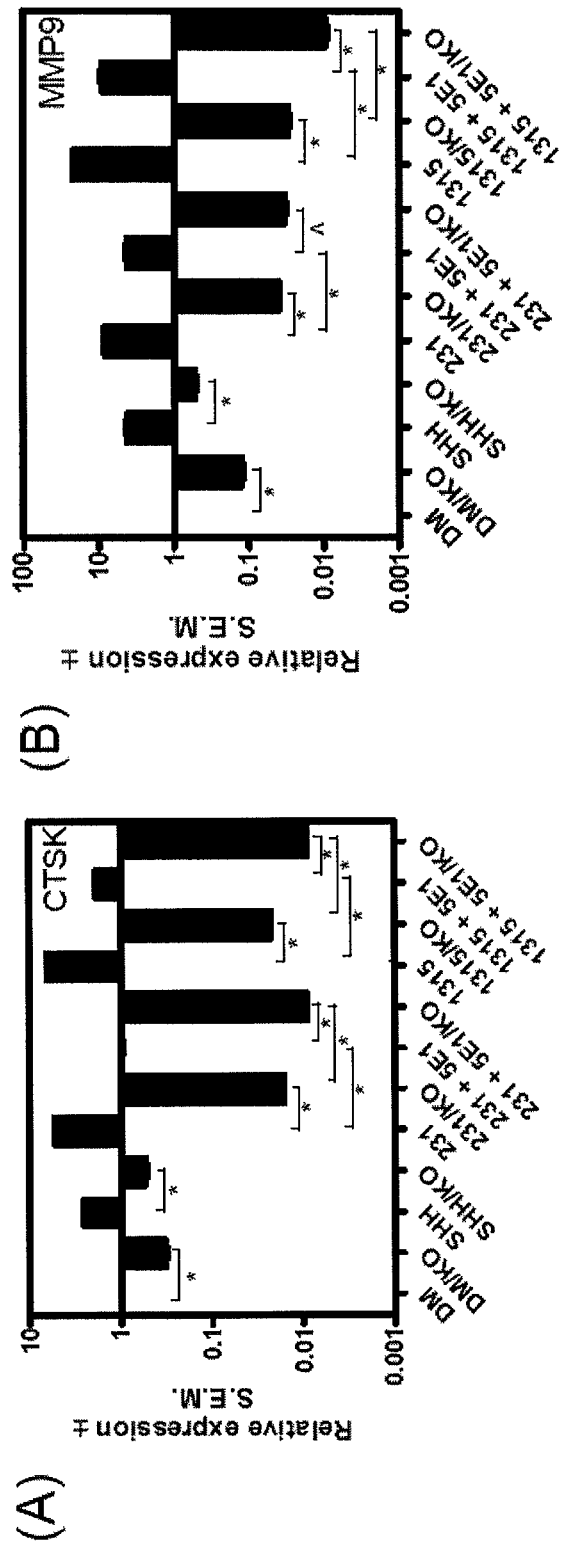
FIG. 59 (panel A) shows a graph depicting relative in various treated cells.
Figure 59:
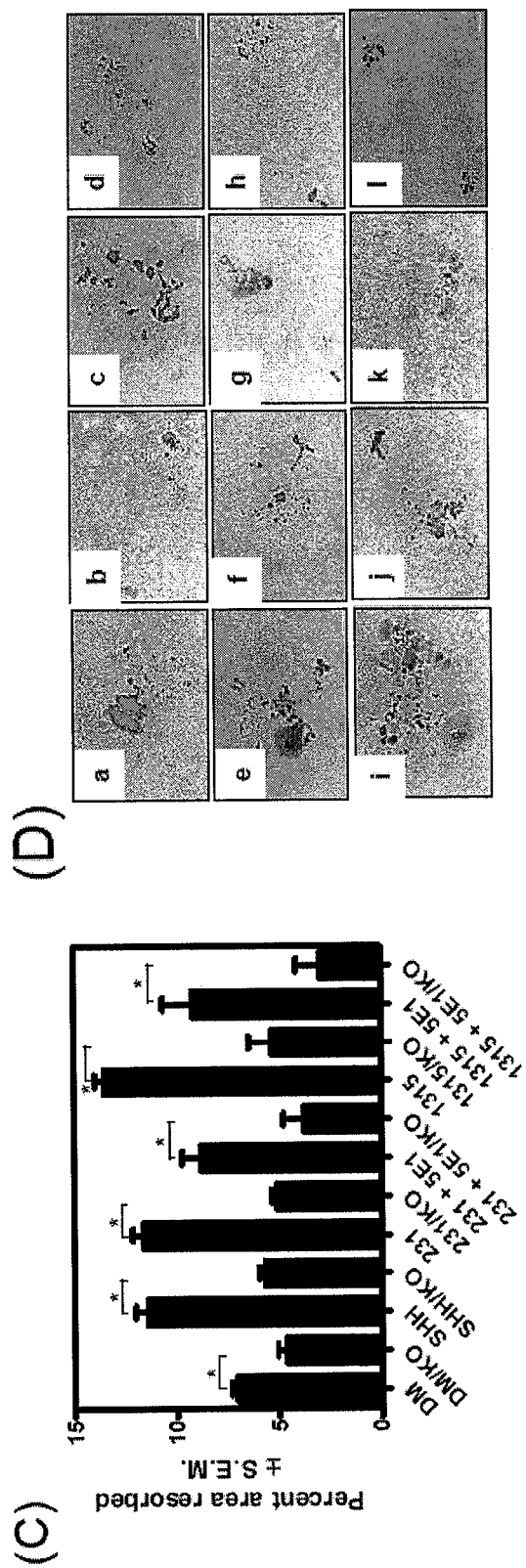

Silencing the expression of endogenous OPN in osteoclasts decreases their ability to express Cathepsin K and MMP9 in response to breast cancer cell conditioned media. RAW254.7 cells were cultured under differentiating conditions for 6 days to allow for complete differentiation. Differentiation conditions included recombinant SHH (100 nM) or conditioned media from breast cancer cells (MDA-MB- 231, SUM159 and SUM1315) with or without the 5E1 antibody (2.5 µg/ml). One set of osteoclasts was silenced on day 6 for OPN expression (KO) using shRNA targeting OPN cloned into pSuper. The expression of FIG. 59 (panel A), Cathepsin K (CTSK) FIG. 59 (panel B), and MMP9 was assessed by real-time quantitative RT-PCR on day 7. The levels of gene expression are represented relative to the expression in DM alone. The extent of CTSK expressed by the groups silenced for OPN is significantly lower (*p<0.0001) compared to their respective control (OPN-expressing) for all groups tested. For both breast cancer cell lines tested, the extent of CTSK expression in the 5E1/KO group is significantly lower (*p<0.0001) than the 5E1 alone supplemented group. Relative to the respective controls, the levels of MMP9 in the groups silenced for OPN is significantly lower (*p<0.0001) for all groups tested. Further, the extent of MMP9 expression in 231+5E1/KO is significantly lower (^ p=0.0002) than the 231+5E1 group but not the 231/KO group. Similarly the 1315+5E1/KO group expresses significantly (p<0.0001) lower levels of MMP9 relative to the 1315+5E1 group and the 1315/KO group. FIG. 59 (panel C), The resorption activity was assessed by conducting the differentiation as described above on OAAS plates, followed by quantitation of the resorbed area as described above. The extent of resorption expressed by the groups silenced for OPN is significantly lower (*p<0.005) compared to their respective control (OPN-expressing) for all groups tested. For both breast cancer cell lines tested, the extent of resorption in the 5E1/KO group is significantly lower (*p<0.05) than the 5E1 alone supplemented group. The difference between the 5E1/KO group was not statistically different relative to the corresponding KO group.

As seen in FIG. 59, silencing OPN in the osteoclasts, significantly decreased the expression of CTSK and MMP9 in response to DM alone. The absence of OPN made the osteoclasts refractory to the stimulative effects of SHH. Abrogating OPN from the osteoclasts also made the osteoclasts non-responsive to the effects of the conditioned media from MDA-MB-231 and SUM1315 cells. This was seen as a marked reduction in the expression of both, CTSK and MMP9. The most remarkable decrease was seen in the response of osteoclasts that were silenced for OPN expression and exposed to differentiation medium that was depleted of the Hh ligands. Thus, overall, the results implicate a role for Hh ligand initiated osteopontin expression in osteoclasts in influencing the expression of proteases, CTSK and MMP9. The expression of OPN by the osteoclasts was also critical for their ability to resorb bone matrix. As seen in FIG. 59 (panel C) and 59 (panel D), abrogating OPN expression from osteoclasts notably compromised (p<0.005) their ability to resorb bone in response to DM alone or DM supplemented with SHH. Even in the presence of conditioned medium from the MDA-MB-231 and the SUM1315 cells, the osteoclasts silenced for OPN expression were compromised (p<0.005) for their resorptive ability. The decrease in resorption in response to depletion of the Hh ligands from the breast cancer cell conditioned medium was further accentuated when the osteoclasts were unable to express OPN. Cumulatively, the data suggests that the enhanced differentiation and resorptive ability of osteoclasts in response to Hh signaling initiated by breast cancer cells is due to the upregulated OPN expression by the osteoclasts. OPN is important to the osteoclast differentiation associated expression of proteases and resorptive ability.

Hh Signaling in the Breast Cancer Cells Ameliorates their Ability to Influence Osteoclast Differentiation and Activity While Hh ligands expressed by the breast cancer cells clearly play a role in influencing osteoclast differentiation and activity, the effect of SUM1315 cells that have been abrogated for the expression of the transcription factor, GLI1, was assessed.

RAW264.7 cells were cultured for 6 days in presence of double strength DM supplemented (1:1) with medium from SUM1315 breast cancer cells. Osteoclast differentiation was assessed by TRAP assay and the activity was assessed by culturing the osteoclasts as described above, on OAAS plates. Relative to untransfected SUM1315 cells and SUM1315 cells transfected with a scrambled control (scr1 (pSuperior.gfp+neo) and scr2 (pSuper)), the medium from the cells silenced for GLI1 expression (KD2) and OPN (OPNi) was significantly less efficient in inducing FIG. 60 (panel A), osteoclast differentiation (*p=0.012 and p=0.0049 respectively) and FIG. 60 (panel C), resorption activity (p=0.0001 and p=0.0005 respectively). Images represent (FIG. 60, panel B) differentiation and (FIG. 60, panel D) resorption. Differentiation and resorption conditions included medium from (a) control SUM1315 cells or (b) cells transfected with vector control (scr1: pSuperior.egfp-.neo) or (c) transfected with shRNA targeting GLI1 or (d) transfected with pSuper vector control (scr2) or (e) transfected with shRNA targeting OPN.

Figure 60:
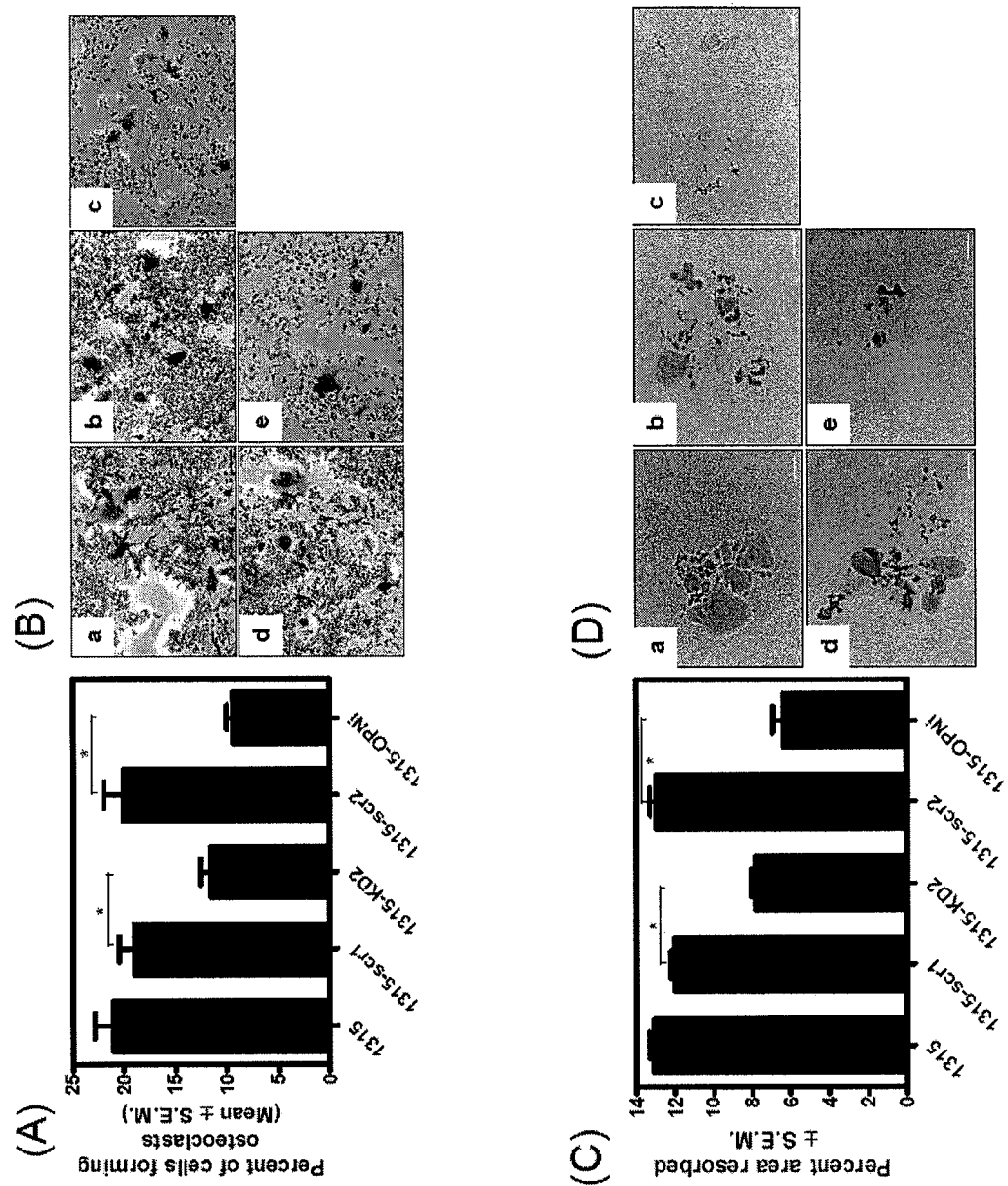
FIG. 60 (panel A) shows a graph depicting percent cells forming osteoclast for various treated cells (*p=0.012 and p=0.0049 respectively).

As seen in FIG. 60, conditioned media from breast cancer cells silenced for GLI1 expression was deficient in inducing differentiation (p<0.05) (FIG. 60, panel A) and activity (p=0.0001) (FIG. 60, panel B) of osteoclasts. Abrogating GLI1 expression in the breast cancer results in a significant decrease (p<0.05) in the expression of OPN and SHH. OPN expression by breast cancer cells enhances osteoclast differentiation and activity. Hh ligands expressed by the breast cancer cells play a vital role in communicating with the osteoclasts. In order to directly determine the role of OPN expressed by the SUM1315 cells, the expression of OPN was silenced and assessed the effect of the conditioned media on osteoclast differentiation and activity was assessed. Abrogating OPN expression from the breast cancer cells significantly diminished their ability to influence osteoclast differentiation (p<0.01) and activity (p=0.0005) (FIG. 60, panel A—60, panel D).

DISCUSSION

Metastases in the bone occur in 60-80% of advanced breast cancer patients. The bone metastases in breast cancer are predominantly osteolytic, characterized by vigorous bone resorption (bone breakdown). The most common mode of transport of breast cancer cells from the breast to bone is through the vertebral-venous system that allows breast cancer cells to come into contact with the axial skeleton, including the ribs, spine, pelvis, and proximal humerus and femur, which is the main distribution of bone metastases in breast cancer patients. Once malignant cells have migrated to the bone, their ability to colonize is facilitated by various growth factors that are secreted by the bone. The crosstalk between tumor cells and the microenvironment promotes a vicious cycle of tumor growth and bone loss that perpetuates the formation of bony lesions. When the bone is lysed by osteoclasts, the factors released stimulate malignant tumor growth, which then increases the number of cells available to release the factors that stimulate osteoclastic activity, so more bone is resorbed and the cycle continues.

Factors, such as MMPs, chemokine receptor 4 (CXCR4), vascular endothelial growth factor (VEGF), and connective tissue growth factor (CTGF) target metastatic tumor cells to bone and facilitate survival within the bone microenvironment. Physical factors within the bone microenvironment, including hypoxia, acidic pH, and extracellular Ca2+, and bone-derived growth factors, such as TGF-β and IGFs, activate tumor expression of osteoblast-stimulatory factors, like vascular endothelial growth factor (VEGF), platelet-derived growth factor (PDGF), and Endothelin (ET-1) (Yin, J. J., et al. (2003) Proc Natl Acad Sci USA 100, 10954-10959. Maturation of osteoblasts is coupled with their release of RANKL that can stimulate osteoclastogenesis. Breast cancer cells also express osteoclast-stimulatory factors, such as PTHrP, TGF-β, and IL-11. In fact, expression of IL-11 and OPN by breast cancer cells has been found to be critical for the osteolytic activity of breast cancer cells.

The Hh signaling pathway involves the binding of a Hh ligand to the receptor PTCH, thereby relieving its inhibitory effect on SMOH, permitting transduction of the Hh signal to intracellular components, culminating in transcriptional activation of downstream genes like GLI1. The Hh ligands were initially thought to be a transmembrane, non-diffusible signal for neighboring cells. Further research revealed that the Hh ligands are secreted after being post-translationally modified and participate in short- and long-range signaling. Data provided herein shows that Hh ligands expressed by breast cancer cells can initiate a crosstalk directly with osteoclasts and promote osteoclast differentiation (assessed by multinucleate cells showing TRAP activity) and resorption activity accompanied by increased expression of OPN, CTSK and MMP9. TRAP, a glycosylated monomeric metalloenzyme, is highly expressed in osteoclasts and has been implicated in the detachment of cells necessary for initiating cell migration. It is upregulated during osteoclastogenesis along with CTSK and as such used as a histochemical marker for differentiated osteoclasts. Multinucleation, an essential step in osteoclast differentiation, is a prerequisite for its efficient bone resorbing ability. Mononuclear osteoclasts fuse repeatedly to form giant multinucleated osteoclasts which after the polarization of the membrane and organization of the cytoskeleton result in a mature bone-resorbing osteoclast.

The bone resorbing ability of mature osteoclast has been attributed to cysteine proteinase CTSK and a host of different matrix metalloproteinases, including MMP9, MMP 13 and MMP14. CTSK with its ability to cleave the native helix of collagen at multiple sites has been implicated as the molecule for matrix solubilisation whereas collagenolysis-enhancing MMP 9 has been found to be critical for osteoclast migration. Enhanced osteoclast differentiation and activation elicited by breast cancer cells was concomitant with significantly increased expression of OPN and the cysteine protease CTSK and MMP9. Moreover, Hh ligands expressed by the breast cancer cells play a critical role in inducing changes in the osteoclasts, since neutralizing the activity of these ligands from the conditioned medium of the breast cancer cells reduces the efficacy of the breast cancer cells to elicit osteoclast differentiation and resorptive activity. Hh ligands expressed by breast cancer cells are also essential for the production of OPN, CTSK and MMP9 by the osteoclasts since squelching them with the 5E1 antibody resulted in a significant decrease in expression.

As such, the data shows that OPN expression is upregulated as a downstream event of Hh signaling initiated by the Hh ligands expressed by the breast cancer cells. OPN is particularly abundant at the attachment sites of osteoclasts and is essential for reorganization of the osteoclast cytoskeleton for osteoclast motility. It is not only responsible for activating the bone resorptive ability of osteoclasts but also for their migration. Further, OPN enhances the differentiation of pre-osteoclasts to osteoclasts, resulting in upregulated expression of CTSK and MMP9. Consequently, resorptive activity of the osteoclasts is also negatively impacted by the inability to express OPN. While Hh signaling in osteoclasts influences their activity, the data reveals that Hh signaling in breast cancer cells is also vital to their ability to elicit osteoclast activation. OPN expressed by breast cancer cells also enhances osteoclast activity. Overall, the study indicates a causal role for Hh signaling in promoting breast cancer cell-mediated osteolyic activity.

Figure 61:
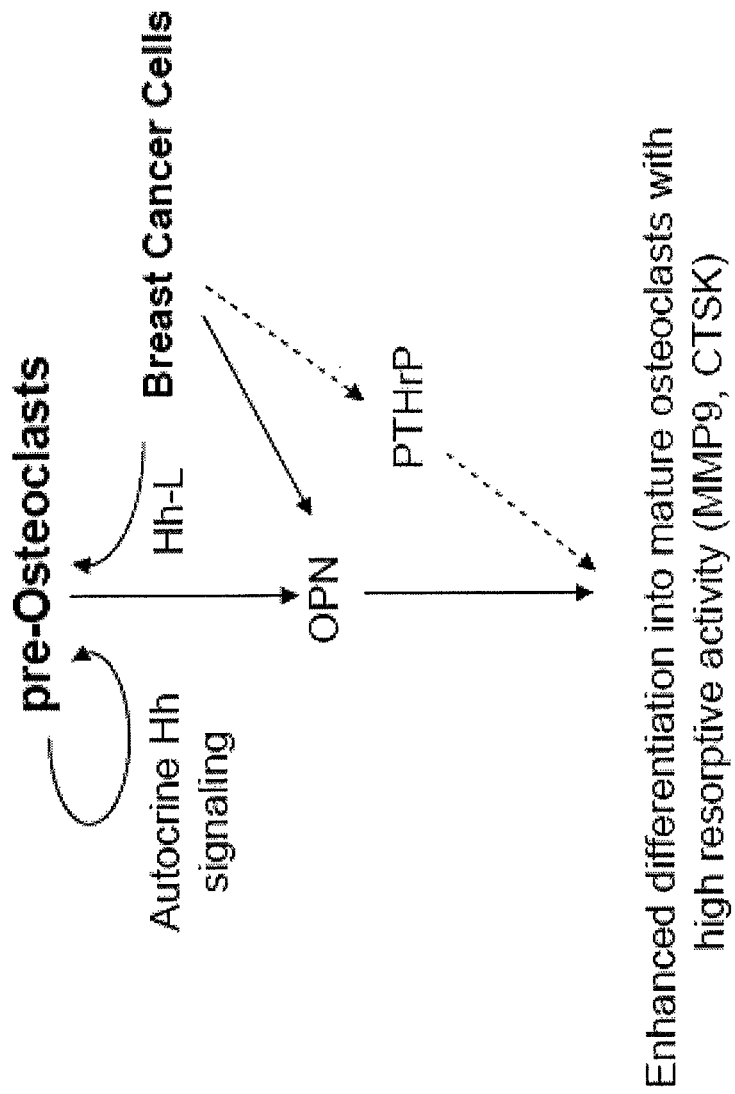
FIG. 61 shows a schematic diagram depicting expression of Hh ligands (Hh-L) in breast cancer cells that activate Hh signaling in preosteoclasts. Breast cancer cells also express OPN that can initiate signaling in pre-osteoclasts. The pre-osteoclasts respond to Hh-L secreted by the breast cancer cells as well as autocrine Hh signaling by expressing OPN and differentiating into mature osteoclasts (characterized by expression of MMP9 and CTSK) with increased resorptive activity. Breast cancer cells also express PTHrP in response to Hh signaling. Thus, overall, Hh signaling-mediated expression of factors such as OPN and PTHrP cumulatively result in enhanced differentiation and resorptive activity of osteoclasts. The dotted lines denote implications from previously published literature, whereas the solid lines depict data from the work described herein.

Hh ligands expressed by breast cancer cells act as conversational molecules and can directly mediate a paracrine crosstalk with osteoclast precursors leading to osteoclastogenesis and the induction of resorptive activity. Osteoclasts respond to the stimulus provided by breast cancer cells by activating Hh signaling and upregulating OPN expression that is vital to their differentiation and resorptive activity. Thus, it is likely that the accumulation of OPN and PTHrP in the bone microenvironment in response to Hh signaling can potentially have a cumulative effect on the osteoclasts resulting in their activation (FIG. 61). Hh signaling determines the potency of breast cancer cells to induce osteoclastogenesis and resorption. Further, inhibiting Hh signaling in osteoclasts resulted in significantly reduced osteolytic activity. Hh inhibitors are in clinical trials to test efficacy in combating several malignancies, including breast cancer. The data demonstrate that these inhibitors can also have an impact on osteoclasts. Specifically, inhibiting the Hh signaling in pre-osteoclasts using cyclopamine hampered the ability of pre-osteoclasts to respond to the stimulatory effects of the breast cancer cells, indicating that Hh signaling is vital to osteoclast activity.

Example 11

Hedgehog Signal in Tumor Cells Facilitates Osteoblast-Enhanced Oteolytic Metastatses In this study, the role of the Hh pathway in the crosstalk between tumor cells and osteoblasts is investigated. Tumor cells are shown to facilitate osteoblast differentiation and deposition of mineralized matrix via Hh signaling. These differentiated osteoblasts express RANKL, that together with OPN and PTHrP tilt the balance in favor of the osteoclasts. As such, these studies highlight the importance of the delicate balance between the activities of osteoblasts and osteoclasts and bring forth the importance of Hh signaling as an important attribute of the tumor cells' ability to cause osteolytic metastases.

Materials and Methods

Cell lines—Human fetal osteoblasts, hFOB 1.19 (ATCC, CRL-11372) cells were cultured in Dulbecco's Modified Eagle's Medium (DMEM/F12; Invitrogen, Carlsbad, Calif.), supplemented with 2 mM Lglutamine, 1 mM sodium pyruvate, 0.02 mM nonessential amino acids, 5% FBS (Atlanta Biologicals, Norcross, Ga.), without antibiotics or antimycotics (DMEM/F12). MC3T3-E1 subclone 14 (ATCC, CRL-2594) murine pre-osteoblast cells capable of differentiation and mineralization in culture (these lines exhibit high levels of osteoblast differentiation after growth in ascorbic acid and 3 to 4 mM inorganic phosphate) were maintained in alpha Minimum Essential Medium (αMEM) (Mediatech, Herndon, Va.) and 10% FBS but devoid of ascorbic acid. RAW 264.7 (ATCC, TIB 71) cells, a murine preosteoclastic line capable of differentiation and mineralization in culture (in presence of RANKL and M-CSF) were grown in DMEM with L-glutamine (ATCC, 30-2002). MDA-MB-231 human metastatic breast cancer cells, SUM1315 (derived from a metastasis in a patient with infiltrating ductal carcinoma), SUM159 cells (derived from a primary breast tumor with metaplastic carcinoma) and MDA-MB-435 (435) cells were cultured as described herein. The generation and culture conditions of 435 cells stably silenced for OPN (OPNi) or GLI1 (KO1 and KO4) is previously described (Das S, et al. The hedgehog pathway transcription factor GLI1 promotes malignant behavior of cancer cells by up-regulating osteopontin. J Biol Chem 2009; 284:22888-97).

Induction of osteoblastic and osteoclastic differentiation—In order to test the effect of conditioned medium from the tumor cells on osteoblast differentiation, a double-strength differentiation medium (DM) was formulated for MC3T3 E1 Sc-14 cells. It comprised αMEM, 20% FBS, 50 µg/ml ascorbic acid and 20 mM β-glycerophosphate. Conditioned media and the double-strength DM were mixed in a 1:1 ratio. 1×DM was used as control. Similarly a double-strength differentiation medium was formulated for RAW 264.7 cell lines. It consisted of 20% FBS, 50 ng/ml of RANKL and 20 ng/ml of M-CSF added to the growth medium. Conditioned media from the tumor cells was mixed 1:1 with the double-strength DM. 1×DM was used as control. Osteoblast differentiation was assessed by alkaline phosphatase (ALP) activity assay in the perspective of total phosphatase. The functional assessment of osteoblast mineralization was quantified by staining with Alizarin Red S and scoring the number of mineralized nodules.

Apoptosis detection—MC3T3 cells were grown under differentiation conditions along with conditioned media from tumor cells for 21 days with media being changed every 3rd day. At the end of 21 days apoptosis was assayed using the In Situ Cell Death Detection Kit (Roche, Indianapolis, Ind.) following the manufacturers' protocol for initial TUNEL staining. Cells were further stained with DAPI (Vectashield, H-1200, Vector Laboratories, Burlingame, Calif.) and phalloidin coupled with AlexaFluor 555 (Molecular Probes, Invitrogen) to visualize the nuclei and cytoskeleton respectively. The latter staining imparted context to the TUNEL staining. Cells were visualized under the Nikon TE2000 microscope and TUNEL positive cells were counted and expressed as a percentage of total cells in each field of view.

Western Blotting Analysis—was Performed as Described Herein

Studies with Hh inhibitor, cyclopamine—Serum-free conditioned medium (SFM) harvested from ~3.0×106 cells after 24 hours was assayed for OPN by immunoblotting. To test the inhibitory effect of cyclopamine on the Hh pathway cells were cultured in DMEM supplemented with 0.5% FBS and treated for the indicated time intervals with DMSO (vehicle control) or cyclopamine (Sigma, St. Louis, Mo.).

Luciferase Assay—was Performed as Described Herein.

Quantitative RT-PCR (qRT-PCR)—cDNA was generated using High Capacity Reverse Transcriptase Kit (Applied Biosystems, Foster City, Calif.). Real time PCR was performed using a BioRad iQ5 Real-Time Detection system (Bio-Rad, Hercules, Calif.). All reactions were done in triplicate. OPN transcript levels were normalized to GAPDH levels (dCT) which was used to calculate changes in OPN expression (2-ddCT). To analyze the effect of cyclopamine treatment on OPN expression untreated samples were set as calibrator (control) and compared to their respective treated samples. The primers used included Sppl (OPN) (Mm 00436767_m1); Bglap (osteocalcin) (Mm 01741771_g1); IBSP (Mm 00492555_m1); PTHrP (Mm 00433057_m1); RANKL (Mm 00441906_m1); GAPDH (Mm 99999915_g1).

Immunohistochemical analyses—Breast tumor tissue microarrays were obtained from the NCI Cooperative Breast Cancer tissue Resource (CBCTR). The tissues were immunohistochemically stained for IHH and GLI1. Immunohistochemical staining was performed using Dako LSAB+ System-HRP reagents in a Dako Autostainer Plus automated immunostainer (Glostrup, Denmark). The intensity of staining was quantitated with computer-assisted image analysis in a Dako ACIS III Image Analysis System (Glostrup, Denmark).

Statistical Analysis—was Performed as Described Herein.

Results

Expression of GLI1 and IHH is Upregulated in Breast Cancer.

Figure 68:
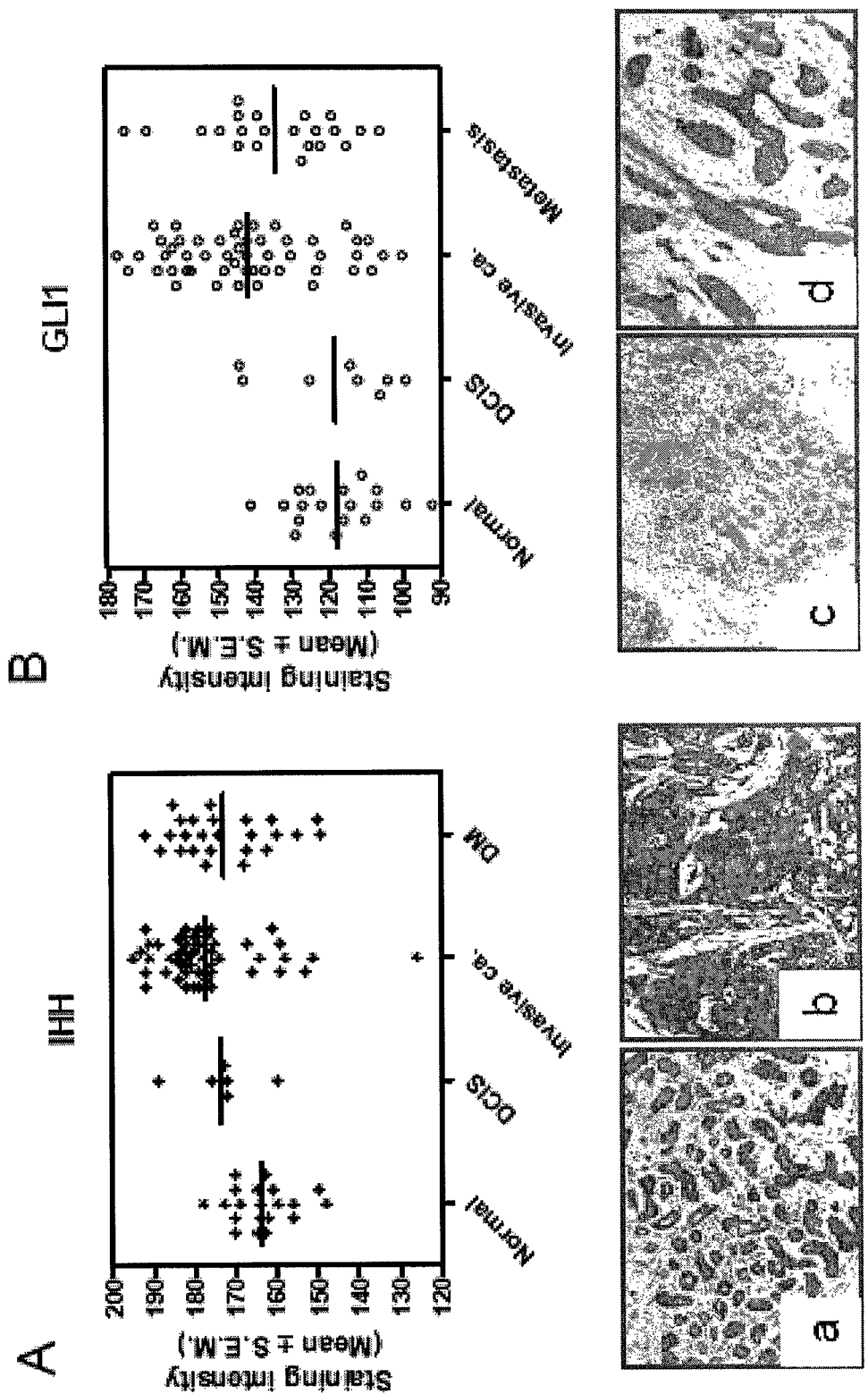
FIG. 68 depicts Hh pathway activation in breast tumors. Breast cancer tissues (n=75) and normal breast tissues (n=9) were immunohistochemically stained for (A) IHH and (B) GLI1 expression. Staining intensities were recorded and represented as a scatter plot. The staining intensities indicating expression levels of IHH and GLI1 were significantly greater (p<0.0001) in the tissues derived from invasive cancer (representing Infiltrating Ductal Carcinoma. Grades II-IV) and from metastatic breast cancer (DM) relative to normal tissues and tissues derived from Ductal Carcinoma In Situ (DCIS). Panels a and b represent normal breast tissue and invasive breast cancer stained for IHH. Panels c and d represent normal breast tissue and invasive breast cancer stained for GLI1.

Using immunohistochemical analyses, the expression of the Hh ligand, IHH and the transcription factor GLI1 were assessed in a tissue array comprising 75 breast cancer tissues and 9 tissues representing normal breast. While the staining intensity of IHH was comparable (p>0.05) in normal tissues and in tissues derived from Ductal Carcinoma. In Situ (DCIS), the tissues derived from invasive cancer (representing Infiltrating Ductal Carcinoma Grades II-IV) and from metastatic breast cancer exhibited significantly (p<0.0001) increased staining intensity for IHH (FIG. 68A; images a and b). Similarly, the staining intensity of GLI1 in tissues from invasive cancer and from metastatic cancer were significantly greater (p<0.0001) compared to normal tissues (FIG. 68B; images c and d).

Hh Signaling Stimulates Osteoblast Differentiation and Mineralization Activity.

Figure 69:
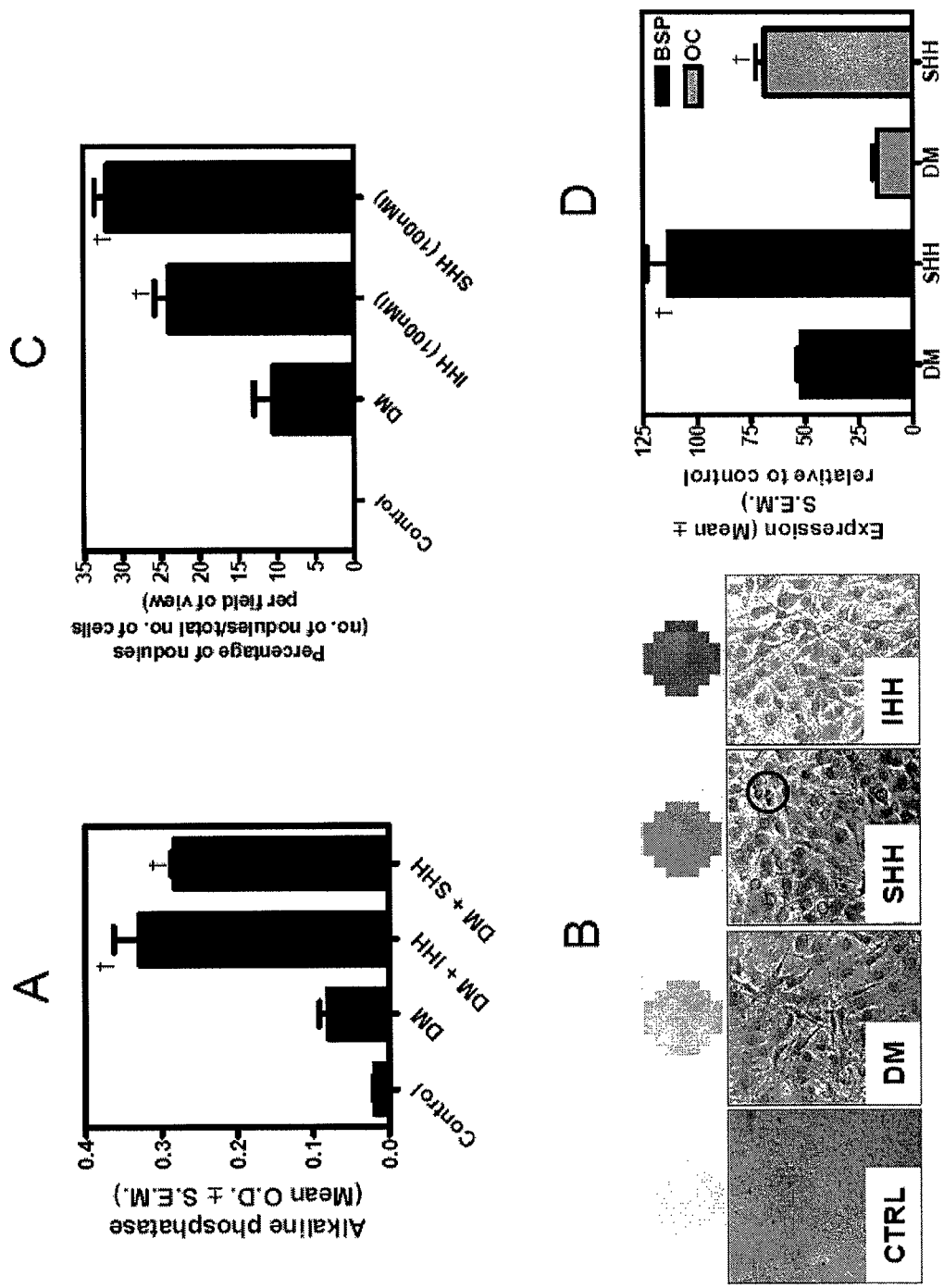
FIG. 69 depicts activation of Hh signaling promoting differentiation and mineralization activity of osteoblasts. MC3T3 E1 Sc-14 cells were grown in differentiation medium (DM) supplemented with either with 100 nM recombinant SHH or IHH or without. Cells grown in normal growth medium were used as control. (A) Differentiation was assessed by alkaline phosphatase (ALP) assay. Under differentiation conditions that included recombinant IHH or SHH, the ALP activity was significantly greater († indicates p<0.0001) relative to DM alone. (B) To visualize differentiated osteoblasts, cells were stained with Alizarin Red and wells scanned at the end of 14 days of differentiation process. Shown are representative well scan images and photomicrographs of differentiated osteoblasts. A representative mineralized nodule is encircled. (C) Relative to control (growth medium), DM induced the formation of mineralized nodules. Relative to DM the media spiked with recombinant IHH and SHH supports the formation of significantly greater number of mineralized nodules († indicates p=0.012 and 0.002, respectively). The number of nodules formed due to each treatment is represented as a percentage of the total number of cells present in each field of view. Control represents growth medium (D) The expression of osteoblast differentiation marker genes, BSP († indicates p=0.0027) and osteocalcin († indicates p=0.0004) is significantly elevated in presence of SHH at the end of 14 days. Cells were harvested and RNA extracted which was used in real time PCR to assay. The fold change in expression is represented relative to control (growth medium).

In order to assess the effect of Hh signaling on the formation of osteoblasts, the monopotential cell line, MC3T3-E1, was used. This cellin is a clonal osteoblastic cell line isolated from calvariae of a late stage mouse embryo. These cells express various osteoblast functions including formation of mineralized bone nodules in long-term culture. The addition of Hh ligands, SHH and IHH to the DM of the MC3T3 cells stimulated differentiation as seen by the increase (p<0.0001) in the ALP activity (FIG. 69A). The resultant osteoblasts exhibited intense staining by Alizarin Red S (FIG. 69B) indicating the presence of mineralized nodules. Overall, a significant increase (p<0.05) in the numbers of mineralized nodules formed in the presence of IHH and SHH was observed (FIG. 69C). This was accompanied by an increase (p<0.005) in the expression of markers of terminally differentiated osteoblasts, bonesialoprotein (BSP) and osteocalcin (FIG. 69D), indicating that stimulating Hh signaling promotes osteoblast differentiation and mineralization activity.

Hh Signaling Upregulates OPN in Osteoblasts

Figure 70:
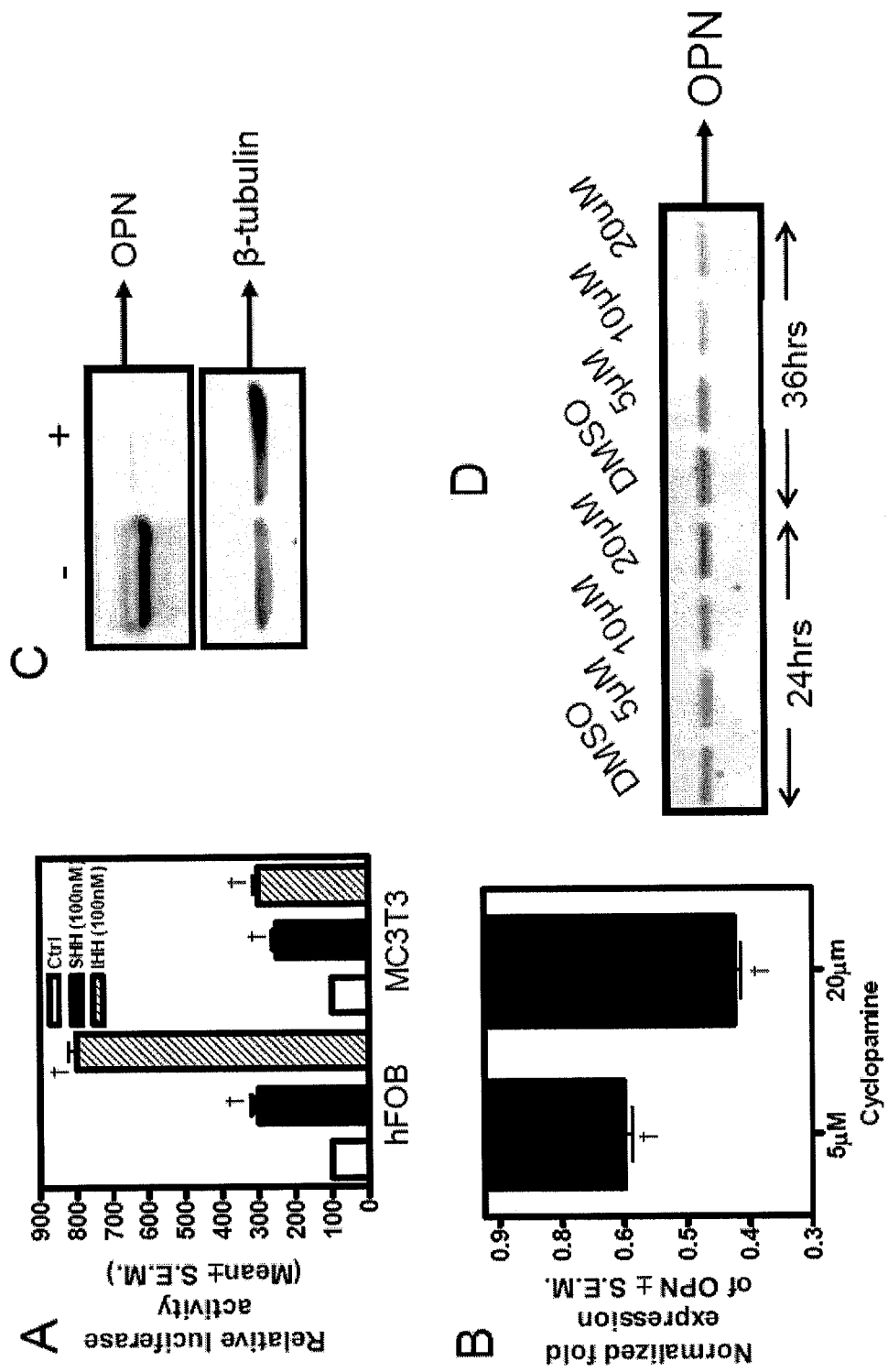
FIG. 70 depicts Hh signaling regulating OPN expression in osteoblastic cells. (A) Hh ligands significantly increase the activity of OPN promoter in the preosteoblastic cell lines hFOB and MC3T3 E1 Sc-14 († indicates p<0.0001 for all indicated groups). Cells were transfected with OPN promoter, treated with Hh ligands and assessed for luciferase activity. (B) The Hh pathway inhibitor, cyclopamine (20 µg/ml), decreased the expression of OPN transcript as assessed by real time PCR († indicates p<0.0001). The expression of total OPN (C) as well as secreted OPN (D) is decreased in presence of cyclopamine. The decrease in the secreted OPN protein level is both, dose (5, 10 and 20 µM) and time dependent.

Hh signaling induces the expression of OPN. OPN promotes adhesion of osteoblasts allowing them to function in osteogenesis. Two osteoblast-forming cells, hFOB and MC3T3 were treated with two Hh ligands, SHH and IHH and assessed the effect on OPN promoter activity. Both ligands caused an upregulation in OPN promoter activity (p<0.0001) (FIG. 70A). Treatment with the Hh inhibitor, cyclopamine, keeps GLI1 sequestered in the cytosolic compartment (FIG. 75A, FIG. 75B) simultaneous with a reduction in the levels of OPN transcript levels (p<0.0001) (FIG. 70B), total OPN protein expression (FIG. 70C) and secreted OPN (FIG. 70D) in the pre-osteoblasts.

Hh Signaling in Tumor Cells Stimulates Differentiation of Osteoblasts as an Early Event and Enhances Expression of RANKL and PTHrP.

Tumor cells express Hh ligands. In order to determine the role of the Hh pathway in mediating the crosstalk between tumor cells and osteoblasts, the effect of conditioned medium from the tumor cells on MC3T3 osteoblast differentiation was assessed after 2 weeks using an ALP activity assay. Relative to DM alone, conditioned medium from the tumor cells caused a significant ($p<0.001$) increase in the ALP activity in 2 weeks. The 5E1 antibody blocks binding of all three mammalian Hh ligands to Ptc1 with low nanomolar affinity, thereby inhibiting Hh signaling. Depleting the Hh ligands from the conditioned medium of the tumor cells using the neutralizing 5E1 antibody caused a decrease in the ALP activity of the differentiated osteoblasts. While the decrease was apparent, although not statistically significant with respect to the conditioned medium from MDA-MB-231 and MDA-MB-435 cells, the decrease was statistically significant ($p<0.05$) with respect to conditioned medium from SUM1315 and SUM159 cells (FIG. 71A). Simultaneous with the reduction in ALP activity, depletion of Hh ligands from the differentiation conditions caused a significant decrease ($p<0.05$) in the expression of (differentiated) osteoblastic proteins, BSP and osteocalcin (FIG. 75C). Functionally, the ability of the osteoblasts to form mineralized nodules was significantly increased ($p<0.0001$) in response to conditioned medium from tumor cells relative to DM alone. Addition of the 5E1 antibody to the differentiation conditions resulted in a significant decrease ($p<0.001$) in the ability of the tumor cell-conditioned medium to elicit osteoblast mineralization activity (FIG. 71B). Differentiated osteoblasts express RANKL and PTHrP and play a role in promoting osteoclast differentiation. Thus, the expression of these two molecules under the conditions used for differentiation was examined. In response to the conditioned medium from breast cancer cells, after 2 weeks of differentiation, the osteoblasts expressed significantly elevated ($p<0.01$) levels of RANKL and PTHrP (FIG. 71C, FIG. 71D). Depletion of Hh ligands from the conditioned medium of the tumor cells resulted in a significant decrease ($p<0.001$) in the levels of RANKL and PTHrP elicited by the conditioned medium. Thus, while Hh ligands from the tumor cell-conditioned medium contributed to osteoblast differentiation, their impact was more pronounced on the expression of RANKL and PTHrP by the differentiated osteoblasts.

OPN Expressed by the Tumor Cells Influences Osteoblast Activity

OPN, a secreted protein expressed by tumor cells, has been implicated as an important regulator of osteoblast differentiation. Both, SUM1315 and MDA-MB-435 cells express OPN. To assess the effect of tumor cell-derived OPN on the osteoblasts, OPN expression was abrogated using shRNA, and the cell-free conditioned medium from these cells was harvested. Osteoblast differentiation was studied in presence of this conditioned medium and the expression of BSP and osteocalcin as indicators of osteoblast differentiation was assessed and measured osteoblast differentiation activity by enumerating the mineralized nodules formed. The conditioned medium from the SUM1315-OPNi and 435-OPNi cells was less efficient ($p<0.005$) in inducing osteoblast differentiation and mineralization (FIG. 72A-72C). Likewise, the expression of RANKL and PTHrP by the osteoblasts was significantly compromised ($p<0.0001$) under differentiation conditions with conditioned medium from tumor cell that were depleted of OPN expression (FIG. 76A). As such, OPN expressed by the tumor cells plays a vital role in the crosstalk between tumor cells and osteoblasts.

Hh Signaling in Tumor Cells Impacts their Ability to Induce Osteoblast Differentiation.

Hh signaling in breast cancer cells also plays a vital role in communication between the breast cancer cells and osteoclasts. In order to assess the role of Hh signaling in tumor cells on their ability to elicit osteoblast differentiation, the expression of GLI1 from the tumor cells was abrogated by shRNA. Conditioned medium from the GLI1-silenced cells was inefficient ($p<0.005$) in inducing osteoblast differentiation as represented in the expression of BSP, osteocalcin (FIG. 72A, FIG. 72B) and the osteoclast differentiation-promoting RANKL and PTHrP proteins ($p<0.05$) (FIG. 72A). Further, the mineralization activity of the osteoblasts was also significantly impaired ($p<0.05$) when the differentiation was elicited for 2 weeks in presence of conditioned medium from cancer cells that were silenced for GLI1 (FIG. 72C), suggesting that active Hh signaling in the tumor cells is vital to their ability to induce osteoblast differentiation.

Figure 71:
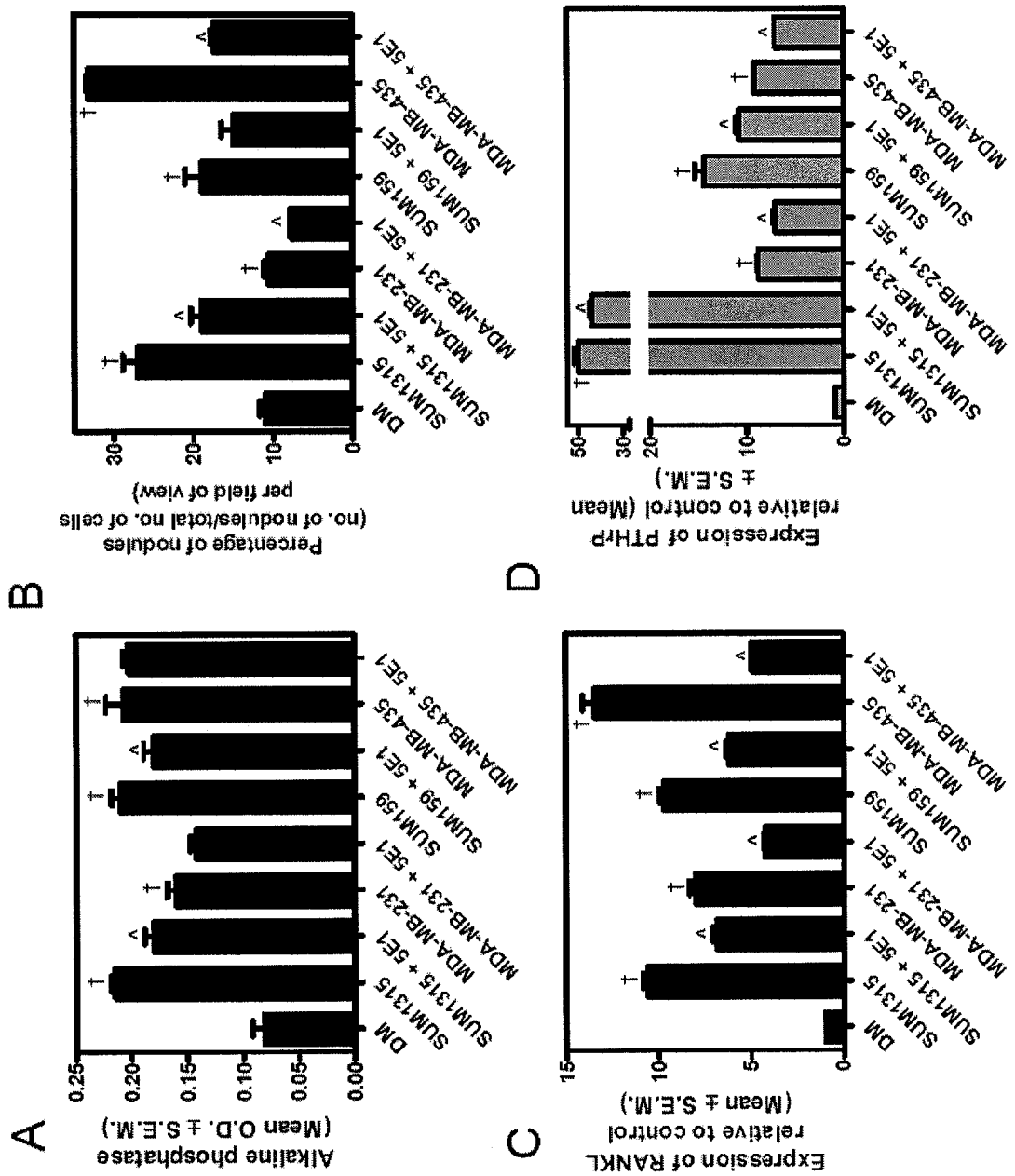
FIG. 71 depicts Hh ligand production by tumor cells impacting the osteoblast differentiation and expression of RANKL and PTHrP. (A) Conditioned media from all four tumor cell lines caused a significant increase in ALP activity of osteoblasts: SUM1315 (†p=0.0002); MDA-MB-231 (†p=0.0035), SUM159 (†p=0.0005), MDAMB-435 (†p=0.0009). Addition of the Hh neutralizing antibody caused a reduction in ALP activity. SUM1315+5E1 (^p=0.014); MDA-MB-231+5E1 (p=0.12), SUM159+5E1 (^p=0.04), MDA-MB-435+5E1 (p=0.6). (B) Tumor cell-conditioned media stimulated mineralization activity of the osteoblasts as evidenced by the numbers of mineralized nodules after Alizarin Red S staining. Nodules were counted and expressed as a percentage of the total number of cells in the field of view. SUM1315 (†p=0.0013); MDA-MB-231 (†p=0.04), SUM159 (†p=0.018), MDA-MB-435 (†p<0.0001). Addition of the Hh neutralizing antibody caused a reduction in numbers of mineralized nodules. SUM1315+5E1 (^p=0.02); MDA-MB-231+5E1 (p=0.0005), SUM159+5E1 (p=0.17), MDA-MB-435+5E1 (p<0.0001). (C) The expression of RANKL by the differentiated osteoblasts was significantly increased in presence of tumor cell-conditioned medium. (†p=0.0013, for all four tumor cell lines). Neutralization of the Hh ligand with the 5E1 antibody caused a reduction in the levels of RANKL expressed. SUM1315+5E1 (^p=0.0004); MDA-MB-231+5E1 (^p=0.0002), SUM159+5E1 (^p=0.0003), MDA-MB-435+5E1 (^p=0.0002). (D) The expression of PTHrP by the osteoblasts was notably greater in presence of conditioned medium from the tumor cells (p<0.0001 for all tumor cells).

Extended Differentiation in Presence of Tumor Cell-Conditioned Media Promotes Osteoblast Apoptosis The data suggested that soluble factors that include OPN and the Hh ligands secreted by tumor cells enhance osteoblast differentiation and mineralization activity. This starkly contradicts the well-established notion that tumor cells causes osteoblasts to undergo apoptosis (Mastro A M, et al. J Cell Biochem 2004; 91:265-76). Notably, these reported studies conducted osteoblast differentiation for longer time periods i.e. 3 weeks or longer. Thus, in order to capture the full impact of the differentiation conditions on the osteoblasts, parallel experiments that were assessed 3 weeks post induction of differentiation were conducted. While differentiation and mineralization activity were already attained at 14 days, the levels of BSP and osteocalcin plummeted sharply ($p<0.001$) at 3 weeks relative to their expression at 2 weeks in differentiation conditions comprising conditioned media from tumor cells (FIG. 73A, FIG. 73B). In contrast, the expression of PTHrP significantly increased ($p<0.001$) in presence of conditioned medium from 3 of the 4 tumor cell lines, whereas RANKL showed variation in the all the four cell systems investigated (FIG. 73C, FIG. 73D). The incidence of apoptosis following 21 days of differentiation in the presence of conditioned media from tumor cells was also assessed. Relative to DM alone, the conditioned medium from all four tumor cells caused a significant increase ($p<0.05$) in the incidence of apoptosis (FIG. 73E), thus corroborating with the published reports. Thus, the data suggests that osteoblasts express osteoclastogenic factors, PTHrP and RANKL in response to OPN and Hh signaling triggered by tumor cells (FIG. 71, FIG. 72, FIG. 76A).

Hh Signaling in Tumor Cells Enhances the Incidence and Intensity of Osteolytic Metastases Intuitively, the data suggests that tumor cells initiate osteoblast differentiation and the expression of osteoclastogenic factors as an early event, followed by elimination of osteoblasts later. Thus, the overall microenvironment appears to shift in favor of osteoclastogenesis. In order to investigate the significance of Hh signaling in the tumor cells with respect to osteolytic metastasis, tumor cells were injected via the left ventricle and assessed the incidence of osteolytic metastases at the tibio-femoral junction 4-6 weeks later. In the mice injected with 435-vector control cells, metastasis in 100% of the mice injected was observed. In contrast, the incidence of mice injected with tumor cells stably silenced for GLI1 was reduced to 60% (FIG. 74 and FIG. 76B). Overall, there was a decrease in the intensity of the osteolytic metastasis as well. The data suggests that Hh signaling in the tumor cells is essential to the development of osteolytic metastases. These cells are also capable of directly activating osteoclast differentiation (assessed by TRAP staining) and stimulating resorption activity (FIG. 76C, FIG. 76D). Moreover, the active Hh signaling and expression of OPN are important attributes for the tumor cells to activate osteoclast differentiation and resorptive activity. Thus, the data suggests that Hh signaling in the tumor cells can directly impact the ability of the cells to cause osteolysis.

DISCUSSION

The Hh pathway plays an essential function in regulating cell fate and in developmental patterning in animals and humans. This pathway is also important in the formation of the skeleton. During skeletogenesis and endochondral ossification Hh signaling coordinates growth and differentiation. In adult animals, systemic administration of the ligand SHH, resulted in a primary increase in osteoblasts and their precursors. Interestingly, this was accompanied by an enhanced osteoclastogenic potential and decreased bone volume due to upregulation of the PTH/PTHrP receptor. Thus, Hh signaling in the adult bone milieu caused stimulatory effects on osteoprogenitors and osteoblasts resulting in bone remodeling and reduced bone strength because of a secondary increase in osteoclastogenesis.

The bone is a common site of metastasis for several malignancies. The impact of metastasized tumor cells in the bone disrupts the balance between the activities of the osteoclasts and osteoblasts. Radiographically, the bone lesions are classified as being osteolytic (bone loss) or osteosclerotic (bone formation) or mixed. Breast cancer bone metastases are usually osteolytic, characterized by excess bone turnover and consequent bone resorption. This is concomitant with the apoptosis and elimination of osteoblasts. In fact, several papers suggest that breast cancer cells limit osteoblasts by either inducing apoptosis or interfering with normal function and thus facilitating osteolysis through increased osteoclast activity. Paradoxically, it must be noted that the basic trigger for the differentiation of pre-osteoclasts to osteoclasts is supplied by the osteoblasts. Osteoblasts produce M-CSF and RANKL that promote pre-osteoclasts to differentiate into multinuclear, activated osteoclasts that adhere to bone and degrade the bone matrix. RANKL and M-CSF activate a dendritic cell-specific transmembrane protein (DCSTAMP) that facilitates cell-cell adhesion and cytoskeletal re-raanagements resulting in a multinucleate osteoclast. Thus, the availability of differentiated osteoblasts is vital to the development of active osteoclasts. Likewise, osteoclasts express BMPs that promote recruitment and proliferation of osteoblasts at resorption sites.

Thus, given the vital role that osteoblasts play in facilitating osteoclast activity, the elimination of osteoblasts by the tumor cells seems counter intuitive and warrants further understanding of the delicate balance between osteoblast and osteoblasts. In this study, the role of Hh signaling in tumor cells on the interaction between tumor cells and osteoblasts was investigated. Breast cancer cells were determined to express elevated staining intensities for the Hh ligand IHH and the transcription factor, GLI1, indicating that the Hh pathway is activated in breast tumor cells. In order to determine the consequences of the interaction between tumor cells and osteoblasts, osteoblast differentiation at early (14 days) and late (21 days) postinitiation of differentiation was investigated in presence of conditioned media from tumor cells. While Hh ligands expressed by the tumor cells enhanced osteoblastogenesis and mineralization activity as an early event, enhanced expression of osteoclastogenesis-promoting factors viz. RANKL and PTHrP in the differentiated osteoblasts was observed. Likewise, OPN expressed by the tumor cells also stimulated osteoblast differentiation. Tumor cells with a competent Hh pathway were more potent at inducing osteoblast differentiation and expression of RANKL and PTHrP. While the expression of osteoblast differentiation markers, BSP and osteocalcin dwindled at a later event (21 days) characterized by increased apoptosis of the osteoblasts, the expression of RANKL and PTHrP continued to be robust, suggesting that the osteoblasts were expressing factors that would propel osteoclastogenesis. Thus, this data suggests that tumor cells initially enhance the differentiation of osteoblasts that in turn, express osteoclastogenesis enhancing factors. Later, as the osteoblasts get eliminated, the availability of RANKL and PTHrP creates an environment that will stimulate osteoclast differentiation and activity. Thus, an active Hh signaling in the tumor cells facilitates the generation of an osteoclast-stimulating milieu by initially kickstarting osteoblast development. This is apparent in the fact that ablating GLI1 severely compromised the ability of the tumor cells to form osteolytic metastasis in an experimental model of bone metastasis.

A role for osteoblast-derived PTHrP as a physiological regulator of bone remodeling has been previously suggested (Miao D, et al. J Clin Invest 2005; 115:2402-11; Miao D, et al. Endocrinology 2004; 145:3554-62). PTHrP is produced by cells of early osteoblast lineage that do not express PTH-receptor. PTHrP acts on receptor-positive committed preosteoblasts, and these cells respond by differentiating into mature osteoblasts. PTHrP acts directly on mature osteoblasts and osteocytes to prevent their apoptosis and is also required to enhance production of RANKL by PTHR1-positive pre-osteoblasts. As a result, osteoclast formation is promoted by interaction of the membrane molecule, RANKL, with its receptor, RANK. It is surmised that a fine balance or spatiotemporal control mechanisms exist to ensure availability of PTHrP for enhancing osteoblast differentiation, as persistently increased local PTHrP levels would favor increased osteoclast formation, through stimulation of RANKL production resulting in increased bone resorption, and high-turnover osteoporosis (Martin T J. J Clin Invest 2005; 115:2322-4.). In fact, the results herein show a steady expression of PTHrP by osteoblasts (at 21 days) and are supported by the fact that Hh signaling competent tumor cells in fact, cause radiographically evident osteolysis in animal models.

Skeletal integrity is an essential survival function of mammals. The findings herein reveal that the tumor cells can alter the balance between the activities of osteoblasts and osteoclasts via Hh signaling. Thus, given the fact that breast cancer cells express Hh ligands (FIG. 75) and that Hh signaling propels breast cancer progression, the studies herein imply that administration of pharmacological Hh inhibitors can inhibit Hh signaling in breast cancer cells, osteoblasts and osteoclasts and may reduce breast cancer-mediated bone loss in metastatic disease. This strategy targets the tumor cells as well as the bone and its microenvironment and can reduce tumor burden and tumor-derived bone lesions.

Example 12

Drug Sensitivity of Cells Transfected with shRNA to GLI1

Figure 62C:
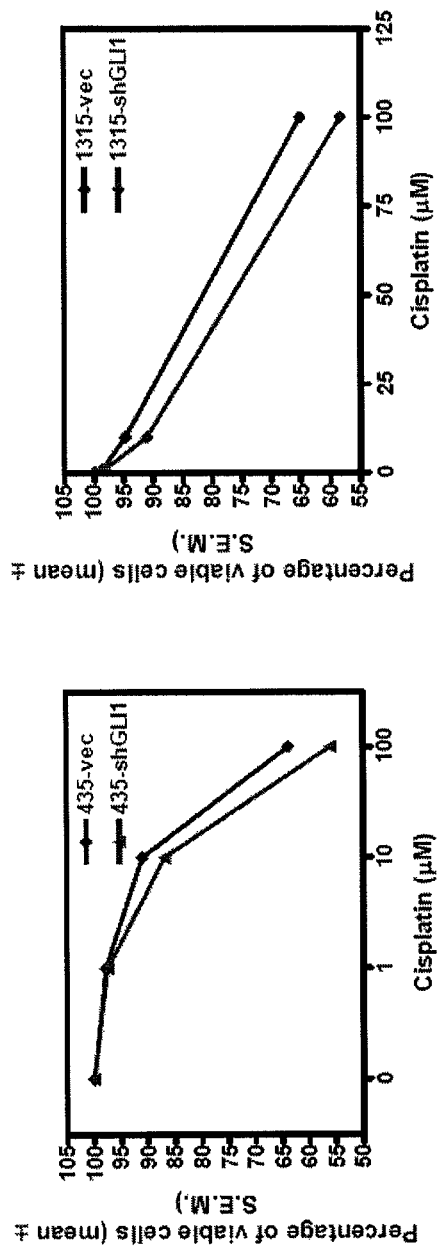
FIG. 62C shows graphs depicting MDA-MB-435 cells (left panel) or SUM1315 cells (right panel) transfected with vector or vector encoding shGLI1 RNA and treated with various concentrations of cisplatin.

MDA-MB-435 (435) and SUM1315 (1315) cells were transfected with either empty vector (vec) or with vector encoding shRNA to GLI1 (shGLI1). Cells were treated with the indicated concentrations of drugs for 24 hours and viability was assessed using an MTS assay (FIG. 62A-FIG. 62C). An increased sensitivity to doxorubicin and taxolin cells transfected with the shRNA to GLI1 was observed. Using real-time quantitative RT-PCR the GLI1 shRNA brings about a decrease of about 50% in the expression of ABCB1 (MDR1) and 90% decrease in ABCG2 (BCRP).

Example 13

Gli1 is Located in the Nucleus of A2780-CP70 Cells

Figure 24:
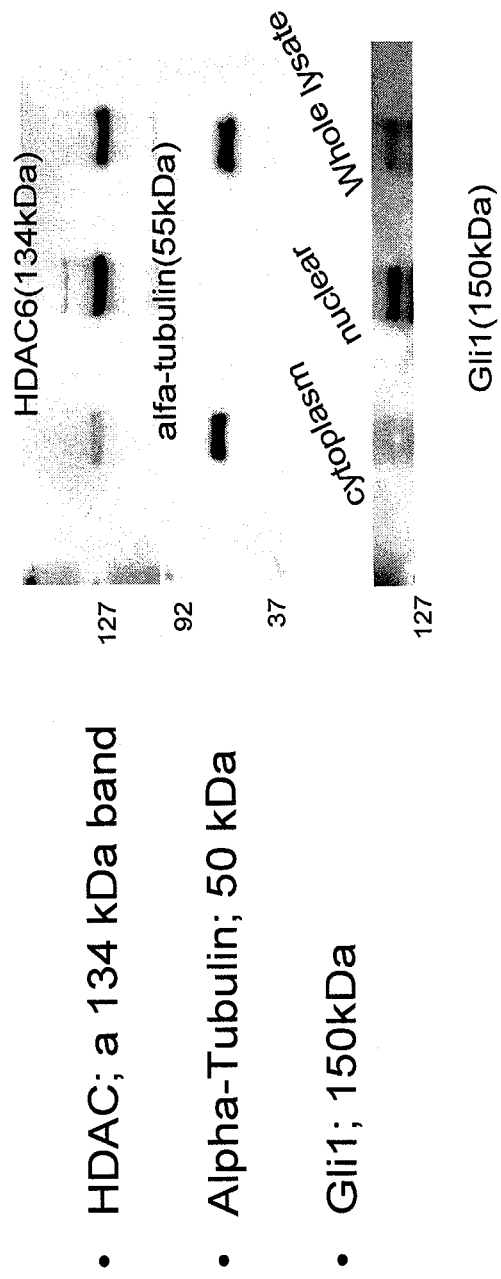
FIG. 24 shows a Western blot of A2780-CP70 cells grown as monolayers and harvested in log phase.

The paired human ovarian cancer cell lines A2780 and A2780-CP70 are cisplatin-sensitive (IC50 ~3 μM), and cisplatin-resistant (IC50 ~40 μM), respectively (Parker, R. J., et al. J Clin Invest, 87:772-777, 1991; Li Q, et al. J Biol Chem, 273:23419-23425, 1998; Bonovich M, et al. Cancer Gene Therapy, 9:62-70, 2002). A2780-CP70 cells were grown in monolayers, harvested in log phase growth, and assessed for the presence of Gli1 in: a) whole cell lysate; b) nuclear fraction; and, c) cytoplasmic fraction using Western blot analysis. Controls included α-tubulin and histone deactylase. Referring to FIG. 24, Gli1 was detected in whole cell lysates and nuclear fractions, but not in cytoplasmic fractions. This suggests that the Hedgehog pathway is activated in A2780-CP70 cells.

Example 14

Gli1 is Present in the Nucleus of A2780 and A2780-CP70 Cells

Figure 25:
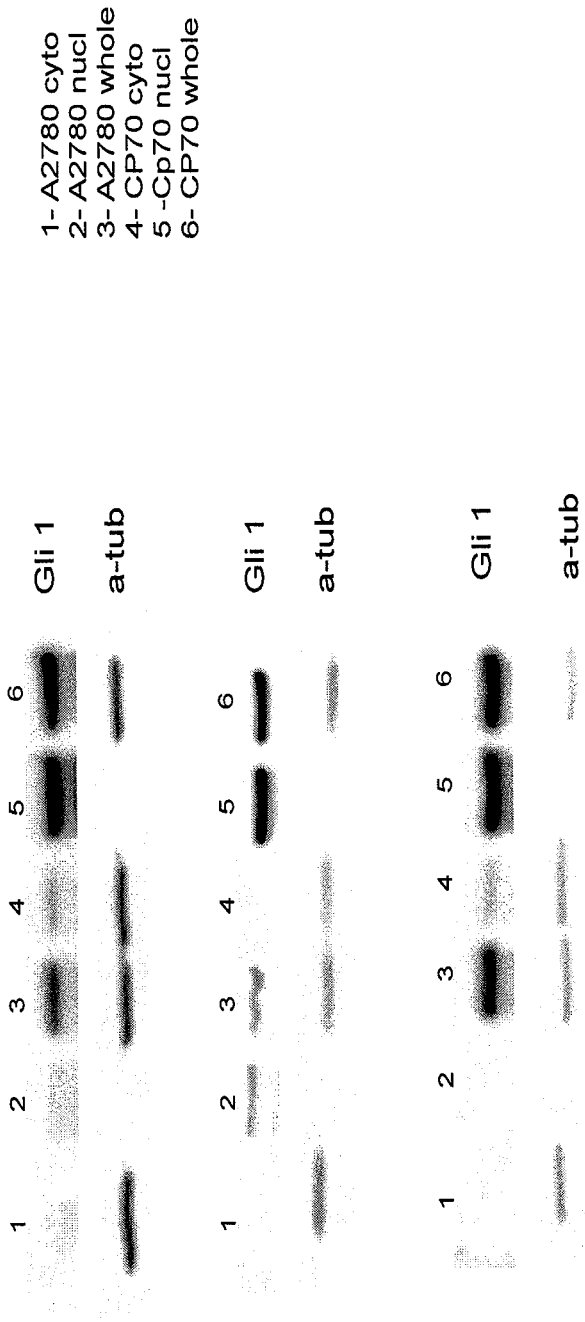
FIG. 25 shows a Western blot of A2780 and A2780-CP70 cells and probed for GLI1 and α-tubulin. A2780 cells: lanes 1, 2, 3. A2780-CP70 cells: lanes 4, 5, 6. Upper, middle and lower panels are from three separate experiments.

Gli1 protein expression was assessed in A2780 and A2780-CP70 cells grown in log phase in monolayers using Western blot analysis.). Gli1 would be expected in the cytosol but not in the nucleus in cells in which the Hedgehog pathway is inactive. Referring to FIG. 25, Gli1 protein was present in the nuclear fractions of A2780 and A2780-CP70 cells. While Gli1 protein was detected in the cytosol of A2780-CP70 cells, the protein was not detected in the cytosolic fraction of A2780 cells. The relative increase in Gli1 protein in A2780-CP70 cells over A2780 cells was estimated using radiodensitometry to be 20- to >30-fold greater (lane 2 compared to lane 5). This suggests that the Hedgehog pathway is activated in both A2780-CP70 and A2780 cells, but more strongly activated in A2780-CP70 cells, and is consistent with the observation that activation of the Hedgehog pathway is associated with the development of drug resistance for example, cisplatin drug resistance.

Example 15

Figure 26:
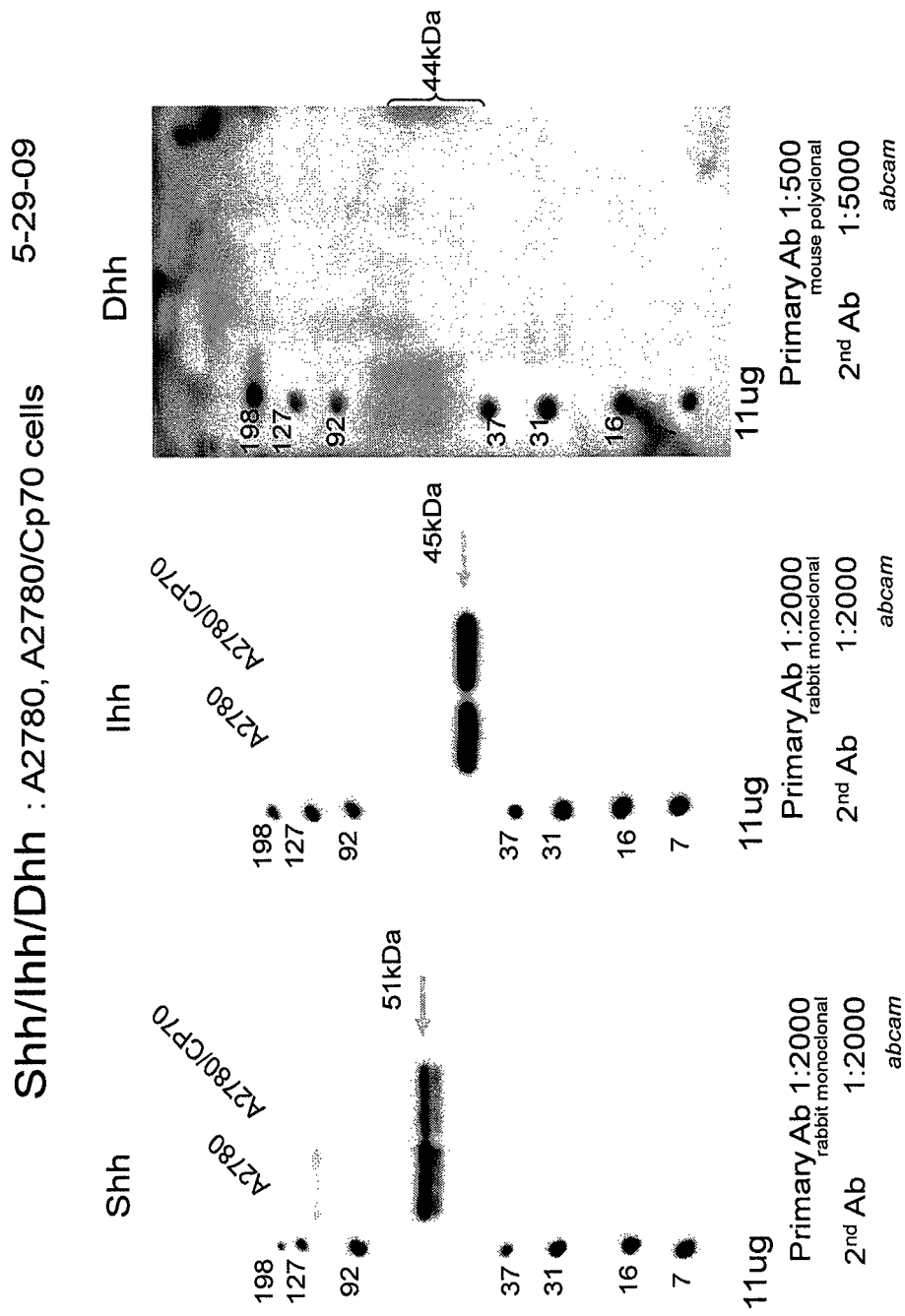
FIG. 26 shows Western blots of A2780 and A2780-CP70 cells and probed SHH (left panel), IHH (center panel), and DHH (right panel).

Indian Hedgehog (IHH), Sonic Hedgehog (SHH), and Desert Hedgehog (DHH) Protein Expression in A2780 and A2780-CP70 Cells To assess whether the Hedgehog pathway is self-driven in A2780 and A2780-CP70 monolayers, cell lysates were assayed for IHH, SHH, and DHH using Western blot analysis. Referring to FIG. 26, SHH (51 kDa) was observed in A2780 and A2780-CP70 cells, but was expressed at greater levels in A2780 cells. IHH (45 kDa) was observed in A2780 and A2780-CP70 cells at similar levels to those observed for SHH. DHH was present in A2780 and A2780-CP70 cells at low levels. This suggests that A2780 and A2780-CP70 monolayers are hedgehog driven.

Example 16

Gli1 Protein Expression in Cyclopamine-Treated A2780-CP70 Cells

Gli1 protein expression was examined in A2780-CP70 cells treated with the Smoothened inhibitor, cyclopamine, using Western blot analysis. A2780-CP70 cells were grown in log phase and treated with 70 μM cyclopamine for 24 hr, 48 hr, and 72 hr. Protein lysates were obtained form adherent cells. Under these conditions, 70 μM cyclopamine is associated with 50-70% cell killing at 72 hr.

Figure 27:
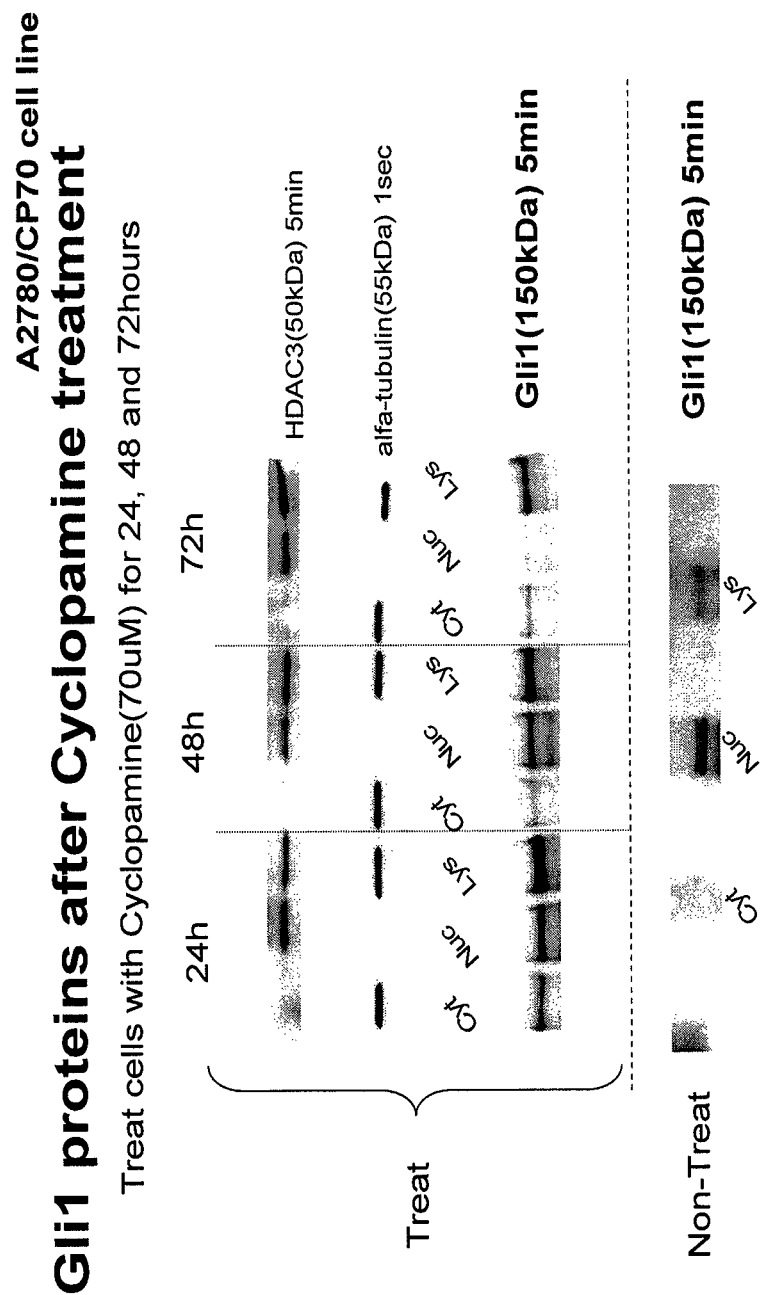
FIG. 27 shows a Western blot of A2780-CP70 cells treated with 70 µM cyclopamine for 24 hr, 48 hr, and 72 hr, and probed for GLI1, α-tubulin, and HDAC3.

Referring to FIG. 27, Gli1 protein was detected in nuclear and cytoplasmic fractions at 24 hr in treated cells. At 48 hr, Gli1 was detected in the nuclear fractions, but only at low levels in cytoplasmic fractions. At 72 hr, Gli1 protein was present in very low levels in nuclear and cytoplasmic fractions. This suggest that cyclopamine inhibits translocation of Gli1 from the cytoplasm into the nucleus due to inhibition of the Gli1-activator, Smoothened. In addition, Gli1 protein levels in the cytoplasm declined over 72 hr, suggesting that cytoplasmic Gli1 protein was degraded. Accordingly, Smoothened may have a role in the production and maintenance of cytoplasmic levels of Gli1 protein.

Transfection of an anti-Gli1 shRNA construct inhibits the Hedgehog pathway. Reduced Gli1 protein and mRNA levels were observed in the nucleus of transfected cisplatin-resistant A2780-CP70 cells. Gli1 mRNA levels rebounded by 72 hr post-transfection. These observations were similar to those observed in A2780-CP70 cells treated with cyclopamine, an inhibitor of the Hedgehog pathway. In addition, transfected A2780-CP70 cells showed stable mRNA levels of c-jun, increased mRNA levels of c-fos. C-fos mRNA levels peaked between 6 and 24 hr post-transfection. These observations were similar to those observed in A2780-CP70 cells treated with cyclopamine.

Example 17

Figure 28:
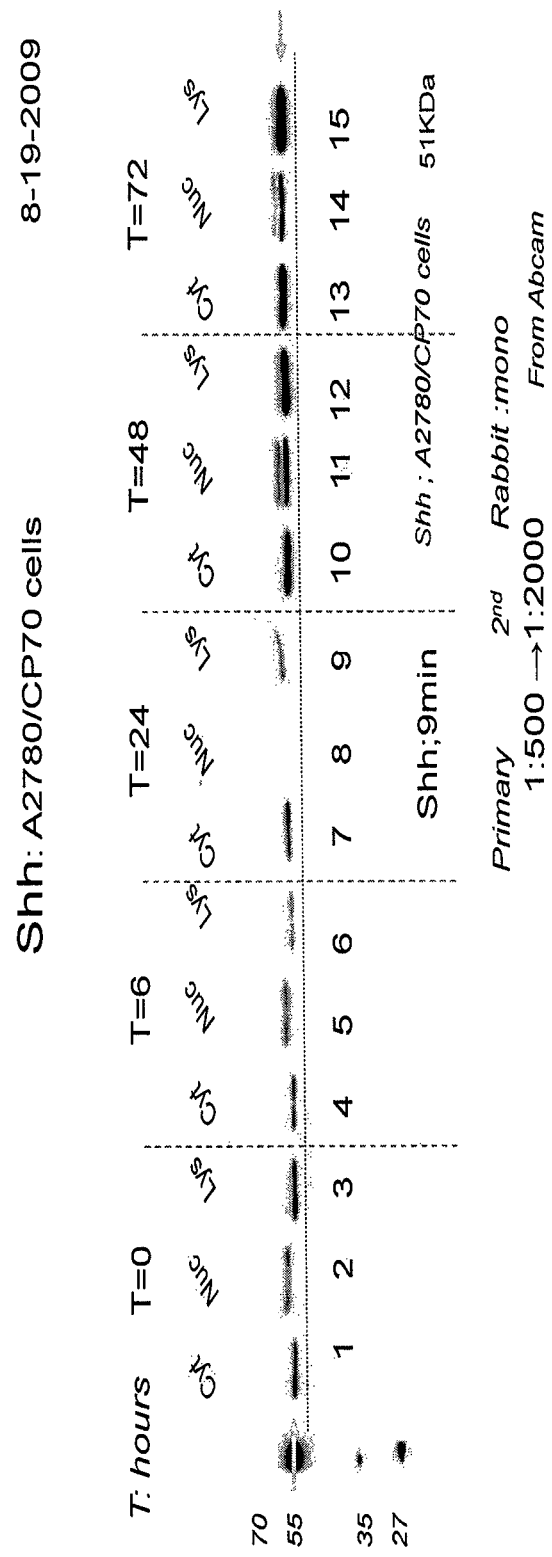
FIG. 28 shows a Western blot of A2780-CP70 cells treated with cyclopamine for 0 hr, 6 hr, 24 hr, 48 hr, and 72 hr, and probed for SM.
Figure 29:
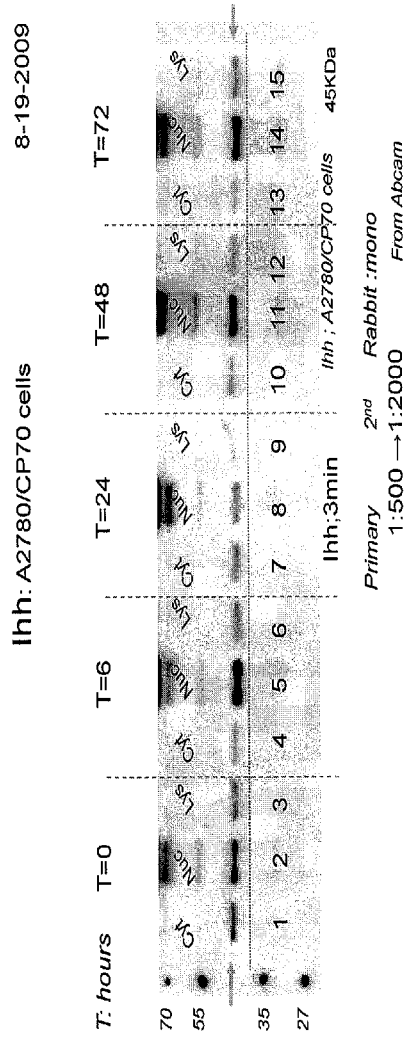
FIG. 29 shows a Western blot of A2780-CP70 cells treated with cyclopamine for 0 hr, 6 hr, 24 hr, 48 hr, and 72 hr, and probed for IHH.

Sonic Hedgehog (SHH) and Indian Hedgehog (IHH) Protein Expression in Cyclopamine-Treated A2780-CP70 Cells SHH and IHH protein levels were assessed in cyclopamine-treated A2780-CP70 cells by Western blot analysis. Referring to FIG. 28, SHH protein (51 kDa) was detected in cytoplasmic fractions, but not nuclear fractions of treated cells at 0 hr. SHH protein levels decreased in cytoplasmic fractions between 6-24 hr of cyclopamine treatment. At 48 hr, SHH protein levels were prominent in cytoplasmic and nuclear fractions, and remained prominent through 72 hr. Referring to FIG. 29, IHH protein (45 kDa) was detected in cytoplasmic and nuclear fractions of treated cells at 0 hr. At 6 hr, IHH protein levels were more prominent in nuclear fractions than in cytoplasmic fractions. At 24 hr, IHH protein levels were low in both nuclear and cytoplasmic fractions. However, at 48 hr IHH protein levels increased in nuclear fractions through to 72 hr. IHH was only weakly present in the cytoplasmic fractions between 48-72 hr. In sum, SHH and IHH protein levels were reduced at 24 hr. After 24 hr SHH and IHH protein levels were similar in nuclear and cytoplasmic fractions. SHH and IHH protein levels rebounded by 48 hr and 72 hr.

Example 18 c-Jun Protein, c-Jun mRNA, and c-Fos mRNA Expression in Cyclopamine-Treated A2780-CP70 Cells c-jun protein expression was assessed in cyclopamine-treated A2780-CP70 cells using Western blot analysis. Controls included α-tubulin and histone deacetylase 3. c-jun antibody recognizes non-phosphorylated c-jun protein.

Figure 30:
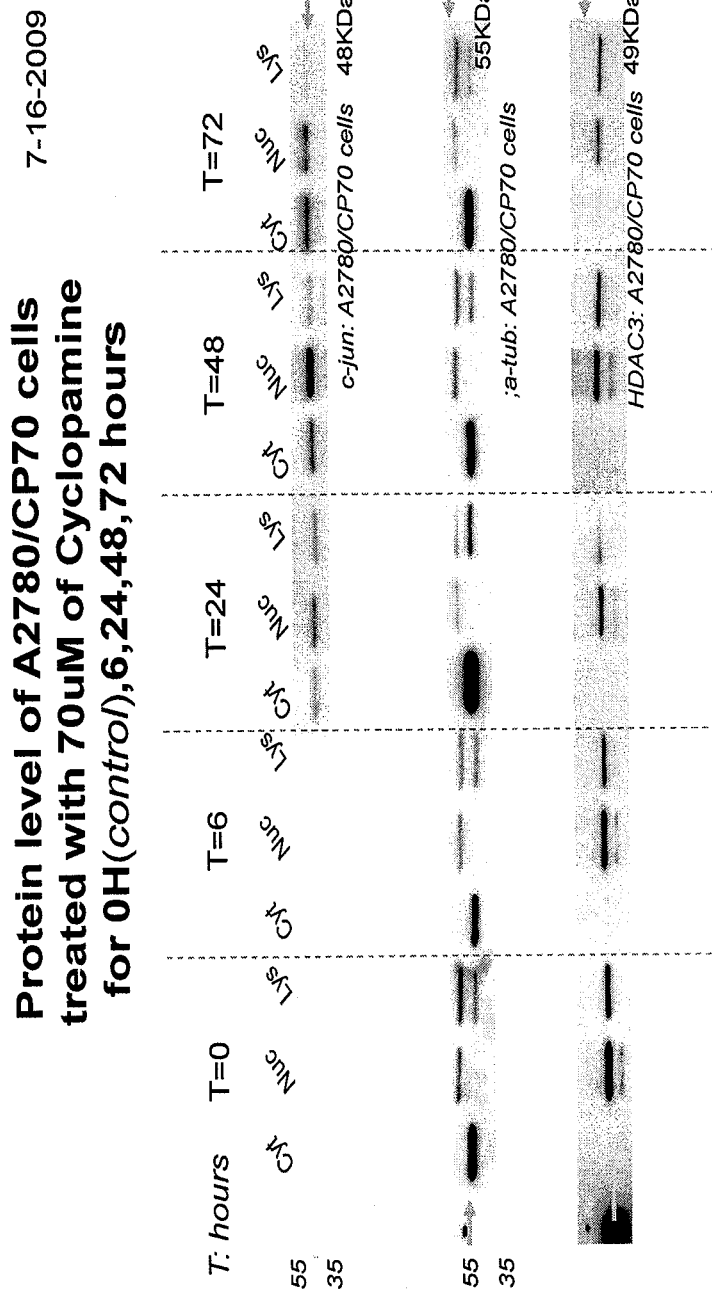
FIG. 30 shows a Western blot of A2780-CP70 cells treated with 70 µM cyclopamine for 0 hr, 6 hr, 24 hr, 48 hr, and 72 hr, and probed for c-jun, α-tubulin, and HDAC3.
Figure 31:
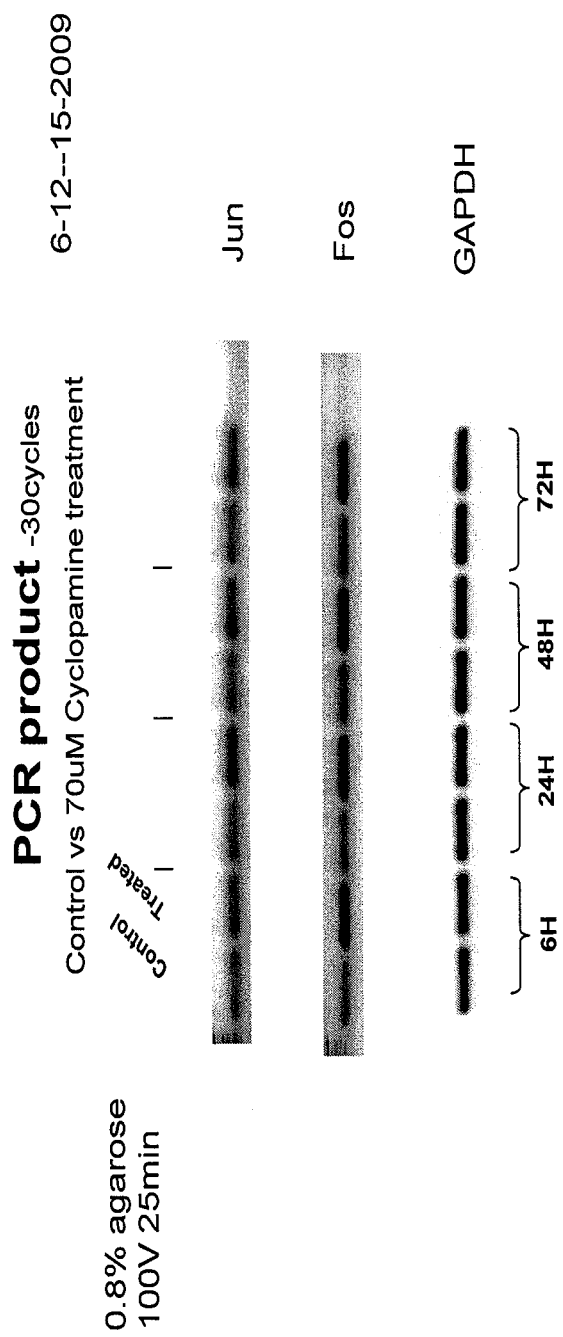
FIG. 31 shows a Southern blot of A2780-CP70 cells treated with 70 cyclopamine for 6 hr, 24 hr, 48 hr, and 72 hr, and reflects a PCR assessment of mRNA levels for c-jun, c-fos, and GAPDH.
Figure 32:
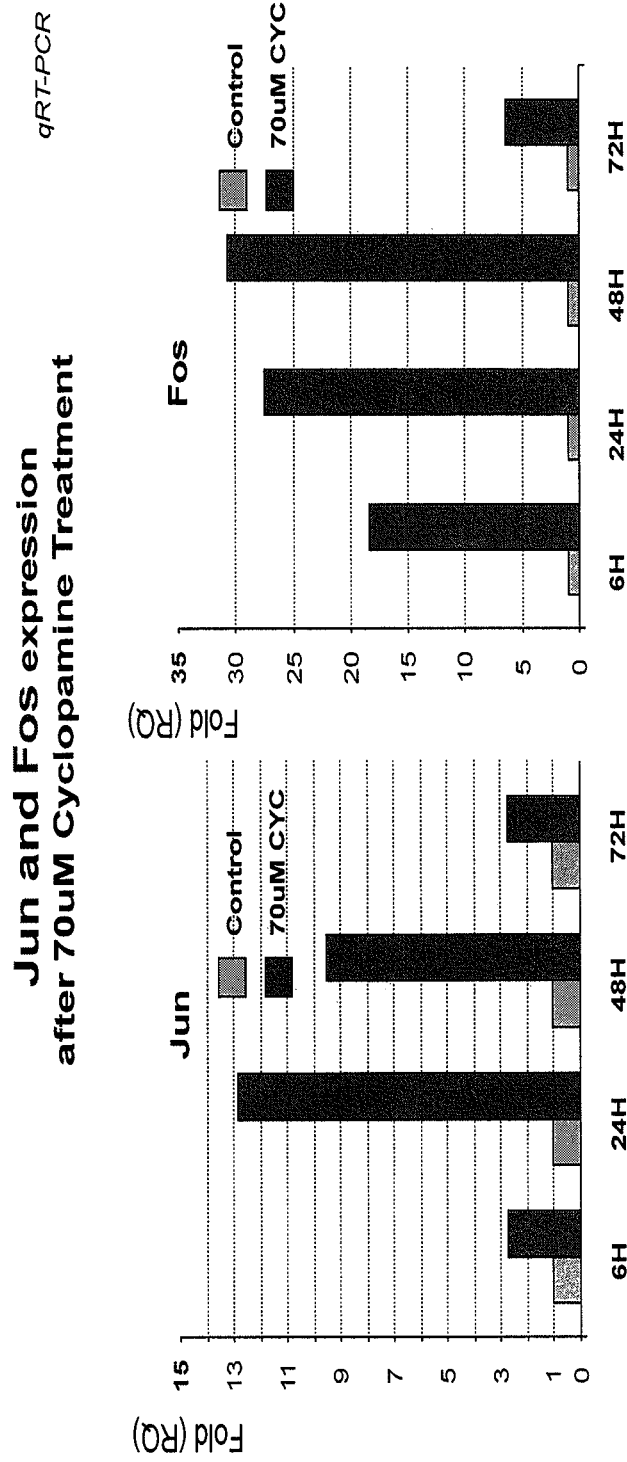
FIG. 32 shows graphs of c-jun (left panel) and c-fos (right panel) expression in A2780-CP70 cells treated with 70 µM cyclopamine for 6 hr, 24 hr, 48 hr, and 72 hr.

Referring to FIG. 30, unphosphorylated c-jun protein levels were low between 0 hr and 6 hr in nuclear and cytoplasmic fractions at 0 hr. At 24 hr, c-jun protein was easily detected levels in nuclear and cytoplasmic fractions. Expression of c-jun protein in nuclear peaked at 48 hr and began to diminish by 72 hr. Expression of c-jun protein in cytoplasmic fractions plateaued between 48 and 72 hr.

c-jun and c-fos mRNA expression was assessed in A2780-CP70 cells treated with cyclopamine using semi-quantative PCR (FIG. 31). c-jun mRNA was detected at low levels at 0 hr. At 6 hr, c-jun mRNA levels has increased by 3-fold. At 24 hr, c-jun mRNA levels peaked with a 13-fold increase over 0 hr. c-jun mRNA levels had decreased at 48 hr. A similar pattern of expression over time was observed for c-fos mRNA levels, however, c-fos mRNA levels peaked at levels 27-fold greater than 0 hr. These results are summarized in FIG. 32. In sum, A2780-CP70 cells exhibited a biphasic response to treatment with 70 μM cyclopamine, with low levels of c-jun for at least 6 hr, followed by increased levels of c-jun and c-fos that peaked at 48 hr. These data suggest that disruption of the Hedgehog pathway using cyclopamine results in suppression of c-jun for an approximate 24 hour period.

Figure 33:
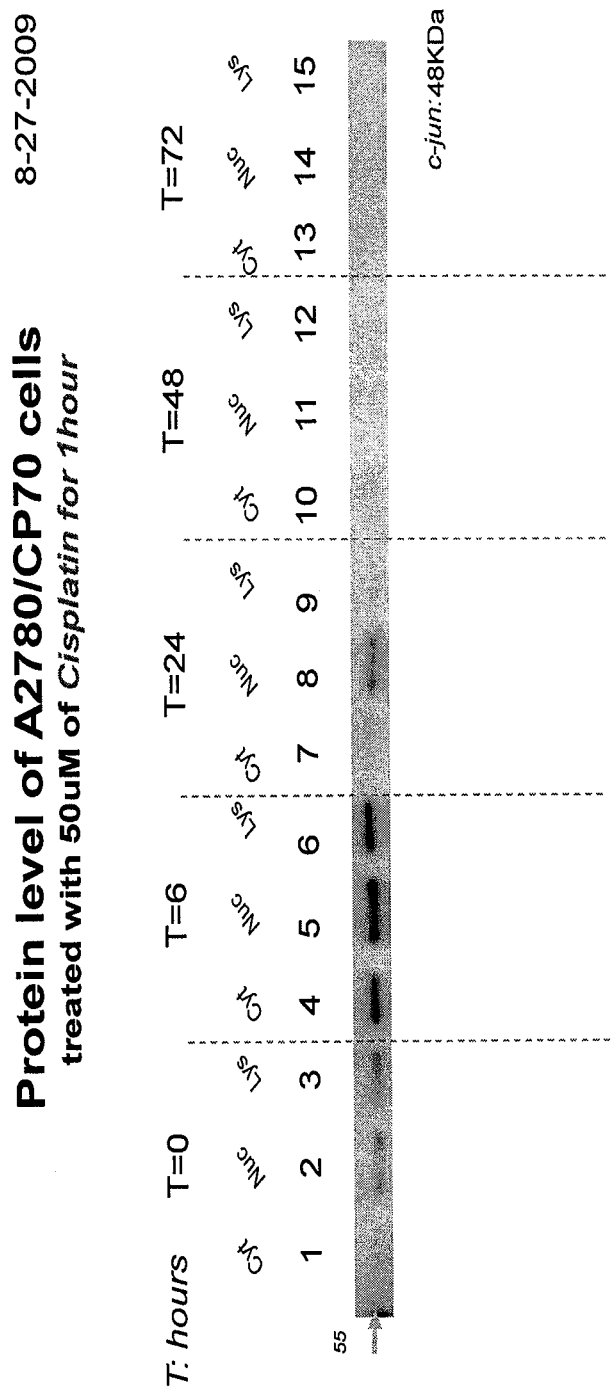
FIG. 33 shows a Western blot of A2780-CP70 cells treated with 50 µM cisplatin for 1 hr and probed for c-jun. Samples were taken 0 hr, 6 hr, 24 hr, 48 hr, and 72 hr post-treatment.

Comparative Example 19 c-Jun Protein Expression in Cisplatin-Treated A2780-CP70 Cells c-jun protein expression was assessed in cisplatin-treated A2780-CP70 cells using Western blot analysis. A2780-CP70 cells were treated with an IC50 dose of cisplatin (Li Q, et al. J Biol Chem, 273:23419-23425, 1998). Referring to FIG. 33, c-jun protein expression increased substantial between 0-6 hr. c-jun protein levels waned between 6-72 hr. c-jun protein expression in cisplatin-treated cells is consistent with previous reports, and different from that observed in cyclopamine-treated A2780-CP70 cells.

The expression pattern of c-jun and c-fos is similar in A2780-CP70 cells treated with cisplatin or phorbol ester (Li Q, et al. International Journal of Oncology, 13:987-992, 1998; Li Q, et al. Cellular and Molecular Life Sciences, 55:456-466, 1999).

Comparative Example 20 c-Jun Protein Expression in A2780-CP70 Cells Treated with Cisplatin

Figure 34:
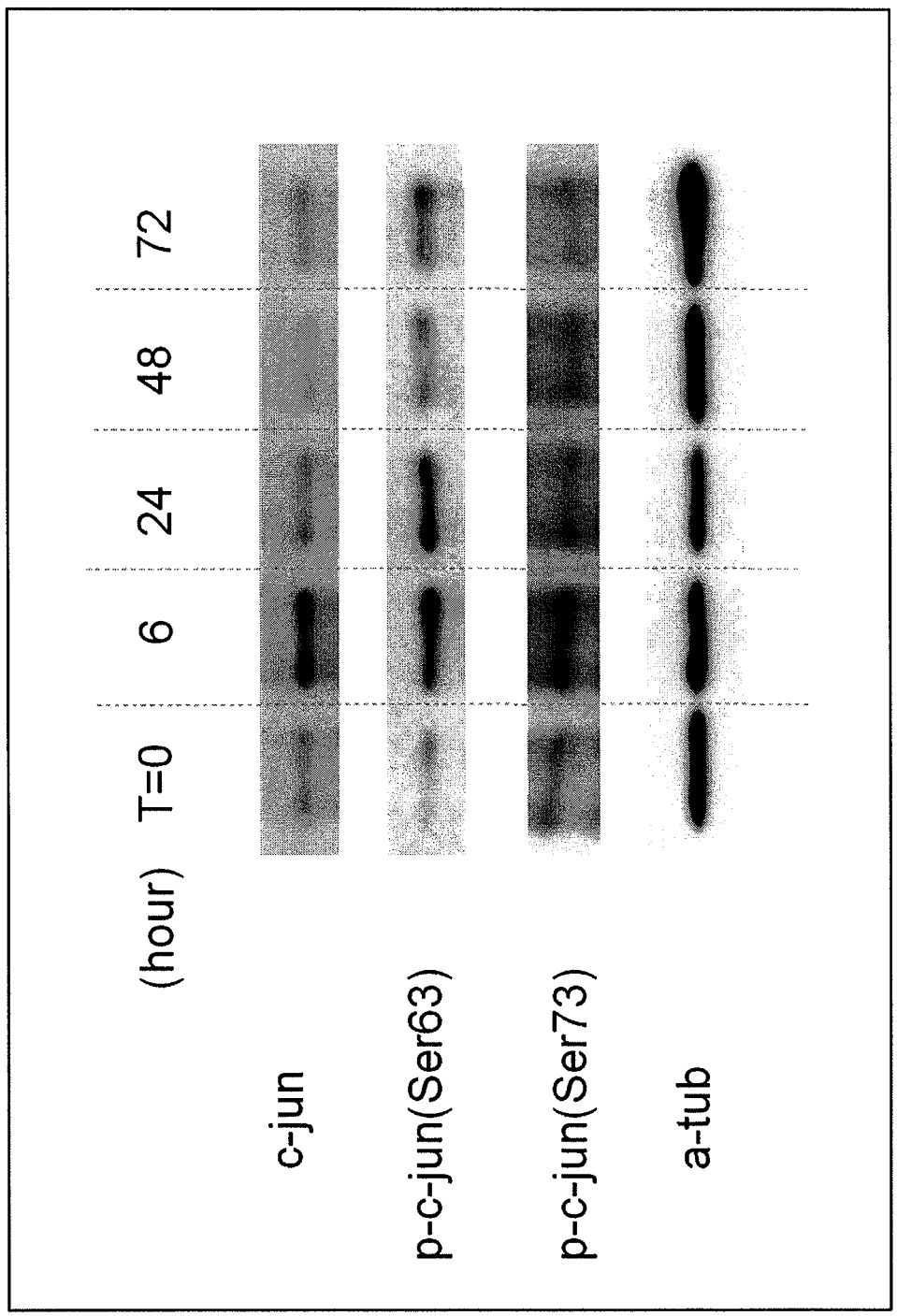
FIG. 34 shows a Western blot of A2780-CP70 cells treated with 50 µM cisplatin for 1 hr and probed for c-jun, phosphorylated c-jun (Ser 63), phosphorylated c-jun (Ser 73), and α-tubulin. Samples were taken 0 hr, 6 hr, 24 hr, 48 hr, and 72 hr post-treatment.

Phosphorylation of c-jun protein in A2780-CP70 cells treated with cisplatin was assessed using Western blot analysis (Li Q, et al. J Biol Chem, 273:23419-23425, 1998) (FIG. 34). C-JUN is unregulated after treatment with cisplatin.

Example 21 c-Fos Protein Expression and c-Jun Protein Phosphorylation in Cyclopamine-Treated A2780-CP70 Cells Protein expression of c-fos and phosphorylation of c-jun in cyclopamine-treated A2780-CP70 cells was assessed using Western blot analysis. Protein levels for c-jun, c-fos, phosphorylated c-jun (Ser 63), phosphorylated c-jun (Ser 73), and phosphorylated c-jun (Thr 91, Thr 93) were tested in cytosolic, nuclear, and whole cell fractions at 0 hr, 6 hr, 24 hr, 48 hr, and 72 hr. Internal controls for cytosolic and nuclear fractions included α-tubulin and histone deacetylase 3.

Figure 35:
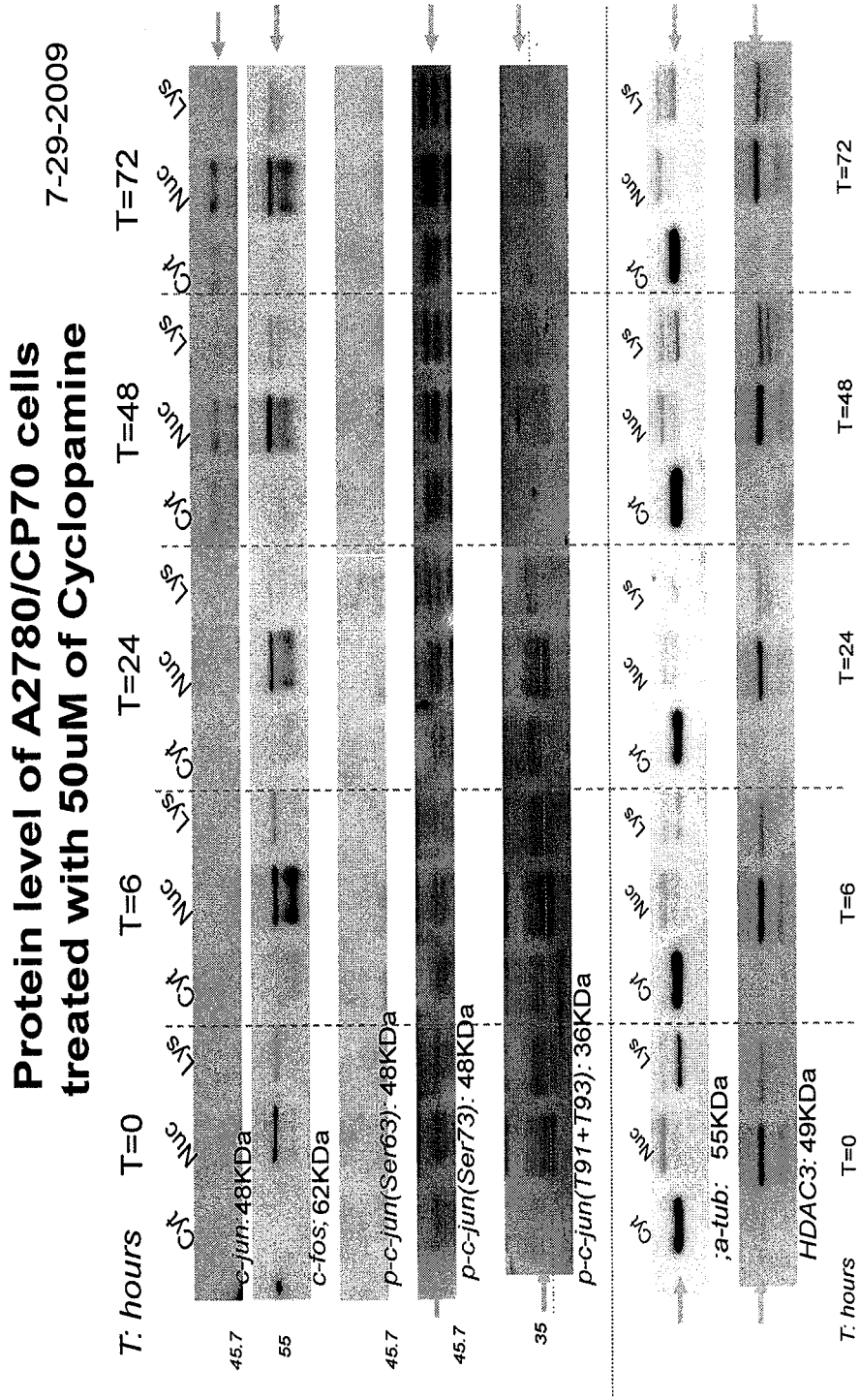
FIG. 35 shows a Western blot of A2780-CP70 cells treated with 50 μM cyclopamine and probed for c-jun, c-fos, phosphorylated c-jun (Ser 63), phosphorylated c-jun (Ser 73), phosphorylated c-jun (Thr 91, Thr 93), HDAC3, and α-tubulin. Samples were taken 0 hr, 6 hr, 24 hr, 48 hr, and 72 hr.

Referring to FIG. 35, c-jun protein levels, were low at 0 hr and 24 hr, but increased in cytosolic and nuclear fractions at 48 hr and 72 hr. For c-fos, protein levels were detected at baseline, increased substantially at 6 hr, and plateaued at 24, 48 and 72 hr. For phosphorylated c-jun (Ser 63), no substantial expression was detected over 72 hr. For phosphorylated c-jun (Ser 73), protein expression was detected at 0 hr and 6 hr in cytosolic and nuclear fractions, with a gradual increase in levels at 24 hour, 48 hr, and 72 hr. For phosphorylated c-jun (Thr 91, Thr 93), protein expression was detected at 0 hr, with peak levels at 6 hr, substantial expression levels at 24 hr, and a gradual decline at 48 hr and 72 hr. Protein was present in the cytosolic and nuclear fractions, with greater levels of protein in the nuclear fraction. In sum, the delayed increase in c-jun, after treatment with cyclopamine, is characterized by increased phosphorylation Thr 91 and Thr 93; but not at Ser 63. Also, the increase at Ser 73 in c-jun, peaks at 48-72 hr.

Figure 36:
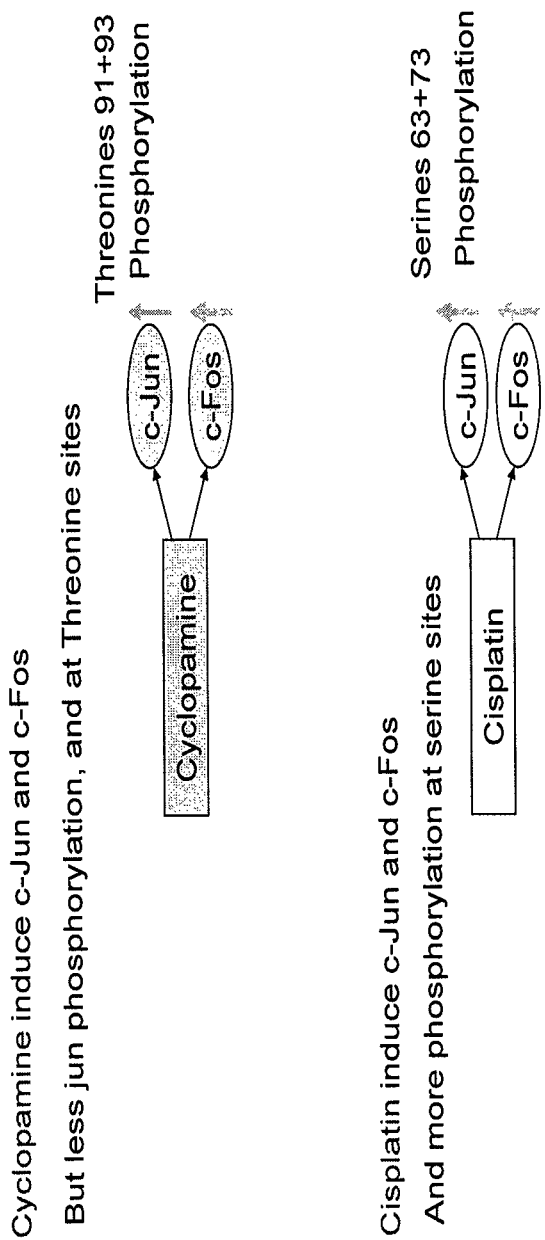
FIG. 36 shows a schematic diagram summarizing differences between c-jun expression in cells treated with cyclopamine or cisplatin.

The observed pattern of c-jun expression was distinct from the pattern observed in A2780-CP70 cells treated with cisplatin (Li Q, et al. J Biol Chem, 273:23419-23425, 1998). In response to cisplatin, c-jun (Ser 63/73) protein levels peaked at 3-5 hr after cisplatin exposure, and dropped dramatically below peak levels by 8 hr after exposure. FIG. 36 summarizes some differences between the c-jun response to cyclopamine, versus the c-jun response to cisplatin, in A2780-CP70 cells.

Accordingly, disruption of the Hedgehog pathway suppresses up-regulation of c-jun. Up-regulation of c-jun is necessary for up-regulation of genes that play a role in resistance to chemotherapeutic agents, such as genes involved in nucleotide excision repair, such as ERCC1 (Reed E. Cisplatin and platinum analogs. in: Cancer Principles and Practice of Oncology; 8th Edition. Lippincott, Williams, and Wilkins; Philadelphia, pp 419-26, 2008; Reed E. Cisplatin, Carboplatin, and Oxaliplatin. in: Cancer Chemotherapy and Biotherapy: Principles and Practice. 4th Edition. Lippincott, Williams & Wilkins, Philadelphia, pp 332-343, 2006; Li Q, et al. AntiCancer Research, 20: 645-652, 2000; Dabholkar, M., et al. J Clin Invest, 94:703-708, 1994; Dabholkar, M., et al. Oncology Reports, 2:209-214, 1995).

Example 22

Transfection of A2780-CP70 Cells with an Anti-GLI1 shRNA Construct

Figure 37:
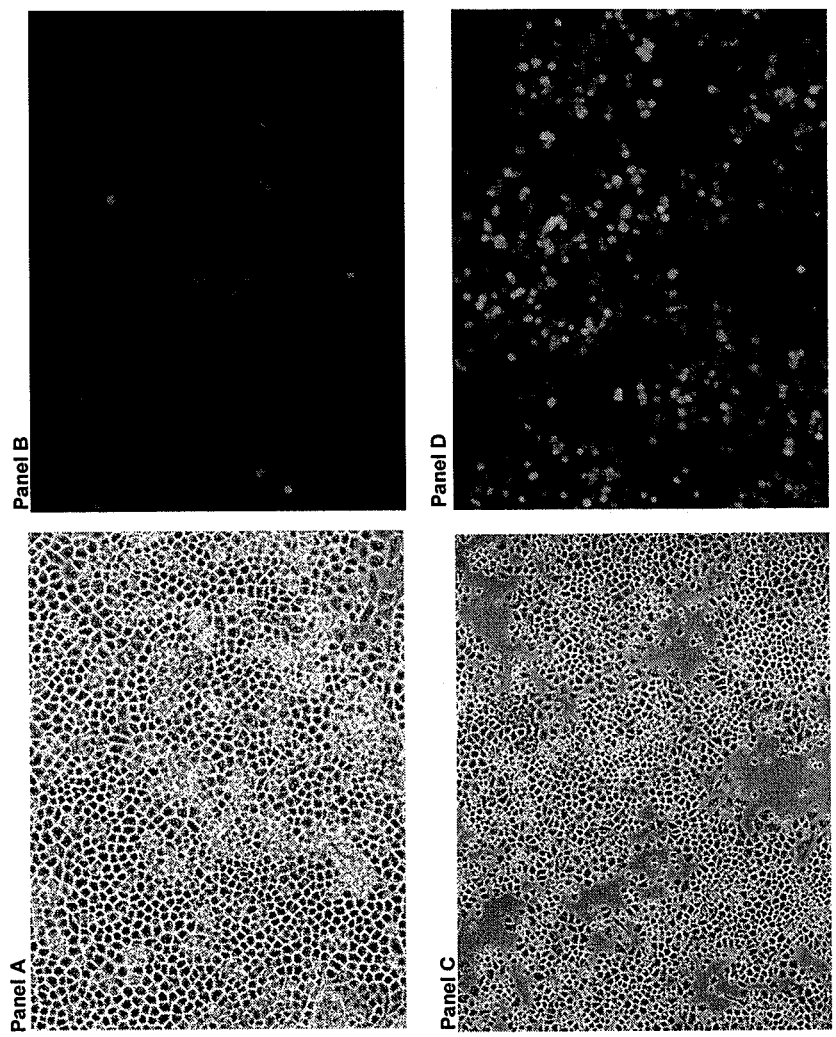
FIG. 37 shows a photomicrograph of A2780-CP70 cells transfected with an anti-GLI1 shRNA construct. Panels A and B show a cell-field immediately after transfection under visible light and fluorescent light conditions, respectively. Panels C and D show a cell-field 24 hr after transfection under visible light and fluorescent light conditions, respectively.

An anti-Gli1 shRNA construct that incorporated an anti-GLI1 shRNA in a pSUPERIOR GFP neo vector was transfected into A2780-CP70 cells. This construct corresponds to GLI1 shRNA-1 construct of Example 4. FIG. 37A and FIG. 37B show a field of cells at 0 hr after transfection. FIG. 37C and FIG. 37D show a field of cells at 24 hr after transfection. At 24 hr after transfection, >70% of cells were transfected with the anti-Gli1 shRNA construct. At this level of transfection, a 50% inhibition of growth was observed. Experiments described herein, were carried out using cells that remained adherent.

Example 23

Figure 38:
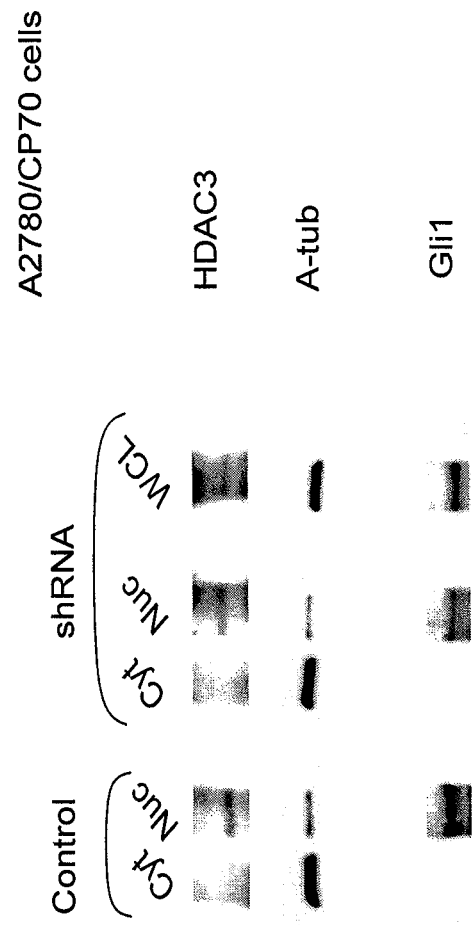
FIG. 38 shows a Western blot of A2780-CP70 cells transfected with anti-GLI1shRNA construct and probed for GLI1, HDAC3, and α-tubulin. Samples were taken 44 hr post-transfection.

Gli1 and Gli2 Expression in A2780-CP70 Cells Transfected with Anti-GLI1 shRNA Construct Gli1 protein expression was examined in nuclear and cytoplasmic fractions of A2780-CP70 cells transfected with anti-GLI1 shRNA construct using Western blot analysis. Referring to FIG. 38, Gli1 protein levels in the nuclear fractions were reduced 44 hr post-transfection in comparison to protein levels at 0 hr.

Figure 39:
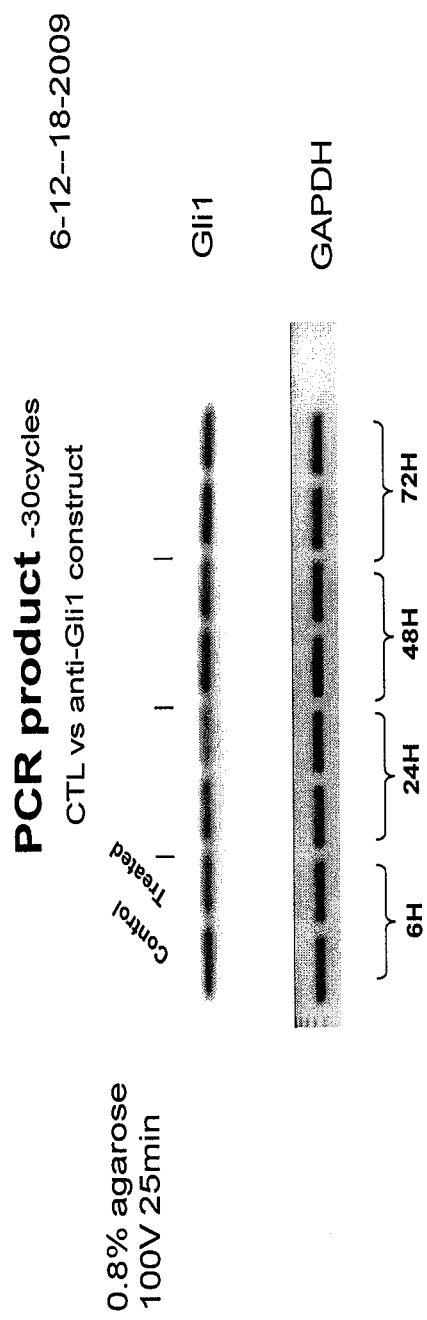
FIG. 39 shows a Southern blot of A2780-CP70 cells transfected with anti-GLI1 shRNA construct, and reflects a PCR assessment of mRNA levels for GLI1 and GAPDH. Samples were taken 6 hr, 24 hr, 48 hr, and 72 hr post-transfection.

GLI1 mRNA expression was examined in A2780-CP70 cells transfected with anti-GLI1 shRNA construct at 6 hr, 24 hr, 48 hr, and 72 hr post-transfection using a semi-quantative PCR analysis (FIG. 39). Blots were assessed by radiodensitometry. At 6 hr, the GLI1 mRNA expression was reduced by approximately half compared to control cells, with further reduction at 24 hr. There was partial recovery at 48 hr. At 72 hr transfected cells and control cells show equivalent levels of GLI1 mRNA expression.

Figure 40:
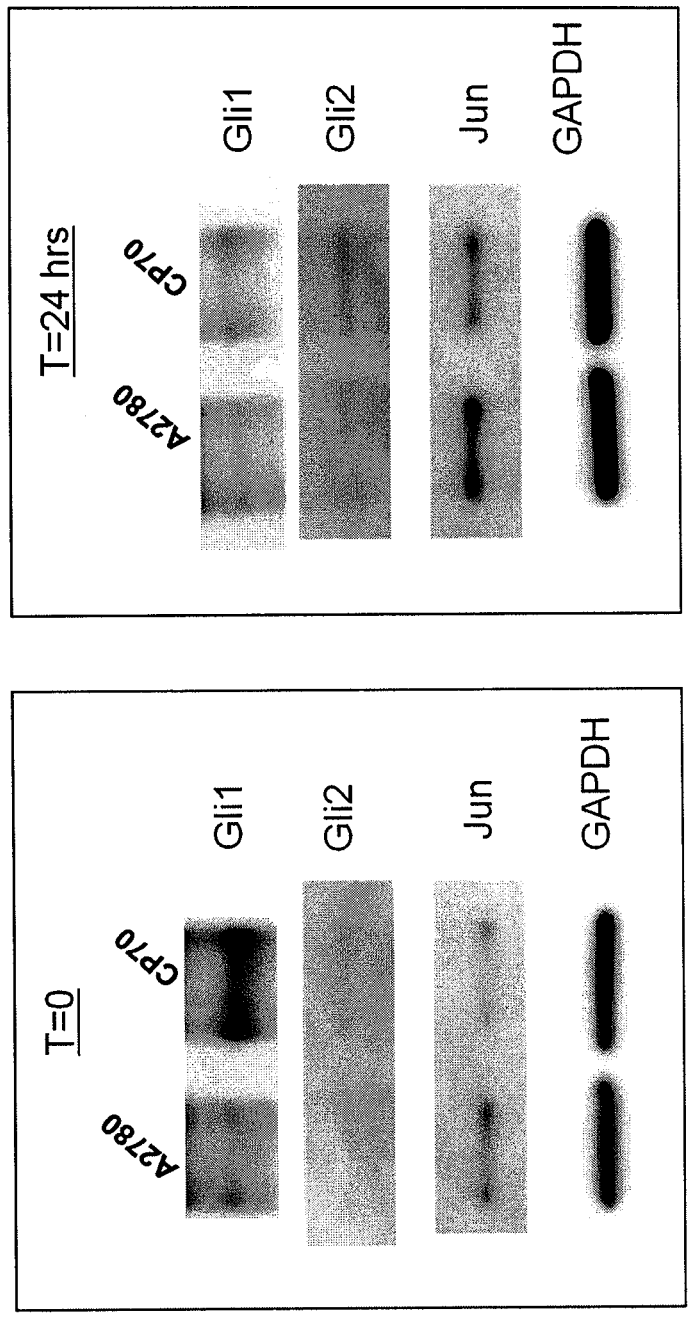
FIG. 40 shows a Western blot of A2780-CP70 and A2780 cells transfected with anti-GLI1 shRNA construct and probed for GLI1, GLI2, c-jun, and GAPDH. Samples were taken 24 hr post-transfection.

Gli2 protein expression was examined in A2780 and A2780-CP70 cells transfected with anti-GLI1 shRNA construct using Western blot analysis. Referring to FIG. 40, in A2780-CP70 cells transfected with anti-GLI1 shRNA construct, Gli2 protein levels remain similar after 24 hr post-transfection.

Figure 41:
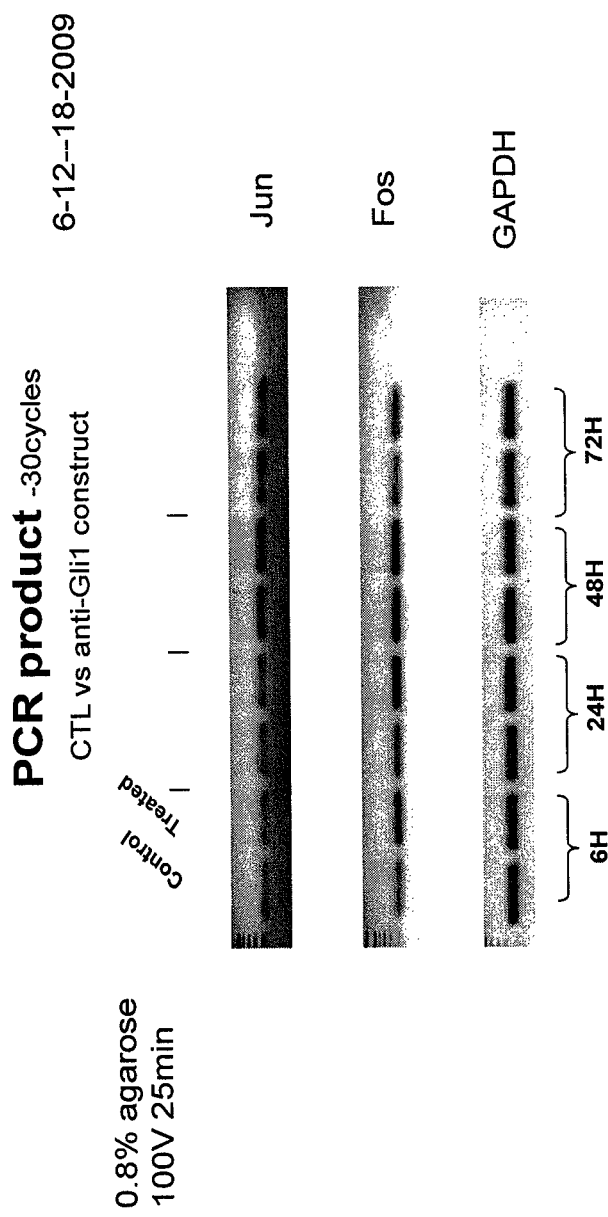
FIG. 41 shows a Southern blot of A2780-CP70 cells transfected with anti-GLI1 shRNA construct, and reflects a PCR assessment of mRNA levels for c-jun, c-fos, and GAPDH. Samples were taken 6 hr, 24 hr, 48 hr, and 72 hr post-transfection.

Example 24 c-Jun and c-Fos Expression in A2780-CP70 Cells Transfected with Anti-GLI1 shRNA Construct c-jun and c-fos mRNA expression was examined in A2780-CP70 cells transfected with anti-GLI1 shRNA construct at 6 hr, 24 hr, 48 hr, and 72 hr post-transfection using semi-quantative PCR analysis (FIG. 41). Transfection of the anti-Gli1 shRNA construct resulted in a 5-6 fold increase in c-fos mRNA compared to control cells at 24 hr, which returned to baseline at 72 hr. For c-jun, there was no substantive difference between transfected and control cells. Comparable changes were observed in c-fos and c-jun protein levels in transfected and control cells. In sum, treatment with anti-Gli1 shRNA construct resulted in stable mRNA levels of c-jun and increased levels of c-fos in A2780-CP70 cells.

These data suggest that the c-jun response in A2780-CP70 cells is similar whether the hedgehog pathway is challenged by inhibiting the plasma transmembrane protein, Smoothened, with cyclopamine, or by reducing the levels of the transcriptional activator, Gli1, by transfecting cells with anti-Gli1 shRNA construct. An increase in c-jun protein expression is suppressed for 6 to 24 hr when the Hedgehog pathway is challenged by methods that result in ~50% cell killing. In contrast, the c-jun response in cells treated with an IC50 dose of cisplatin is very different. Suppression of the Hedgehog pathway results in suppression of c-jun expression.

The Hedgehog pathway acting through Gli1 may allow for the rapid up-regulation of c-jun after treatment of cells with cisplatin. Rapid up-regulation of c-jun would allow for rapid up-regulation of ERCC1 and other NER genes that play a role in removal of platinum-DNA damage.

The >20-fold higher levels of Gli1 that are observed in cisplatin-resistant A2780-CP70 cells (as compared to cisplatin-sensitive A2780 cells), would allow for greater up-regulation of NER. This greater up regulation of NER would be consistent with previous observations, when comparing these two cell lines for platinum-DNA adduct repair. Such an interaction between Gli1 and Jun has been described on non-NER genes.

Figure 42:
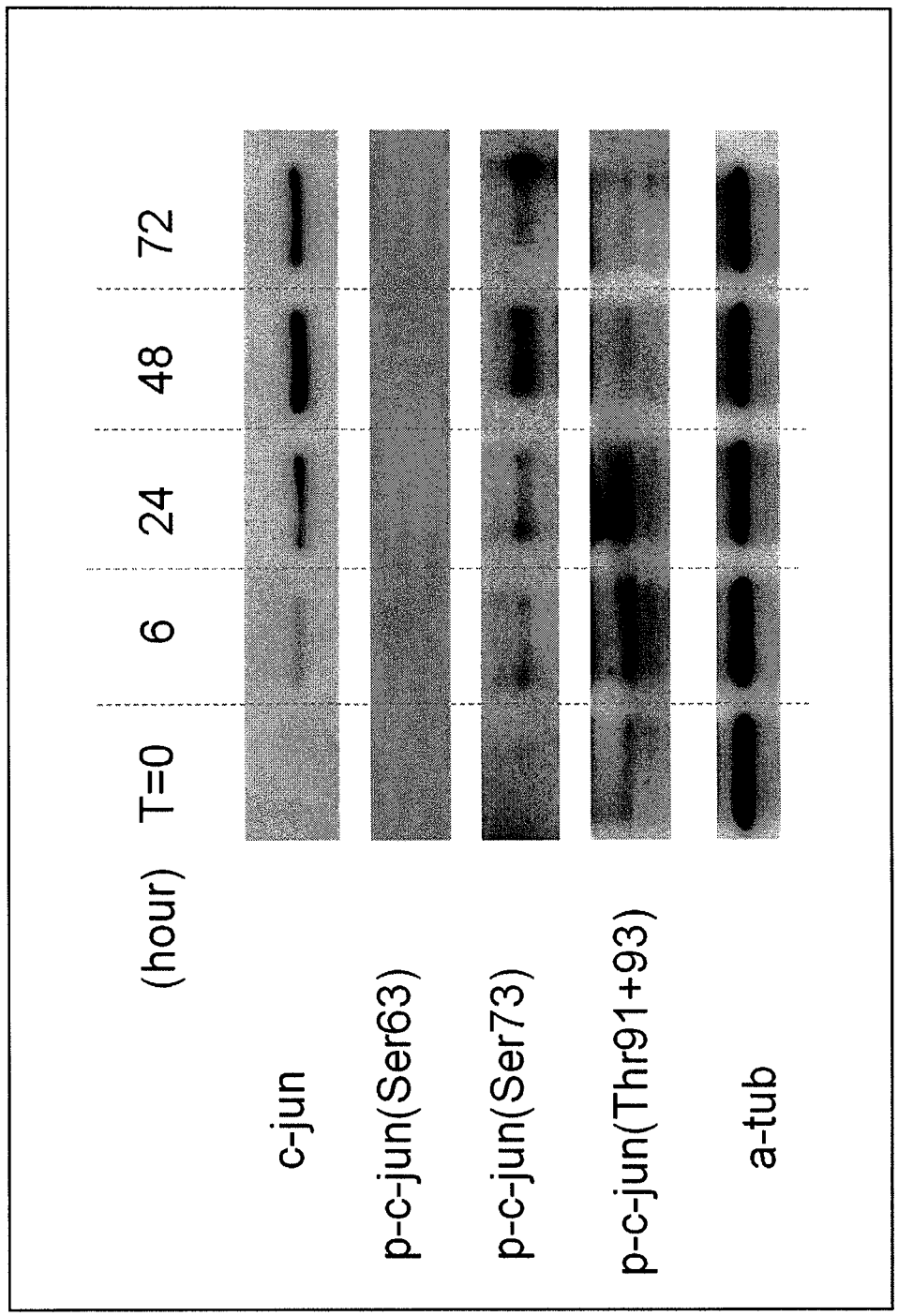
FIG. 42 shows a Western blot of A2780-CP70 cells transfected with anti-GLI1 shRNA construct and probed c-jun, c-fos, phosphorylated c-jun (Ser 63), phosphorylated c-jun (Ser 73), phosphorylated c-jun (Thr 91, Thr 93), and α-tubulin. Samples were taken 0 hr, 6 hr, 24 hr, 48 hr, and 72 hr post-transfection.

Example 25 c-Jun Protein Phosphorylation in A2780-CP70 Cells Transfected with Anti-GLI1 shRNA Construct Phosphorylation of c-jun in A2780-CP70 cells transfected with anti-GLI1 shRNA construct was assessed using Western blot analysis. Protein levels for c-jun, phosphorylated c-jun (Ser 63), phosphorylated c-jun (Ser 73), and phosphorylated c-jun (Thr 91, Thr 93) were examined at 0 hr, 6 hr, 24 hr, 48 hr, and 72 hr. Referring to FIG. 42, c-jun (Ser 63) upregulation is inhibited in cells transfected with anti-GLI1 shRNA construct; c-jun (Thr 91, Thr 93) is upregulated.

The anti-GLI1 shRNA construct inhibits phosphorylation of c-jun at Ser 63. c-jun (Ser 63) plays a role in cellular resistance to chemotherapeutic agents, and DNA repair, such as ERCC1-related DNA repair. Accordingly, inhibition of Gli1 is likely to block the up-regulation of the c-jun (Ser 63) cascade and inhibit DNA repair mechanisms, such as those in which ERCC1 plays a role.

Gli1 and c-jun may co-operate in the transcriptional regulation of some genes (Laner-Plamberger S, et al. Oncogene 28:1639-1651, 2009). The data presented here suggests that Gli1 and c-jun cooperate in the transcriptional regulation of at least ERCC1 and other DNA repair genes.

Example 26

Figure 43:
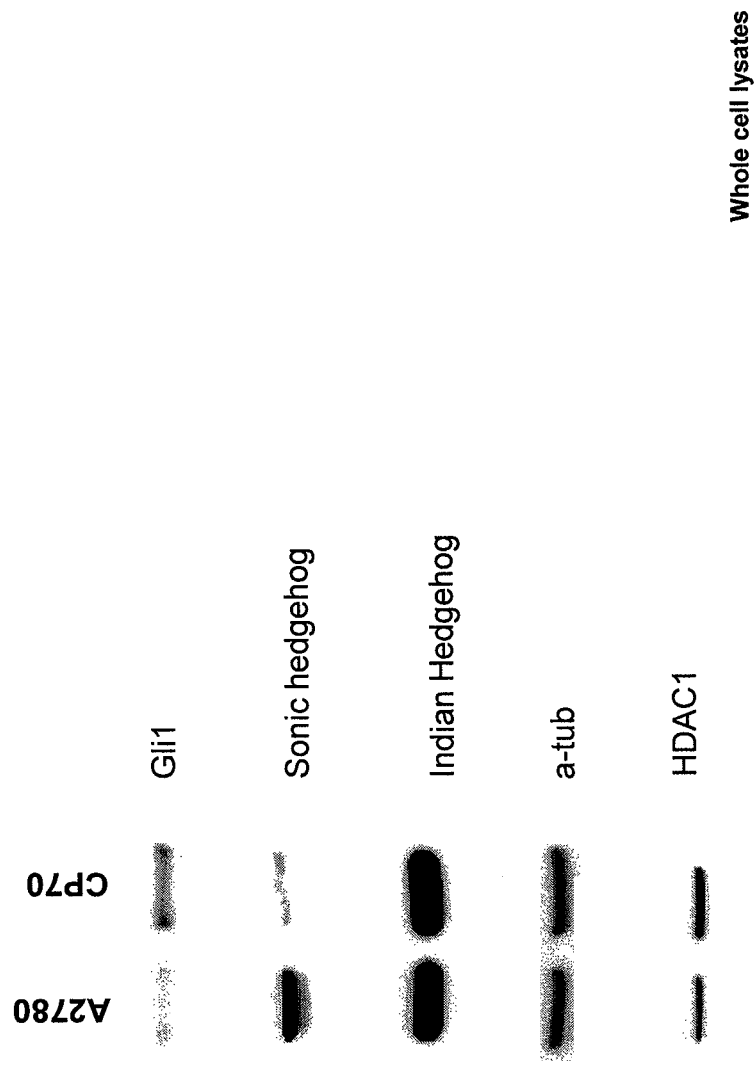
FIG. 43 shows a Western blot of A2780-CP70 and A2780 cells transfected with anti-GLI1 shRNA construct and probed GLI1, SSH, IHH, α-tubulin, and HDAC1. Samples were taken 24 hr post-transfection.

Sonic Hedgehog (SHH) and Indian Hedgehog (IHH) Expression in A2780 and A2780-CP70 Cells Transfected with Anti-GLI1 shRNA Construct Monolayers of A2780 cells or A2780-CP70 cells were transfected with anti-GLI1 shRNA construct. SHH and IHH protein expression was examined 24 hr post-transfection on whole cell lysates using Western blot analysis. Referring to FIG. 43, at 24 hr post-transfection, IHH protein levels were similar in A2780 and A2780-CP70 cells, while SHH protein levels were >10 fold higher in A2780 cells compared to A2780-CP70 cells. At 24 hr post-transfection, IHH levels were >5 fold and >20 fold greater than SHH levels in A2780 cells and A2780-CP70 cells, respectively. These differences contrast to those seen in A2780-CP70 cells treated with cyclopamine where IHH and SHH protein levels were virtually the same.

Figure 44:
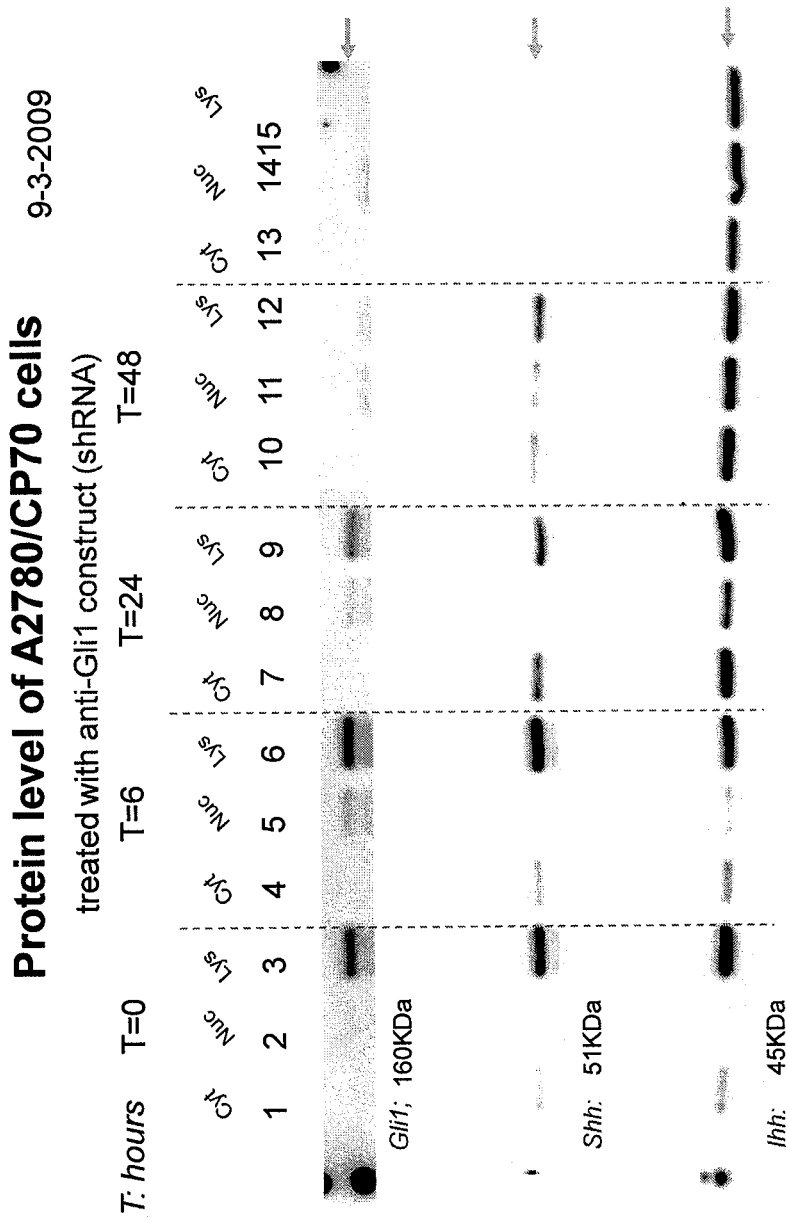
FIG. 44 shows a Western blot of A2780-CP70 cells transfected with anti-GLI1 shRNA construct and probed GLI1, SSH, and IHH. Samples were taken 0 hr, 6 hr, 24 hr, and 48 hr post-transfection.

Protein levels of Gli1, SHH, and IHH in A2780-CP70 cells were examined at 0 hr, 6 hr, 24 hr, 48 hr, and 72 hr post-transfection in cytosolic and nuclear fractions and whole cell lysates using Western blot analysis. Referring to FIG. 44, Gli1 protein levels peaked at 6 hr, were reduced at 24 hr, and not detected at 48 and 72 hr. SHH ligand protein levels peaked at 24 hr in cytosolic fractions, and decreased thereafter. In nuclear fractions, SHH protein levels remained low and peaked at 48 hr. In whole cell lysates, SHH protein levels exceeded the sum of the levels observed in the cytosolic and nuclear fractions, suggesting that SHH may accumulate in a cell membrane fraction in these assays. IHH ligand protein levels gradually increased over the initial 24 hr in the cytosolic and nuclear fractions, and those levels were maintained at hr 48 and 72. FIG. 44 also shows that IHH ligand protein levels were greater than SHH ligand protein level in A2780-CP70 cells at 24 hr post-transfection. In sum, treatment of cisplatin-sensitive and cisplatin-resistant human ovarian cancer cells with an anti-Gli1 shRNA construct has different effects on the cellular protein levels of SHH and IHH.

Example 27

ERCC1, XPD, or XRCC1 mRNA Levels in A2780-CP70 Cells Treated with Cyclopamine or Transfected with Anti-Gli1 shRNA Construct Cellular insults that result in 50% cell killing in A2780-CP70 cells can result in up-regulation of the JUN-kinase pathway and/or the ERK pathway (Li Q, et al. J Biol Chem, 273:23419-23425, 1998; Li Q, et al. International Journal of Oncology, 13:987-992, 1998; Li Q, et al. Cellular and Molecular Life Sciences, 55:456-466, 1999). Up-regulation of these pathways can result in up-regulation of ERCC1 and other essential DNA repair genes. To determine whether the Hedgehog pathway plays a role in up-regulation of ERCC1, the Hedgehog pathway was inhibited in conditions that resulted in 50% cell killing.

Figure 45:
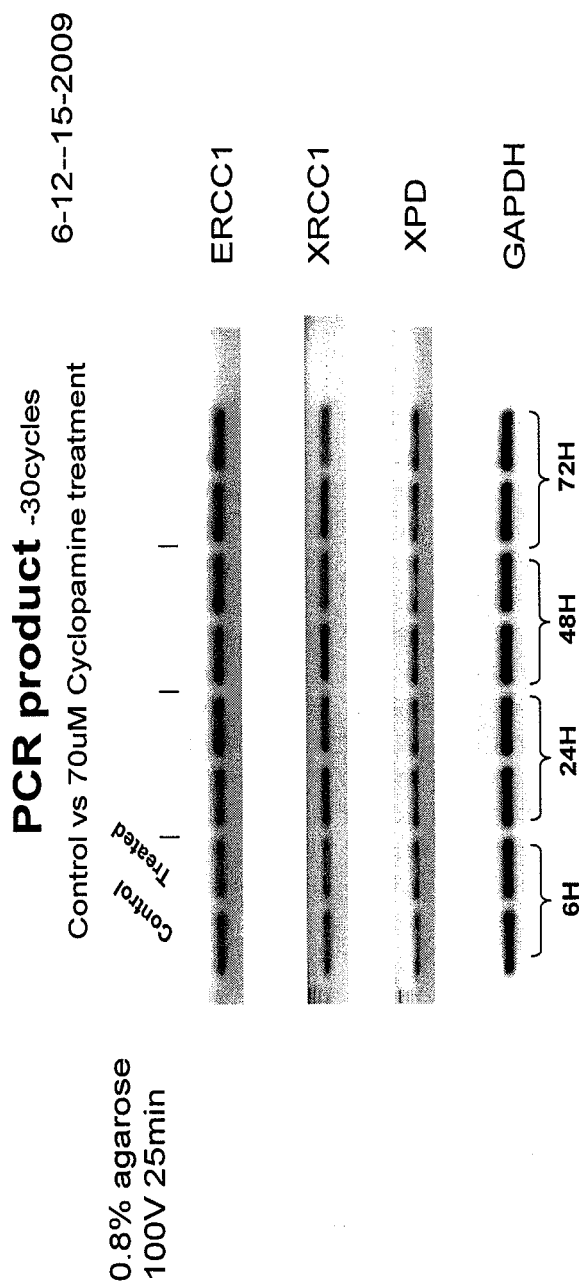
FIG. 45 shows a Southern blot of A2780-CP70 cells treated with 70 μM cyclopamine, and reflects a PCR assessment of mRNA levels for ERCC1, XRCC1, XPD, and GAPDH. Samples were taken at 6 hr, 24 hr, 48 hr, and 72 hr.

A2780-CP70 cells were treated with 70 μM cyclopamine, a concentration that causes 50-70% cell death. mRNA levels for ERCC1 and XPD of the NER pathway, and XRCC1 of the base excision repair pathway were determined at 6 hr, 24 hr, 48 hr, and 72 hr in treated and non-treated cells using semi-quantative PCR. Referring to FIG. 45, there was no increase in mRNAs for ERCC1, XPD, or XRCC1 following cyclopamine treatment in A2780-CP70 cells.

Figure 46:
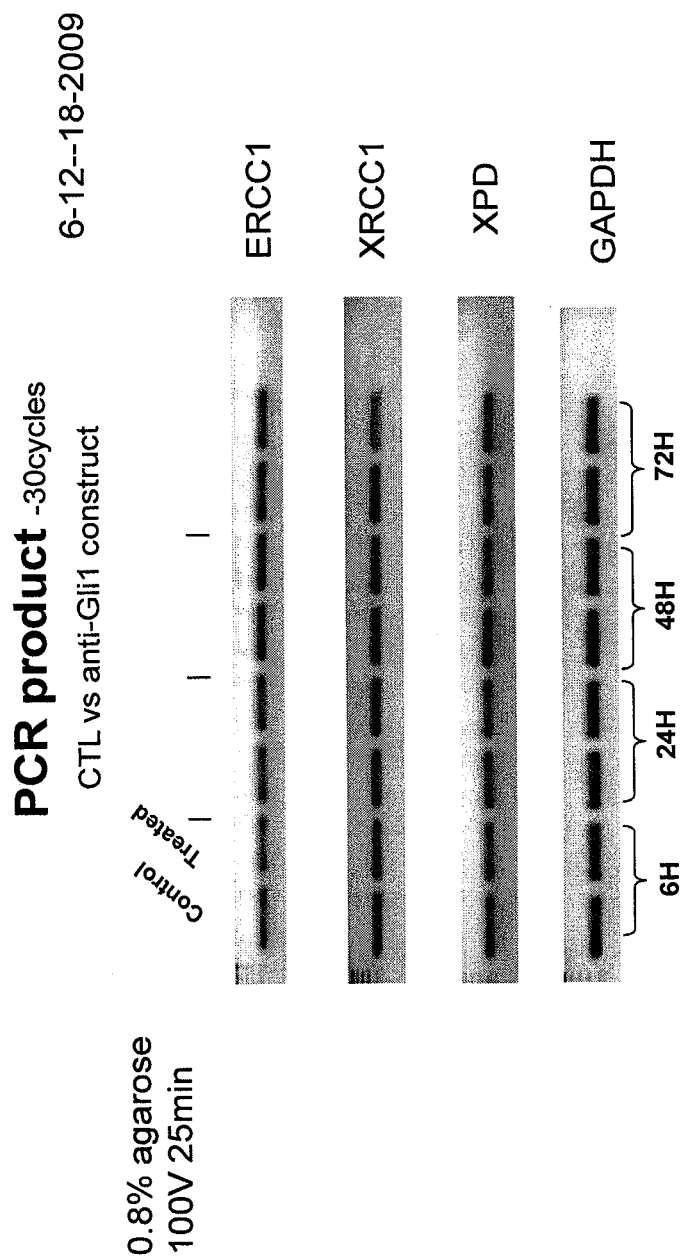
FIG. 46 shows a Southern blot of A2780-CP70 cells transfected with anti-GLI1 shRNA construct and, reflects a PCR assessment of mRNA levels for ERCC1, XRCC1, XPD, and GAPDH. Samples were taken at 6 hr, 24 hr, 48 hr, and 72 hr.

In another experiment, A2780-CP70 cells were transfected with anti-Gli1 shRNA construct. mRNA levels for ERCC1 and XPD of the NER pathway, and XRCC1 of the base excision repair pathway were determined at 6 hr, 24 hr, 48 hr, and 72 hr in transfected and control cells using semi-quantative PCR. Referring to FIG. 46, there was no increase in mRNAs for ERCC1, XPD, or XRCC1 in A2780-CP70 cells transfected with anti-Gli1 shRNA construct.

In sum, A2780-CP70 cells treated with cyclopamine or transfected with anti-Gli1 shRNA construct at levels that are associated with 50% cell killing had no detected effect on mRNA levels for ERCC1, XPD, or XRCC1. This observation contrasts with previous experiments where ERCC1, XPD, or XRCC1 were up-regulated in A2780-CP70 cells treated with other agents that invoke >50% cell death, including cisplatin and phorbol ester at IC50 doses.

Example 28

Figure 47:
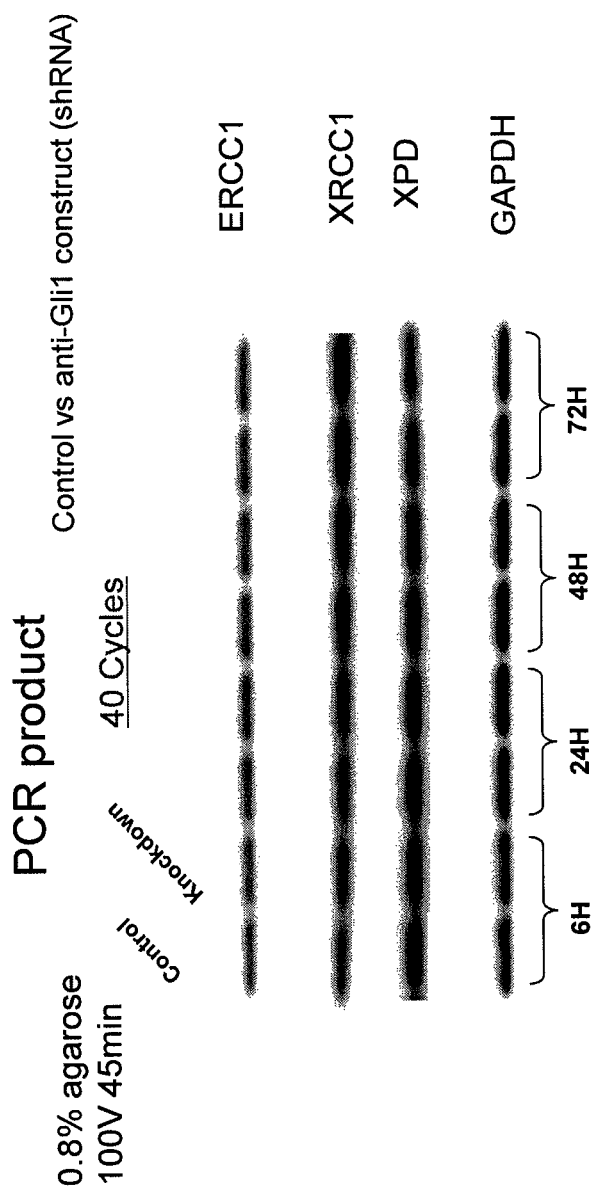
FIG. 47 shows a Southern blot of A2780-CP70 cells transfected with anti-GLI1 shRNA construct and treated with 40 μM cisplatin for 1 hr (IC50 dose), and reflects a PCR assessment of mRNA levels for ERCC1, XRCC1, XPD, and GAPDH. Samples were taken at 6 hr, 24 hr, 48 hr, and 72 hr.
Figure 48:
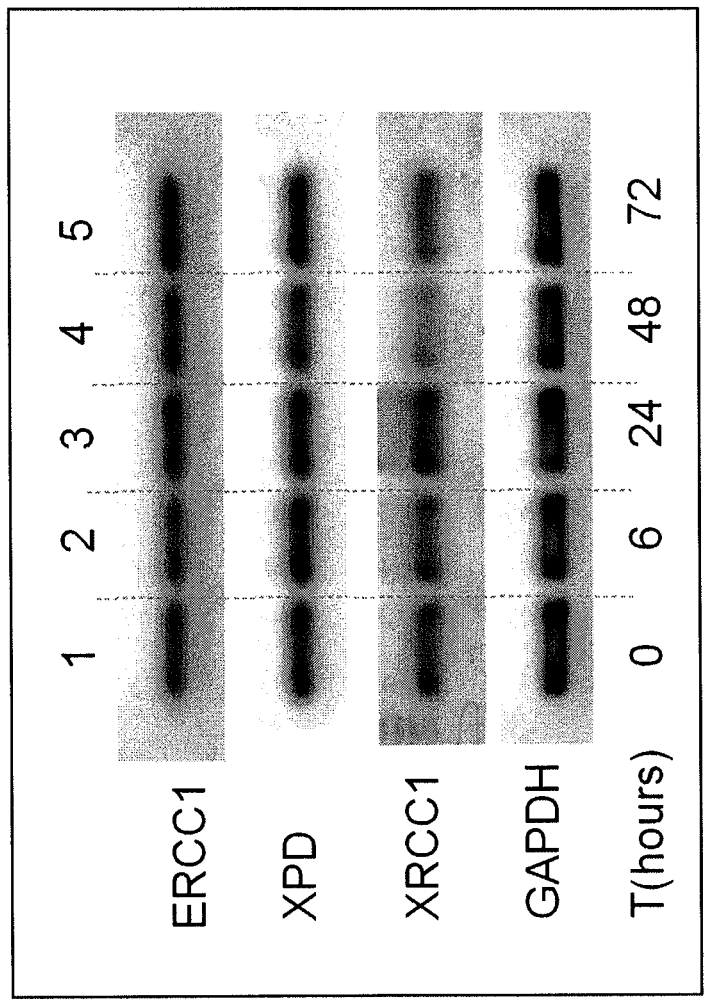
FIG. 48 shows a Southern blot of A2780-CP70 cells transfected with anti-GLI1 shRNA construct and treated with 40 μM cisplatin for 1 hr (IC50 dose), and reflects a PCR assessment of mRNA levels for ERCC1, XRCC1, XPD, and GAPDH. Samples were taken at 0 hr, 6 hr, 24 hr, 48 hr, and 72 hr.

ERCC1, XPD, or XRCC1 mRNA Levels in Anti-Gli1 shRNA Construct—Transfected A2780-CP70 Cells Treated with Cisplatin A2780-CP70 cells were transfected with anti-Gli1 shRNA construct at levels associated with 50% cell death. Cells were treated 24 hr post-transfection with 40 cisplatin for 1 hr (IC50 dose). mRNA levels of ERCC1, XPD, or XRCC1 were measured in adherent cells 6 hr, 24, hr, 48 hr, and 72 hr post-treatment using semi-quantative PCR. Referring to FIG. 47, mRNA levels of ERCC1, XPD, or XRCC1 were similar at each time point. This observation contrasts with an expected 6-fold increase in ERCC1 mRNA levels, in cells treated with cisplatin only (Li Q, et al. Modulation of ERCC-1 mRNA expression by pharmacological agents in human ovarian cancer cells. Biochemical Pharmacology, 57:347-353, 1999; Li Q, et al. Effect of interleukin-1 and tumor necrosis factor on cisplatin-induced ERCC1 mRNA expression in a human ovarian carcinoma cell line. Anticancer Research, 18: 2283-2287, 1998). FIG. 48 shows the results of a similar experiment. Surprisingly, transfection with anti-Gli1 shRNA construct for 24 hr, then treatment with an IC50 dose of cisplatin in A2780-CP70 cells, results in the absence of an expected cisplatin-related up-regulation of the mRNA of ERCC1, XRCC1, and XPD In sum, in cells treated with cisplatin, expression levels of ERCC1, XPD, and XRCC1 proteins increase 5-fold. However, in cells pretreated with anti-Gli1 shRNA construct, the expression levels of ERCC1, XPD, and XRCC1 do not increase in response to treatment to cisplatin.

Example 29

Figure 49:
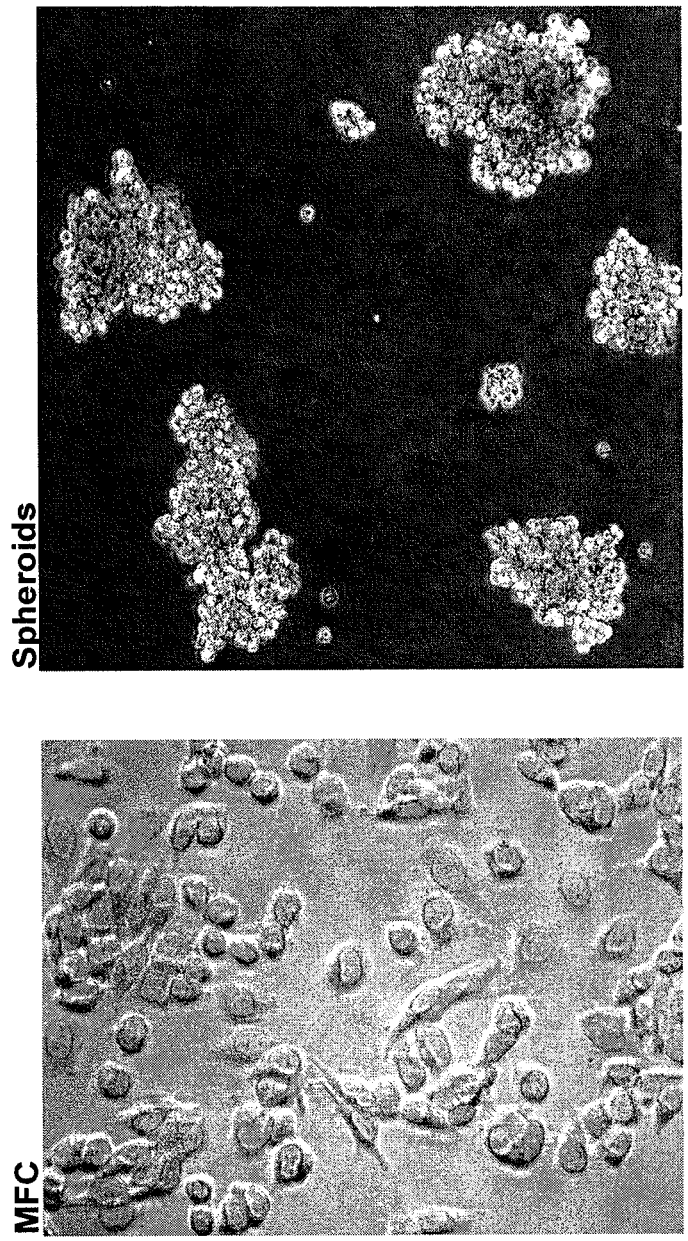
FIG. 49 shows photomicrographs of A2780 cells cultured in monolayers (left panel), or spheroids (right panel).

CD44, CD117 (c-Kit), and Gli1 Protein Levels in A2780 Cell Monolayers, Spheroids, and Monolayers Derived from Spheroids A2780 and A2780-CP70 cells can be cultured to have stem cell-like phenotypes by inducing spheroids in spheroid-forming non-adherent culture conditions. CD44, CD117 (c-Kit), and Gli1 protein expression was assessed using Western blot analysis in A2780 cells grown in monolayers (MFC—monolayer forming cells), spheroids, and monolayers derived from spheroids (SFC—spheroid forming cells), monolayers derived from spheroids were cultured as described in (Zhang S, et al. Cancer Res 68:4311-4320, 2008). FIG. 49 shows A2780 human ovarian cancer cells in two growth forms: a) MFC=monolayer forming cells; and, b) spheroids.

Figure 50:
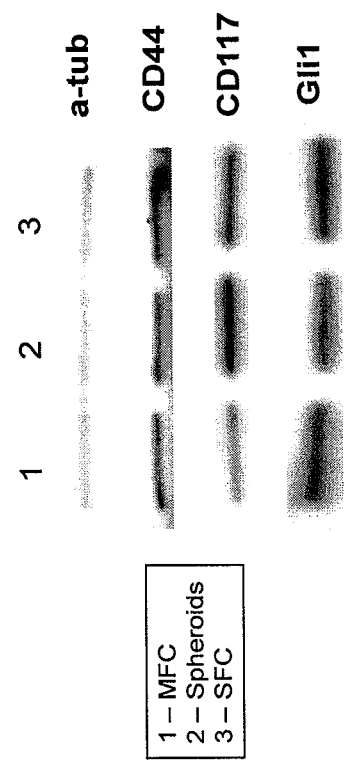
FIG. 50 shows a Western blot of A2780 cells probed GLI1, CD117, CD44, and α-tubulin. Lanes: 1-MFC (cells cultured in monolayers); 2-spheroids (cells cultured as spheroids); and 3-SFC (monolayers of cells derived from spheroids).

Referring to FIG. 50, protein expression for CD44, CD117 (c-Kit), and Gli1 was detected in A2780 cell monolayers, spheroids, and monolayers derived from spheroids. Expression of CD117 (c-Kit) was greatest in A2780 spheroids (lane 2). Protein expression for CD44 or Gli1 was similar in A2780 cell monolayers, spheroids, and monolayers derived from spheroids. Gli1 protein expression may be greater in monolayers derived from spheroids than in spheroids.

Example 30

Figure 51:
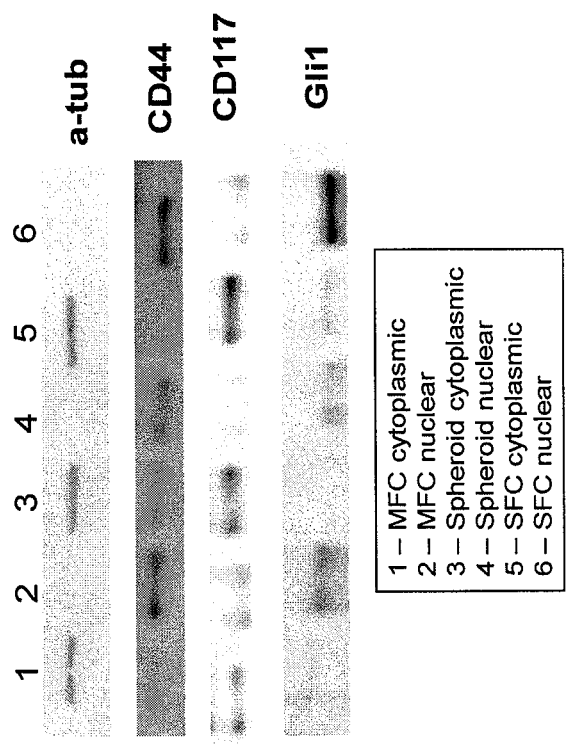
FIG. 51 shows a Western blot of A2780 cells probed GLI1, CD117, CD44, and α-tubulin. Lanes: 1-MFC (cells cultured in monolayers) nuclear fraction; 2-MFC (cells cultured in monolayers) cytoplasmic fraction; 3-spheroids (cells cultured as spheroids) nuclear fraction; 4-spheroids (cells cultured as spheroids) cytoplasmic fraction; and 5-SFC (monolayers of cells derived from spheroids) nuclear fraction; and 6-SFC (monolayers of cells derived from spheroids) cytoplasmic fraction.

Localization of CD44, CD117 (c-Kit), and Gli1 Protein Expression in A2780 Cell Monolayers, Spheroids, and Monolayers Derived from Spheroids CD117 (c-Kit), and Gli1 protein expression in A2780 cell monolayers, spheroids, and monolayers derived from spheroids was assessed in cytoplasmic and nuclear fractions using Western blot analysis. Referring to FIG. 51, CD117 was detected in cytoplasmic fractions of cells cultured as monolayers, spheroids, or monolayers derived from spheroids. Moreover, Gli1 was detected mostly in nuclear fractions. CD44 was detected in mostly in the nuclear fraction of cells grown as monolayers derived from sphereoids.

Example 31

Figure 52A:
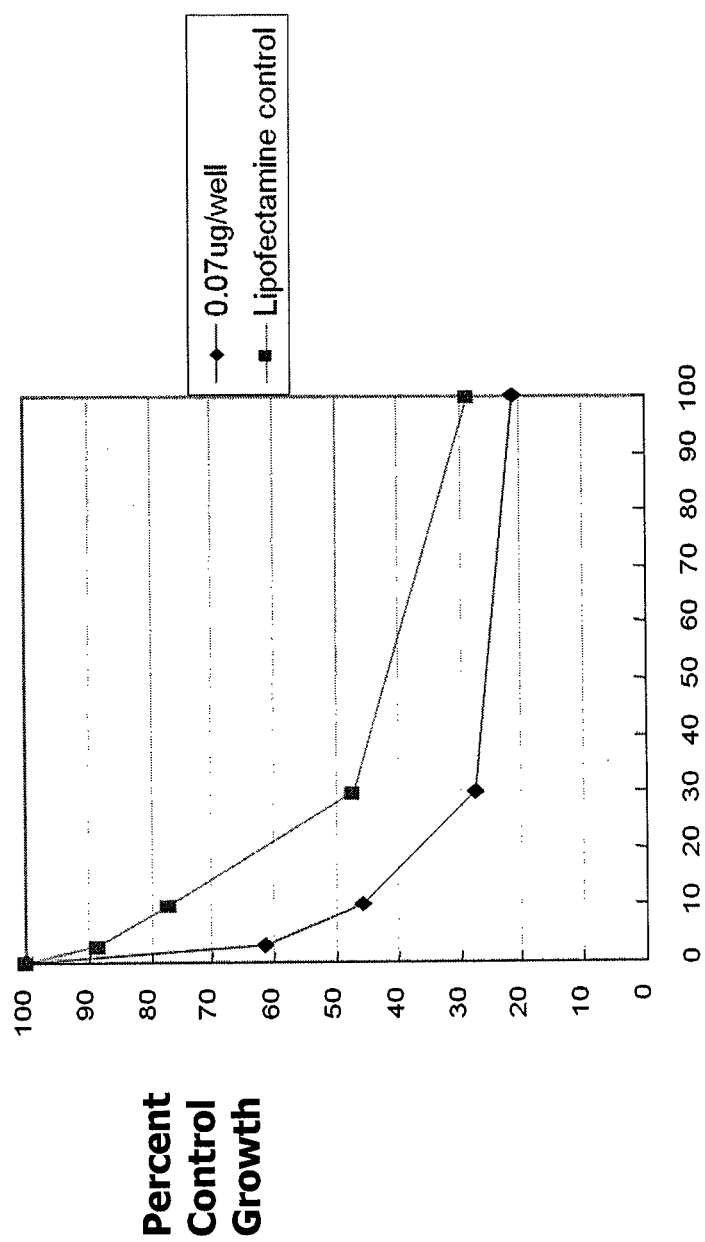
FIGS. 52A and 52B show graphs depicting of percent growth of A2780-CP70 cells transfected with anti-Gli1 shRNA construct and treated with various concentrations of cisplatin.
Figure 52B:
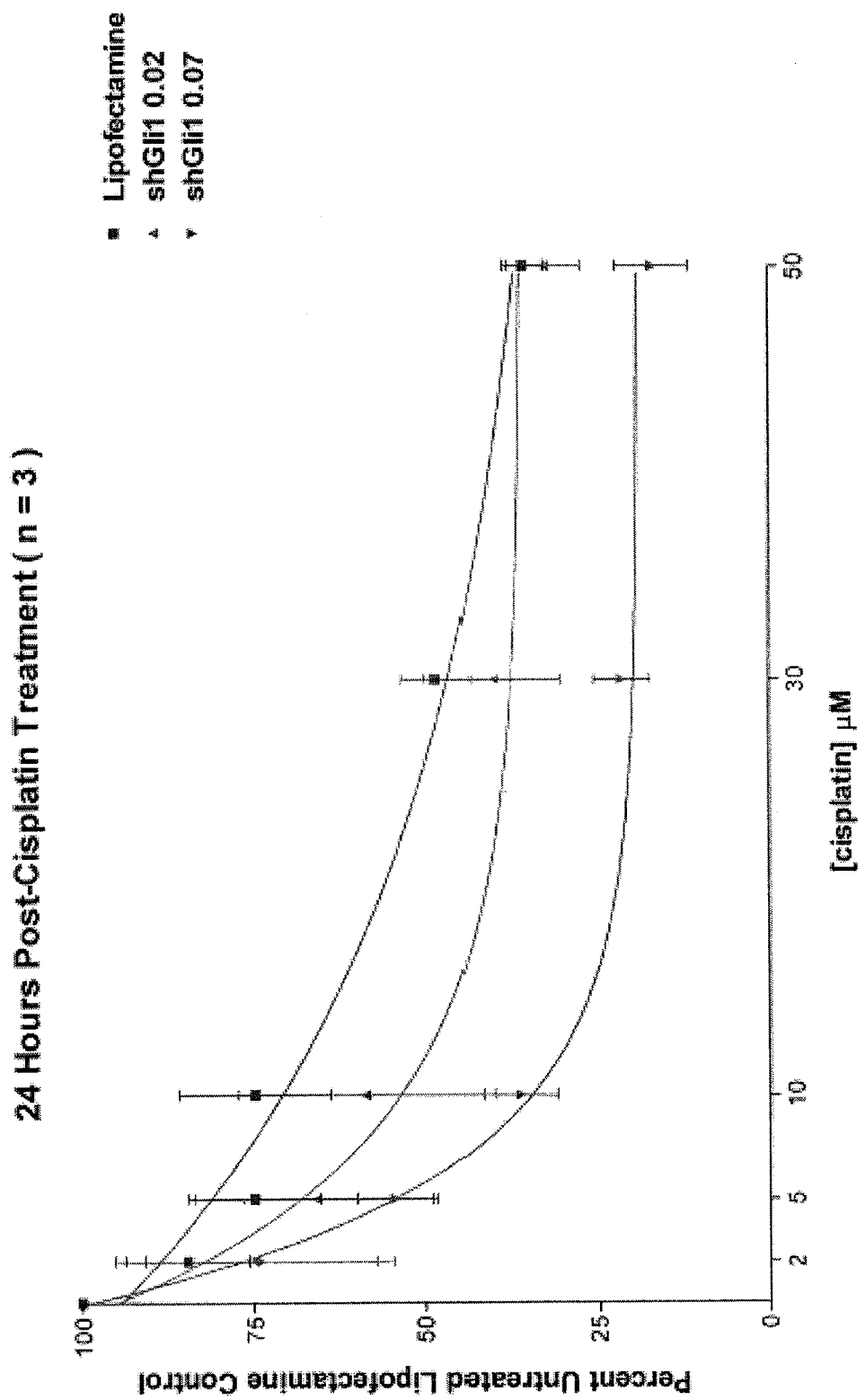

IC50 Cisplatin Dose in A2780-CP70 Cells Transfected with Anti-Gli1 shRNA Construct A2780-CP70 cells were transfected with 0.07 µg/well anti-Gli1 shRNA construct or control. Transfected cells were treated with 0 µM, 10 µM, 30 µM, and 100 µM cisplatin at 24 hr post-transfection. Percent cell growth was determined relative to control cells. Referring to FIG. 52A, cells transfected with anti-Gli1 shRNA construct had an IC50 of 8 µM cisplatin, compared to control cells with an IC50 of 28 µM cisplatin. In another experiment, A2780-CP70 cells were transfected with 0.02 µg/well or 0.07 µg/well anti-Gli1 shRNA construct. Transfected cells were treated with 0 µM, 2 µM, 5 µM, 10 µM, 30 µM, and 50 µM cisplatin at 24 hr post-transfection. Percent cell growth was determined relative to control cells (FIG. 52B). These results show that transfection with anti-Gli1 shRNA construct increases the sensitivity of A2780-CP70 cells to cisplatin.

Example 32

Figure 53:
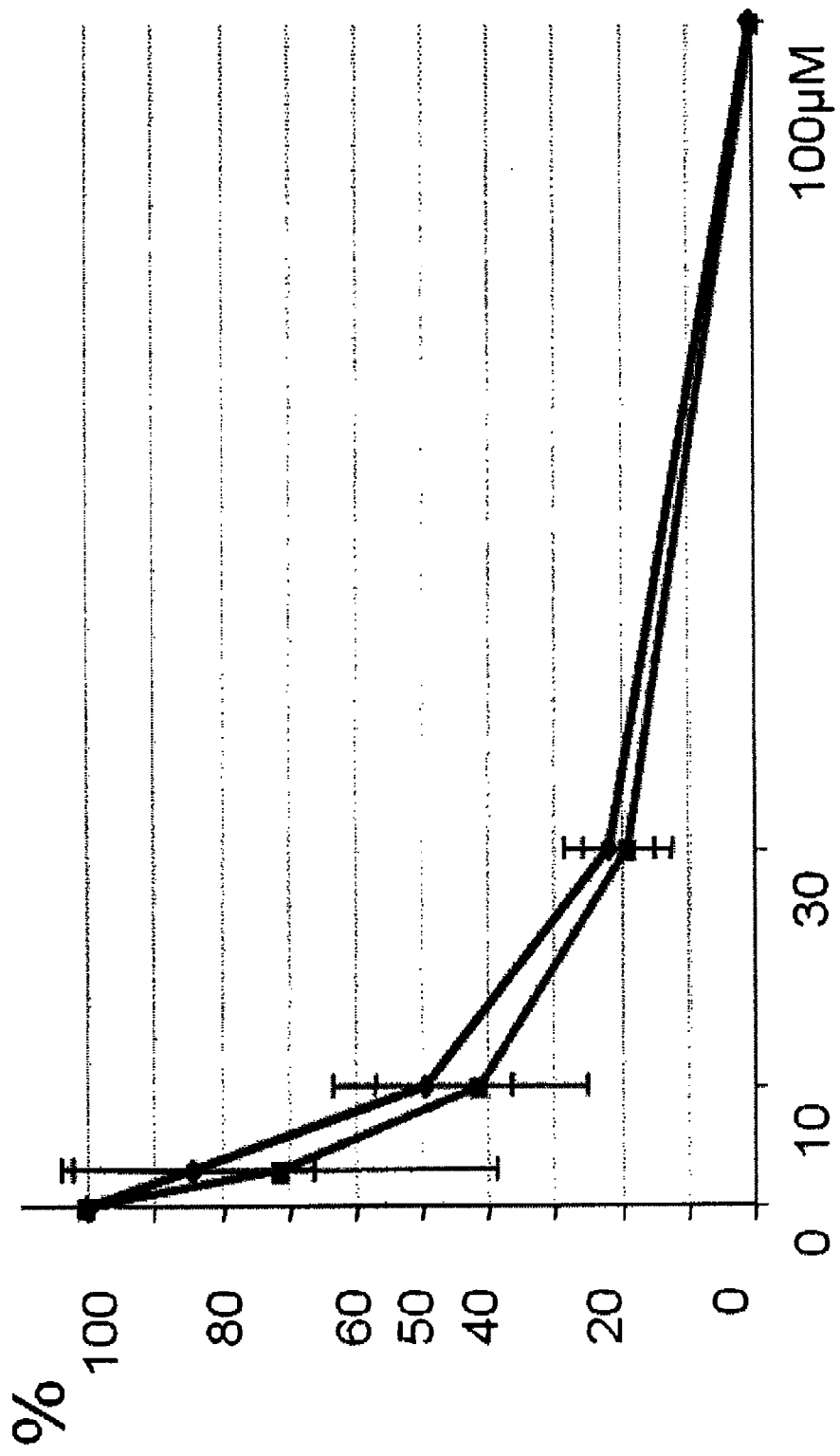
FIG. 53 shows a graph of percent growth of A2780-CP70 cells transfected with anti-Gli1 shRNA construct and treated with 20 μM cyclopamine for 1 hr, and 0 μM, 10 μM, 30 μM, or 100 μM cisplatin. Control cells were treated with cisplatin only.

IC50 Cisplatin Dose in A2780-CP70 Cells Treated with Cisplatin and Cyclopamine A2780-CP70 cells were treated with 20 µM cyclopamine for 1 hr, and 0 µM, 10 µM, 30 µM, or 100 µM cisplatin at 24 hr post-transfection. Control cells were treated with cisplatin only. Percent cell growth was determined relative to control cells. Referring to FIG. 53, levels of cell killing were similar for cells treated with cisplatin and cyclopamine as for cells treated with cisplatin only. These results suggest that the action of cyclopamine does not synergize with the action of cisplatin.

Example 33

A2780-CP70 Cells Transfected with Anti-Gli1 shRNA Construct

Figure 63:
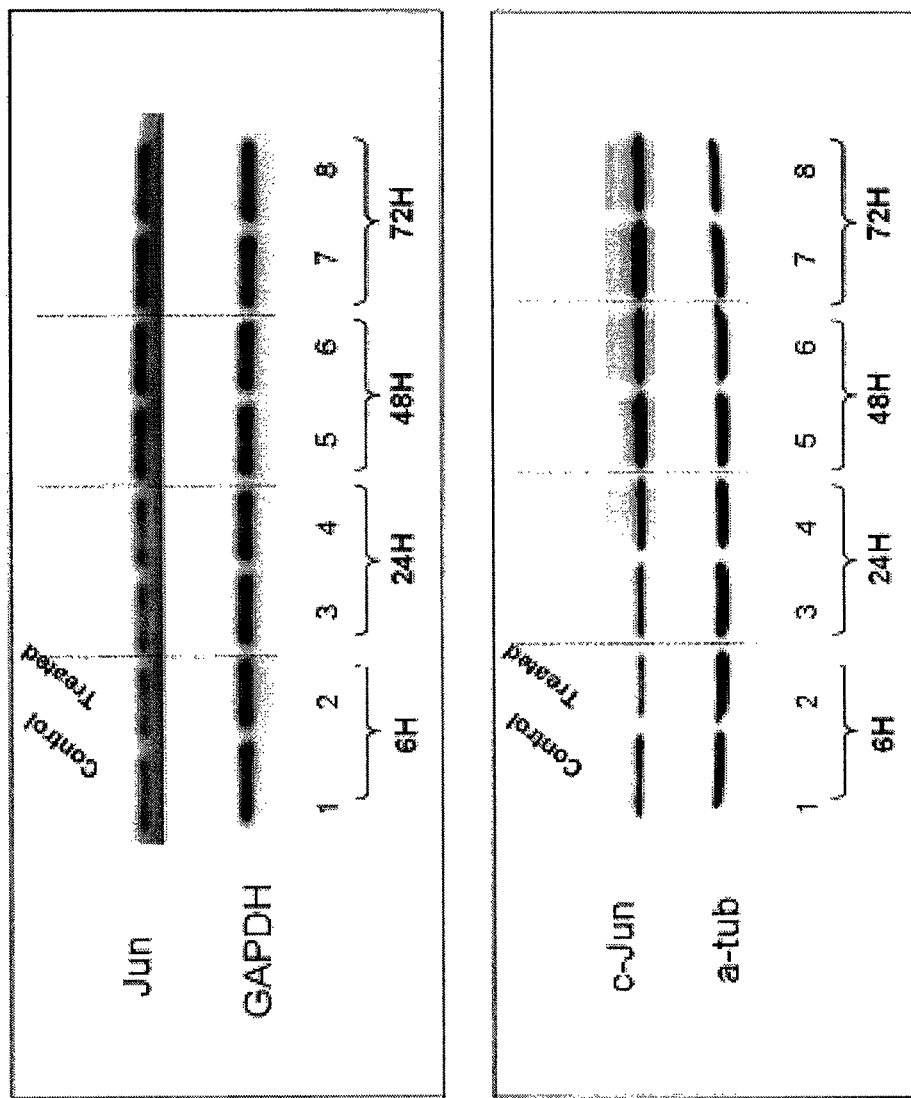
FIG. 63 (upper panel) and FIG. 63 (lower) show Northern and Western blots, respectively, of c-jun expression in A2780-CP70 cells treated with anti-Gli1 shRNA over time.

A2780-CP70 cells were transfected with an IC50 dose of anti-Gli1 shRNA (treated) construct or vector (control). Total intracellular c-jun mRNA and c-jun protein was measured at 6 hr, 24 hr, 48 hr, and 72 hr. FIG. 63 (upper panel) and FIG. 63 (lower) show Northern and Western blots, respectively, of c-jun expression in A2780-CP70 cells treated with anti-Gli1 shRNA over time. Treatment with an anti-Gli1 shRNA did not result in upregulation of total c-jun protein or mRNA. Transfection of a construct encoding anti-Gli1 shRNA does not result in upregulation of total intracellular c-jun mRNA or c-jun protein.

Example 34

Identification of a GLI1 Isoform Binding the C-JUN Promoter

A2780-CP70 cells treated with cisplatin results in upregulation of phosphorylation of c-jun protein (Ser 63/73); upregulation of c-jun (Ser 63/73) results in upregulation of AP-1; upregulation of AP-1 results in upregulation of genes including ERRC1, XPD, XPA, XRCC1, and other NER and BER genes. Upregulation of ERCC1 does not occur if upregulation of c-jun or AP-1 is blocked.

FIG. 52B shows a show depicting a cell survival assay in which human ovarian cells were treated with various concentrations of cisplatin in the presence of an anti-Gli1 shRNA. From FIG. 52B, increasing concentrations of an anti-Gli1 shRNA resulted in increased percentage of cell survival of cells treated with cisplatin.

Figure 64:
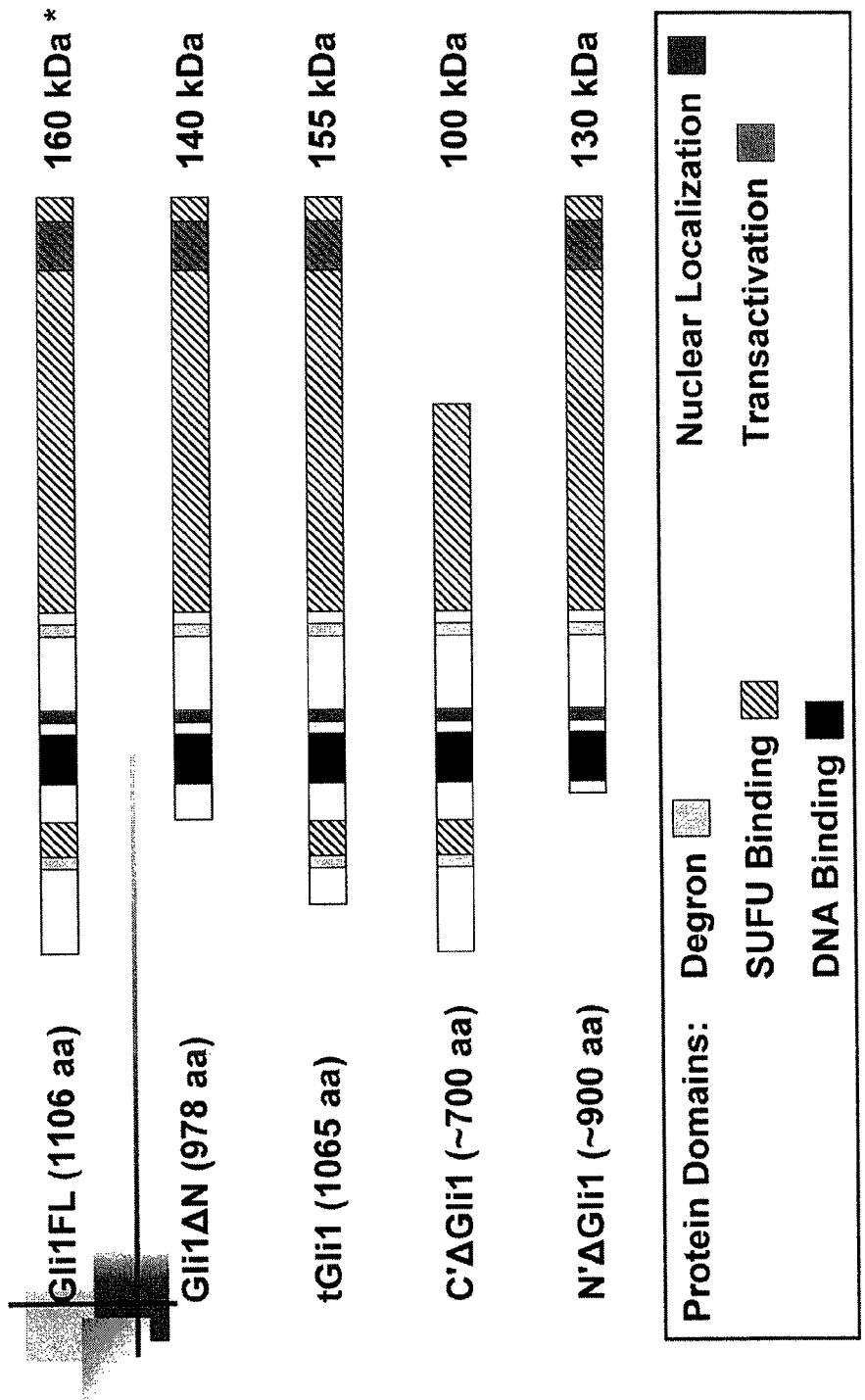
FIG. 64 shows a schematic diagram of the primary structures of several GLI1 protein isoforms.

FIG. 64 shows a schematic diagram of the primary structures of several GLI1 protein isoforms. GLI1FL represents a full-length isoform of 1106 residues; GLI1ΔN represents an isoform of 978 residues with an N-terminal truncation; tGLI1 represents an isoform of 1065 residues with an N-terminal truncation; C'ΔGLI1 represents an isoform of about 700 residues with a C-terminal truncation; and N'ΔGLI1 represents an isoform of about 900 residues with an N-terminal truncation. Domains in the isoforms include: a Degron domain that includes a residues that direct the starting place of degradation; a SuFu binding domain; a DNA binding domain; a nuclear localization signal; and a transactivation domain. GLI1ΔN and tGLI1 are two alternatively spliced GLI1 variants (See, e.g., Zhu H. and Lo H., Current Genomics 11, 238, 2010, the disclosure of which is incorporated herein by reference in its entirety). The N'ΔGLI1 (GLI1-130) protein isoform can be phosphylated or unphosphorylated; N'ΔGLI1 (GLI1-130) may be a post-translational product from GLIFL (Stecca et al., EMBO J. (2009) 28:663-676, the disclosure of which is incorporated herein by reference in its entirety; Ruiz A. (1999) Development 126: 3205-3216, the disclosure of which is incorporated herein by reference in its entirety). Table 4 summarizes GLI1 protein isoforms.

TABLE 4

| Name | Alternative name | Residues | Example amino acid sequence | *Weight (kDa) |
|---|---|---|---|---|
| GLI1 isoform 1 | GLI1FL | 1106 | SEQ ID NO: 19 | 160 |
| GLI1 isoform 2 | GLI1ΔN | 978 | SEQ ID NO: 20 | 140 |
| GLI1 isoform 3 | tGLI1 | 1065 | SEQ ID NO: 21 | 155 |
|  | C'ΔGLI1 | ~900 |  | 100 |
|  | N'ΔGLI1 | ~700 |  | 130 |

*Approximate molecular weight on denaturing polyacylamide gel

Figure 65:
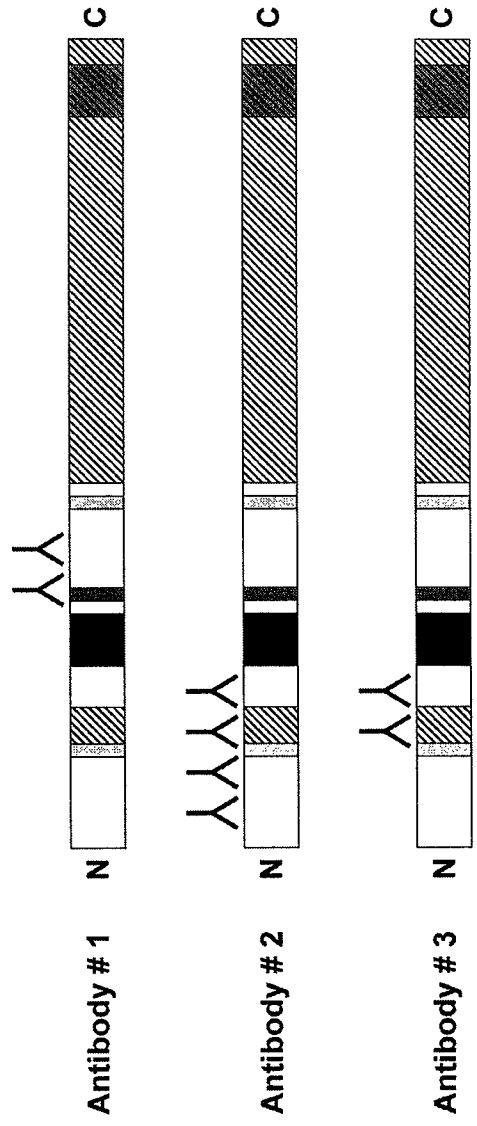
FIG. 65 shows a schematic diagram of the binding domains for three commercial antibodies (#1, #2, and #3) to the full length isoform of GLI1 protein.
Figure 66:
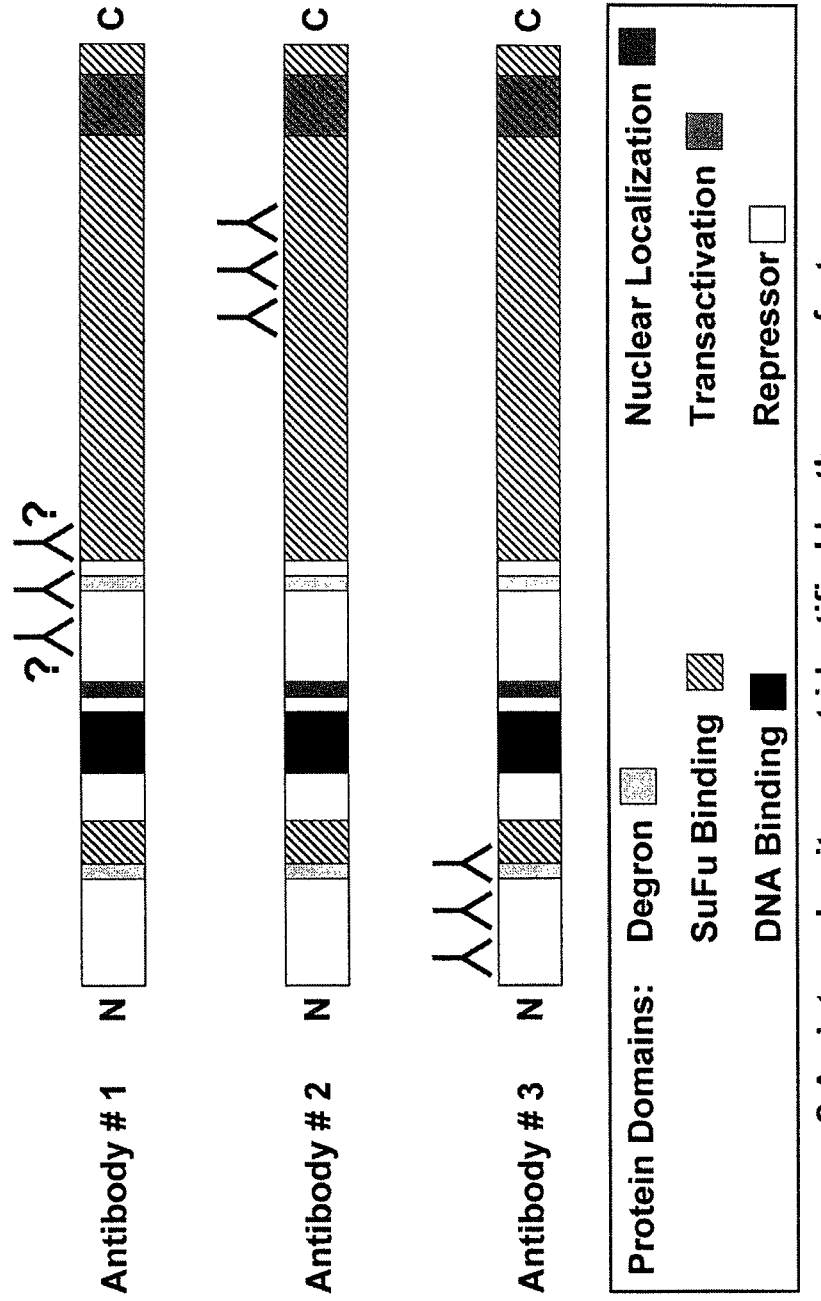
FIG. 66 shows the binding domains for three commercial antibodies (#1, #2, and #3) to the full length isoform of GLI2 protein.

FIG. 65 shows the binding domains for three commercial antibodies (#1, #2, and #3) to the full length isoform of GLI1 protein. FIG. 66 shows the binding domains for three commercial antibodies (#1, #2, and #3) to the full length isoform of GLI2 protein.

Figure 67:
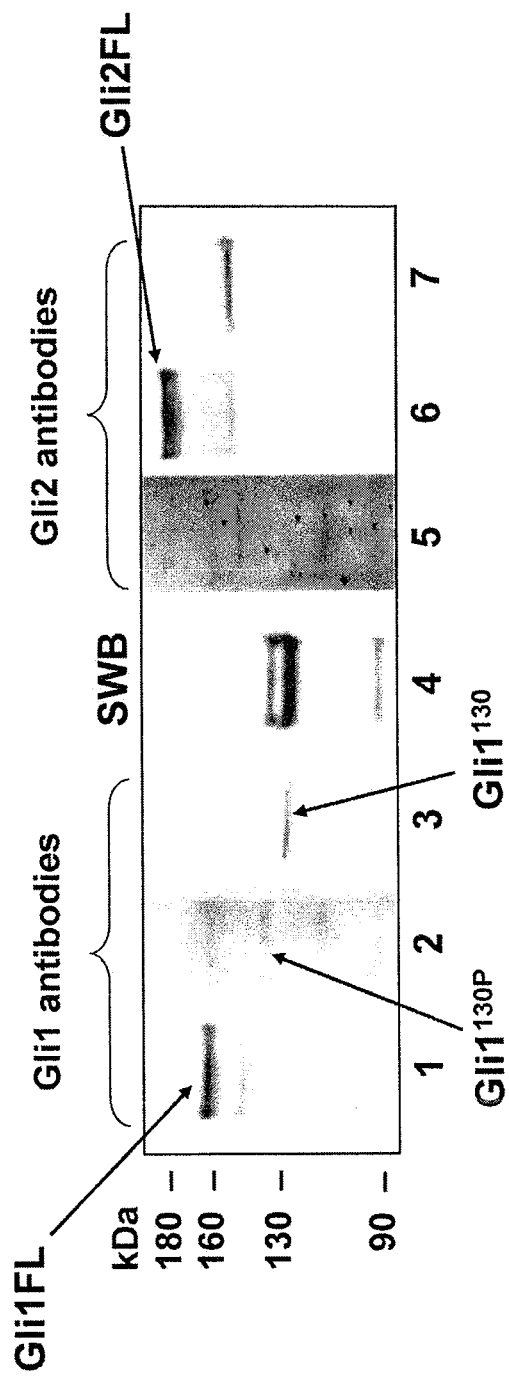
FIG. 67 depicts Western blots and a SouthWestern blot prepared from nuclear lysate of A2780-CP70 cells and probed with GLI1 antibodies #1, #2, and #3, and GLI2 antibodies #1, #2, and #3, and a DNA probe to the c-jun promoter.

FIG. 67 depicts Western blots and a SouthWestern blot prepared from nuclear lysate of A2780-CP70 cells and probed with GLI1 antibodies #1, #2, and #3, and GLI2 antibodies #1, #2, and #3, and a DNA probe to the c-jun promoter and comprising the GLI1 binding site. GLI1 antibodies #2 and #3 bind to bands that correspond to GLI1-130 in phosporylated and unphosphorylated states, respectively (FIG. 67, lanes 2 and 3 of). Nuclear lysate probed with a c-jun promoter probe binds to bands that correspond to GLI1-130 in phosporylated and unphosphorylated states (FIG. 67, lane 4). Thus, GLI-130 binds to the c-jun promoter and suggests that GLI-130 plays a role in AP-1 inhibition.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method for treating or ameliorating a disorder in a subject with a reduced dosage of a therapeutic agent, said method comprising:
reducing the level of a nucleic acid encoding GLI1 or the level of GLI1 protein in a cell of the subject, and
administering an effective amount of the therapeutic agent to the subject, wherein the effective amount of the therapeutic agent is less than the effective amount of the therapeutic agent in the absence of the reduction of the level of a nucleic acid encoding GLI1 or the level of GLI1 protein in a cell of the subject.

2. The method of claim 1, wherein the level of a nucleic acid encoding GLI1 or the level of GLI1 protein is reduced by administering to the subject an isolated nucleic acid selected from a small hairpin RNA (shRNA), a small interfering RNA (siRNA), a micro RNA (miRNA), an antisense polynucleotide, and a ribozyme.

3. The method of claim 2, wherein the isolated nucleic acid comprises a sequence encoding GLI1 or a fragment thereof, a sequence encoding antisense GLI1 or a fragment thereof, or an antisense nucleic acid complementary to a sequence encoding GLI1 or a fragment thereof.

4. The method of claim 3, wherein the nucleic acid comprises a sequence selected from SEQ ID NO.s:01-10.

5. The method of claim 4, wherein the nucleic acid comprises SEQ ID NO:01.

6. The method of claim 1, wherein the therapeutic agent comprises a chemotherapeutic agent.

7. The method of claim 6, wherein the chemotherapeutic agent is selected from a platinum-based compound such as cisplatin, carboplatin, nedaplatin, oxaliplatin, satraplatin, and triplatin tetranitrate, a nitrogen mustard such as cyclophosphamide, mechlorethamine, uramustine, melphalan, chlorambucil, and ifosfamide, a nitrosoureas such as carmustine, lomustine, and streptozocin, an alkyl sulfonate such as busulfan, thiotepa, procarbazine, and altretamine.

8. The method of claim 7, wherein the chemotherapeutic agent comprises a platinum-based compound.

9. The method of claim 8, wherein the platinum-based compound comprises cisplatin.

10. The method of claim 6, wherein the chemotherapeutic agent is selected from the group consisting of taxol and doxirubicin.

11. The method of claim 3, wherein increased expression of ERRC1, XPD, or XRCC1 results in increased cellular resistance to the therapeutic agent.

12. The method of claim 3, wherein increased activity of a nucleotide excision repair pathway results in increased cellular resistance to the therapeutic agent.

13. The method of claim 3, wherein increased activity of a base excision repair pathway results in increased cellular resistance to the therapeutic agent.

14. The method of claim 12, wherein the cellular resistance further comprises clinical resistance to the therapeutic agent.

15. The method of claim 3, wherein the disorder comprises cancer.

16. The method of claim 15, wherein the cancer is selected from breast cancer, melanoma, prostate cancer, colorectal cancer, head and neck cancer, lung cancer, colon cancer, oesophageal cancer, gastric cancer, testicular cancer, and ovarian cancer.

17. The method of claim 1, wherein the subject is a mammal.

18. The method of claim 17, wherein the mammal is a human.

19. The method of claim 1, wherein the nucleic acid encoding GLI1 comprises a nucleic acid encoding GLI1-130, or the GLI1 protein comprises GLI1-130 isoform.

20. A method for reducing the dosage of a therapeutic agent needed to treat a disorder in a subject comprising administering to the subject a nucleic acid comprising a sequence selected from SEQ ID NO.s:01-10, wherein the administration reduces the level of a nucleic acid encoding GLI1 or the level of GLI1 protein in a cell of the subject.

21. The method of claim 1, wherein said disorder is ovarian cancer and said therapeutic agent is a platinum-based chemotherapeutic compound.

22. The method of claim 21, wherein said platinum-based chemotherapeutic compound comprises cisplatin.

* * * * *

UNITED STATES PATENT AND TRADEMARK OFFICE
CERTIFICATE OF CORRECTION

PATENT NO.      : 9,540,647 B2
APPLICATION NO. : 14/919448
DATED           : January 10, 2017
INVENTOR(S)     : Lalita Samant et al.

It is certified that error appears in the above-identified patent and that said Letters Patent is hereby corrected as shown below:

On the Title Page

In Column 2 (page 1, item (56)) at Line 33, Under Other Publications, change "the" to --The--.

In Column 2 (page 1, item (56)) at Line 46, Under Other Publications, change "1990)" to --(1990)--.

In Column 1 (page 2, item (56)) at Line 22, Under Other Publications, change "-phospate" to -- -phosphate--.

In Column 1 (page 2, item (56)) at Line 58, Under Other Publications, after "Methods" insert --in--.

In Column 2 (page 2, item (56)) at Line 34, Under Other Publications, change "Melonoma" to --Melanoma--.

In Column 1 (page 3, item (56)) at Line 8, Under Other Publications, change "facor" to --factor--.

In Column 1 (page 3, item (56)) at Line 8, Under Other Publications, change "Gen" to --Gene--.

In Column 1 (page 3, item (56)) at Line 32, Under Other Publications, change "Proliveration," to --Proliferation,--.

In Column 2 (page 3, item (56)) at Line 49, Under Other Publications, change "1997)" to --(1997)--.

In Column 2 (page 3, item (56)) at Line 59, Under Other Publications, change "Elextroporation." to --Electroporation.--.

In Column 2 (page 4, item (56)) at Line 22, Under Other Publications, change "ten" to --Ten--.

Signed and Sealed this
Twenty-third Day of May, 2017

Michelle K. Lee
*Director of the United States Patent and Trademark Office*

CERTIFICATE OF CORRECTION (continued)
U.S. Pat. No. 9,540,647 B2

In Column 2 (page 4, item (56)) at Line 27, Under Other Publications, change "(2003) 1198-1205." to --(2003) 22:(8): 1198-1205.--.

In Column 2 (page 4, item (56)) at Line 36, Under Other Publications, change "riboyme" to -- ribozyme--.

In Column 2 (page 4, item (56)) at Line 44, Under Other Publications, change "Beno" to --Benzo--.

In the Drawings

Sheet 3 of 99 (Y-Axis, FIG. 2, Continued) at Line 1, Change "Luicferase" to --Luciferase--.

Sheet 5 of 99 (Y-Axis, FIG. 2, Continued) at Line 1, Change "Luicferase" to --Luciferase--.

Sheet 39 of 99 (FIG. 24) at Line 3, Change "deactylase" to --deacetylase--.

Sheet 63 of 99 (FIG. 48) at Line 7, Change "after after" to --after--.

In the Specification

In Column 2 at Line 4, After "an" delete "the".

In Column 2 at Lines 18-19, Change "rhabdomysocarcomas," to --rhabdomyosarcomas,--.

In Column 5 at Line 24, Change "doxirubicin." to --doxorubicin.--.

In Column 6 at Line 28, Change "doxirubicin." to --doxorubicin.--.

In Column 8 at Line 20, After "cancer" insert --.--.

In Column 10 at Line 20, Change "or or" to --or--.

In Column 12 at Line 60, Change "MCC12A, MCC12F" to --MCC012A, MCC012F--.

In Column 13 at Line 51, After "endogenous" insert --GLI1.--.

In Column 13 at Line 67, After "EMT" insert --.--.

In Column 15 at Line 3, After "invade" insert --.--.

In Column 15 at Line 21, After "IHH" insert --.--.

In Column 16 at Line 5, Change "(Tartarate" to --(Tartrate--.

In Column 16 at Line 49, Change "SM." to --SHH.--.

CERTIFICATE OF CORRECTION (continued)
U.S. Pat. No. 9,540,647 B2

In Column 16 at Line 57, After "70" insert --µM--.

In Column 17 at Line 21, Change "anti-GLI1shRNA" to --anti-GLI1 shRNA--.

In Column 20 at Line 27, Change "(*p<0.0001)." to --(*p≤0.0001).--.

In Column 23 at Line 38, Change "435: p<0.0001)." to --435: † p<0.0001).--.

In Column 32 at Line 6, Change "endometriod," to --endometrioid,--.

In Column 34 at Line 39, After "Methods" insert --in--.

In Column 42 at Line 64, Change "a" to --α--.

In Column 43 at Line 29, Change "TNF a," to --TNF α,--.

In Column 43 at Line 34, Change "α-1" to --α-I--.

In Column 49 at Line 11, Change "of of" to --of--.

In Column 49 at Line 67, Change "Brelsow" to --Breslow--.

In Column 50 at Line 1, Change "Brelsow" to --Breslow--.

In Column 51 at Line 67, After "GLI1" insert --.--.

In Column 54 at Line 64, Change "-MO2;" to -- -M02;--.

In Column 57 at Line 4, Change "K," to --K.,--.

In Column 57 at Line 17, After "This" delete "that".

In Column 57 at Line 22, Change "RedS" to --Red S--.

In Column 58 at Line 23, Change "(tartarate" to --(tartrate--.

In Column 59 at Line 24, After "(Oligoengine)" insert --.--.

In Column 59 at Line 25, Change "Tartarate" to --Tartrate--.

In Column 60 at Line 42, Change "(Ctsk;" to --(CTSK;--.

In Column 60 at Line 53 (approx.), Change "Pre-Osteclasts" to --Pre-Osteoclasts--.

In Column 61 at Lines 10-11 (approx.), Change "osteoclasts." to --osteoclasts.--.

CERTIFICATE OF CORRECTION (continued)
U.S. Pat. No. 9,540,647 B2

In Column 61 at Line 63, Change "(p<0.01)," to --(p≤0.01),--.

In Column 62 at Line 15, Change "(FIG." to --(FIGS.--.

In Column 62 at Line 43, Change "FIG." to --FIGS.--.

In Column 64 at Line 41, Change "(FIG." to --(FIGS.--.

In Column 65 at Line 43, Change "MMP 13" to --MMP13--.

In Column 65 at Line 47, Change "MMP 9" to --MMP9--.

In Column 66 at Line 11, Change "osteolyic" to --osteolytic--.

In Column 66 at Line 37 (approx.), Change "Oteolytic Metastatses" to --Osteolytic Metastases--.

In Column 66 at Line 55, Change "Lglutamine," to --L-glutamine,--.

In Column 67 at Line 66, Change "Sppl" to --Spp1--.

In Column 68 at Lines 8-9 (approx.), Change "LSAB+ System-HRP" to --LSAB+System-HRP--.

In Column 68 at Line 25, Change "Carcinoma." to --Carcinoma--.

In Column 71 at Line 50, Change "re-raanagements" to --re-arrangements--.

In Column 73 at Line 11 (approx.), Change "taxolin" to --taxol in--.

In Column 74 at Line 19, Change "form" to --from--.

In Column 75 at Line 25, Change "semi-quantative" to --semi-quantitative--.

In Column 76 at Line 2, Change "unregulated" to --upregulated--.

In Column 77 at Line 24, Change "semi-quantative" to --semi-quantitative--.

In Column 77 at Line 46, Change "semi-quantative" to --semi-quantitative--.

In Column 79 at Line 37, Change "semi-quantative" to --semi-quantitative--.

In Column 79 at Line 45, Change "semi-quantative" to --semi-quantitative--.

In Column 79 at Line 65, After "40" insert --µM--.

In Column 80 at Line 1, Change "semi-quantative" to --semi-quantitative--.

CERTIFICATE OF CORRECTION (continued)
U.S. Pat. No. 9,540,647 B2

In Column 80 at Line 16 (approx.), After "XPD" insert --.--.

In Column 82 at Line 21 (approx.), Change "phosphylated" to --phosphorylated--.

In Column 82 at Line 39 (approx.), Change "polyacylamide" to --polyacrylamide--.

In Column 82 at Line 52, Change "phosporylated" to --phosphorylated--.

In Column 82 at Line 55, Change "phosporylated" to --phosphorylated--.

In the Claims

In Column 109 at Line 3, In Claim 10, change "doxirubicin." to --doxorubicin.--.

```
                          SEQUENCE LISTING

<160> NUMBER OF SEQ ID NOS: 21

<210> SEQ ID NO 1
<211> LENGTH: 19
<212> TYPE: DNA
<213> ORGANISM: Homo sapiens
<220> FEATURE:
<221> NAME/KEY: misc_binding
<222> LOCATION: (1)...(19)
<223> OTHER INFORMATION: GLI1 transcript

<400> SEQUENCE: 1
cctcgtagct ttcatcaac                                                     19

<210> SEQ ID NO 2
<211> LENGTH: 19
<212> TYPE: DNA
<213> ORGANISM: Homo sapiens
<220> FEATURE:
<221> NAME/KEY: misc_binding
<222> LOCATION: (1)...(19)
<223> OTHER INFORMATION: GLI1 transcript

<400> SEQUENCE: 2
tcatcaactc gcgatgcac                                                     19

<210> SEQ ID NO 3
<211> LENGTH: 19
<212> TYPE: DNA
<213> ORGANISM: Homo sapiens
<220> FEATURE:
<221> NAME/KEY: misc_binding
<222> LOCATION: (1)...(19)
<223> OTHER INFORMATION: GLI1 transcript

<400> SEQUENCE: 3
ccaaacgcta tacagatcc                                                     19

<210> SEQ ID NO 4
<211> LENGTH: 19
<212> TYPE: DNA
<213> ORGANISM: Homo sapiens
<220> FEATURE:
<221> NAME/KEY: misc_binding
<222> LOCATION: (1)...(19)
<223> OTHER INFORMATION: GLI1 transcript

<400> SEQUENCE: 4
ccctcgtagc tttcatcaa                                                     19

<210> SEQ ID NO 5
<211> LENGTH: 19
```

```
<212> TYPE: DNA
<213> ORGANISM: Homo sapiens
<220> FEATURE:
<221> NAME/KEY: misc_binding
<222> LOCATION: (1)...(19)
<223> OTHER INFORMATION: GLI1 transcript

<400> SEQUENCE: 5
cgtagctttc atcaactcg                                                 19

<210> SEQ ID NO 6
<211> LENGTH: 19
<212> TYPE: DNA
<213> ORGANISM: Homo sapiens
<220> FEATURE:
<221> NAME/KEY: misc_binding
<222> LOCATION: (1)...(19)
<223> OTHER INFORMATION: GLI1 transcript

<400> SEQUENCE: 6
gtagctttca tcaactcgc                                                 19

<210> SEQ ID NO 7
<211> LENGTH: 19
<212> TYPE: DNA
<213> ORGANISM: Homo sapiens
<220> FEATURE:
<221> NAME/KEY: misc_binding
<222> LOCATION: (1)...(19)
<223> OTHER INFORMATION: GLI1 transcript

<400> SEQUENCE: 7
tagctttcat caactcgcg                                                 19

<210> SEQ ID NO 8
<211> LENGTH: 19
<212> TYPE: DNA
<213> ORGANISM: Homo sapiens
<220> FEATURE:
<221> NAME/KEY: misc_binding
<222> LOCATION: (1)...(19)
<223> OTHER INFORMATION: GLI1 transcript

<400> SEQUENCE: 8
ttcatcaact cgcgatgca                                                 19

<210> SEQ ID NO 9
<211> LENGTH: 19
<212> TYPE: DNA
<213> ORGANISM: Homo sapiens
<220> FEATURE:
<221> NAME/KEY: misc_binding
<222> LOCATION: (1)...(19)
<223> OTHER INFORMATION: GLI1 transcript

<400> SEQUENCE: 9
catcaactcg cgatgcaca                                                 19

<210> SEQ ID NO 10
<211> LENGTH: 19
<212> TYPE: DNA
<213> ORGANISM: Homo sapiens
<220> FEATURE:
<221> NAME/KEY: misc_binding
<222> LOCATION: (1)...(9)
<223> OTHER INFORMATION: GLI1 transcript

<400> SEQUENCE: 10
```

```
atcaactcgc gatgcacat                                                 19

<210> SEQ ID NO 11
<211> LENGTH: 3618
<212> TYPE: DNA
<213> ORGANISM: Homo sapiens
<220> FEATURE:
<221> NAME/KEY: gene
<222> LOCATION: (1)...(3618)
<223> OTHER INFORMATION: GLI1 gene

<400> SEQUENCE: 11
cccagactcc agccctggac cgcgcatccc gagcccagcg cccagacaga gtgtccccac     60
accctcctct gagacgccat gttcaactcg atgaccccac caccaatcag tagctatggc    120
gagccctgct gtctccggcc cctccccagt caggggccc  ccagtgtggg gacagaagga    180
ctgtctggcc cgcccttctg ccaccaagct aacctcatgt ccggccccca cagttatggg    240
ccagccagag agaccaacag ctgcaccgag ggcccactct tttcttctcc ccggagtgca    300
gtcaagttga ccaagaagcg ggcactgtcc atctcacctc tgtcggatgc cagcctggac    360
ctgcagacgg ttatccgcac ctcacccagc tccctcgtag cttttcatca actcgcgatgc    420 acatctccag gaggctccta cggtcatctc tccattggca ccatgagccc atctctggga    480
ttcccagccc agatgaatca ccaaaaaggg ccctcgcctt cctttggggt ccagccttgt    540
ggtccccatg actctgcccg gggtgggatg atccccacatc ctcagtcccg ggacccttc    600 ccaacttgcc agctgaagtc tgagctggac atgctggttg caagtgccg  ggaggaaccc    660 ttggaaggtg atatgtccag ccccaactcc acaggcatac aggatcccct gttggggatg    720
ctggatgggc gggaggacct cgagagagag gagaagcgtg agcctgaatc tgtgtatgaa    780
actgactgcc gttgggatgg ctgcagccag gaatttgact cccaagagca gctggtgcac    840
cacatcaaca gcgagcacat ccacggggag cggaaggagt tcgtgtgcca ctgggggggc    900
tgctccaggg agctgaggcc cttcaaagcc cagtacatgc tggtggttca catgcgcaga    960
cacactggcg agaagccaca caagtgcacg tttgagggt gccggaagtc atactcacgc   1020
ctcgaaaacc tgaagacgca cctgcggtca cacgggtg agaagccata catgtgtgag   1080
cacgagggct gcagtaaagc cttcagcaat gccagtgacc gagccaagca ccagaatcgg   1140
acccattcca atgagaagcc gtatgtatgt aagctccctg ctgcaccaa acgctataca   1200 gatcctagct cgctgcgaaa acatgtcaag acagtgcatg gtcctgacgc ccatgtgacc   1260
aaacggcacc gtgggatgg ccccctgcct cgggcaccat ccatttctac agtgagcccc   1320
aagagggagc gggaaggagg tcccatcagg gaggaaagca gactgactgt gccagagggt   1380
gccatgaagc cacagccaag ccctgggcc cagtcatcct gcagcagtga ccactccccg   1440
gcagggagtg cagccaatac agacagtggt gtggaaatga ctggcaatgc aggggcagc   1500 actgaagacc tctccagctt ggacgaggga ccttgcattg ctggcactgg tctgtccact   1560
cttcgccgcc ttgagaacct caggctggac cagctacatc aactccggcc aataggggacc   1620 cggggtctca aactgcccag cttgtcccac accggtacca ctgtgtcccg ccgcgtgggc   1680 ccccagtct ctcttgaacg ccgcagcagc agctccagca gcatcagctc tgcctatact   1740
gtcagccgcc gctcctccct ggcctctcct ttcccccctg ctccccacc agagaatgga   1800 gcatcctccc tgcctggcct tatgcctgcc cagcactacc tgcttcgggc aagatatgct   1860
tcagccagag ggggtggtac ttcgcccact gcagcatcca gcctggatcg gataggtggt   1920
cttcccatgc ctccttggag aagccgagcc gagtatccag gatacaaccc caatgcaggg   1980
```

```
gtcacccgga gggccagtga cccagcccag gctgctgacc gtcctgctcc agctagagtc    2040
cagaggttca agagcctggg ctgtgtccat accccaccca ctgtggcagg gggaggacag    2100
aactttgatc cttacctccc aacctctgtc tactcaccac agccccccag catcactgag    2160
aatgctgcca tggatgctag agggctacag gaagagccag aagttgggac ctccatggtg    2220
ggcagtggtc tgaaccccta tatggacttc ccacctactg atactctggg atatggggga    2280
cctgaagggg cagcagctga gccttatgga gcgagggtc caggctctct gcctcttggg    2340
cctggtccac ccaccaacta tggccccaac ccctgtcccc agcaggcctc atatcctgac    2400
cccacccaag aaacatgggg tgagttccct tcccactctg gctgtaccc aggccccaag    2460 gctctaggtg aacctacag ccagtgtcct cgacttgaac attatggaca agtgcaagtc    2520
aagccagaac agggtgccc agtggggtct gactccacag gactggcacc ctgcctcaat    2580
gcccacccca gtgaggggcc cccacatcca cagcctctct tttcccatta ccccagccc    2640 tctcctcccc aatatctcca gtcaggcccc tatacccagc caccccctga ttatcttcct    2700
tcagaaccca ggccttgcct ggactttgat tccccaccc attccacagg gcagctcaag    2760
gctcagcttg tgtgtaatta tgttcaatct caacaggagc tactgtggga gggtgggggc    2820
agggaagatg ccccgccca ggaaccttcc taccagagtc ccaagtttct gggggttcc    2880 caggttagcc caagccgtgc taaagctcca gtgaacacat atggacctgg ctttggaccc    2940
aacttgccca atcacaagtc aggttcctat cccacccctt caccatgcca tgaaaatttt    3000
gtagtggggg caaataggc ttcacatagg gcagcagcac cacctcgact tctgccccca    3060
ttgcccactt gctatgggcc tctcaaagtg ggaggcacaa accccagctg tggtcatcct    3120
gaggtgggca ggctaggagg gggtcctgcc ttgtaccctc ctcccgaagg acaggtatgt    3180
aaccccctgg actctcttga tcttgacaac actcagctgg actttgtggc tattctggat    3240
gagccccagg ggctgagtcc tcctccttcc catgatcagc ggggcagctc tggacatacc    3300
ccacctccct ctgggccccc caacatggct gtgggcaaca tgagtgtctt actgagatcc    3360
ctacctgggg aaacagaatt cctcaactct agtgcctaaa gagtagggaa tctcatccat    3420
cacagatcgc atttcctaag gggtttctat ccttccagaa aaattggggg agctgcagtc    3480
ccatgcacaa gatgccccag ggatgggagg tatgggctgg gggctatgta tagtctgtat    3540
acgttttgag gagaaatttg ataatgacac tgtttcctga taataaagga actgcatcag    3600
aaaaaaaaaa aaaaaaaa                                                  3618
```

<210> SEQ ID NO 12
<211> LENGTH: 17
<212> TYPE: DNA
<213> ORGANISM: Homo sapiens
<220> FEATURE:
<221> NAME/KEY: misc_binding
<222> LOCATION: (1)...(17)
<223> OTHER INFORMATION: GLI1-binding site

<400> SEQUENCE: 12

```
tgctgaatgc ccatccc                                                     17
```

<210> SEQ ID NO 13
<211> LENGTH: 28
<212> TYPE: DNA
<213> ORGANISM: Artificial Sequence
<220> FEATURE:
<223> OTHER INFORMATION: Primer

```
<400> SEQUENCE: 13
ctcagcggcc gctaataaat gaaaaagc                                          28

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
gttagcggcc gctgagagtt ccaggaag                                          28

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gtttttccct actttctccc                                                   20

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
ccaaaaacgc acacacac                                                     18

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17 ttcccctac caaatgttca                                                    20

<210> SEQ ID NO 18
<211> LENGTH: 22
<212> TYPE: DNA
<213> ORGANISM: Artificial Sequence
<220> FEATURE:
<223> OTHER INFORMATION: Artificial Sequence

<400> SEQUENCE: 18
tgctgcaaaa gtaattgtgg tt                                                22

<210> SEQ ID NO 19
<211> LENGTH: 1106
<212> TYPE: PRT
<213> ORGANISM: Homo sapiens

<400> SEQUENCE: 19
```

Met Phe Asn Ser Met Thr Pro Pro Ile Ser Ser Tyr Gly Glu Pro
 1               5                  10                  15

Cys Cys Leu Arg Pro Leu Pro Ser Gln Gly Ala Pro Ser Val Gly Thr
                20                  25                  30

Glu Gly Leu Ser Gly Pro Pro Phe Cys His Gln Ala Asn Leu Met Ser

```
            35                  40                  45
Gly Pro His Ser Tyr Gly Pro Ala Arg Glu Thr Asn Ser Cys Thr Glu
 50                  55                  60
Gly Pro Leu Phe Ser Ser Pro Arg Ser Ala Val Lys Leu Thr Lys Lys
 65                  70                  75                  80
Arg Ala Leu Ser Ile Ser Pro Leu Ser Asp Ala Ser Leu Asp Leu Gln
                     85                  90                  95
Thr Val Ile Arg Thr Ser Pro Ser Ser Leu Val Ala Phe Ile Asn Ser
                100                 105                 110
Arg Cys Thr Ser Pro Gly Gly Ser Tyr Gly His Leu Ser Ile Gly Thr
                115                 120                 125
Met Ser Pro Ser Leu Gly Phe Pro Ala Gln Met Asn His Gln Lys Gly
                130                 135                 140
Pro Ser Pro Ser Phe Gly Val Gln Pro Cys Gly Pro His Asp Ser Ala
145                 150                 155                 160
Arg Gly Gly Met Ile Pro His Pro Gln Ser Arg Gly Pro Phe Pro Thr
                165                 170                 175
Cys Gln Leu Lys Ser Glu Leu Asp Met Leu Val Gly Lys Cys Arg Glu
                180                 185                 190
Glu Pro Leu Glu Gly Asp Met Ser Ser Pro Asn Ser Thr Gly Ile Gln
                195                 200                 205
Asp Pro Leu Leu Gly Met Leu Asp Gly Arg Glu Asp Leu Glu Arg Glu
210                 215                 220
Glu Lys Arg Glu Pro Glu Ser Val Tyr Glu Thr Asp Cys Arg Trp Asp
225                 230                 235                 240
Gly Cys Ser Gln Glu Phe Asp Ser Gln Glu Gln Leu Val His His Ile
                245                 250                 255
Asn Ser Glu His Ile His Gly Glu Arg Lys Glu Phe Val Cys His Trp
                260                 265                 270
Gly Gly Cys Ser Arg Glu Leu Arg Pro Phe Lys Ala Gln Tyr Met Leu
                275                 280                 285
Val Val His Met Arg Arg His Thr Gly Glu Lys Pro His Lys Cys Thr
                290                 295                 300
Phe Glu Gly Cys Arg Lys Ser Tyr Ser Arg Leu Glu Asn Leu Lys Thr
305                 310                 315                 320
His Leu Arg Ser His Thr Gly Glu Lys Pro Tyr Met Cys Glu His Glu
                325                 330                 335
Gly Cys Ser Lys Ala Phe Ser Asn Ala Ser Asp Arg Ala Lys His Gln
                340                 345                 350
Asn Arg Thr His Ser Asn Glu Lys Pro Tyr Val Cys Lys Leu Pro Gly
                355                 360                 365
Cys Thr Lys Arg Tyr Thr Asp Pro Ser Ser Leu Arg Lys His Val Lys
                370                 375                 380
Thr Val His Gly Pro Asp Ala His Val Thr Lys Arg His Arg Gly Asp
385                 390                 395                 400
Gly Pro Leu Pro Arg Ala Pro Ser Ile Ser Thr Val Glu Pro Lys Arg
                405                 410                 415
Glu Arg Glu Gly Gly Pro Ile Arg Glu Glu Ser Arg Leu Thr Val Pro
                420                 425                 430
Glu Gly Ala Met Lys Pro Gln Pro Ser Pro Gly Ala Gln Ser Ser Cys
                435                 440                 445
Ser Ser Asp His Ser Pro Ala Gly Ser Ala Ala Asn Thr Asp Ser Gly
                450                 455                 460
```

```
Val Glu Met Thr Gly Asn Ala Gly Gly Ser Thr Asp Leu Ser Ser
465                 470                 475                 480

Leu Asp Glu Gly Pro Cys Ile Ala Gly Thr Gly Leu Ser Thr Leu Arg
                485                 490                 495

Arg Leu Glu Asn Leu Arg Leu Asp Gln Leu His Gln Leu Arg Pro Ile
                500                 505                 510

Gly Thr Arg Gly Leu Lys Leu Pro Ser Leu Ser His Thr Gly Thr Thr
            515                 520                 525

Val Ser Arg Arg Val Gly Pro Pro Val Ser Leu Glu Arg Arg Ser Ser
530                 535                 540

Ser Ser Ser Ser Ile Ser Ser Ala Tyr Thr Val Ser Arg Arg Ser Ser
545                 550                 555                 560

Leu Ala Ser Pro Phe Pro Pro Gly Ser Pro Glu Asn Gly Ala Ser
                565                 570                 575

Ser Leu Pro Gly Leu Met Pro Ala Gln His Tyr Leu Leu Arg Ala Arg
            580                 585                 590

Tyr Ala Ser Ala Arg Gly Gly Gly Thr Ser Pro Thr Ala Ala Ser Ser
            595                 600                 605

Leu Asp Arg Ile Gly Gly Leu Pro Met Pro Pro Trp Arg Ser Arg Ala
            610                 615                 620

Glu Tyr Pro Gly Tyr Asn Pro Asn Ala Gly Val Thr Arg Arg Ala Ser
625                 630                 635                 640

Asp Pro Ala Gln Ala Ala Asp Arg Pro Ala Pro Ala Arg Val Gln Arg
                645                 650                 655

Phe Lys Ser Leu Gly Cys Val His Thr Pro Pro Thr Val Ala Gly Gly
                660                 665                 670

Gly Gln Asn Phe Asp Pro Tyr Leu Pro Thr Ser Val Tyr Ser Pro Gln
            675                 680                 685

Pro Pro Ser Ile Thr Glu Asn Ala Ala Met Asp Ala Arg Gly Leu Gln
            690                 695                 700

Glu Glu Pro Glu Val Gly Thr Ser Met Val Gly Ser Gly Leu Asn Pro
705                 710                 715                 720

Tyr Met Asp Phe Pro Pro Thr Asp Thr Leu Gly Tyr Gly Gly Pro Glu
                725                 730                 735

Gly Ala Ala Ala Glu Pro Tyr Gly Ala Arg Gly Pro Gly Ser Leu Pro
                740                 745                 750

Leu Gly Pro Gly Pro Pro Thr Asn Tyr Gly Pro Asn Pro Cys Pro Gln
            755                 760                 765

Gln Ala Ser Tyr Pro Asp Pro Thr Gln Glu Thr Trp Gly Glu Phe Pro
            770                 775                 780

Ser His Ser Gly Leu Tyr Pro Gly Pro Lys Ala Leu Gly Gly Thr Tyr
785                 790                 795                 800

Ser Gln Cys Pro Arg Leu Glu His Tyr Gly Gln Val Gln Val Lys Pro
                805                 810                 815

Glu Gln Gly Cys Pro Val Gly Ser Asp Ser Thr Gly Leu Ala Pro Cys
                820                 825                 830

Leu Asn Ala His Pro Ser Glu Gly Pro Pro His Pro Gln Pro Leu Phe
            835                 840                 845

Ser His Tyr Pro Gln Pro Ser Pro Gln Tyr Leu Gln Ser Gly Pro
            850                 855                 860

Tyr Thr Gln Pro Pro Pro Asp Tyr Leu Pro Ser Glu Pro Arg Pro Cys
865                 870                 875                 880
```

```
Leu Asp Phe Asp Ser Pro Thr His Ser Thr Gly Gln Leu Lys Ala Gln
                885                 890                 895

Leu Val Cys Asn Tyr Val Gln Ser Gln Gln Glu Leu Leu Trp Glu Gly
            900                 905                 910

Gly Gly Arg Glu Asp Ala Pro Ala Gln Glu Pro Ser Tyr Gln Ser Pro
            915                 920                 925

Lys Phe Leu Gly Gly Ser Gln Val Ser Pro Ser Arg Ala Lys Ala Pro
            930                 935                 940

Val Asn Thr Tyr Gly Pro Gly Phe Gly Pro Asn Leu Pro Asn His Lys
945                 950                 955                 960

Ser Gly Ser Tyr Pro Thr Pro Ser Pro Cys His Glu Asn Phe Val Val
            965                 970                 975

Gly Ala Asn Arg Ala Ser His Arg Ala Ala Ala Pro Pro Arg Leu Leu
            980                 985                 990

Pro Pro Leu Pro Thr Cys Tyr Gly Pro Leu Lys Val Gly Gly Thr Asn
            995                1000                1005

Pro Ser Cys Gly His Pro Glu Val Gly Arg Leu Gly Gly Gly Pro Ala
           1010                1015                1020

Leu Tyr Pro Pro Pro Glu Gly Gln Val Cys Asn Pro Leu Asp Ser Leu
1025                1030                1035                1040

Asp Leu Asp Asn Thr Gln Leu Asp Phe Val Ala Ile Leu Asp Glu Pro
           1045                1050                1055

Gln Gly Leu Ser Pro Pro Pro Ser His Asp Gln Arg Gly Ser Ser Gly
           1060                1065                1070

His Thr Pro Pro Pro Ser Gly Pro Pro Asn Met Ala Val Gly Asn Met
           1075                1080                1085

Ser Val Leu Leu Arg Ser Leu Pro Gly Glu Thr Glu Phe Leu Asn Ser
           1090                1095                1100

Ser Ala
1105

<210> SEQ ID NO 20
<211> LENGTH: 978
<212> TYPE: PRT
<213> ORGANISM: Homo sapiens

<400> SEQUENCE: 20

Met Ser Pro Ser Leu Gly Phe Pro Ala Gln Met Asn His Gln Lys Gly
 1               5                  10                  15

Pro Ser Pro Ser Phe Gly Val Gln Pro Cys Gly Pro His Asp Ser Ala
            20                  25                  30

Arg Gly Gly Met Ile Pro His Pro Gln Ser Arg Gly Pro Phe Pro Thr
        35                  40                  45

Cys Gln Leu Lys Ser Glu Leu Asp Met Leu Val Gly Lys Cys Arg Glu
    50                  55                  60

Glu Pro Leu Glu Gly Asp Met Ser Ser Pro Asn Ser Thr Gly Ile Gln
65                  70                  75                  80

Asp Pro Leu Leu Gly Met Leu Asp Gly Arg Glu Asp Leu Glu Arg Glu
                85                  90                  95

Glu Lys Arg Glu Pro Glu Ser Val Tyr Glu Thr Asp Cys Arg Trp Asp
            100                 105                 110

Gly Cys Ser Gln Glu Phe Asp Ser Gln Glu Gln Leu Val His His Ile
        115                 120                 125

Asn Ser Glu His Ile His Gly Glu Arg Lys Glu Phe Val Cys His Trp
    130                 135                 140
```

```
Gly Gly Cys Ser Arg Glu Leu Arg Pro Phe Lys Ala Gln Tyr Met Leu
145                 150                 155                 160

Val Val His Met Arg Arg His Thr Gly Glu Lys Pro His Lys Cys Thr
            165                 170                 175

Phe Glu Gly Cys Arg Lys Ser Tyr Ser Arg Leu Glu Asn Leu Lys Thr
            180                 185                 190

His Leu Arg Ser His Thr Gly Glu Lys Pro Tyr Met Cys Glu His Glu
            195                 200                 205

Gly Cys Ser Lys Ala Phe Ser Asn Ala Ser Asp Arg Ala Lys His Gln
            210                 215                 220

Asn Arg Thr His Ser Asn Glu Lys Pro Tyr Val Cys Lys Leu Pro Gly
225                 230                 235                 240

Cys Thr Lys Arg Tyr Thr Asp Pro Ser Ser Leu Arg Lys His Val Lys
            245                 250                 255

Thr Val His Gly Pro Asp Ala His Val Thr Lys Arg His Arg Gly Asp
            260                 265                 270

Gly Pro Leu Pro Arg Ala Pro Ser Ile Ser Thr Val Glu Pro Lys Arg
            275                 280                 285

Glu Arg Glu Gly Pro Ile Arg Glu Glu Ser Arg Leu Thr Val Pro
290                 295                 300

Glu Gly Ala Met Lys Pro Gln Pro Ser Pro Gly Ala Gln Ser Ser Cys
305                 310                 315                 320

Ser Ser Asp His Ser Pro Ala Gly Ser Ala Ala Asn Thr Asp Ser Gly
            325                 330                 335

Val Glu Met Thr Gly Asn Ala Gly Gly Ser Thr Glu Asp Leu Ser Ser
            340                 345                 350

Leu Asp Glu Gly Pro Cys Ile Ala Gly Thr Gly Leu Ser Thr Leu Arg
            355                 360                 365

Arg Leu Glu Asn Leu Arg Leu Asp Gln Leu His Gln Leu Arg Pro Ile
            370                 375                 380

Gly Thr Arg Gly Leu Lys Leu Pro Ser Leu Ser His Thr Gly Thr Thr
385                 390                 395                 400

Val Ser Arg Arg Val Gly Pro Pro Val Ser Leu Glu Arg Arg Ser Ser
            405                 410                 415

Ser Ser Ser Ser Ile Ser Ser Ala Tyr Thr Val Ser Arg Arg Ser Ser
            420                 425                 430

Leu Ala Ser Pro Phe Pro Pro Gly Ser Pro Pro Glu Asn Gly Ala Ser
            435                 440                 445

Ser Leu Pro Gly Leu Met Pro Ala Gln His Tyr Leu Leu Arg Ala Arg
            450                 455                 460

Tyr Ala Ser Ala Arg Gly Gly Gly Thr Ser Pro Thr Ala Ala Ser Ser
465                 470                 475                 480

Leu Asp Arg Ile Gly Gly Leu Pro Met Pro Pro Trp Arg Ser Arg Ala
            485                 490                 495

Glu Tyr Pro Gly Tyr Asn Pro Asn Ala Gly Val Thr Arg Arg Ala Ser
            500                 505                 510

Asp Pro Ala Gln Ala Ala Asp Arg Pro Ala Pro Ala Arg Val Gln Arg
            515                 520                 525

Phe Lys Ser Leu Gly Cys Val His Thr Pro Thr Val Ala Gly Gly
            530                 535                 540

Gly Gln Asn Phe Asp Pro Tyr Leu Pro Thr Ser Val Tyr Ser Pro Gln
545                 550                 555                 560
```

-continued

```
Pro Pro Ser Ile Thr Glu Asn Ala Ala Met Asp Ala Arg Gly Leu Gln
            565                 570                 575

Glu Glu Pro Glu Val Gly Thr Ser Met Val Gly Ser Gly Leu Asn Pro
            580                 585                 590

Tyr Met Asp Phe Pro Pro Thr Asp Thr Leu Gly Tyr Gly Gly Pro Glu
            595                 600                 605

Gly Ala Ala Ala Glu Pro Tyr Gly Ala Arg Gly Pro Gly Ser Leu Pro
    610                 615                 620

Leu Gly Pro Gly Pro Thr Asn Tyr Gly Pro Asn Pro Cys Pro Gln
625                 630                 635                 640

Gln Ala Ser Tyr Pro Asp Pro Thr Gln Glu Thr Trp Gly Glu Phe Pro
                645                 650                 655

Ser His Ser Gly Leu Tyr Pro Gly Pro Lys Ala Leu Gly Gly Thr Tyr
            660                 665                 670

Ser Gln Cys Pro Arg Leu Glu His Tyr Gly Gln Val Gln Val Lys Pro
        675                 680                 685

Glu Gln Gly Cys Pro Val Gly Ser Asp Ser Thr Gly Leu Ala Pro Cys
        690                 695                 700

Leu Asn Ala His Pro Ser Glu Gly Pro Pro His Pro Gln Pro Leu Phe
705                 710                 715                 720

Ser His Tyr Pro Gln Pro Ser Pro Pro Gln Tyr Leu Gln Ser Gly Pro
                725                 730                 735

Tyr Thr Gln Pro Pro Asp Tyr Leu Pro Ser Glu Pro Arg Pro Cys
                740                 745                 750

Leu Asp Phe Asp Ser Pro Thr His Ser Thr Gly Gln Leu Lys Ala Gln
            755                 760                 765

Leu Val Cys Asn Tyr Val Gln Ser Gln Gln Glu Leu Leu Trp Glu Gly
    770                 775                 780

Gly Gly Arg Glu Asp Ala Pro Ala Gln Glu Pro Ser Tyr Gln Ser Pro
785                 790                 795                 800

Lys Phe Leu Gly Gly Ser Gln Val Ser Pro Ser Arg Ala Lys Ala Pro
                805                 810                 815

Val Asn Thr Tyr Gly Pro Gly Phe Gly Pro Asn Leu Pro Asn His Lys
            820                 825                 830

Ser Gly Ser Tyr Pro Thr Pro Ser Pro Cys His Glu Asn Phe Val Val
        835                 840                 845

Gly Ala Asn Arg Ala Ser His Arg Ala Ala Pro Pro Arg Leu Leu
        850                 855                 860

Pro Pro Leu Pro Thr Cys Tyr Gly Pro Leu Lys Val Gly Gly Thr Asn
865                 870                 875                 880

Pro Ser Cys Gly His Pro Glu Val Gly Arg Leu Gly Gly Pro Ala
                885                 890                 895

Leu Tyr Pro Pro Pro Glu Gly Gln Val Cys Asn Pro Leu Asp Ser Leu
            900                 905                 910

Asp Leu Asp Asn Thr Gln Leu Asp Phe Val Ala Ile Leu Asp Glu Pro
        915                 920                 925

Gln Gly Leu Ser Pro Pro Ser His Asp Gln Arg Gly Ser Ser Gly
    930                 935                 940

His Thr Pro Pro Pro Ser Gly Pro Pro Asn Met Ala Val Gly Asn Met
945                 950                 955                 960

Ser Val Leu Leu Arg Ser Leu Pro Gly Glu Thr Glu Phe Leu Asn Ser
                965                 970                 975

Ser Ala
```

<210> SEQ ID NO 21
<211> LENGTH: 1065
<212> TYPE: PRT
<213> ORGANISM: Homo sapiens

<400> SEQUENCE: 21

```
Met Phe Asn Ser Met Thr Pro Pro Ile Ser Ser Tyr Gly Glu Pro
 1               5                  10                  15

Cys Cys Leu Arg Pro Leu Pro Ser Gln Gly Ala Pro Ser Val Gly Thr
                20                  25                  30

Glu Val Lys Leu Thr Lys Lys Arg Ala Leu Ser Ile Ser Pro Leu Ser
                35                  40                  45

Asp Ala Ser Leu Asp Leu Gln Thr Val Ile Arg Thr Ser Pro Ser Ser
            50                  55                  60

Leu Val Ala Phe Ile Asn Ser Arg Cys Thr Ser Pro Gly Gly Ser Tyr
 65                 70                  75                  80

Gly His Leu Ser Ile Gly Thr Met Ser Pro Ser Leu Gly Phe Pro Ala
                85                  90                  95

Gln Met Asn His Gln Lys Gly Pro Ser Pro Ser Phe Gly Val Gln Pro
                100                 105                 110

Cys Gly Pro His Asp Ser Ala Arg Gly Gly Met Ile Pro His Pro Gln
            115                 120                 125

Ser Arg Gly Pro Phe Pro Thr Cys Gln Leu Lys Ser Glu Leu Asp Met
        130                 135                 140

Leu Val Gly Lys Cys Arg Glu Glu Pro Leu Glu Gly Asp Met Ser Ser
145                 150                 155                 160

Pro Asn Ser Thr Gly Ile Gln Asp Pro Leu Leu Gly Met Leu Asp Gly
                165                 170                 175

Arg Glu Asp Leu Glu Arg Glu Glu Lys Arg Glu Pro Glu Ser Val Tyr
                180                 185                 190

Glu Thr Asp Cys Arg Trp Asp Gly Cys Ser Gln Glu Phe Asp Ser Gln
            195                 200                 205

Glu Gln Leu Val His His Ile Asn Ser Glu His Ile His Gly Glu Arg
        210                 215                 220

Lys Glu Phe Val Cys His Trp Gly Gly Cys Ser Arg Glu Leu Arg Pro
225                 230                 235                 240

Phe Lys Ala Gln Tyr Met Leu Val Val His Met Arg Arg His Thr Gly
                245                 250                 255

Glu Lys Pro His Lys Cys Thr Phe Glu Gly Cys Arg Lys Ser Tyr Ser
                260                 265                 270

Arg Leu Glu Asn Leu Lys Thr His Leu Arg Ser His Thr Gly Glu Lys
            275                 280                 285

Pro Tyr Met Cys Glu His Glu Gly Cys Ser Lys Ala Phe Ser Asn Ala
        290                 295                 300

Ser Asp Arg Ala Lys His Gln Asn Arg Thr His Ser Asn Glu Lys Pro
305                 310                 315                 320

Tyr Val Cys Lys Leu Pro Gly Cys Thr Lys Arg Tyr Thr Asp Pro Ser
                325                 330                 335

Ser Leu Arg Lys His Val Lys Thr His Gly Pro Asp Ala His Val
                340                 345                 350

Thr Lys Arg His Arg Gly Asp Gly Pro Leu Pro Arg Ala Pro Ser Ile
            355                 360                 365

Ser Thr Val Glu Pro Lys Arg Glu Arg Glu Gly Gly Pro Ile Arg Glu
```

```
                370               375               380
Glu Ser Arg Leu Thr Val Pro Glu Gly Ala Met Lys Pro Gln Pro Ser
385               390               395               400

Pro Gly Ala Gln Ser Ser Cys Ser Ser Asp His Ser Pro Ala Gly Ser
              405               410               415

Ala Ala Asn Thr Asp Ser Gly Val Glu Met Thr Gly Asn Ala Gly Gly
              420               425               430

Ser Thr Glu Asp Leu Ser Ser Leu Asp Glu Gly Pro Cys Ile Ala Gly
          435               440               445

Thr Gly Leu Ser Thr Leu Arg Arg Leu Glu Asn Leu Arg Leu Asp Gln
          450               455               460

Leu His Gln Leu Arg Pro Ile Gly Thr Arg Gly Leu Lys Leu Pro Ser
465               470               475               480

Leu Ser His Thr Gly Thr Thr Val Ser Arg Arg Val Gly Pro Pro Val
              485               490               495

Ser Leu Glu Arg Arg Ser Ser Ser Ser Ile Ser Ser Ala Tyr
              500               505               510

Thr Val Ser Arg Arg Ser Ser Leu Ala Ser Pro Phe Pro Pro Gly Ser
              515               520               525

Pro Pro Glu Asn Gly Ala Ser Ser Leu Pro Gly Leu Met Pro Ala Gln
530               535               540

His Tyr Leu Leu Arg Ala Arg Tyr Ala Ser Ala Arg Gly Gly Gly Thr
545               550               555               560

Ser Pro Thr Ala Ala Ser Ser Leu Asp Arg Ile Gly Gly Leu Pro Met
              565               570               575

Pro Pro Trp Arg Ser Arg Ala Glu Tyr Pro Gly Tyr Asn Pro Asn Ala
              580               585               590

Gly Val Thr Arg Arg Ala Ser Asp Pro Ala Gln Ala Ala Asp Arg Pro
              595               600               605

Ala Pro Ala Arg Val Gln Arg Phe Lys Ser Leu Gly Cys Val His Thr
              610               615               620

Pro Pro Thr Val Ala Gly Gly Gln Asn Phe Asp Pro Tyr Leu Pro
625               630               635               640

Thr Ser Val Tyr Ser Pro Gln Pro Pro Ser Ile Thr Glu Asn Ala Ala
              645               650               655

Met Asp Ala Arg Gly Leu Gln Glu Glu Pro Glu Val Gly Thr Ser Met
              660               665               670

Val Gly Ser Gly Leu Asn Pro Tyr Met Asp Phe Pro Pro Thr Asp Thr
              675               680               685

Leu Gly Tyr Gly Gly Pro Glu Gly Ala Ala Ala Glu Pro Tyr Gly Ala
          690               695               700

Arg Gly Pro Gly Ser Leu Pro Leu Gly Pro Gly Pro Thr Asn Tyr
705               710               715               720

Gly Pro Asn Pro Cys Pro Gln Gln Ala Ser Tyr Pro Asp Pro Thr Gln
              725               730               735

Glu Thr Trp Gly Glu Phe Pro Ser His Ser Gly Leu Tyr Pro Gly Pro
              740               745               750

Lys Ala Leu Gly Gly Thr Tyr Ser Gln Cys Pro Arg Leu Glu His Tyr
              755               760               765

Gly Gln Val Gln Val Lys Pro Glu Gln Gly Cys Pro Val Gly Ser Asp
          770               775               780

Ser Thr Gly Leu Ala Pro Cys Leu Asn Ala His Pro Ser Glu Gly Pro
785               790               795               800
```

-continued

```
Pro His Pro Gln Pro Leu Phe Ser His Tyr Pro Gln Pro Ser Pro Pro
            805                 810                 815

Gln Tyr Leu Gln Ser Gly Pro Tyr Thr Gln Pro Pro Pro Asp Tyr Leu
            820                 825                 830

Pro Ser Glu Pro Arg Pro Cys Leu Asp Phe Asp Ser Pro Thr His Ser
            835                 840                 845

Thr Gly Gln Leu Lys Ala Gln Leu Val Cys Asn Tyr Val Gln Ser Gln
            850                 855                 860

Gln Glu Leu Leu Trp Glu Gly Gly Arg Glu Asp Ala Pro Ala Gln
865                 870                 875                 880

Glu Pro Ser Tyr Gln Ser Pro Lys Phe Leu Gly Gly Ser Gln Val Ser
            885                 890                 895

Pro Ser Arg Ala Lys Ala Pro Val Asn Thr Tyr Gly Pro Gly Phe Gly
            900                 905                 910

Pro Asn Leu Pro Asn His Lys Ser Gly Ser Tyr Pro Thr Pro Ser Pro
            915                 920                 925

Cys His Glu Asn Phe Val Val Gly Ala Asn Arg Ala Ser His Arg Ala
            930                 935                 940

Ala Ala Pro Pro Arg Leu Leu Pro Pro Leu Pro Thr Cys Tyr Gly Pro
945                 950                 955                 960

Leu Lys Val Gly Gly Thr Asn Pro Ser Cys Gly His Pro Glu Val Gly
            965                 970                 975

Arg Leu Gly Gly Gly Pro Ala Leu Tyr Pro Pro Pro Glu Gly Gln Val
            980                 985                 990

Cys Asn Pro Leu Asp Ser Leu Asp Leu Asp Asn Thr Gln Leu Asp Phe
            995                 1000                1005

Val Ala Ile Leu Asp Glu Pro Gln Gly Leu Ser Pro Pro Pro Ser His
            1010                1015                1020

Asp Gln Arg Gly Ser Ser Gly His Thr Pro Pro Pro Ser Gly Pro Pro
1025                1030                1035                1040

Asn Met Ala Val Gly Asn Met Ser Val Leu Leu Arg Ser Leu Pro Gly
            1045                1050                1055

Glu Thr Glu Phe Leu Asn Ser Ser Ala
            1060                1065
```